(12) United States Patent
Morriello et al.

(10) Patent No.: US 10,357,481 B2
(45) Date of Patent: Jul. 23, 2019

(54) SUBSTITUTED TRIAZOLO BICYCLIC COMPOUNDS AS PDE2 INHIBITORS

(71) Applicants: MERCK SHARP & DOHME CORP., Rahway, NJ (US); Gregori J. Morriello, Rahway, NJ (US); Lehua Chang, Rahway, NJ (US); Ashley Forster, Rahway, NJ (US); Yili Chen, Rahway, NJ (US); Michael P. Dwyer, Rahway, NJ (US); Zack Zhiqiang Guo, Rahway, NJ (US); Ming Wang, Rahway, NJ (US); Shimin Xu, Beijing (CN); Yingjian Bo, Beijing (CN); Jianmin Fu, Beijing (CN)

(72) Inventors: Gregori J. Morriello, Rahway, NJ (US); Lehua Chang, Rahway, NJ (US); Ashley Forster, Rahway, NJ (US); Yili Chen, Rahway, NJ (US); Michael P. Dwyer, Rahway, NJ (US); Zack Zhiqiang Guo, Rahway, NJ (US); Ming Wang, Rahway, NJ (US); Shimin Xu, Beijing (CN); Yingjian Bo, Beijing (CN); Jianmin Fu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/579,878

(22) PCT Filed: Jun. 27, 2016

(86) PCT No.: PCT/US2016/039478
§ 371 (c)(1),
(2) Date: Dec. 5, 2017

(87) PCT Pub. No.: WO2017/003894
PCT Pub. Date: Jan. 5, 2017

(65) Prior Publication Data
US 2018/0169072 A1 Jun. 21, 2018

(30) Foreign Application Priority Data
Jul. 1, 2015 (WO) ................ PCT/CN2015/083060

(51) Int. Cl.
| | | |
|---|---|---|
| *A61K 31/4196* | (2006.01) | |
| *C07D 471/04* | (2006.01) | |
| *C07D 487/04* | (2006.01) | |
| *A61P 25/28* | (2006.01) | |
| *A61P 25/22* | (2006.01) | |
| *A61P 25/18* | (2006.01) | |
| *A61P 25/16* | (2006.01) | |
| *A61P 25/06* | (2006.01) | |
| *A61K 31/52* | (2006.01) | |

(52) U.S. Cl.
CPC .......... *A61K 31/4196* (2013.01); *A61K 31/52* (2013.01); *A61P 25/06* (2018.01); *A61P 25/16* (2018.01); *A61P 25/18* (2018.01); *A61P 25/22* (2018.01); *A61P 25/28* (2018.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 6,573,263 B2 | 6/2003 | Niewohner et al. | |
| 7,419,969 B2 | 9/2008 | Naidu et al. | |
| 8,598,155 B2 | 12/2013 | Helal et al. | |
| 8,642,660 B2 * | 2/2014 | Goldfarb ............. | A61K 31/122 514/18.9 |
| 8,680,116 B2 | 3/2014 | DeLeon et al. | |

(Continued)

FOREIGN PATENT DOCUMENTS

| | | |
|---|---|---|
| CN | 1849070 | 10/2006 |
| CN | 1894245 | 1/2007 |

(Continued)

OTHER PUBLICATIONS

Gujjar, R. et al., J. Med. Chem. (2011), 54(11), pp. 3935-3949.*

(Continued)

*Primary Examiner* — Heidi Reese

(74) *Attorney, Agent, or Firm* — Sylvia A. Ayler; John C. Todaro

(57) ABSTRACT

The present invention is directed to substituted triazolo bicyclic compounds of formula I which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

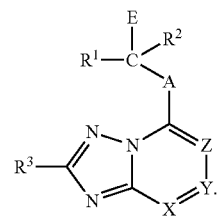

I

8 Claims, No Drawings

(56) References Cited

U.S. PATENT DOCUMENTS

| | | | |
|---|---|---|---|
| 2007/0135457 A1 | 6/2007 | Beyer et al. | |
| 2007/0275961 A1* | 11/2007 | Bower | A61K 31/519 |
| | | | 514/233.2 |
| 2007/0281917 A1 | 12/2007 | Naidu et al. | |
| 2009/0182142 A1* | 7/2009 | Furukubo | C07D 487/04 |
| | | | 544/122 |
| 2009/0253677 A1 | 10/2009 | Beaulieu et al. | |
| 2012/0214791 A1 | 8/2012 | Helal et al. | |

FOREIGN PATENT DOCUMENTS

| | | | |
|---|---|---|---|
| EP | 1097706 A1 | 5/2001 | |
| EP | 1097707 A1 | 5/2001 | |
| EP | 1430898 A1 | 6/2004 | |
| EP | 1956009 A1 | 8/2008 | |
| GB | 1148629 A * | 4/1969 | C07D 487/04 |
| WO | WO2003035076 | 5/2003 | |
| WO | WO2003035077 A1 | 5/2003 | |
| WO | WO2005041957 | 10/2004 | |
| WO | WO2004096128 | 11/2004 | |
| WO | WO2005061497 | 7/2005 | |
| WO | WO2006024640 | 3/2006 | |
| WO | WO200672615 | 7/2006 | |
| WO | WO2007058646 | 5/2007 | |
| WO | WO2009016498 | 2/2009 | |
| WO | WO2009080546 | 7/2009 | |
| WO | WO2009117540 | 9/2009 | |
| WO | WO2010136493 | 12/2010 | |
| WO | WO2012080727 A2 | 6/2012 | |
| WO | WO2012114222 | 8/2012 | |
| WO | WO2013034758 | 9/2012 | |
| WO | WO2013034761 | 9/2012 | |
| WO | WO2012151567 | 11/2012 | |
| WO | WO201300924 | 1/2013 | |
| WO | WO2013034755 | 3/2013 | |
| WO | WO2013098373 | 7/2013 | |
| WO | 2013161913 | 10/2013 | |
| WO | WO2014010732 | 1/2014 | |
| WO | WO2014019979 | 2/2014 | |
| WO | WO2014139983 | 9/2014 | |
| WO | WO2015012328 | 1/2015 | |
| WO | WO2005063723 | 7/2017 | |

OTHER PUBLICATIONS

Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 Is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Boyd et al., 2-Substituted -4,5-Dihydroxypyrimidine-6-Carboxamide Antiviral Targeted Libraries, J. Comb. Chem, 2009, 1100-1104, 11.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Columbus Ohio, US Chemical Abstracts Service Database Reg, Jul. 19, 2013, RN1178021-74-3; RN1306099-73-9; RN1303743-34-1; RN1223719-29-6; RN1223520-51-1; RN1223423-44-6; RN1223259-98-0; RN1154011-32-1; RN1062264-55-4; RN41062254-33-4; RN1223491-75-5; RN1050683-37-8; RN144105-20-4; RN1445736-38-8.

Cote et al., Comparative Involvement of Cyclic Nucleotide, Endocrinology, 1999, 3594-3601, 140.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.
Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Gergega et al., Systematic Effect of Benzo-Annelation on Oxo-Hydroxy Tautomerism of Heterocyclic, J. Phys. Chem A., 2007, 4934-4943, 111.
Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.
Haynes et al., Erythro-9-(2-Hydroxy-3-Nonyl) Adenine Inhibits Cyclic-3',5' Guanosine Monophosphate -Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Huang et al., A Fluroescence Polarization Assay for Cyclic Nucleotide Phosphodiesterases, J. of Biomolecular Screening, 2002, pp. 215-222, 7.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kheifets et al., Structure and Amide -Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.

(56) References Cited

OTHER PUBLICATIONS

Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
P. C. Tfelt-Hansen et al., One Hundred Years of Migraine Research: Major Clinical and, Headache, 2011, 752-778, 51.
Pace et al., Dihydroxypyrimidine-4-Carboxamides as Novel Poten and Selective HIV Integrase Inhibitors, J. Med Chem., 2007, 2225-2239, 50.
Petrocchi et al., From dihydroxypyrimidine carboxylic acids to carboxamide, Bioorganic & Medicinal Chemistry Letters, 2007, 350-353, 17.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.
Plummer et al., Discovery of potent selective bioavailable phosphodiesterase, Bioorganic & Medicinal Chemistry Letters, 2013, 3443-3447, 23.
Pubchem: SID 166318194. Nov. 30, 2013. Retrieved Feb. 8, 2016. Retrieved from the Internet. https://pubchem.ncbi.nlm.nih.gov/substance/1663181914.
Pubchem: SID 233296808, Feb. 12, 2005. Retrieved Dec. 10, 2016, Retrieved from the Internet. URL:https://pubchem.ncbl.nlm.nih.gov/substance/233296808

Reierson et al., Repeated antidepressant therapy increases cyclic GMP signaling, Neurosci Letter, 2009, 149-153, 466 (3).
Rivet-Bastide et al., cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Sanchez et al., Gas-Phase Tautomeric Equilibrium of 4-Hydroxypyrimidine, J. Am. Chem Soc., 2007, 6287-6290, 129.
Savai et al., Targeting Cancer with Phosphodiesterase Inhibitors, Expert Opinion, 2010, 117-131, 19.
Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.
Jensen, T et al, The identification of GPR3 inverse agonist AF64394; The first small molecule inhibitor of GPR3 receptor function, Bioorganic & Medicinal Chemistry Letters, 2014, 5195-5198, 24(22).
Vidler, LR et al, Discovery of Novel Small-Molecule Inhibitors of BRD4 Using Structure-Based Virtual Screening, Journal of Medicinal Chemistry, 2013, 8073-8088, 56(20).

\* cited by examiner

SUBSTITUTED TRIAZOLO BICYCLIC COMPOUNDS AS PDE2 INHIBITORS

CROSS REFERENCE TO RELATED APPLICATIONS

This application is the National Stage of International Application No. PCT/US2016/039478 filed on Jun. 27, 2016, which claims the benefit under International Application PCT/CN2015/083060 filed on Jul. 1, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary mesengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001)); platelet aggregation (R. J. Haslam, et Al., Biochem. J., 323, 371 (1997); female sexual arousal disorder (C. P. Wayman, et al., EP Patent Publications EP10977707 and EP1097706); osteoarthritis pain (M. Plummer et, al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et al., J. Pharm. Exp. Ther., 276, 752 (1996)). See also 2-Substituted-4,5-dihydroxypyrimidine-6-carboxamide Antiviral Targeted Libraries, Vincent Boyd et al., Journal of Combinatorial Chemistry (2009), 11(6), 1100-1104; From Dihydroxypyrimidine Carboxylic Acids to Carboxamide HIV-1 Integrase Inhibitors: SAR Around the Amide Moiety, Alessia Petrocchi et al., Bioorganic & Medicinal Chemistry Letters (2007), 17(2), 350-353; Dihydroxypyrimidine-4-carboxamides as Novel Potent and Selective HIV Integrase Inhibitors, Paola Pare et al., Journal of Medicinal Chemistry (2007), 50(9), 2225-2239; US2007135457, WO2012151567, US20090253677, US20070281917, WO2004096128, WO2003035077, WO2003035076, WO2007058646, WO2009117540, and U.S. Pat. No. 7,419, 969.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7):1081-92, 2004). PDE2A inhibition was also shown to improve cognitive deficits that develop in aging and Alzheimer's disease (Domek-Lopacinska and Strosznaj der, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263, 8,598,155, and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al, *Differential Regulation of Endothelial Cell Permeability by cGMP via Phosphodieserase 2 and 3*, Circulation Research, 2007; 101, pgs: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating PDE2 conditions, diseases or disorders associated with PDE2 such as Alzheimer's disease, cognitive impairment associated with schizophrenia, depression, migraines, and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to substituted triazolo bicyclic compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to substituted triazolo bicyclic compounds of formula I:

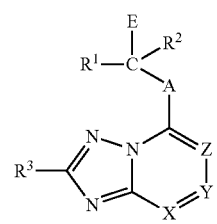

or a pharmaceutically acceptable salt thereof, wherein:
A represents NR, or O;
E represents phenyl, indolyl, naphthyl, or pyridyl, said phenyl, indolyl, naphthyl, and pyridyl, optionally substituted with 1 to 3 groups of $R^a$,
X, Y, and Z are represented respectively as follows:
X=N, Y=$CR^{4a}$, Z=$CR^{4b}$;
X=CH, Y=$CR^{4a}$, Z=N;
X=CH, Y=N, Z=$CR^{4b}$;
X=N, Y=N, Z=$CR^{4b}$;
X=CH, Y=$CR^{4a}$, Z=$CR^{4b}$;
$R^1$ and $R^2$ are independently selected from the group consisting of H, $C_{1-6}$alkyl, and $C_{3-10}$cycloalkyl, said alkyl and cycloalkyl optionally substituted with 1 to 3 groups of $R^a$; or $R^1$ and $R^2$ can combine with the carbon to which they are attached to form $C_{3-10}$cycloalkyl or $C_{3-10}$heterocycloalkyl, said cycloalkyl and heterocycloalkyl optionally substituted with 1 to 3 groups of $R^a$;
$R^3$ represents H, $C_{1-6}$alkyl, $C_{1-4}$haloalkyl, $C_{3-10}$cycloalkyl, $NR_2$, said alkyl and cycloalkyl optionally substituted with 1 to 3 groups of $R^a$;
$R^{4a}$ and $R^{4b}$ independently are selected from the group consisting of hydrogen, OR, $C_{1-6}$alkyl, $C_{1-4}$haloalkyl, $C_{3-10}$cycloalkyl, halo, and $NR_2$, said alkyl and cycloalkyl optionally substituted with one to three groups of $R^a$;
$R^a$ is selected from the group consisting of halo, CN, $C_{1-6}$alkyl, $(CH_2)_nOR$, $(O)_pC_{1-4}$haloalkyl, $NR_2$, $SCF_3$, $SF_5$, $C_{3-10}$cycloalkyl, $C_{6-10}$aryl, and $C_{4-10}$heterocyclyl; said alkyl, cycloalkyl and heterocyclyl optionally substituted with one to three groups selected from halo, and $C_{1-6}$alkyl; two adjacent $R^a$ groups on the phenyl of E together with the atoms to which they are attached can combine to form a cyclic ring, said ring optionally interrupted by 1 to 2 heteroatoms selected from N, S, and O;
R represents H or $C_{1-6}$alkyl,
n represents 0, 1, 2, 3, or 4;
p represents 0 or 1.

An embodiment of the invention of formula I is realized when A is NR. A subembodiment of this aspect of the invention of formula I is realized when A is NH. Another subembodiment of this aspect of the invention of formula I is realized when A is $NCH_3$.

Another embodiment of the invention of formula I is realized when A is O.

Another embodiment of the invention of formula I is realized when E is optionally substituted phenyl. A subembodiment of this aspect of the invention of formula I is realized when E is phenyl optionally substituted with 1 to 3 groups selected from halo, $(CH_2)_nCF_3$, $OCF_3$, $C(CH_3)_3$, $CHF_2$, $SF_5$, $SCF_3$, $OCHF_2$, $CH(CH_3)_2$, $CF_2CH_3$, cyclopropyl, phenyl, and pyridyl, said cyclopropyl, phenyl, and pyridyl optionally substituted with 1 to 3 groups selected from halo, and $C_{1-6}$alkyl. Another subembodiment of this aspect of the invention of formula I is realized when E is phenyl substituted with 1 to 3 groups selected from halo, $(CH_2)_nCF_3$, and $OCF_3$. Still another subembodiment of this aspect of the invention of formula I is realized when E is phenyl substituted with 1 to 3 groups selected from fluorine, chlorine, $CF_3$, and $OCF_3$.

Another embodiment of the invention of formula I is realized when E is optionally substituted indolyl.

Another embodiment of the invention of formula I is realized when E is optionally substituted naphthyl.

Another embodiment of the invention of formula I is realized when E is optionally substituted pyridyl.

Another embodiment of the invention of formula I is realized when $R^3$ is hydrogen.

Another embodiment of the invention of formula I is realized when $R^3$ is optionally substituted $C_{1-6}$alkyl. A subembodiment of this aspect of the invention of formula I is realized when $R^3$ is $CH_3$, $(CH_2)_nOH$, or $CH_2CH_3$.

Another embodiment of the invention of formula I is realized when $R^3$ is $C_{1-4}$haloalkyl. A subembodiment of this aspect of the invention is realized when $R^3$ is selected from the group consisting of $CF_2CH_3$, $CHF_2$, $CH_2F$, and $CF_3$.

Another embodiment of the invention of formula I is realized when $R^3$ is $NR_2$. A subembodiment of this aspect of the invention is realized when $R^3$ is selected from the group consisting of $NH_2$, $NHCH_3$, and $N(CH_3)_2$.

Another embodiment of the invention of formula I is realized when $R^3$ is optionally substituted $C_{3-6}$cycloalkyl. A subembodiment of this aspect of the invention is realized when $R^3$ is selected from the group consisting of optionally substituted cyclopropyl, cyclobutyl, cyclopentyl, and cyclohexyl. Another subembodiment of this aspect of the invention is realized when $R^3$ is optionally substituted cyclopropyl.

Still another embodiment of the invention of formula I is realized when X, Y, and Z, respectively, represent X=N, Y=$CR^{4a}$, Z=$CR^{4b}$. A subembodiment of this aspect of the invention of formula I is realized when $R^{4a}$ and $R^{4b}$ are selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl. Another subembodiment of this aspect of the invention of formula I is realized when one of $R^{4a}$ and $R^{4b}$ is hydrogen or $CH_3$ and the other is selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl. Still another subembodiment of this aspect of the invention of formula I is realized when one of $R^{4a}$ and $R^{4b}$ is hydrogen and the other is selected from the group consisting of $CH_3$, $(CH_2)_nOH$, and $CF_3$.

Still another embodiment of the invention of formula I is realized when X, Y, and Z, respectively, represent X=CH, Y=$CR^{4a}$, Z=N. A subembodiment of this aspect of the invention of formula I is realized when $R^{4a}$ is selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl. Another subembodiment of this aspect of the invention of formula I is realized when $R^{4a}$ is selected from the group consisting of $CH_3$, $(CH_2)_nOH$, and $CF_3$.

Still another embodiment of the invention of formula I is realized when X, Y, and Z, respectively, represent X=CH, Y=N, Z=$CR^{4b}$. A subembodiment of this aspect of the invention of formula I is realized when $R^{4b}$ is selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl. Another subembodiment of this aspect of the invention of formula I is realized when $R^{4b}$ is hydrogen.

Still another embodiment of the invention of formula I is realized when X, Y, and Z, respectively, represent X=CH, Y=$CR^{4a}$, Z=$CR^{4b}$. A subembodiment of this aspect of the invention of formula I is realized when $R^{4a}$ and $R^{4b}$ are selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl. Another subembodiment of this aspect of the invention of formula I is realized when $R^{4a}$ and $R^{4b}$ are both hydrogen.

Another embodiment of the invention of formula I is realized when X, Y, and Z, respectively, represent X=N, Y=N, Z=$CR^{4b}$. A subembodiment of this aspect of the invention of formula I is realized when $R^{4b}$ is selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl. Another subembodiment of this aspect of the invention of formula I is realized when $R^{4b}$ is hydrogen.

Yet another embodiment of the invention of formula I is realized when $R^1$ and $R^2$ are selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_n$ $OCH_3$. A subembodiment of this aspect of the invention of formula I is realized when one of $R^1$ and $R^2$ is hydrogen. Another subembodiment of the invention of formula I is realized when one of $R^1$ and $R^2$ is hydrogen and the other is selected from the group consisting of $CH_3$, $CH(CH_3)_2$, $C(CH_3)_2OH$, $C(CH_3)_3$, $(CH_2)_nOH$, and $(CH_2)_n$ $OCH_3$. Still another subembodiment of the invention of formula I is realized when one of $R^1$ and $R^2$ is hydrogen and the other is $CH_3$.

Still another embodiment of the invention of formula I is realized when $R^1$ and $R^2$ independently are selected from the group consisting of optionally substituted cyclopropyl, cyclobutyl, cyclopentyl and cyclohexyl.

Yet another embodiment of the invention of formula I is realized when $R^1$ and $R^2$ combine with the carbon to which they are attached to form an optionally substituted $C_{3-10}$cycloalkyl or $C_{3-10}$heterocycloalkyl. In particular embodiments $R^1$ and $R^2$ combine to form cyclopropyl, cyclobutyl, cyclopentyl, cyclohexyl, and oxetanyl. A subembodiment of this aspect of the invention of formula I is realized when $R^1$ and $R^2$ combine with the carbon to which they are attached to form an optionally substituted cyclopropyl.

Another embodiment of the invention of formula I is realized when two adjacent $R^a$ groups on the phenyl of E together with the atoms to which they are attached can combine to form benzodioxolyl.

Another embodiment of the invention of formula I is realized when $R^a$ is selected from H, OH, halo, $(CH_2)_nCH_3$, $CH(CH_3)_2$, $C(CH_3)_3$, $(CH_2)_nOCH_3$, $CF_2CH_3$, $CH_2F$, $CHF_2$, $(CH_2)_nCF_3$, $OCHF_2$, $OCF_3$, $SCF_3$, $SF_5$, $CH_2NH_2$, $(CH_2)_nN(CH_3)_2$, and optionally substituted cyclobutyl, cyclopropyl, phenyl, naphthyl, pyrimidinyl, and pyridyl.

Another embodiment of the invention of formula I is realized when n is 0. Another embodiment of the invention of formula I is realized when n is 1. Another embodiment of the invention of formula I is realized when n is 2. Another embodiment of the invention of formula I is realized when n is 3. Still another embodiment of the invention of formula I is realized when n of $R^a$ is 0-1, 0-2, or 0-3.

Still another embodiment of the invention is realized when it is represented by structural formula Ia:

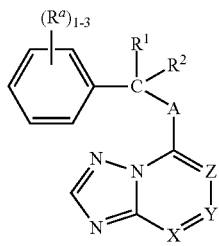

Ia or a pharmaceutically acceptable salt thereof. An embodiment of the invention of formula Ia is realized when $R^a$ is selected from halo, $(CH_2)_nCF_3$, $OCF_3$, $C(CH_3)_3$, $CHF_2$, $SF_5$, $SCF_3$, $OCHF_2$, $CH(CH_3)_2$, cyclopropyl, and pyridyl, said cyclopropyl and pyridyl optionally substituted with 1 to 3 groups of $C_{1-6}$ alkyl, X, Y, and Z, respectively, represents X=N, Y=$CR^{4a}$, Z=$CR^{4b}$, wherein $R^{4a}$ and $R^{4b}$ are selected from the group consisting of H, $CH_3CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl and $R^1$ and $R^2$ are selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $C(CH_3)_2CH_2OR$, $(CH_2)_nOCH_3$.

A subembodiment of this aspect of the invention of formula Ia is realized when $R^a$ is selected from the group consisting of halo, (CH2)nCF3, and OCF3, one of $R^{4a}$ and $R^{4b}$ is hydrogen or CH3 and the other is selected from the group consisting of H, CH3, CH(CH3)2, (CH3)2OH, C(CH3)3, CH2CH3, CH(CH3)OH, (CH2)nOH, CHF2, CH2F, CF3, CF2CF3, NH2, N(CH3)2, NHCH3, OCH2CH3, (CH2)nOCH3, halo and optionally substituted cyclopropyl, and one of $R^1$ and $R^2$ is hydrogen and the other is selected from the group consisting of CH3, CH(CH3)2, C(CH3)2OH, C(CH3)3, (CH2)nOH, and (CH2)nOCH3.

Still another subembodiment of this aspect of the invention of formula Ia is realized when $R^a$ is selected from the group consisting of fluorine, chlorine, CF3 and OCF3, one of $R^{4a}$ and $R^{4b}$ is hydrogen and the other is selected from the group consisting of CH3, (CH2)nOH, and CF3, and one of $R^1$ and $R^2$ is hydrogen and the other is CH3.

Yet another embodiment of the invention of formula Ia is realized when $R^a$ is selected from the group consisting of fluorine, chlorine, $CF_3$, and $OCF_3$, one of $R^{4a}$ and $R^{4b}$ is hydrogen and the other is selected from the group consisting of $CH_3$, $(CH_2)_nOH$, and $CF_3$, and $R^1$ and $R^2$ combine with the carbon to which they are attached to form optionally substituted cyclopropyl, cyclobutyl, cyclopentyl, cyclohexyl, or oxetanyl.

Another embodiment of the invention of formula Ia is realized when $R^a$ is selected from halo, $(CH_2)_nCF_3$, $OCF_3$, $C(CH_3)_3$, $CHF_2$, $SF_5$, $SCF_3$, $OCHF_2$, $CH(CH_3)_2$, cyclopropyl, and pyridyl, said cyclopropyl and pyridyl optionally substituted with 1 to 3 groups of $C_{1-6}$ alkyl, X, Y, and Z, respectively, represent X=CH, Y=$CR^{4a}$, Z=N, wherein $R^{4a}$ is selected from H, $CH_3$, $CH(CH_3)_2$, $(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl and optionally substituted cyclopropyl and $R^1$ and $R^2$ are selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_nOCH_3$.

Another embodiment of the invention of formula Ia is realized when $R^a$ is selected from halo, $(CH_2)_nCF_3$, $OCF_3$, $C(CH_3)_3$, $CHF_2$, $SF_5$, $SCF_3$, $OCHF_2$, $CH(CH_3)_2$, cyclopropyl, and pyridyl, said cyclopropyl and pyridyl optionally substituted with 1 to 3 groups of $C_{1-6}$ alkyl, X, Y, and Z, respectively, represent X=CH, Y=N, Z=$CR^{4b}$, wherein $R^{4b}$ is hydrogen and $R^1$ and $R^2$ are selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_nOCH_3$.

Another embodiment of the invention of formula Ia is realized when $R^a$ is selected from halo, $(CH_2)_nCF_3$, $OCF_3$, $C(CH_3)_3$, $CHF_2$, $SF_5$, $SCF_3$, $OCHF_2$, $CH(CH_3)_2$, cyclopropyl, and pyridyl, said cyclopropyl and pyridyl optionally substituted with 1 to 3 groups of $C_{1-6}$ alkyl, X, Y, and Z, respectively, represents X=CH, Y=$CR^{4a}$, Z=$CR^{4b}$, wherein $R^{4a}$ and $R^{4b}$ both are hydrogen and $R^1$ and $R^2$ are selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_nOCH_3$.

Another embodiment of the invention of formula Ia is realized when $R^a$ is selected from halo, $(CH_2)_nCF_3$, $OCF_3$, $C(CH_3)_3$, $CHF_2$, $SF_5$, $SCF_3$, $OCHF_2$, $CH(CH_3)_2$, cyclopropyl, and pyridyl, said cyclopropyl and pyridyl optionally substituted with 1 to 3 groups of $C_{1-6}$ alkyl, X, Y, and Z, respectively, represents X=N, Y=N, Z=$CR^{4b}$, wherein $R^{4b}$ is hydrogen and $R^1$ and $R^2$ are selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_nOCH_3$.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, Parkinson's disease, Parkinson's disease dementia (PDD), or Huntington's disease, and those associated with striatal hypofunction or basal ganglia dysfunction using the compounds of formula I.

Examples of compounds of the invention can be found throughout the specification.

The invention also encompasses pharmaceutical compositions containing a compound of formula I, and methods for treatment or prevention of phosphodiesterase mediated diseases using compounds of formula I.

Where a variable occurs more than once in any formula of the invention, or in a substituent thereof, the individual occurrences of that variable are independent of each other, unless otherwise specified. Also, combinations of substituents or variables are permissible only if such combinations result in stable compounds and valency is permissible.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein the term "heterocycloakyl" means a cycloalkyl containing heteroatom selected from N, S, O.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties and heterocycloalkyl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. "Haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

Where possible, compounds of this invention may exist in several tautomeric forms as be appreciated by any one skilled in the art. Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and Ia and they are intended to represent all possible tautomeric forms for these compounds without regard to what actually is the predominant tautomeric form in existence for a particular compound.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, crystalline products or crystalline intermediates that are derivatized, if necessary, with a reagent containing an asymmetric center of known absolute configuration.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I and Ia. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formula I and Ia can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc or EA=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOAt=1-Hydroxy-7-azabenzotriazole
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanesulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Pd(dppf)Cl$_2$=1,1'-Bis(diphenylphosphino)ferrocenepalladiumdichloride
Ph=phenyl PPTS=pyridinium p-toluene sulfonate
pTSA=p-toluene sulfonic acid
PyH.Br$_3$=pyridine hydrobromide perbromide
r.t./RT=room temperature
rac.=racemic
T3P=2,4,6-Tripropyl-1,3,5,2,4,6-trioxatriphosphinane 2,4,6-trioxide
TBAF=tetrabutylammonium fluoride
TFA=trifluoroacetic acid
TfO=trifluoromethanesulfonate=triflate
THF=tetrahydrofuran
TLC=thin layer chromatography
TMSCl=trimethylsilyl chloride All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 function or activity in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1 inhibiting the disease state, i.e., arresting the development of the disease state or its clinical symptoms; 2) or relieving the disease state, i.e., causing temporary or permanent regression of the disease state or its clinical symptoms.

The invention is also directed to use of the compounds to prevent the disease state.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "'selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEi's such as Aricept (donepezil) and Exelon (rivastigmine) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwise noted.

The progress of reactions was often monitored by TLC or LC-MS. The LC-MS was recorded using one of the following methods.

Method A: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 µM $NH_4HCO_3$), hold 1 min; 3.6 minute total run time.

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

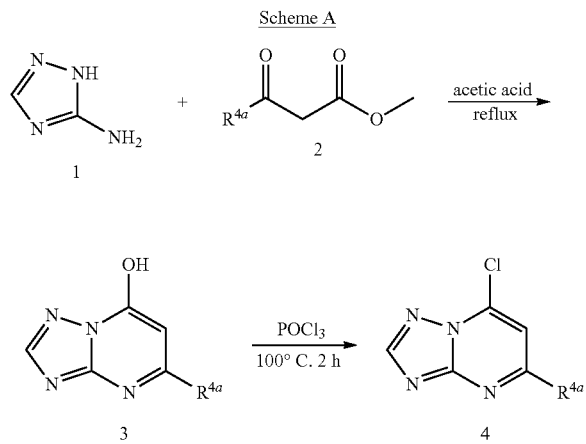

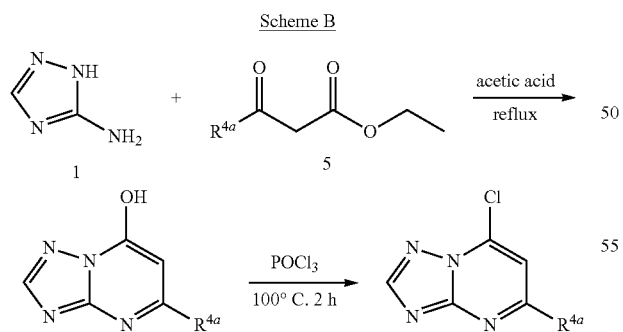

Schemes A and B demonstrate the synthesis of 7-substituted triazolopyrimidine cores (4) by use of various malonate esters. 3-Amino-[1,2,4]-triazole 1 is condensed with the substituted malonate ester 2 or 5 to form the substituted 7-hydroxy-[1,2,4]-triazolo[1,5-a]pyrimidine 3. Chlorination with phosphorous oxychloride gives the corresponding 7-chloro-[1,2,4]-triazolo[1,5-a]pyrimidine.

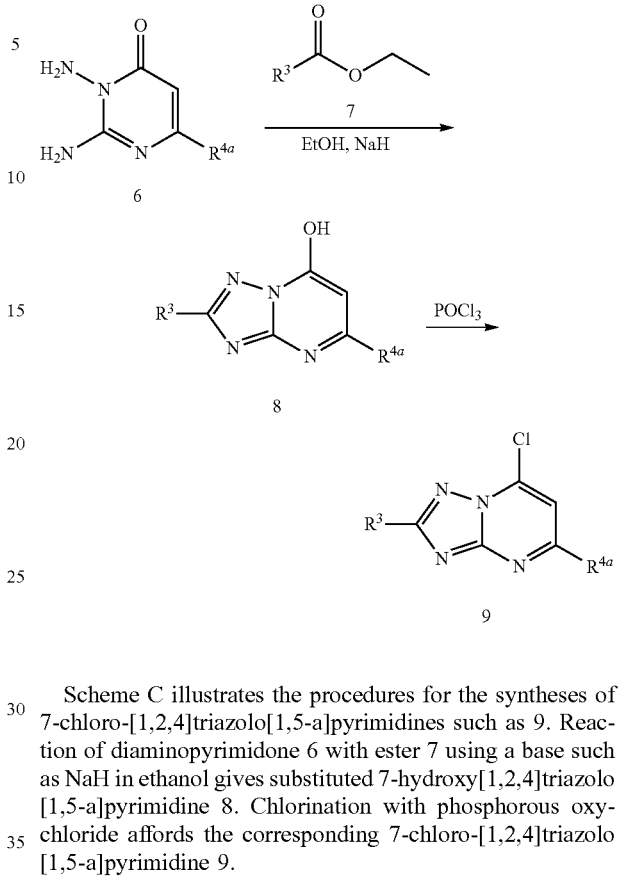

Scheme C illustrates the procedures for the syntheses of 7-chloro-[1,2,4]triazolo[1,5-a]pyrimidines such as 9. Reaction of diaminopyrimidone 6 with ester 7 using a base such as NaH in ethanol gives substituted 7-hydroxy[1,2,4]triazolo[1,5-a]pyrimidine 8. Chlorination with phosphorous oxychloride affords the corresponding 7-chloro-[1,2,4]triazolo[1,5-a]pyrimidine 9.

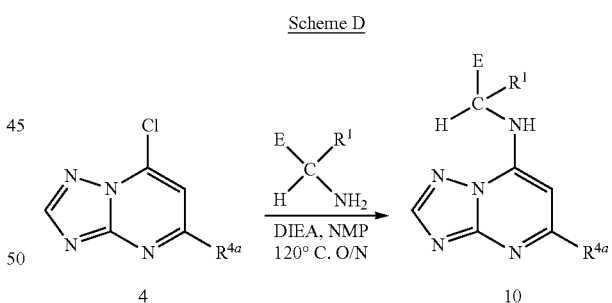

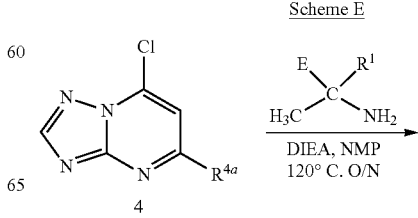

Scheme F

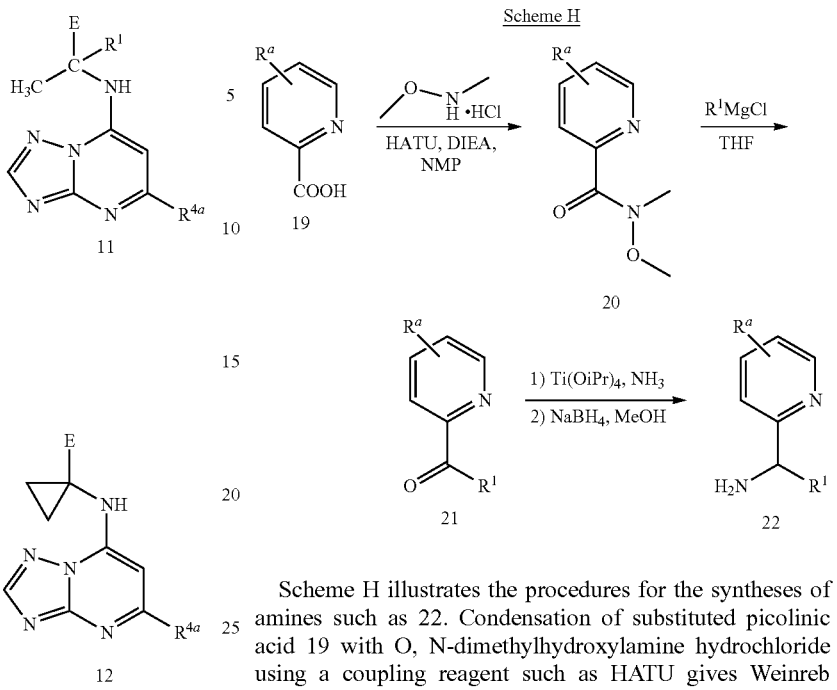

$S_NAr$ displacement of the chloride intermediate with various alpha-substituted amines lead to the final PDE2 compounds 10, 11, and 12. Scheme F is specific to the fused cyclopropyl benzyl amines 12.

Scheme G

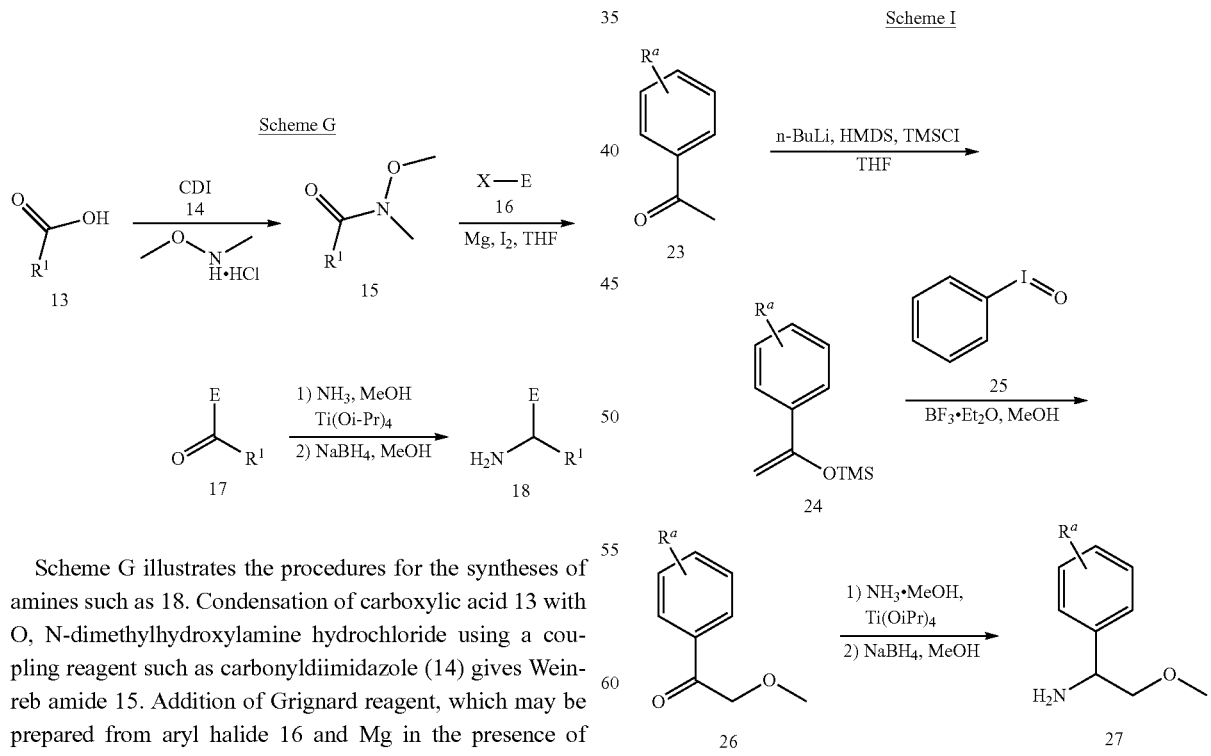

Scheme G illustrates the procedures for the syntheses of amines such as 18. Condensation of carboxylic acid 13 with O, N-dimethylhydroxylamine hydrochloride using a coupling reagent such as carbonyldiimidazole (14) gives Weinreb amide 15. Addition of Grignard reagent, which may be prepared from aryl halide 16 and Mg in the presence of iodine in THF, to the Weinreb amide 15 forms ketone 17. Reductive amination of ketone 17 using titanium isopropoxide, methanolic ammonia solution and a reducing reagent such as sodium borohydride gives amine 18.

Scheme H illustrates the procedures for the syntheses of amines such as 22. Condensation of substituted picolinic acid 19 with O, N-dimethylhydroxylamine hydrochloride using a coupling reagent such as HATU gives Weinreb amide 20. Addition of Grignard reagent to Weinreb amide 20 forms ketone 21. Reductive amination of ketone 21 using titanium isopropoxide, methanolic ammonia solution and a reducing reagent such as sodium borohydride affords amine 22.

Scheme I illustrates the procedures for the syntheses of amines such as 27. Substituted acetophenone 23 is converted to the corresponding silyl enol ether 24 using TMSCl and a base such as LiHMDS (formed in situ) in THF. Oxidation of silyl enol ether 24 using iodosobenzene (25) and boron trifluoride affords α-methoxy ketone 26. Reductive amination of ketone 26 using titanium isopropoxide, methanolic ammonia solution and a reducing reagent such as sodium borohydride gives amine 27.

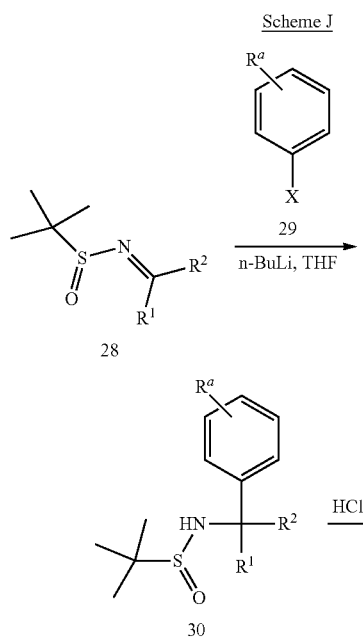

Scheme J illustrates the procedures for the syntheses of amines such as 31. Addition of lithium reagent formed by metal-halogen exchange of aryl halide 29 using n-BuLi, to N-sulfinyl imine 28 forms sulfinamide 30. Acid treatment readily removes the N-sulfinyl group in the sulfinamide 30 to give amine 31.

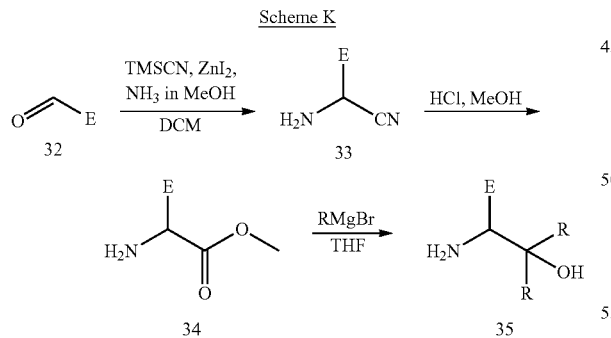

Scheme K illustrates the procedures for the syntheses of amino alcohols such as 35. Treatment of aromatic aldehyde 32 with TMSCN in the presence of catalytic amounts of $ZnI_2$ followed by exposure to saturated methanolic ammonia solution gives α-amino nitrile 33. Substituted α-amino acid ester 34 is obtained by reacting α-amino nitrile 33 with saturated methanolic HCl solution. Addition of a Grignard reagent to substituted α-amino acid ester 34 affords the corresponding racemic amino alcohol 35.

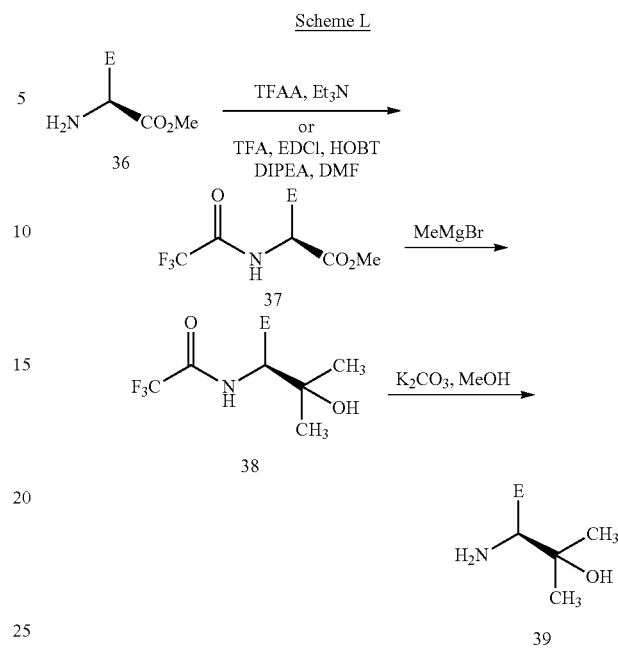

Scheme L outlines the procedure to synthesis the 2-methylpropan-2-ol benzyl amines 39 from commercially available (S)-aminoesters 36. The amine is first protected as the trifluoroacetamide 37 which is then treated with an excess of Grignard reagent. Once isolated, the trifluoroacetamide 38 can be deprotected with base to yield the desired 2-methylpropan-2-ol benzyl amine 39. In some cases, minor racemazation (5-15%) is seen and the enantiomers may be separated via chiral column separation. This same set of conditions can be done with the (R)-aminoesters; if the (R)-stereochemistry is desired.

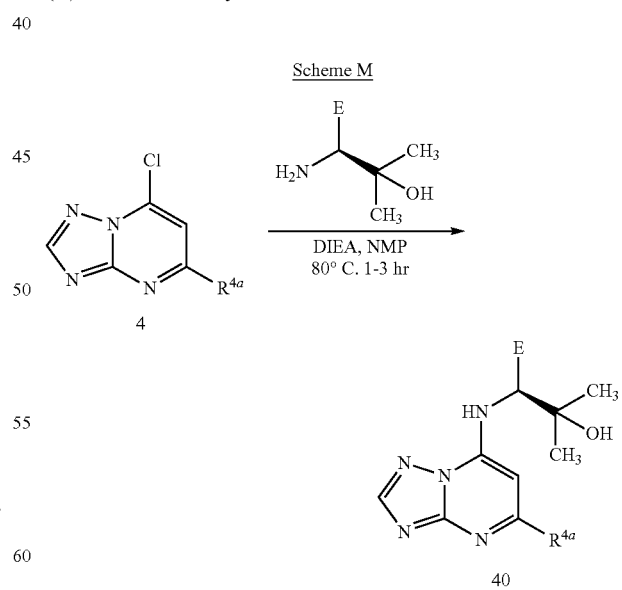

Scheme M illustrates the $S_NAr$ displacement of the chloride intermediate with various alpha-substituted amines (synthesis outlined in Scheme L)which lead to the final PDE2 compounds 40.

Scheme N

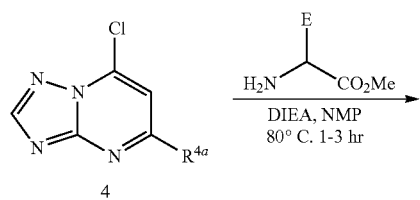
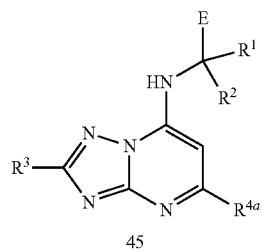

Scheme O illustrates the procedures for the syntheses of substituted triazolopyrimidine compounds such as 45. Coupling of substituted 7-chloro-[1,2,4]triazolo[1,5-a]pyrimidine 9 and α-amino alcohol 44 using a base such as DIEA affords corresponding substituted 7-amino alcohol triazolopyrimidine compound 45.

Scheme P

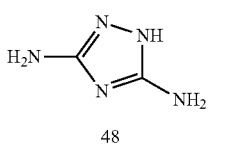

Scheme P illustrates a procedure for the synthesis of tertiary amines such as 47.

Alkylation of the secondary amine 46 using a methylating reagent such as CH₃I and a base such as KOtBu gives tertiary amine 47.

An alternative route to the 2-methylpropan-2-ol amine PDE2 compounds addressed in the prior Scheme M, is outlined is Scheme N. S$_N$Ar displacement of the chloro-substituted triazolopyrimidine intermediate is done with the commercially available racemic aryl substituted aminoesters. The product 41 is then treated with methyl Grignard to convert it to the 2-methylpropan-2-ol substituted compounds 42. Enantiomers (40 and 43) are then separated via chiral column purification.

Scheme O

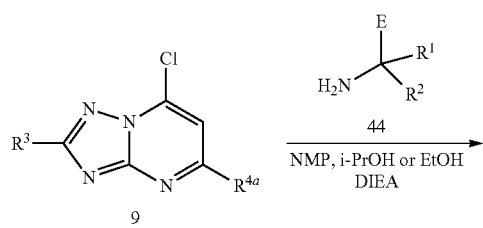

Scheme Q

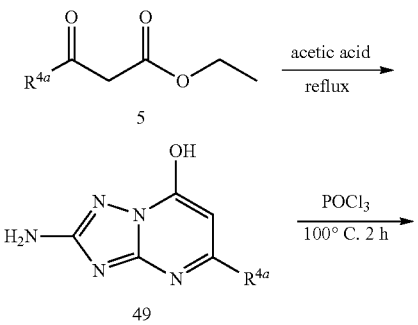

-continued

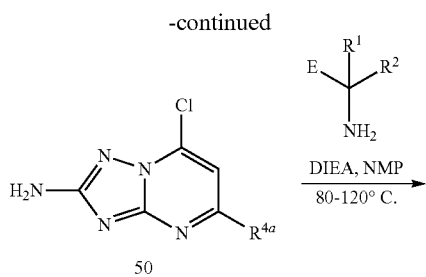

Scheme R illustrates the procedures for the syntheses of 5-methoxy 7-amino alcohol triazolopyrimidines such as 54 and 55. 5-chloro 7-amino alcohol triazolopyrimidine 52 is transformed to 5-methoxy 7-amino alcohol triazolopyrimidine 53 using sodium methoxide in dioxane. The enantiomers 54 and 55 are obtained after chiral separation of 5-methoxy 7-amino alcohol triazolopyrimidine 53.

Scheme S

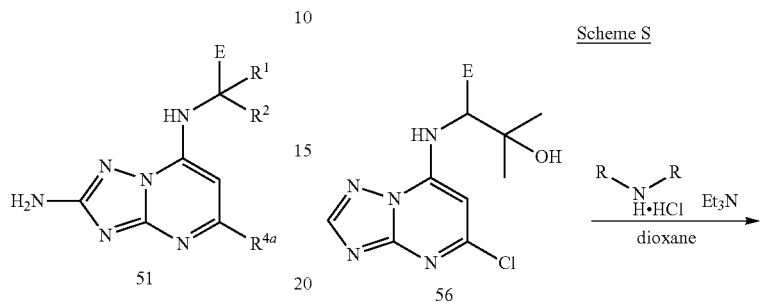

Scheme Q illustrates the procedure for the synthesis of amino substituents on the carbon of the triazole ring. The procedure is similar to Schemes A and B, but starts with 1H-[1,2,4]-triazole-3,5-diamine 48 which is condensed with the substituted malonate ester 5 to form the 5-substituted-2-amino-[1,2,4]triazolo[1,5-a]pyrimidin-7-ol 49. Chlorination with phosphorous oxychloride gives the corresponding 5-substituted-7-chloro-[1,2,4]-triazolo[1,5-a]pyrimidine 50. Finally, S$_N$Ar displacement of the chloro-substituent with a substituted benzyl amine via addition of base such as DIEA upon heating affords the product 51.

Scheme R

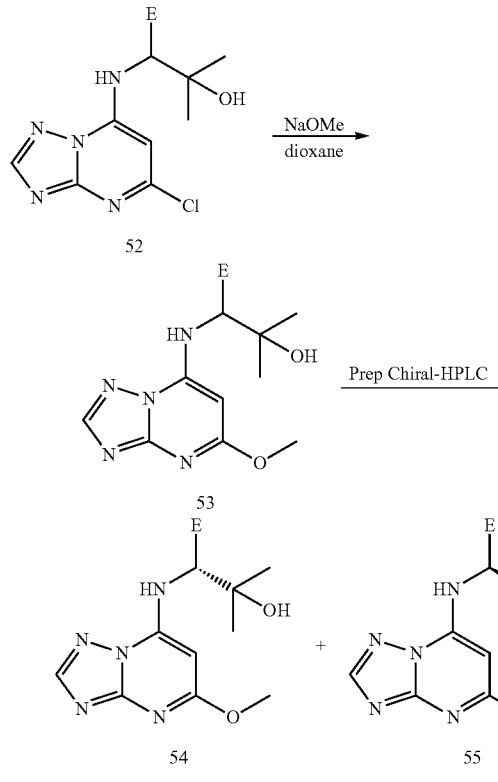

Scheme S illustrates the procedures for the syntheses of 5-amino 7-amino alcohol triazolopyrimidines such as 57. 5-Halogen 7-amino alcohol triazolopyrimidine 56 is transformed to 5-amino 7-amino alcohol triazolopyrimidine 57 using corresponding amine in dioxane. The enantiomer 58 and 59 are obtained after chiral separation of triazolopyrimidine 57.

Scheme T

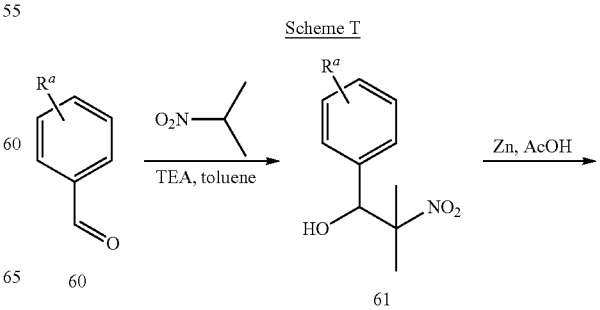

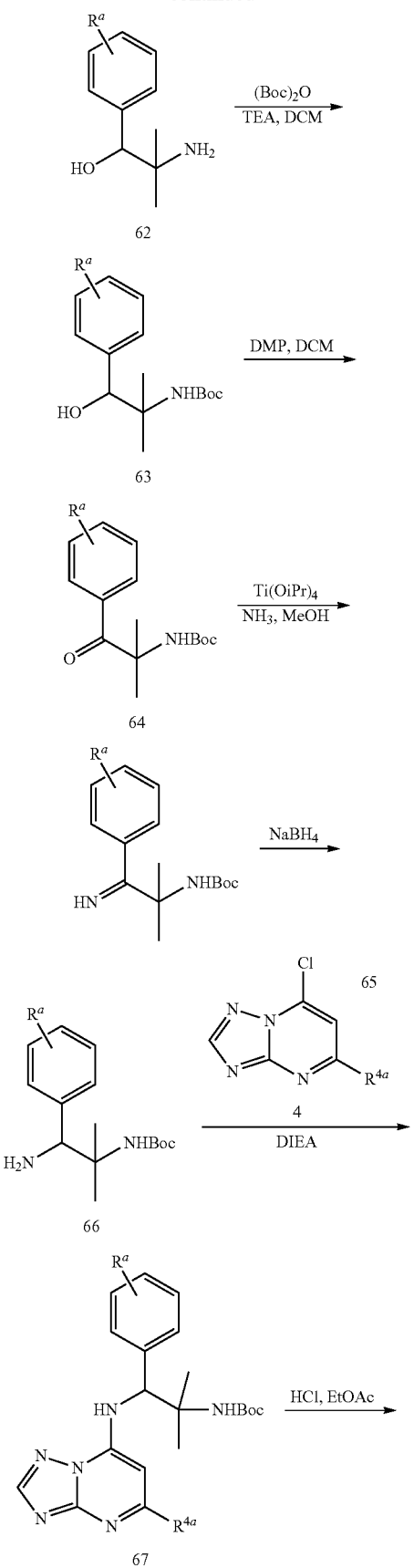

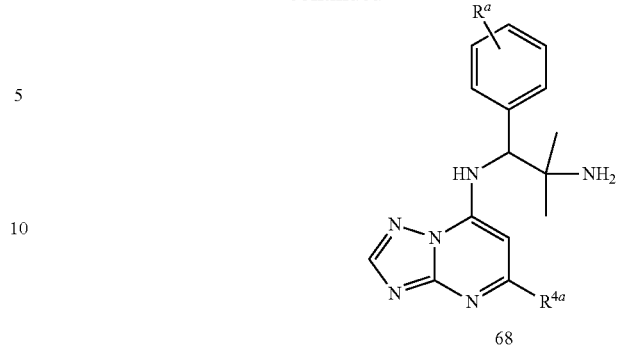

Scheme T illustrates the procedure for the syntheses of triazolopyrimidines such as 68. 2-Nitropropane is deprotonated and added with substituted benzaldehyde 60 to give benzylalcohol 61, which is reduced to give amino benzylalcohol 62. The amino group is protected selectively by a protecting group such as Boc to afford 63, which is then oxidized to arylalkylketone 64. Reductive amination of 64 occurs via imine 65 to give benzylamine 66. Coupling of benzylamine 66 and aromatic heterocyclic halide 4 gives 67, which is deprotected to afford compound 68.

Scheme U

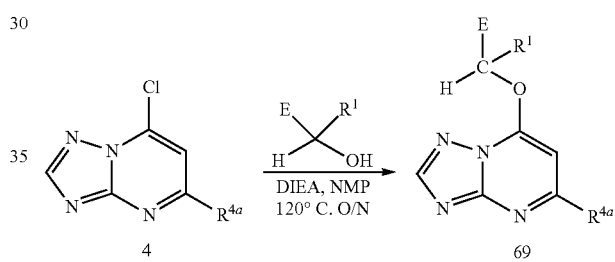

Ether compounds can also be synthesized via $S_NAr$ displacement with alpha benzyl substituted alcohols.

Scheme V

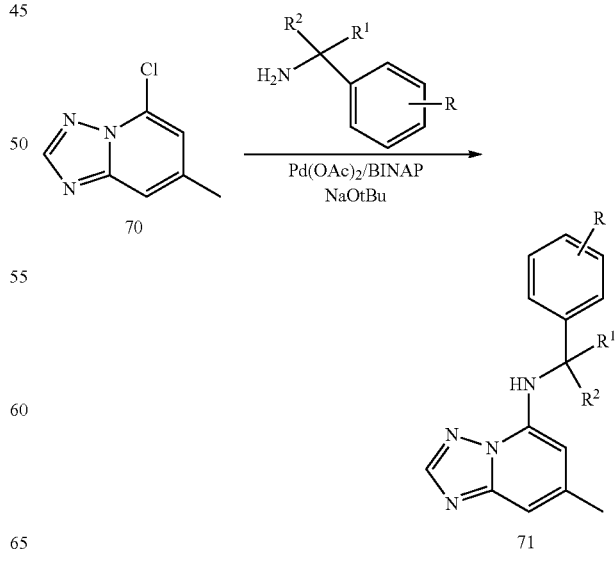

Scheme V demonstrates the synthesis of triazolopyridines via Buchwald C—N coupling of the commercially available 70 with substituted benzyl amines to afford the desired product 71.

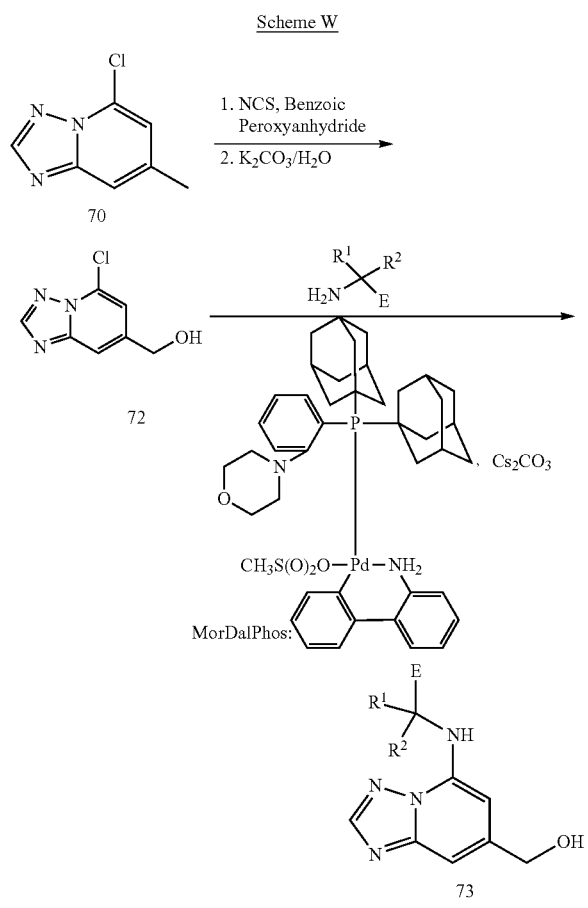

The methyl hydroxyl containing compounds can also be synthesized from the comercially available 70. Hydroxylation of the methyl group with NCS and benzoyl peroxide, affords 72 which is followed by Buchwald C—N coupling to afford the final PDE2 compounds 73.

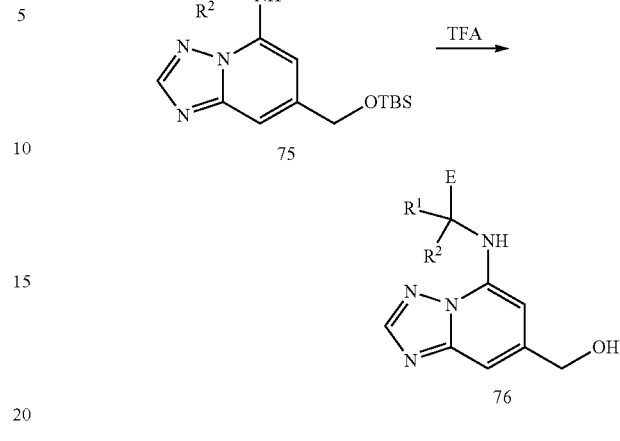

An alternate route to the methyl hydroxyl compounds is outlined in Scheme X. Protection of the alcohol as a TBDMS ether, followed by Buchwald amination of 74 gives amine 75. Deprotection of the silyl ether with TFA provides 76.

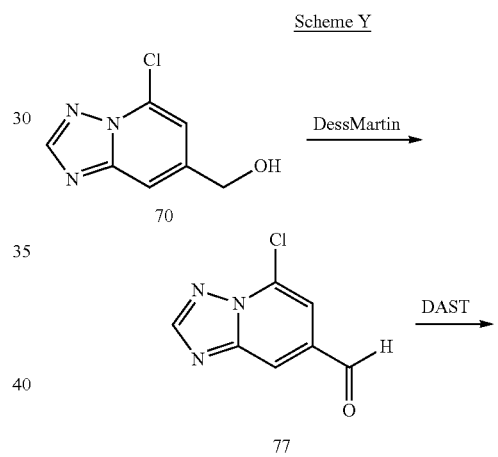

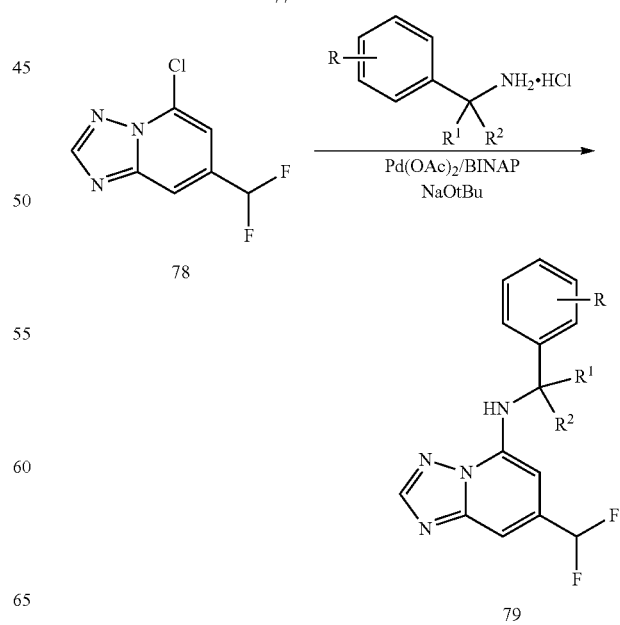

Scheme Y illustrates the synthesis of 5-di-fluoro substituted triazolopyridine analogs. Starting with the methyl hydroxyl intermediate 70, oxidation to the aldehyde 77 is accomplished with Dess Martin reagent and then the hydroxyl group is converted to di-fluoro 78 via treatment with DAST. Buchwald C—N coupling, as outlined in the previous schemes, affords compounds 79.

Scheme Z demonstrates the synthesis of secondary hydroxyl substituted analogues. The aldehyde 77 is treated with the appropriate methyl Grignard reagent to afford the secondary alcohol 80. The hydroxyl group is then protected with TBS via treatment with TBDMS-Cl in the presence of a base. Compound 81 is then converted to compound 82 by similar procedures outlined in the previous schemes. Final deprotection with acid, such as TFA or HCl, in an organic/aqueous mixture afforded the final PDE2 compounds 83.

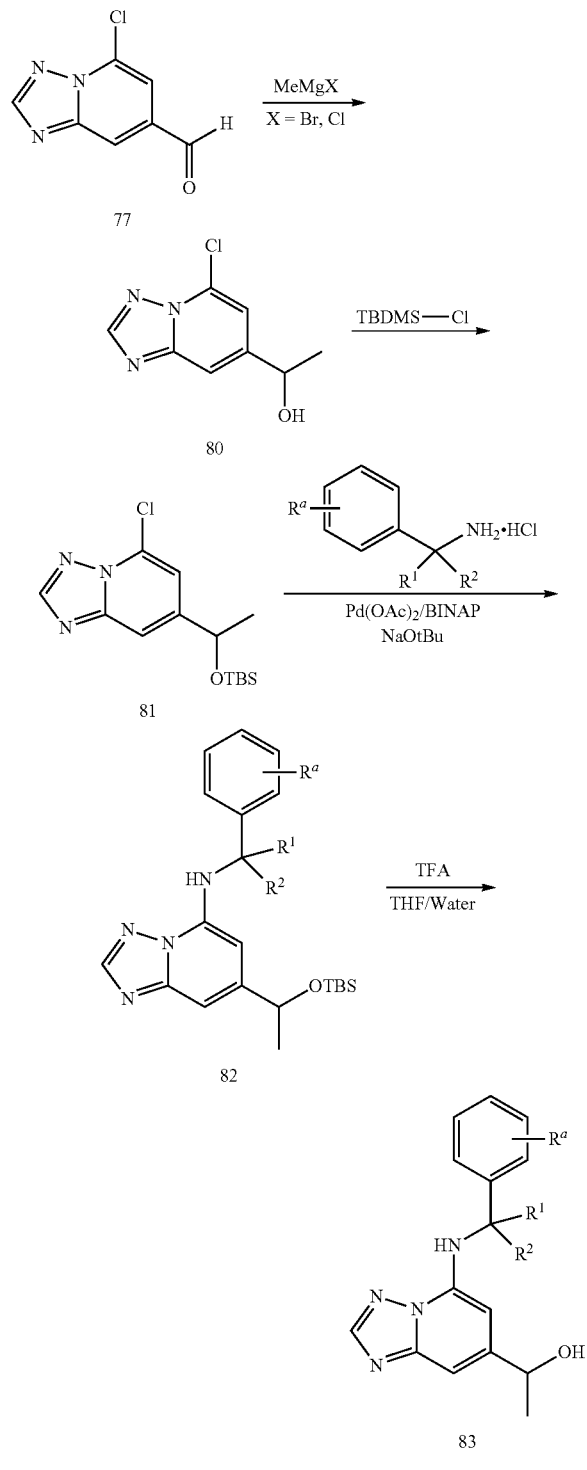

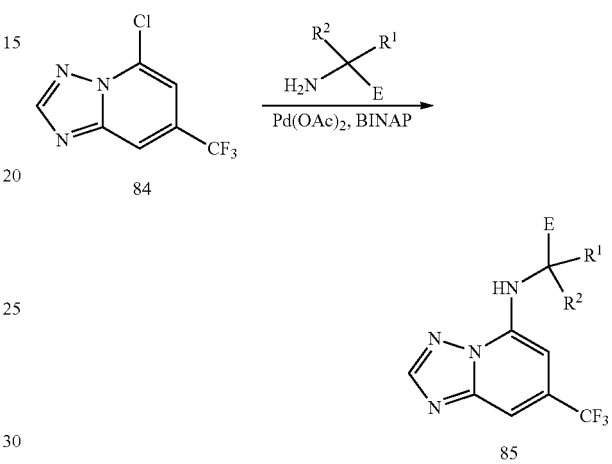

Scheme AA demonstrates the Buchwald C—N coupling of 5-chloro-7-(trifluoromethyl)-[1,2,4]triazolo[1,5-a]pyridine 84 from patent reference WO 2011090127A1 and the appropriate substituted benzyl amines to afford the final PDE2 analogues 85.

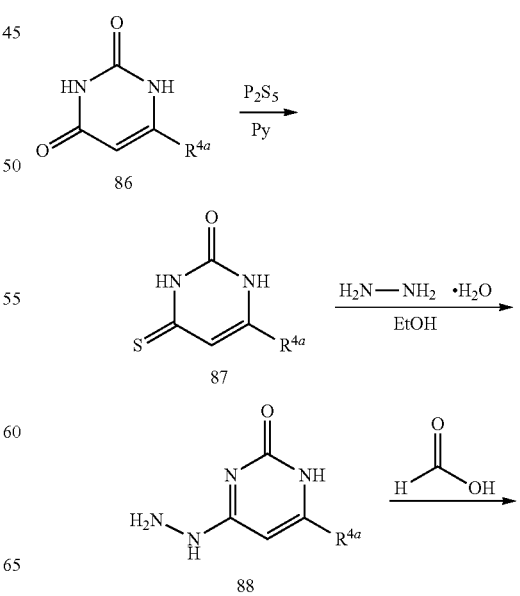

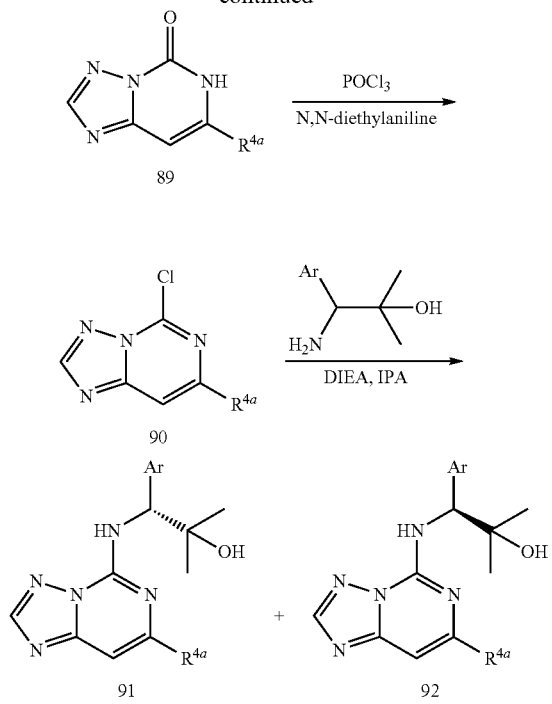

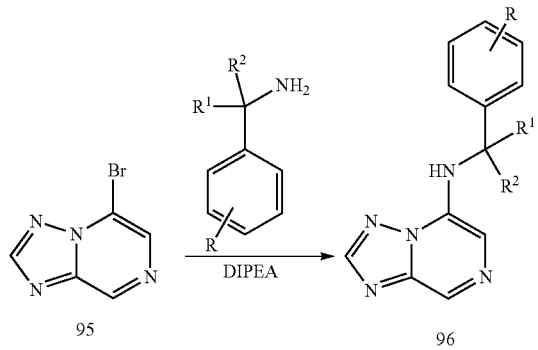

Scheme BB illustrates the procedures for the syntheses of 7-substituted 5-amino alcohol [1,2,4]triazolo[1,5-J]pyrimidin-5(6H)-ones such as 91 and 92. Treatment of 6-substituted pyrimidine-2,4(1H,3H)-dione 86 with phosphorus pentasulfide in pyridine gives 6-substituted 4-thioxo-3,4-dihydropyrimidin-2(1H)-one 87 which is converted to hydrazinopyrimidinone 88 using hydrazine hydrate. Cyclization of hydrazinopyrimidinone 88 with formic acid followed by rearrangement yields 7-substituted [1,2,4]triazolo[1,5-J]pyrimidin-5(6H)-one 89. Chlorination of 7-substituted [1,2,4]triazolo[1,5-J]pyrimidin-5(6H)-one 89 with phosphoryl chloride gives the corresponding chloro derivative 90 which reacts with α-amino alcohol to afford 7-substituted 5-amino alcohol [1,2,4]triazolo[1,5-J]pyrimidin-5(6H)-ones 91 and 92 after chiral separation.

Schemes CC and DD illustrate the syntheses of regioisomeric triazolopyrimidines. The commercially available halo-substituted triazolopyrimidines (93, 95) are converted to the desired compounds (94, 96) via $S_NAr$ displacement with chosen substituted benzyl amines.

PREPARATORY EXAMPLES

Preparatory Example 1

7-Chloro-5-ethyl-[1,2,4]-triazolo[1,5-a]pyrimidine

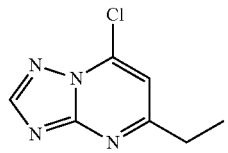

Step 1: 5-Ethyl-[1,2,4]triazolo[1,5-a]pyrimidin-7-ol

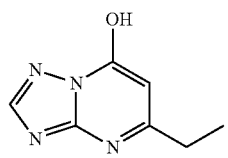

A solution of 1H-1,2,4-triazol-5-amine (513 mg, 6.10 mmol) and methyl-3-oxopentanoate (1 g, 5.81 mmol) in 20 mL acetic acid in a 100 mL round bottom flask (set with condensor) was heated to reflux (via oil bath) under nitrogen atmosphere overnight. The mixture was cooled and the acetic acid removed under reduced pressure to afford a white solid. The solid was suspended in 5 mL of methanol. The solid was filtered off and washed with 10 mL of methanol. LC-MS of the methanol filtrate showed that it contained the desired material. The solvent was removed under reduced pressure and the residue taken up in 4 mL of 10% methanol in DCM. The material was placed on preparative TLC plates (3×1000 μM, silica gel) and developed with 10% methanol in DCM. The bands containing the product were then removed and the product eluted off the silica gel with 250 mL 15% methanol in DCM. The solvent was removed under reduced pressure to afford the product as a solid. LC-MS Scheme CC

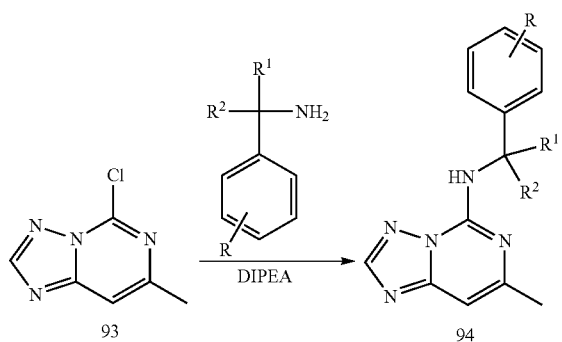

(+ESI) m/z=165. $^1$H NMR (500 MHz, CD$_3$OD) δ: 8.22 (s, 1H), 5.80 (s, 1H), 2.02 (q, J=6.7 Hz, 2H), 1.25 (t, J=6.8 Hz, 3H).

Step 2: 7-Chloro-5-ethyl-[1,2,4]-triazolo[1,5-a]pyrimidine

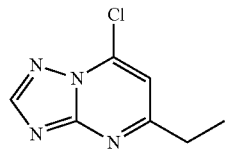

5-Ethyl-[1,2,4]triazolo[1,5-a]pyrimidin-7-ol (200 mg, 1.35 mmol) was taken up into POCl$_3$ (1.88 ml, 20.2 mmol) and heated to 100° C. via oil bath; After 2 hrs, the mixture was allowed to cool to room temperature and then to 0° C. via ice bath. The mixture was partitioned between ethyl acetate and water. The organics were collected and dried over sodium sulfate, filtered, and concentrated. The material was taken up in 2 mL DCM and placed onto preparative TLC plates (2×1000 μM, silica gel) and the plates developed with 7.5% methanol in DCM. The bands containing the compound were removed from the plates and the product eluted off with 15% methanol in DCM (200 mL). The solvent was removed under reduced pressure to afford a solid. LC-MS (+ESI) m/z=183 (M+H) and 185 (M+2+H).

The following compounds in Table P1 were prepared using procedures similar to those described in Preparatory Example 1 using appropriate starting materials.

TABLE P1

| Preparatory Example # | Structure | IUPAC Name | Mass [M + H]$^+$ |
|---|---|---|---|
| 2 | 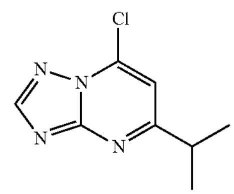 | 7-Chloro-5-isopropyl-[1,2,4]-triazolo[1,5-a]pyrimidine | 197.0<br>199.0 (M + 2 + H) |
| 3 | 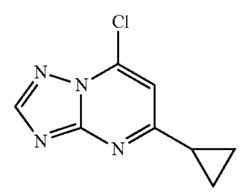 [SMILES: Clc1cc(C2CC2)nc2ncnn12] | 7-Chloro-5-cyclopropyl-[1,2,4]-triazolo[1,5-a]pyrimidine | 195.0<br>197.0 (M + 2 + H) |
| 4 | 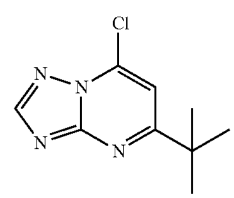 | 7-Chloro-5-tert-butyl-[1,2,4]-triazolo[1,5-a]pyrimidine | 211.0<br>213.0 (M + 2 + H) |
| 5 | 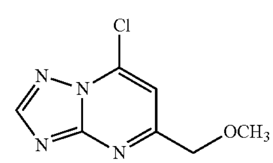 [SMILES: COCc1cc(Cl)n2ncnc2n1] | 7-Chloro-5-(methoxymethyl)-[1,2,4]-triazolo[1,5-a]pyrimidine | 199.0<br>201.0 (M + 2 + H) |
| 6 | 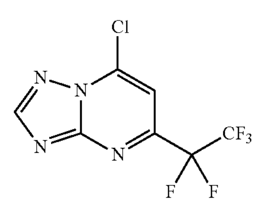 [SMILES: FC(F)(F)C(F)(F)c1cc(Cl)n2ncnc2n1] | 7-Chloro-5-(pentafluoroethyl)-[1,2,4]-triaozlo[1,5-a]pyrimidine | 273.0<br>275.0 (M + 2 + H) |

Preparatory Example 7

7-Chloro-5-(trifluoromethyl)-[1.24]-triazolo[1,5-a]pyrimidine

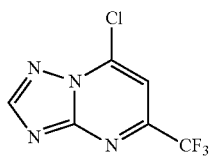

Step 1: 5-(Trifluoromethyl)-[1,2,4]triazolo[1,5-a]pyrimidin-7-ol

To a solution of ethyl 4,4,4-trifluoro-3-oxobutanoate (4.99 g, 27.1 mmol) in AcOH (15 mL) was added 1H-1,2,4-triazol-5-amine (2.28 g, 27.1 mmol). The solution was stirred at 100° C. for 6 h. Then the reaction solution was cooled to room temperature and filtered. The filter cake was washed with ethanol (2×10 mL) and dried to afford the crude title compound as a solid which was used in next step directly without further purification. MS (+ESI) m/z=204.9.

Step 2: 7-Chloro-5-(trifluoromethyl)-[1,2,4]triazolo[1,5-a]pyrimidine

To 5-(trifluoromethyl)-[1,2,4]triazolo[1,5-a]pyrimidin-7-ol (0.770 g, 3.8 mmol) was added POCl$_3$ (2.1 mL, 22.6 mmol). The reaction mixture was stirred at 110° C. for 16 h. The resulting mixture was cooled to room temperature and the solvent was removed under reduced pressure. The residue was quenched by ice-water (15 mL) and extracted with ethyl acetate (3×15 mL). The combined organic layers were washed with brine (15 mL), dried over anhydrous sodium sulfate and filtered. The filtrate was concentrated to afford the title compound as a solid which was used in next step directly without further purification. MS (+ESI) m/z=222.9; 224.9.

Preparatory Example 8

7-Chloro-5-(difluoromethyl)-[124]-triazolo[1,5-a]pyrimidine

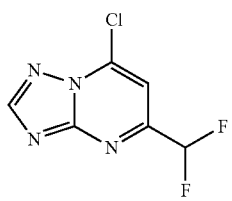 [SMILES: FC(F)c1cc(Cl)n2ncnc2n1]

The following example was prepared using similar procedures as in Preparatory Example 7 using ethyl 4,4-difluoro-3-oxobutanoate as starting material. LC-MS (+ESI) m/z=204.9; 206.9 (M+2+H).

Preparatory Example 9

7-Chloro-2-(fluoromethyl)-5-methyl-[1,2,4]triazolo[1,5-a]pyrimidine

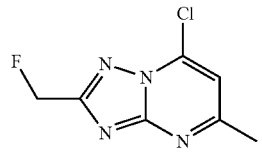

Step 1: 2-(Fluoromethyl)-5-methyl-[1,2,4]triazolo[1,5-a]pyrimidin-7-ol

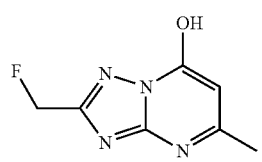

To a solution of 2,3-diamino-6-methylpyrimidin-4(3H)-one (0.200 g, 1.43 mmol) in ethanol (3 mL) was added ethyl 2-fluoroacetate (2.27 g, 21.4 mmol). This was followed by the addition of sodium hydride (0.171 g, 7.14 mmol). The reaction was stirred for 16 h at 90° C. The resulting mixture was cooled to room temperature and concentrated under reduced pressure. The residue was purified by column chromatography over silica gel using gradient 0-18% of MeOH in DCM as eluent. The title compound was obtained as a solid. $^1$H NMR (300 MHz, MeOD-d$_4$) δ: 5.88 (s, 1H), 5.50 (s, 1H), 5.35 (s, 1H), 2.39 (s, 3H).

Step 2: 7-Chloro-2-(fluoromethyl)-5-methyl-[1,2,4]triazolo[1,5-a]pyrimidine

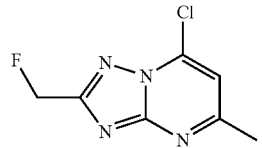

To phosphoryl trichloride (0.253 g, 1.65 mmol) was added 2-(fluoromethyl)-5-methyl-[1,2,4]triazolo[1,5-a]pyrimidin-7-ol (0.150 g, 0.823 mmol). The reaction mixture was stirred at 100° C. for 2 h. The resulting mixture was cooled to room temperature and quenched by ice water (20 mL). Then the pH value of the mixture was adjusted to 10 with sat'd. aqueous Na$_2$CO$_3$ and extracted with DCM (3×20 mL). The combined organic layers were washed with water (20 mL), dried over anhydrous sodium sulfate and filtered. The filtrate was concentrated under reduced pressure. The residue was purified by column chromatography over silica gel using gradient 0-54% of ethyl acetate in petroleum ether as eluent. The title compound was obtained as a solid. MS (+ESI) m/z=200.9; 202.9.

The following compounds in Table P2 were prepared using procedures similar to those described in Preparatory Example 9 using appropriate starting materials.

TABLE P2

| Preparatory Example # | Structure | IUPAC Name | Mass [M + H]+ No MS obtained |
|---|---|---|---|
| 10 | 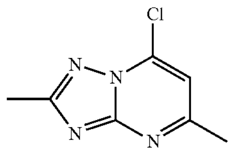 | 7-Chloro-2,5-dimethyl-[1,2,4]triazolo[1,5-a]pyrimidine | 183.1 185.1 (M + 2 + H) |
| 11 | 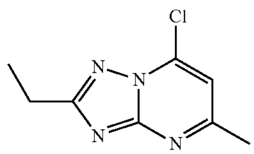 | 7-Chloro-2-ethyl-5-methyl-[1,2,4]triazolo[1,5-a]pyrimidine | 197.1 199.1 (M + 2 + H) |
| 12 | 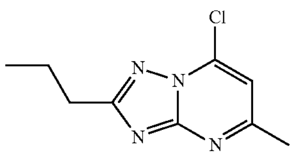 | 7-Chloro-5-methyl-2-propyl-[1,2,4]triazolo[1,5-a]pyrimidine | 211.0 212.8 (M + 2 + H) |
| 13 | 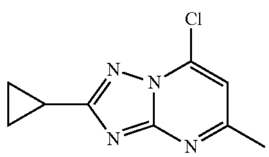 | 7-Chloro-2-cyclopropyl-5-methyl-[1,2,4]triazolo[1,5-a]pyrimidine | ¹H NMR (300 MHz CD₃OD) δ: 7.80 (s, 1H), 2.75 (s, 3H), 2.32-2.25 (m, 1H), 1.40-1.20 (m, 4H) |
| 14 | 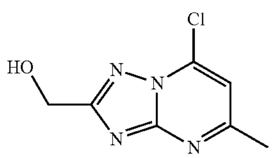 | (7-Chloro-5-methyl-[1,2,4]triazolo[1,5-a]pyrimidin-2-yl)methanol | 199.0 201.0 (M + 2 + H) |
| 15 | 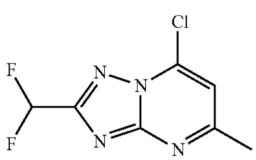 | 7-Chloro-2-(difluoromethyl)-5-methyl-[1,2,4]triazolo[1,5-a]pyrimidine | 218.9 221.0 (M + 2 + H) |

Preparatory Example 16

[3-Fluoro-4-(trifluoromethoxy)phenyl](oxetan-3-yl)methanamine

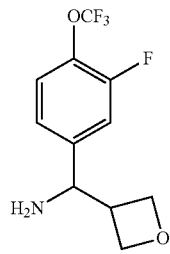

Step 1:
N-Methoxy-N-methyloxetane-3-carboxamide

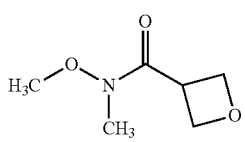

To a solution of oxetane-3-carboxylic acid (0.500 g, 4.90 mmol) and N,O-dimethylhydroxylamine hydrochloride (0.478 g, 4.9 mmol) in DCM (10 mL) was added 1,1-carbonyldiimidazole (0.874 g, 5.4 mmol). The reaction mixture was stirred at 25° C. for 16 h. Then the reaction mixture was diluted with brine (5 mL) and extracted with ethyl acetate (3×5 mL). The combined organic layers were washed with water (2×5 mL), brine (2×5 mL), dried over anhydrous sodium sulfate and filtered. The filtrate was concentrated under reduced pressure. The residue was purified by column chromatography over silica gel using gradient 1-99% of ethyl acetate in petroleum ether as eluent. The fractions containing desired product were combined and concentrated. The title compound was obtained as a liquid. MS (+ESI) m/z=146.2.

Step 2: [3-Fluoro-4-(trifluoromethoxy)phenyl](oxetan-3-yl)methanone

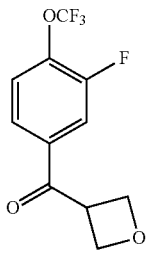

A mixture of magnesium (0.201 g, 8.3 mmol) and iodine (0.210 g, 0.83 mmol) in THF (5 mL) was purged with nitrogen for 3 times and stirred under nitrogen atmosphere at 25° C. This was followed by the addition of a solution 4-bromo-2-fluoro-1-(trifluoromethoxy)benzene (2.14 g, 8.3 mmol) in THF (5 mL) dropwise with stirring at room temperature. The resulting mixture was refluxed for 1 h, then the resulting mixture was cooled to room temperature. To the reaction mixture was added a solution of N-methoxy-N-methyloxetane-3-carboxamide (0.200 g, 1.4 mmol) in THF (2 mL) dropwise and stirred at room temperature for 2 h. The resulting mixture was quenched with brine (5 mL) and extracted with ethyl acetate (3×5 mL). The combined organic layers were washed with water (2×5 mL), brine (2×5 mL), dried over anhydrous sodium sulfate and filtered. The filtrate was concentrated under reduced pressure. The residue was purified by column chromatography over silica gel using gradient 1-50% of ethyl acetate in petroleum ether as eluent. The fractions containing desired product were combined and concentrated. The title compound was obtained as a liquid. MS (+ESI) m/z=264.0.

Step 3: [3-Fluoro-4-(trifluoromethoxy)phenyl](oxetan-3-yl)methanamine

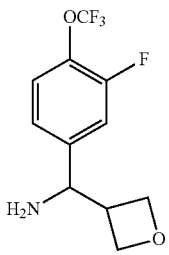

To a solution of [3-fluoro-4-(trifluoromethoxy)phenyl](oxetan-3-yl)methanone (0.150 g, 0.570 mmol) in NH$_3$ (2 M in MeOH, 5 mL) was added titanium(IV) isopropoxide (0.323 g, 1.14 mmol). The reaction mixture was stirred at 60° C. for 16 h. The resulting mixture was cooled room temperature. Then to the reaction mixture was added sodium borohydride (71.9 mg, 1.9 mmol). The resulting reaction mixture was stirred at 25° C. for 3 h. The resulting mixture was then quenched by water (20 mL) and extracted with EtOAc (3×20 mL). The combined organic layers was washed with brine (20 mL), dried over anhydrous sodium sulfate and filtered. The filtrate was concentrated under reduced pressure. The title compound was obtained as a solid which was used in the next step without further purification. MS (+ESI) m/z=266.0.

Preparatory Example 17

2-Methyl-1-(5-(trifluoromethyl)pyridin-2-yl)propan-1-amine

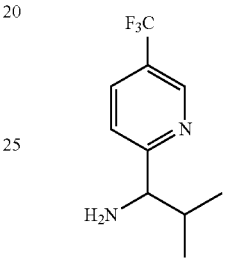

Step 1: N-Methoxy-N-methyl-5-(trifluoromethyl)picolinamide

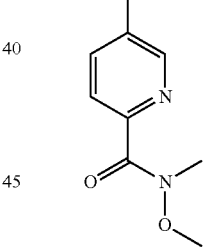

To a solution of 5-(trifluoromethyl)picolinic acid (2.00 g, 10.5 mmol) in NMP (20 mL) were added N,O-dimethylhydroxylamine hydrochloride (1.33 g, 13.6 mmol), HATU (3.98 g, 10.5 mmol) and DIEA (5.5 mL, 31.4 mmol) at 0° C. The reaction mixture was stirred at room temperature for 16 h. Then the mixture was diluted with ethyl acetate (20 mL) and washed with brine (3×20 mL). The organic phase was dried over anhydrous sodium sulfate and filtered. The filtrated was concentrated under reduced pressure. The residue was purified by column chromatography over silica gel using gradient 0-30% of ethyl acetate in petroleum ether as eluent. The title compound was obtained as a liquid. $^1$H NMR (400 MHz, CDCl$_3$) δ: 8.89 (s, 1H), 8.04 (d, J=7.6 Hz, 1H), 7.85-7.65 (m, 1H), 3.75 (s, 3H), 3.41 (s, 3H).

Step 2: 2-Methyl-1-(5-(trifluoromethyl)pyridin-2-yl)propan-1-one

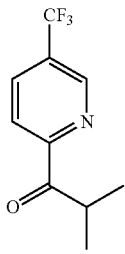

To a solution of N-methoxy-N-methyl-5-(trifluoromethyl)picolinamide (2.10 g, 9.0 mmol) in THF (20 mL) was added dropwise isopropylmagnesium bromide (1 M in THF, 17.9 mL, 17.9 mmol) at 0° C. The reaction solution was warmed to room temperature and stirred for 2 h. Then the reaction solution was quenched with sat'd NH$_4$Cl (100 mL) and extracted with ethyl acetate (3×100 mL). The combined organic layers was washed with brine (200 mL), dried over anhydrous sodium sulfate and filtered. The filtrate was concentrated under reduced pressure. The residue was purified by column chromatography over silica gel using isocratic 20% of ethyl acetate in petroleum ether as eluent. The fractions containing desired product were combined and concentrated. The title compound was obtained as a liquid. $^1$H NMR (400 MHz, CDCl$_3$) δ: 8.96 (s, 1H), 8.17 (d, J=8.0 Hz, 1H), 8.09 (d, J=8.0 Hz, 1H), 4.38-3.87 (m, 1H), 1.24 (d, J=7.2 Hz, 6H).

Step 3: 2-Methyl-1-(5-(trifluoromethyl)pyridin-2-yl)propan-1-amine

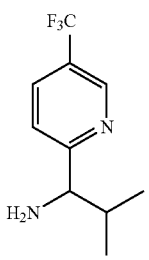

The title compound was prepared using procedures similar to those described in Step 3 of Preparatory Example 16 using 2-methyl-1-(5-(trifluoromethyl)pyridin-2-yl)propan-1-one to afford the title compound as a liquid which was used in the next step without further purification. $^1$H NMR (400 MHz, DMSO-d$_6$) δ: 9.05 (s, 1H), 8.58 (br, 2H), 8.34 (d, J=8.4 Hz, 1H), 7.76 (d, J=8.4 Hz, 1H), 4.37-4.34 (m, 1H), 2.25-2.16 (m, 1H), 0.98 (d, J=6.4 Hz, 3H), 0.86 (d, J=6.4 Hz, 3H).

Preparatory Example 18

1-[3-Fluoro-4-(trifluoromethyl)phenyl]-2-methoxyethanamine

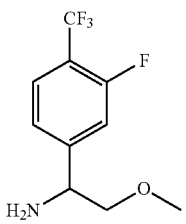 [SMILES: COCC(N)c1ccc(C(F)(F)F)c(F)c1]

Step 1: {[1-(3-Fluoro-4-(trifluoromethyl)phenyl)vinyl]oxy}trimethylsilane

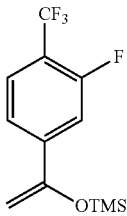

To a solution of hexamethyldisilazane (1.03 g, 6.40 mmol) in THF (5 mL) at −78° C. was added n-butyllithium (2.5 M in hexane, 2.56 mL, 6.4 mmol). The reaction solution was stirred at −78° C. for 1 h. Into the reaction solution was added a solution of 1-(3-fluoro-4-(trifluoromethyl)phenyl)ethanone (1.20 g, 5.80 mmol) in THF (3 mL) at −78° C. The solution was stirred at −78° C. for 30 min followed by the addition of chlorotrimethylsilane (0.632 g, 5.80 mmol). The reaction mixture was then slowly warmed to room temperature and was stirred for additional 3 h. The resulting mixture was quenched with water (5 mL) and extracted with ethyl acetate (3×20 mL). The combined organic fractions were washed with brine (2×10 mL), dried with anhydrous sodium sulfate and filtered. The filtrate was concentrated under reduced pressure. The title compound was obtained as a liquid and used in the next step without further purification. $^1$H NMR (400 MHz, DMSO-d$_6$) δ: 7.78-7.74 (m, 1H), 7.68-7.60 (m, 2H), 5.34 (d, J=2.4 Hz, 1H), 4.65 (d, J=2.4 Hz, 1H), 0.26 (s, 9H).

Step 2: 1-[3-Fluoro-4-(trifluoromethyl)phenyl]-2-methoxyethanone

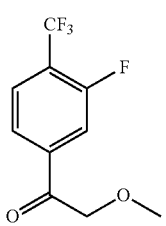

To a solution of iodosylbenzene (1.304 g, 5.93 mmol) in methanol (20 mL) were added boron trifluoride diethyl etherate (1.37 mL, 10.8 mmol) and ((1-(3-fluoro-4-(trifluoromethyl)phenyl) vinyl)oxy)trimethylsilane (1.50 g, 5.4 mmol) at −78° C. The reaction mixture was stirred at −78° C. for 1 h and then warmed to room temperature in 2 h. The reaction mixture was stirred at room temperature for additional 30 min. The resulting mixture was concentrated under reduced pressure and diluted with water (20 mL). The resulting mixture was neutralized with 5% aqueous sodium bicarbonate. The resulting mixture was extracted with DCM (3×40 mL). The combined organic layers were dried over sodium sulfate and concentrated under reduced pressure. The residue was purified by column chromatography over silica gel using isocratic 20% of ethyl acetate in petroleum ether as eluent. The title compound was obtained as a liquid. $^1$H NMR (300 MHz, CDCl$_3$) δ: 7.83-7.71 (m, 3H), 4.65 (s, 2H), 3.51 (s, 3H).

Step 3: 1-(3-Fluoro-4-(trifluoromethyl)phenyl)-2-methoxyethanamine

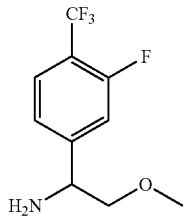 [SMILES: COCC(N)c1ccc(C(F)(F)F)c(F)c1]

The title compound was prepared using procedures similar to those described in Step 3 of Preparatory Example 16 using 1-(3-fluoro-4-(trifluoromethyl)phenyl)-2-methoxyethanone to afford the title compound as a solid which was used in the next step without further purification. $^1$H NMR (300 MHz, CDCl$_3$) δ: 7.64-7.55 (m, 3H), 4.18-4.15 (m, 1H), 3.44-3.41 (m, 2H), 3.30 (s, 3H).

Preparatory Examples 19 and 20

3-(3-Fluoro-4-(trifluoromethyl)phenyl)oxetan-3-amine and 3-(2-Fluoro-3-(trifluoromethyl)phenyl)oxetan-3-amine

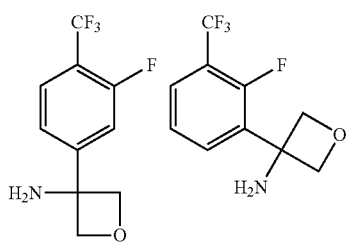

Step 1: N-(3-(3-fluoro-4-(trifluoromethyl)phenyl)oxetan-3-yl)-2-methylpropane-2-sulfinamide and N-(3-(2-fluoro-3-(trifluoromethyl)phenyl)oxetan-3-yl)-2-methylpropane-2-sulfinamide

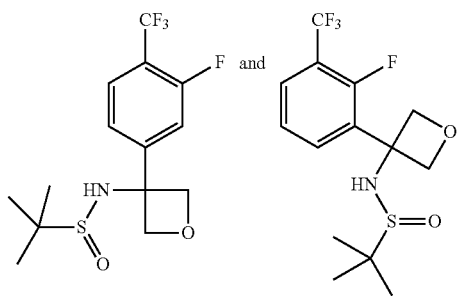 [SMILES: CC(C)(C)S(=O)NC1(c2ccc(C(F)(F)F)c(F)c2)COC1 ; "and" ; CC(C)(C)S(=O)NC1(c2cccc(C(F)(F)F)c2F)COC1]

To a solution of 4-bromo-2-fluoro-1-(trifluoromethyl)benzene (0.416 g, 1.7 mmol) in THF (3 mL) was added dropwise n-BuLi (2.5 M in hexane, 0.64 mL, 1.6 mmol) at −78° C. The reaction solution was stirred for 1 h at −78° C. To the reaction solution was added dropwise a solution of 2-methyl-N-(oxetan-3-ylidene)propane-2-sulfinamide (0.200 g, 1.1 mmol) in THF (7 mL) at −78° C. The reaction solution was warmed slowly to room temperature and stirred for 16 h. The reaction solution was quenched with sat'd. aqueous NH$_4$Cl (10 mL). The mixture was extracted with EtOAc (3×30 mL). The combined organic fractions was washed with brine (2×10 mL), dried with anhydrous sodium sulfate and filtered. The filtrate was concentrated under reduced pressure. The residue was purified by column chromatography over silica gel, using gradient 0-70% of ethyl acetate in petroleum ether as eluent. One isomer of the title compound N-(3-(3-fluoro-4-(trifluoromethyl) phenyl) oxetan-3-yl)-2-methylpropane-2-sulfinamide was obtained as a liquid. $^1$H NMR (400 MHz, CDCl$_3$) δ: 7.70-7.66 (m, 1H), 7.37 (d, J=8.4 Hz, 1H), 7.31 (d, J=11.2 Hz, 1H), 5.10 (s, 2H), 5.03 (d, J=7.2 Hz, 1H), 4.87 (d, J=6.8 Hz, 1H), 1.25 (s, 9H). Another isomer of the title compound N-(3-(2-fluoro-3-(trifluoromethyl)phenyl)oxetan-3-yl)-2-methylpropane-2-sulfinamide was obtained as a liquid. $^1$H NMR (400 MHz, CDCl$_3$) δ: 7.54-7.49 (m, 3H), 5.25-5.22 (m, 2H), 4.88 (d, J=7.2 Hz, 1H), 4.30 (d, J=6.8 Hz, 1H), 1.25 (s, 9H).

Step 2: 3-(3-Fluoro-4-(trifluoromethyl)phenyl)oxetan-3-amine

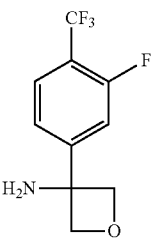

To a solution of N-(3-(3-fluoro-4-(trifluoromethyl)phenyl)oxetan-3-yl)-2-methylpropane-2-sulfinamide (0.250 g, 0.74 mmol) in THF (1 mL) was added HCl (4 M in dioxane, 2.5 mL, 7.5 mmol). The solution was stirred at room temperature for 30 min. The pH value of the mixture was adjusted to 8 with sat'd. aqueous K₂CO₃. The resulting mixture was extracted with EtOAc (40 mL). The organic layer was washed with water (2×10 mL), brine (10 mL), dried over anhydrous sodium sulfate and filtered. The filtrate was concentrated under vacuum to afford the crude title compound as a solid. MS (+ESI) m/z=236.0.

Step 3: 3-(2-Fluoro-3-(trifluoromethyl)phenyl)oxetan-3-amine

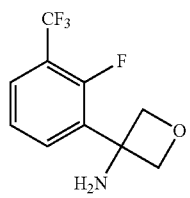 [SMILES: NC1(c2cccc(C(F)(F)F)c2F)COC1]

To sat'd. hydrogen chloride in ethyl acetate (3 mL) was added N-(3-(2-fluoro-3-(trifluoromethyl) phenyl)oxetan-3-yl)-2-methylpropane-2-sulfinamide (0.300 g, 0.9 mmol). The reaction solution was stirred at room temperature for 30 min. The resulting mixture was diluted with water (10 mL). The pH value of the mixture was adjusted to 10 with K₂CO₃. The organic layer was separated. The aqueous phase was extracted with EtOAc (3×20 mL). The combined organic layers was dried over sodium sulfate and filtered. The filtrate was concentrated under reduced pressure to give crude title compound as a solid. MS (+ESI) m/z=235.9.

Preparatory Examples 21

3-(4-(Trifluoromethyl)phenyl)oxetan-3-amine

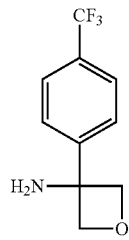

The following example was prepared using similar procedures as in Preparatory Examples 19 and 20 using 4-bromo-1-(trifluoromethyl)benzene as starting material. LC-MS (+ESI) m/z=218.1.

Preparatory Example 22

Methyl 2-amino-2-(3-fluoro-4-(trifluoromethyl)phenyl)acetate

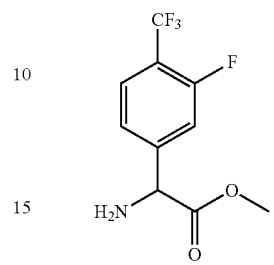

Step 1: 2-Amino-2-(3-fluoro-4-(trifluoromethyl)phenyl)acetonitrile

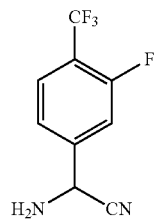

To a solution of 3-fluoro-4-(trifluoromethyl)benzaldehyde (1.00 g, 5.2 mmol) in DCM (10 mL) were added trimethylsilanecarbonitrile (0.516 g, 5.21 mmol) and zinc iodide (0.166 g, 0.52 mmol) at 0° C. After stirred at 0° C. for 10 min, ammonia (saturated in methanol, 5 mL) was added to the reaction mixture, which was then stirred at 60° C. for 3 h. The resulting mixture was quenched with brine (35 mL) and extracted with ethyl acetate (3×15 mL). The combined organic layers were washed with water (2×15 mL), brine (2×15 mL), dried over anhydrous sodium sulfate and filtered. The filtrate was concentrated under reduced pressure. The residue was purified by column chromatography over silica gel using gradient 1-30% of ethyl acetate in petroleum ether as eluent. The title compound was obtained as a liquid. ¹H NMR (300 MHz, CDCl₃) δ: 7.71-7.61 (m, 1H), 7.50-7.45 (m, 2H), 4.97 (s, 1H), 2.00 (br, 2H).

Step 2: Methyl 2-amino-2-(3-fluoro-4-(trifluoromethyl)phenyl)acetate

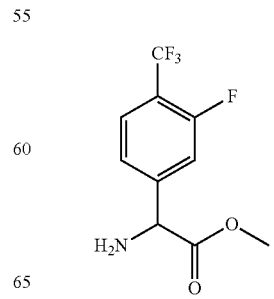

To 2-amino-2-(3-fluoro-4-(trifluoromethyl)phenyl)acetonitrile (0.680 g, 3.12 mmol) in MeOH (10 mL) was added HCl (3 M in dioxane, 10 mL) at 25° C. The reaction mixture was stirred at 60° C. for 3 h. The resulting mixture was cooled, quenched with brine (25 mL) and the pH value was adjusted to 8 with sat'd. aqueous sodium hydroxide. The resulting mixture was extracted with ethyl acetate (3×15 mL). The combined organic layers were washed with water (2×15 mL), brine (2×15 mL), dried over anhydrous sodium sulfate and filtered. The filtrate was concentrated under reduced pressure. The residue was purified by column chromatography over silica gel using gradient 1-70% of ethyl acetate in petroleum ether as eluent. The title compound was obtained as a liquid. MS (+ESI) m/z=252.1.

The following compounds in Table P3 were prepared using procedures similar to those described in Preparatory Example 22 using appropriate starting materials.

TABLE P3

| Preparatory Example # | Structure | IUPAC Name | Mass [M + H]$^+$ or $^1$H NMR |
|---|---|---|---|
| 23 | 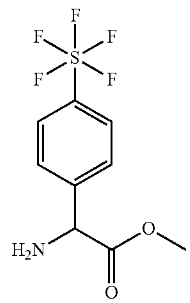 [SMILES: COC(=O)C(N)c1ccc(S(F)(F)(F)(F)F)cc1] | Methyl 2-amino-2-(4-(pentafluorothio)phenyl)acetate | $^1$H NMR (400 MHz, CDCl$_3$) δ: 7.75 (d, J = 8.4 Hz, 2H), 7.52 (d, J = 8.4 Hz, 2H), 4.71 (s, 1H), 3.73 (s, 3H), 2.10 (br, 2H). |
| 24 | 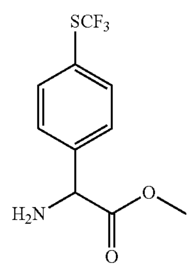 | Methyl 2-amino-2-(4-(trifluoromethylthio)phenyl)acetate | 266.1. |
| 25 | 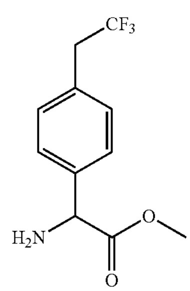 [SMILES: COC(=O)C(N)c1ccc(CC(F)(F)F)cc1] | Methyl 2-amino-2-(4-(2,2,2-trifluoroethyl)phenyl)acetate | 248.0. |
| 26 | 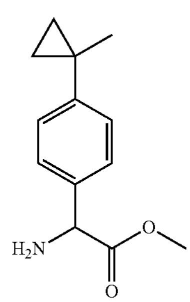 [SMILES: COC(=O)C(N)c1ccc(C2(C)CC2)cc1] | Methyl 2-amino-2-(4-(1-methylcyclopropyl)phenyl)acetate | $^1$H NMR (400 MHz, CDCl$_3$) δ: 7.73-7.21 (m, 4H), 4.59 (s, 1H), 3.72 (s, 3H), 1.95 (br, 2H), 1.41 (s, 3H), 0.85-0.80 (m, 2H), 0.75-0.70 (m, 2H). |

TABLE P3-continued

| Preparatory Example # | Structure | IUPAC Name | Mass [M + H]+ or ¹H NMR |
|---|---|---|---|
| 27 | 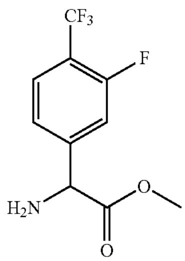 [SMILES: COC(=O)C(N)c1ccc(C(F)(F)F)c(F)c1] | Methyl 2-amino-2-(3-fluoro-4-(trifluoromethyl)phenyl)acetate | Calc'd 252.1 found 251.9. |
| 28 | 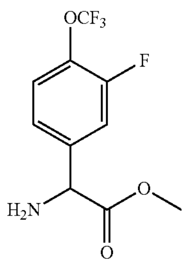 [SMILES: COC(=O)C(N)c1ccc(OC(F)(F)F)c(F)c1] | Methyl 2-amino-2-(3-fluoro-4-(trifluoromethoxy)phenyl)acetate | ¹H NMR (400 MHz, CDCl₃) δ: 7.32-7.21 (m, 3H), 4.65 (s, 1H), 3.74 (s, 3H), 2.05 (br, 2H). |
| 29 | 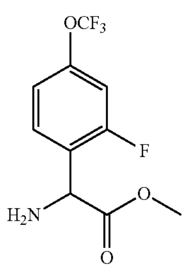 [SMILES: COC(=O)C(N)c1ccc(OC(F)(F)F)cc1F] | Methyl 2-amino-2-(2-fluoro-4-(trifluoromethoxy)phenyl)acetate | 268.1. |
| 30 | 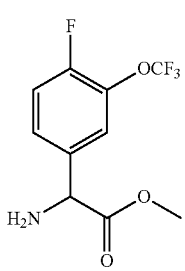 [SMILES: COC(=O)C(N)c1ccc(F)c(OC(F)(F)F)c1] | Methyl 2-amino-2-(4-fluoro-3-(trifluoromethoxy)phenyl)acetate | 268.1. |
| 31 | 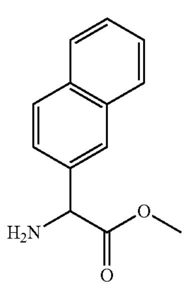 [SMILES: COC(=O)C(N)c1ccc2ccccc2c1] | Methyl 2-amino-2-(naphthalen-2-yl)acetate | ¹H NMR (400 MHz, CD₃OD) δ: 7.90-7.80 (m, 4H), 7.51-7.44 (m, 3H), 4.74 (s, 1H), 3.68 (s, 3H). |

TABLE P3-continued

| Preparatory Example # | Structure | IUPAC Name | Mass [M + H]+ or ¹H NMR |
|---|---|---|---|
| 32 | 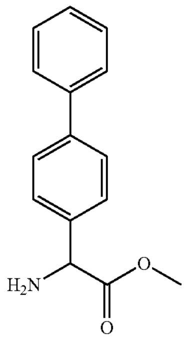 [SMILES: COC(=O)C(N)c1ccc(-c2ccccc2)cc1] | Methyl 2-amino-2-(biphenyl-4-yl)acetate | ¹H NMR (400 MHz, DMSO-d₆) δ: 7.66-7.62 (m, 4H), 7.48-7.44 (m, 4H), 7.38-7.34 (m, 1H), 4.58 (s, 1H), 3.62 (s, 3H), 2.30 (br, 2H). |
| 33 | 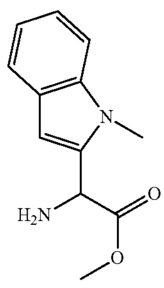 [SMILES: COC(=O)C(N)c1cc2ccccc2n1C] | Methyl 2-amino-2-(1-methyl-1H-indol-2-yl)acetate | 219.1 |
| 34 | 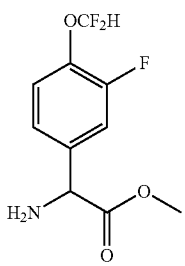 | Methyl 2-amino-2-(4-(difluoromethoxy)-3-fluorophenyl)acetate | 249.9 |
| 35 | 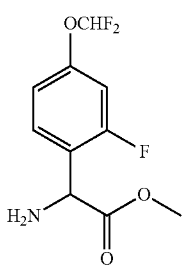 [SMILES: COC(=O)C(N)c1ccc(OC(F)F)cc1F] | Methyl 2-amino-2-(4-(difluoromethoxy)-2-fluorophenyl)acetate | 249.9 |
| 36 | 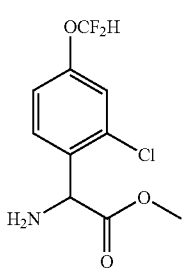 | Methyl 2-amino-2-(2-chloro-4-(difluoromethoxy)phenyl)acetate | 265.9 267.9 (M + 2 + H) |

TABLE P3-continued

| Preparatory Example # | Structure | IUPAC Name | Mass [M + H]+ or ¹H NMR |
|---|---|---|---|
| 37 | 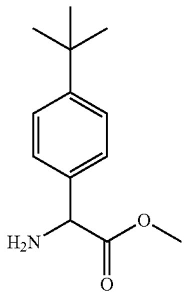 [SMILES: COC(=O)C(N)c1ccc(C(C)(C)C)cc1] | Methyl 2-amino-2-(4-tert-butylphenyl)acetate | 222.0 |
| 38 | 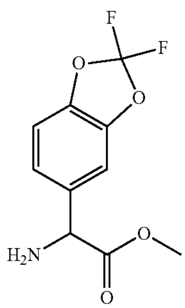 [SMILES: COC(=O)C(N)c1ccc2c(c1)OC(F)(F)O2] | Methyl 2-amino-2-(2,2-difluorobenzo[d][1,3]dioxol-5-yl)acetate | 246.0. |
| 39 | 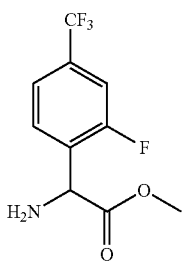 [SMILES: COC(=O)C(N)c1ccc(C(F)(F)F)cc1F] | Methyl 2-amino-2-(2-fluoro-4-(trifluoromethyl)phenyl)acetate | 252.0. |
| 40 | 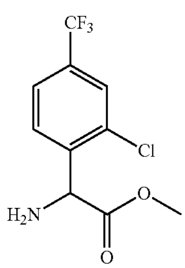 [SMILES: COC(=O)C(N)c1ccc(C(F)(F)F)cc1Cl] | Methyl 2-amino-2-(2-chloro-4-(trifluoromethyl)phenyl)acetate | 268.0 270.0 (M + 2 + H) |
| 41 | 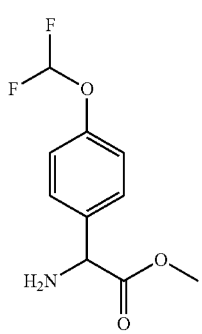 [SMILES: COC(=O)C(N)c1ccc(OC(F)F)cc1] | Methyl 2-amino-2-(4-(difluoromethoxy)phenyl)acetate | 232.0 |

TABLE P3-continued

| Preparatory Example # | Structure | IUPAC Name | Mass [M + H]+ or ¹H NMR |
|---|---|---|---|
| 42 | 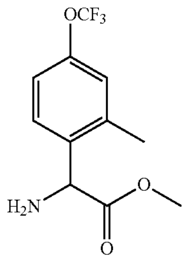 [SMILES: COC(=O)C(N)c1ccc(OC(F)(F)F)cc1C] | Methyl 2-amino-2-(2-methyl-4-(trifluoromethoxy)phenyl)acetate | 264.0 |
| 43 | 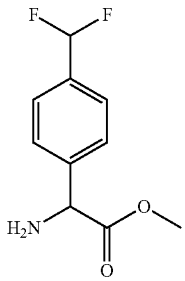 | Methyl 2-amino-2-(4-(difluoromethyl)phenyl)acetate | 216.0 |

Preparatory Example 44

(S)-1-Amino-2-methyl-1-(4-(trifluoromethyl)phenyl)propan-2-ol

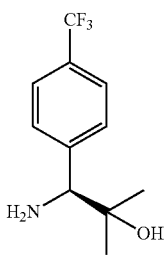

Step 1: Methyl (S)-2-(2,2,2-trifluoroacetamido)-2-(4-(trifluoromethyl)phenyl)acetate

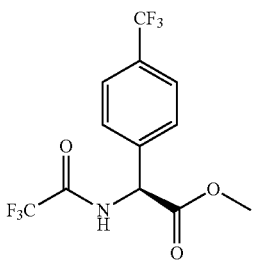 [SMILES: COC(=O)[C@@H](NC(=O)C(F)(F)F)c1ccc(C(F)(F)F)cc1]

To a solution of (S)-methyl 2-amino-2-(4-(trifluoromethyl)phenyl)acetate hydrochloride (360 mg, 1.335 mmol) and DIEA (0.3 mL, 1.67 mmol) in DCM (2 mL) was added trifluoroacetic anhydride (0.23 mL, 1.60 mmol) and the resulting solution stirred at room temperature for 2 hours. The reaction was quenched by addition of 1N aqueous HCl (2 mL) and diluted with DCM (5 mL). The organic layer was separated, washed with saturated aqueous solution of sodium bicarbonate (2 mL) and then brine (2 mL). The organic layer was dried over sodium sulfate, filtered and then the filtrate concentrated under reduced pressure. The residue was purified via preparative TLC plates (3×1000 μM, silica gel) developing with 25% ethyl acetate in hexane. The solvent was removed under reduced pressure to afford the title compound as a solid. LC-MS (+ESI) m/z=330. ¹H NMR (500 MHz, CD₃OD) δ: 7.70 (d, J=8.2 Hz, 2H), 7.53 (d, J=8.2 Hz, 2H), 5.63 (d, J=6.6 Hz, 1H), 3.82 (s, 3H).

Step 2: (S)-2,2,2-Trifluoro-N-(2-hydroxy-2-methyl-1-(4 (trifluoromethyl)phenyl)propyl) acetamide

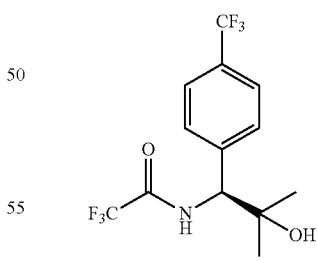

To a stirring solution of methyl (S)-2-(2,2,2-trifluoroacetamido)-2-(4-(trifluoromethyl)phenyl)acetate (400 mg, 1.215 mmol) in THF (6 mL) cooled to 0° C. via ice/water bath under nitrogen atmosphere was added via syringe a 3.0 M solution of methylmagnesium bromide in THF (4.05 mL, 12.15 mmol) and the resulting solution stirred for 2 hours at 0° C. TLC and LC-MS showed that reaction was complete. The reaction mixture was quenched with aqueous saturated ammonium chloride solution (7 mL) and diluted with ethyl acetate (10 mL). The biphasic solution was separated and the aqueous layer washed with ethyl acetate (2×10 mL). The organics were combined, dried over sodium sulfate, filtered and the filtrate concentrate to dryness under reduced pressure. The residue was taken up in 2 mL DCM and purified via prep TLC plates (2×1000 µM, silica gel) developing with 25% ethyl acetate in hexane. The bands containing the product were removed from the plates and the product eluted off with ethyl acetate. The solvent was removed under reduced pressure to afford the compound as a solid. LC-MS (+ESI) m/z=330 and 312 (M-OH)$^+$. $^1$H NMR (500 MHz, CD$_3$OD) δ: 7.65 (d, J=8.1 Hz, 2H), 7.48 (d, J=8.1 Hz, 2H), 4.83 (d, J=8.6 Hz, 1H), 1.42 (s, 3H), 1.08 (s, 3H).

Step 3: (S)-1-Amino-2-methyl-1-(4-(trifluoromethyl)phenyl)propan-2-ol

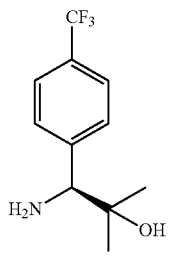

To a solution of (S)-2,2,2-trifluoro-N-(2-hydroxy-2-methyl-1-(4-(trifluoromethyl)phenyl)propyl)acetamide (130 mg, 0.395 mmol) in methanol/water (7:3) was added K$_2$CO$_3$ and the resulting suspension heated to 60° C. via oil bath. All material went into solution after 30 minutes and then the homogeneous solution was stirred for another 16 hours at 60° C. The solvent was then removed under reduced pressure and the aqueous was then extracted with ethyl acetate (3×5 mL). The organics were then combined, dried over sodium sulfate, filtered and the filtrate concentrated to dryness under reduced pressure to afford the title compound. The material was used for the next reaction without further purification. LC-MS (+ESI) m/z=234. $^1$H NMR (500 MHz, CD$_3$OD) δ: 7.60 (d, J=8.3 Hz, 2H), 7.48 (d, J=8.3 Hz, 2H), 3.90 (s, 1H), 1.25 (s, 3H), 1.05 (s, 3H).

The following compounds in Table P4 were prepared using procedures similar to those described in Preparatory Example 44 using appropriate starting materials.

TABLE P4

| Preparatory Example # | Structure | IUPAC Name | Mass [M + H]$^+$ |
| --- | --- | --- | --- |
| 45 | ![structure] | (S)-1-Amino-1-[3-fluoro-4-(trifluoromethyl)phenyl]-2-methylpropan-2-ol | 252.1 |
| 46 | ![structure] | (S)-1-Amino-1-[3-fluoro-4-(trifluoromethoxy)phenyl]-2-methylpropan-2-ol | 268.0 |
| 47 | ![structure] | (S)-1-Amino-1-[2-fluoro-4-(trifluoromethoxy)phenyl]-2-methylpropan-2-ol | 268.0 |

Preparatory Example 48

3-(Amino(3-fluoro-4-(trifluoromethyl)phenyl)methyl)pentan-3-ol

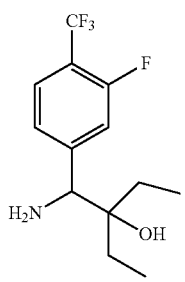

Step 1: 2-Amino-2-(3-fluoro-4-(trifluoromethyl)phenyl)acetonitrile

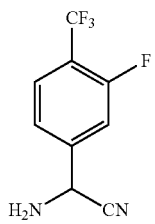

The title compound was prepared using procedures similar to those described in Step 1 of Preparatory Example 22 using 3-fluoro-4-(trifluoromethyl)benzaldehyde to afford the title compound as a liquid. $^1$H NMR (300 MHz, CDCl$_3$) δ: 7.71-7.61 (m, 1H), 7.50-7.45 (m, 2H), 4.97 (s, 1H), 2.00 (br, 2H).

Step 2: Methyl 2-amino-2-(3-fluoro-4-(trifluoromethyl)phenyl)acetate

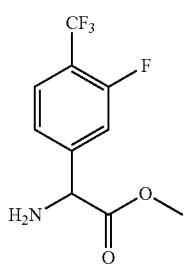 [SMILES: COC(=O)C(N)c1ccc(C(F)(F)F)c(F)c1]

The title compound was prepared using procedures similar to those described in Step 2 of Preparatory Example 22 using 2-amino-2-(3-fluoro-4-(trifluoromethyl)phenyl)acetonitrile to afford the title compound as a liquid. MS (+ESI) m/z=252.1.

Step 3: 3-(Amino(3-fluoro-4-(trifluoromethyl)phenyl)methyl)pentan-3-ol

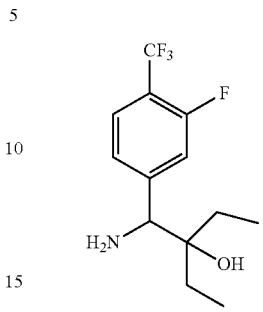

To a solution of methyl 2-amino-2-(3-fluoro-4-(trifluoromethyl)phenyl)acetate (0.100 g, 0.4 mmol) in THF (3 mL) was added ethylmagnesium bromide (1M in THF, 4.0 mL, 4.0 mmol) at −78° C. The solution was warmed to room temperature and stirred for 3 h. The reaction was quenched with sat'd. aqueous NH$_4$Cl (10 mL) and extracted with EtOAc (3×30 mL). The combined organic layers was washed with brine (2×10 mL), dried over anhydrous sodium sulfate and filtered. The filtrate was concentrated under reduced pressure. The residue was purified by column chromatography over silica gel using gradient 0-12% of methanol in DCM as eluent. The title compound was obtained as a solid. MS (+ESI) m/z=280.0.

The following compounds in Table P5 were prepared using procedures similar to those described in Preparatory Example 48 using appropriate starting materials.

TABLE P5

| Preparatory Example # | Structure | IUPAC Name | Mass [M + H]$^+$ |
|---|---|---|---|
| 49 | SCF$_3$ | 1-Amino-2-methyl-1-(4-(trifluoromethylthio)phenyl)propan-2-ol | 266.0 |
| 50 | OCF$_3$ | 1-Amino-1-(2-fluoro-4-(trifluoromethoxy)phenyl)-2-methylpropan-2-ol | 268.0 |

TABLE P5-continued

| Preparatory Example # | Structure | IUPAC Name | Mass [M + H]+ |
|---|---|---|---|
| 51 | 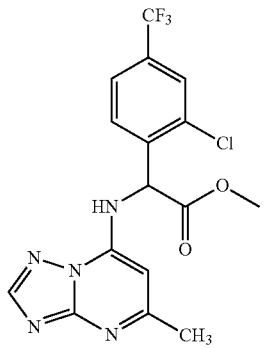 [SMILES: COC(=O)C(Nc1cc(C)nc2ncnn12)c1ccc(C(F)(F)F)cc1Cl] | 1-Amino-2-methyl-1-(6-(trifluoromethyl)pyridin-3-yl)propan-2-ol | 235.0 |

Preparatory Example 52

Methyl 2-(2-chloro-4-(trifluoromethyl)phenyl)-2-(5-methyl-[1,2,4]triazolo[1,5-a]pyrimidin-7-ylamino)acetate

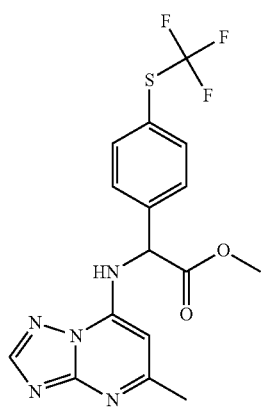

To a solution of methyl 2-amino-2-(2-chloro-4-(trifluoromethyl)phenyl)acetate (0.100 g, 0.400 mmol) in NMP (0.5 mL) was added 7-chloro-5-methyl-[1,2,4]triazolo[1,5-a]pyrimidine (60.0 mg, 0.4 mmol). This was followed by the addition of DIEA (0.12 mL, 0.7 mmol). The reaction mixture was stirred at 80° C. for 2 h. The resulting mixture was cooled to room temperature, diluted with water (10 mL) and extracted with ethyl acetate (3×15 mL). The combined organic layers were washed with water (3×10 mL), brine (3×10 mL), dried over anhydrous sodium sulfate and filtered. The filtrate was concentrated under vacuum. The residue was purified by column chromatography over silica gel using gradient 0-52% of ethyl acetate in petroleum ether as eluent. The title crude compound was further purified by Prep-HPLC with the following conditions: Instrument, GILSON (GX-281); Column: X Bridge $C^{18}$, 19×150 mm, 5 um; Mobile Phase A:Water/0.05% TFA, Mobile Phase B: ACN; Flow rate: 20 mL/min; Gradient: 30% B to 70% B in 10 min; 254 nm. The fractions containing desired product were combined and concentrated to afford the title compound as a liquid. MS (+ESI) m/z=400.0; 402.1.

The following compounds in Table P6 were prepared using procedures similar to those described in Preparatory Example 52 using appropriate starting materials.

TABLE P6

| Preparatory Example # | Structure | IUPAC Name | Mass [M + H]+ | *Coupling method |
|---|---|---|---|---|
| 53 | 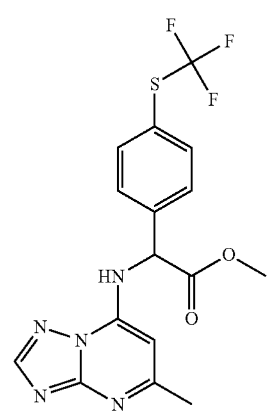 [SMILES: COC(=O)C(Nc1cc(C)nc2ncnn12)c1ccc(SC(F)(F)F)cc1] | Methyl 2-(5-methyl-[1,2,4]triazolo[1,5-a]pyrimidin-7-ylamino)-2-(4-(trifluoromethylthio)phenyl)acetate | 398.0 | A |

TABLE P6-continued

| Preparatory Example # | Structure | IUPAC Name | Mass [M + H]+ | *Coupling method |
|---|---|---|---|---|
| 54 | 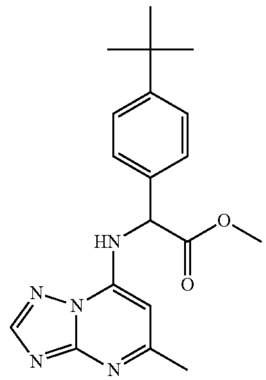 [SMILES: COC(=O)C(Nc1cc(C)nc2ncnn12)c1ccc(C(C)(C)C)cc1] | Methyl 2-(4-tert-butylphenyl)-2-(5-methyl-[1,2,4]triazolo[1,5-a]pyrimidin-7-ylamino)acetate | 354.2 | A |
| 55 | 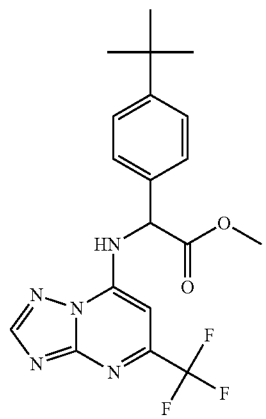 [SMILES: COC(=O)C(Nc1cc(C(F)(F)F)nc2ncnn12)c1ccc(C(C)(C)C)cc1] | Methyl 2-(4-tert-butylphenyl)-2-(5-(trifluoromethyl)-[1,2,4]triazolo[1,5-a]pyrimidin-7-ylamino)acetate | 408.2 | A |
| 56 | 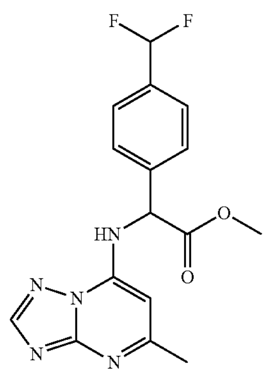 [SMILES: COC(=O)C(Nc1cc(C)nc2ncnn12)c1ccc(C(F)F)cc1] | Methyl 2-(4-(difluoromethyl)phenyl)-2-(5-methyl-[1,2,4]triazolo[1,5-a]pyrimidin-7-ylamino)acetate | 348.0 | A |
| 57 | 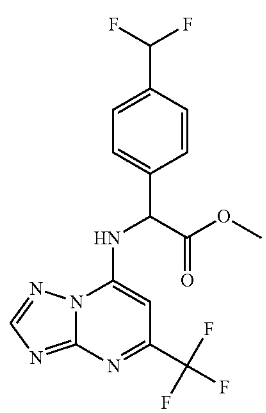 [SMILES: COC(=O)C(Nc1cc(C(F)(F)F)nc2ncnn12)c1ccc(C(F)F)cc1] | Methyl 2-(4-(difluoromethyl)phenyl)-2-(5-(trifluoromethyl)-[1,2,4]triazolo[1,5-a]pyrimidin-7-ylamino)acetate | 402.1 | B |

TABLE P6-continued

| Preparatory Example # | Structure | IUPAC Name | Mass [M + H]+ | *Coupling method |
|---|---|---|---|---|
| 58 | 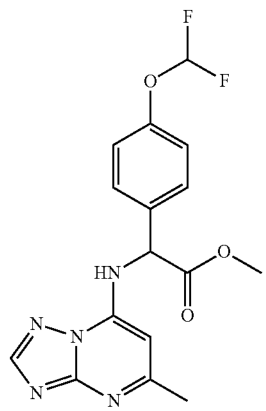 [SMILES: COC(=O)C(Nc1cc(C)nc2ncnn12)c1ccc(OC(F)F)cc1] | Methyl 2-(4-(difluoromethoxy)phenyl)-2-(5-methyl-[1,2,4]triazolo[1,5-a]pyrimidin-7-ylamino)acetate | 364.2 | A |
| 59 | 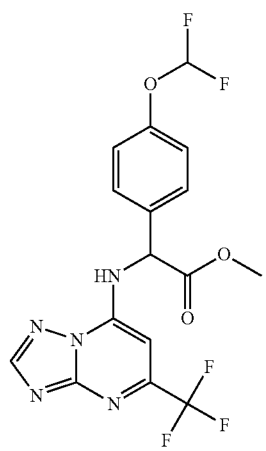 [SMILES: COC(=O)C(Nc1cc(C(F)(F)F)nc2ncnn12)c1ccc(OC(F)F)cc1] | Methyl 2-(4-(difluoromethoxy)phenyl)-2-(5-(trifluoromethyl)-[1,2,4]triazolo[1,5-a]pyrimidin-7-ylamino)acetate | 418.1 | B |
| 60 | 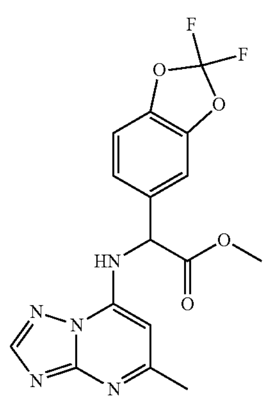 [SMILES: COC(=O)C(Nc1cc(C)nc2ncnn12)c1ccc2c(c1)OC(F)(F)O2] | Methyl 2-(2,2-difluorobenzo[d][1,3]dioxol-5-yl)-2-(5-methyl-[1,2,4]triazolo[1,5-a]pyrimidin-7-ylamino)acetate | 378.2 | A |

TABLE P6-continued

| Preparatory Example # | Structure | IUPAC Name | Mass [M + H]+ | *Coupling method |
|---|---|---|---|---|
| 61 | 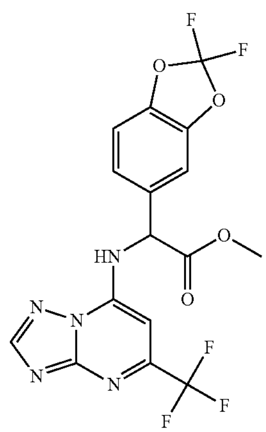 [SMILES: COC(=O)C(Nc1cc(C(F)(F)F)nc2ncnn12)c1ccc2c(c1)OC(F)(F)O2] | Methyl 2-(2,2-difluorobenzo[d][1,3]dioxol-5-yl)-2-(5-(trifluoromethyl)-[1,2,4]triazolo[1,5-a]pyrimidin-7-ylamino)acetate | 432.2 | B |
| 62 | 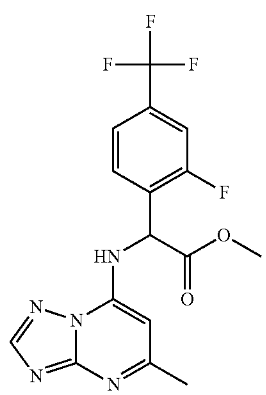 [SMILES: COC(=O)C(Nc1cc(C)nc2ncnn12)c1ccc(C(F)(F)F)cc1F] | Methyl 2-(2-fluoro-4-(trifluoromethyl)phenyl)-2-(5-methyl-[1,2,4]triazolo[1,5-a]pyrimidin-7-ylamino)acetate | 384.1 | A |
| 63 | 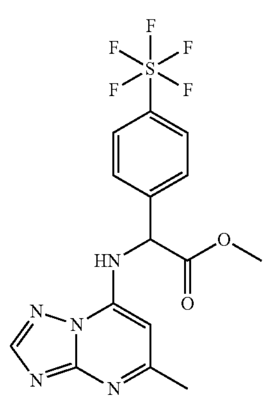 [SMILES: COC(=O)C(Nc1cc(C)nc2ncnn12)c1ccc(S(F)(F)(F)(F)F)cc1] | Methyl 2-(5-methyl-[1,2,4]triazolo[1,5-a]pyrimidin-7-ylamino)-2-(4-(pentafluorothio)phenyl)acetate | 424.0 | A |

TABLE P6-continued

| Preparatory Example # | Structure | IUPAC Name | Mass [M + H]+ | *Coupling method |
|---|---|---|---|---|
| 64 | 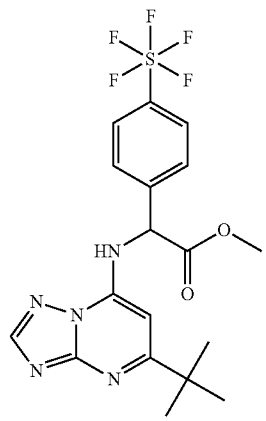 [SMILES: COC(=O)C(Nc1cc(C(C)(C)C)nc2ncnn12)c1ccc(S(F)(F)(F)(F)F)cc1] | Methyl 2-(5-tert-butyl-[1,2,4]triazolo[1,5-a]pyrimidin-7-ylamino)-2-(4-(pentafluorothio)phenyl)acetate | 466.0 | B |
| 65 | 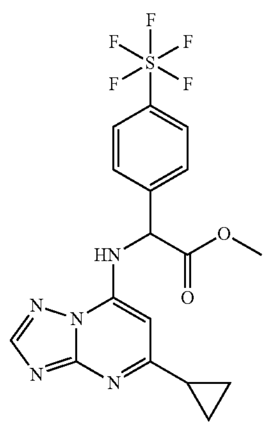 [SMILES: COC(=O)C(Nc1cc(C2CC2)nc2ncnn12)c1ccc(S(F)(F)(F)(F)F)cc1] | Methyl 2-(5-cyclopropyl-[1,2,4]triazolo[1,5-a]pyrimidin-7-ylamino)-2-(4-(pentafluorothio)phenyl)acetate | 450.0 | B |
| 66 | 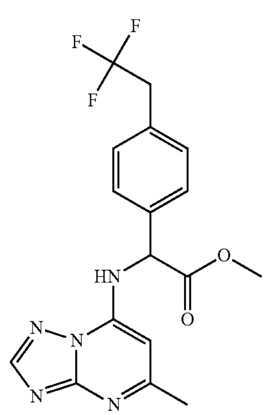 [SMILES: COC(=O)C(Nc1cc(C)nc2ncnn12)c1ccc(CC(F)(F)F)cc1] | Methyl 2-(5-methyl-[1,2,4]triazolo[1,5-a]pyrimidin-7-ylamino)-2-(4-(2,2,2-trifluoroethyl)phenyl)acetate | 380.0 | B |

TABLE P6-continued
| Preparatory Example # | Structure | IUPAC Name | Mass [M + H]+ | *Coupling method |
|---|---|---|---|---|
| 67 | 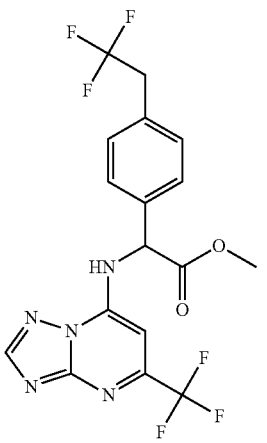 [SMILES: COC(=O)C(Nc1cc(C(F)(F)F)nc2ncnn12)c1ccc(CC(F)(F)F)cc1] | Methyl 2-(4-(2,2,2-trifluoroethyl)phenyl)-2-(5-(trifluoromethyl)-[1,2,4]triazolo[1,5-a]pyrimidin-7-ylamino)acetate | 433.9 | B |
| 68 | 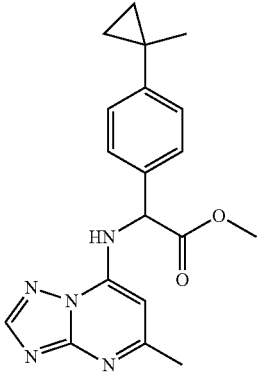 [SMILES: COC(=O)C(Nc1cc(C)nc2ncnn12)c1ccc(C2(C)CC2)cc1] | Methyl 2-(5-methyl-[1,2,4]triazolo[1,5-a]pyrimidin-7-ylamino)-2-(4-(1-methylcyclopropyl)phenyl)acetate | 352.0 | B |
| 69 | 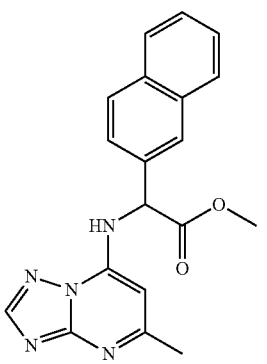 [SMILES: COC(=O)C(Nc1cc(C)nc2ncnn12)c1ccc2ccccc2c1] | Methyl 2-(5-methyl-[1,2,4]triazolo[1,5-a]pyrimidin-7-ylamino)-2-(naphthalen-2-yl)acetate | 348.1 | B |

TABLE P6-continued

| Preparatory Example # | Structure | IUPAC Name | Mass [M + H]+ | *Coupling method |
|---|---|---|---|---|
| 70 | 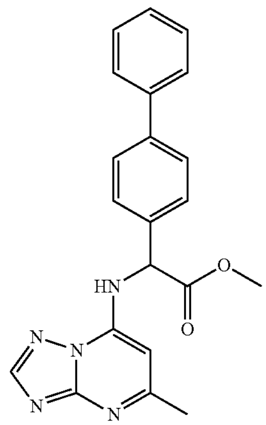 [SMILES: COC(=O)C(Nc1cc(C)nc2ncnn12)c1ccc(-c2ccccc2)cc1] | Methyl 2-(biphenyl-4-yl)-2-(5-methyl-[1,2,4]triazolo[1,5-a]pyrimidin-7-ylamino)acetate | 374.1 | A |
| 71 | 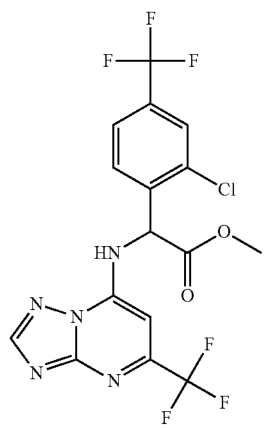 [SMILES: COC(=O)C(Nc1cc(C(F)(F)F)nc2ncnn12)c1ccc(C(F)(F)F)cc1Cl] | Methyl 2-(2-chloro-4-(trifluoromethyl)phenyl)-2-(5-(trifluoromethyl)-[1,2,4]triazolo[1,5-a]pyrimidin-7-ylamino)acetate | 454.0; 456.0 (M + 2 + H) | A |
| 72 | 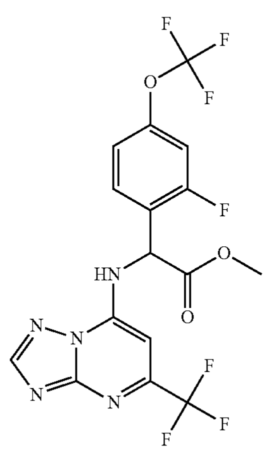 [SMILES: COC(=O)C(Nc1cc(C(F)(F)F)nc2ncnn12)c1ccc(OC(F)(F)F)cc1F] | Methyl 2-(2-fluoro-4-(trifluoromethoxy)phenyl)-2-(5-(trifluoromethyl)-[1,2,4]triazolo[1,5-a]pyrimidin-7-ylamino)acetate | 454.0 | B |

TABLE P6-continued

| Preparatory Example # | Structure | IUPAC Name | Mass [M + H]+ | *Coupling method |
|---|---|---|---|---|
| 73 | 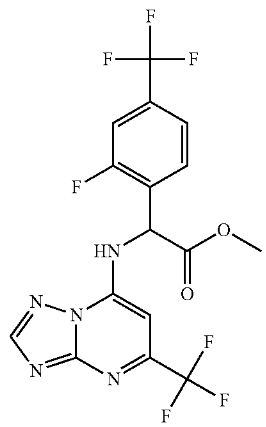 [SMILES: COC(=O)C(Nc1cc(C(F)(F)F)nc2ncnn12)c1ccc(C(F)(F)F)cc1F] | Methyl 2-(2-fluoro-4-(trifluoromethyl)phenyl)-2-(5-(trifluoromethyl)-[1,2,4]triazolo[1,5-a]pyrimidin-7-ylamino)acetate | 438.1 | B |
| 74 | 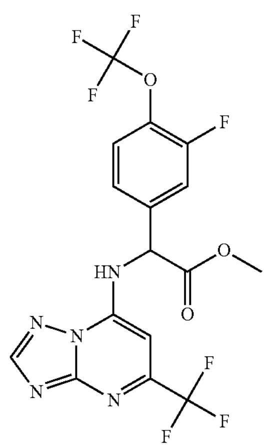 [SMILES: COC(=O)C(Nc1cc(C(F)(F)F)nc2ncnn12)c1ccc(OC(F)(F)F)c(F)c1] | Methyl 2-(3-fluoro-4-(trifluoromethoxy)phenyl)-2-(5-(trifluoromethyl)-[1,2,4]triaozlo[1,5-a]pyrimidin-7-ylamino)acetate | 454.0 | B |
| 75 | 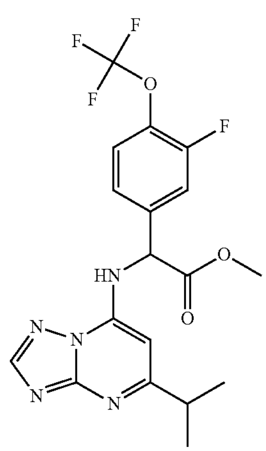 [SMILES: COC(=O)C(Nc1cc(C(C)C)nc2ncnn12)c1ccc(OC(F)(F)F)c(F)c1] | Methyl 2-(3-fluoro-4-(trifluoromethoxy)phenyl)-2-(5-isopropyl-[1,2,4]triazolo[1,5-a]pyrimidin-7-ylamino)acetate | 428.0 | B |

TABLE P6-continued

| Preparatory Example # | Structure | IUPAC Name | Mass [M + H]+ | *Coupling method |
|---|---|---|---|---|
| 76 | 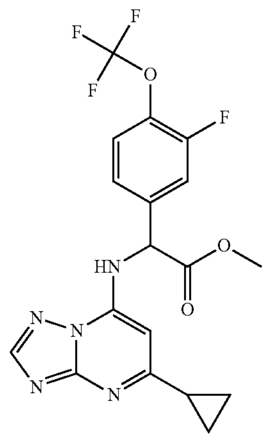 [SMILES: COC(=O)C(Nc1cc(C2CC2)nc2ncnn12)c1ccc(OC(F)(F)F)c(F)c1] | Methyl 2-(5-cyclopropyl-[1,2,4]triazolo[1,5-a]pyrimidin-7-ylamino)-2-(3-fluoro-4-(trifluoromethoxy)phenyl)acetate | 426.0 | B |
| 77 | 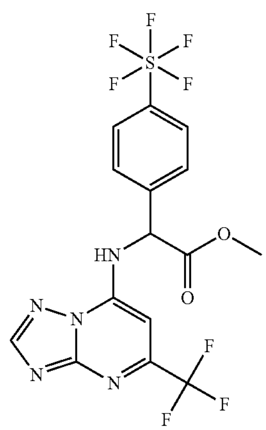 [SMILES: COC(=O)C(Nc1cc(C(F)(F)F)nc2ncnn12)c1ccc(S(F)(F)(F)(F)F)cc1] | Methyl 2-(5-(trifluoromethyl)-[1,2,4]triazolo[1,5-a]pyrimidin-7-ylamino)-2-(4-(pentafluorothio)phenyl)acetate | 477.9 | B |
| 78 | 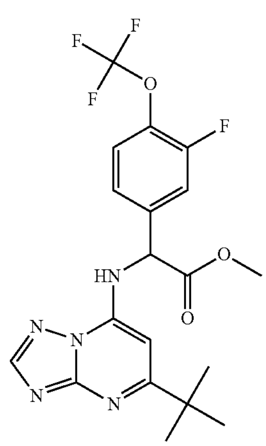 [SMILES: COC(=O)C(Nc1cc(C(C)(C)C)nc2ncnn12)c1ccc(OC(F)(F)F)c(F)c1] | Methyl 2-(5-tert-butyl-[1,2,4]triazolo[1,5-a]pyrimidin-7-ylamino)-2-(3-fluoro-4-(trifluoromethoxy)phenyl)acetate | 442.2 | B |

TABLE P6-continued

| Preparatory Example # | Structure | IUPAC Name | Mass [M + H]+ | *Coupling method |
|---|---|---|---|---|
| 79 | 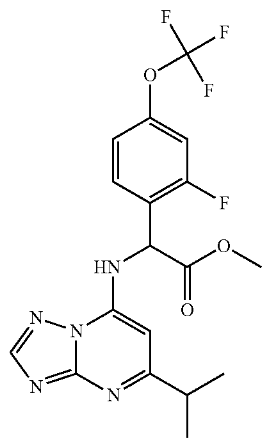 [SMILES: COC(=O)C(Nc1cc(C(C)C)nc2ncnn12)c1ccc(OC(F)(F)F)cc1F] | Methyl 2-((5-isopropyl-[1,2,4]triazolo[1,5-a]pyrimidin-7-yl)amino)-2-(2-fluoro-4-(trifluoromethoxy)phenyl)acetate | 428.1 | A |
| 80 | 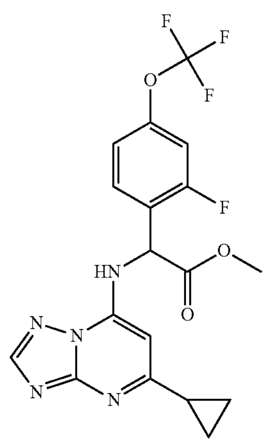 [SMILES: COC(=O)C(Nc1cc(C2CC2)nc2ncnn12)c1ccc(OC(F)(F)F)cc1F] | Methyl 2-((5-cyclopropyl-[1,2,4]triazolo[1,5-a]pyrimidin-7-yl)amino)-2-(2-fluoro-4-(trifluoromethoxy)phenyl)acetate | 425.9 | A |
| 81 | 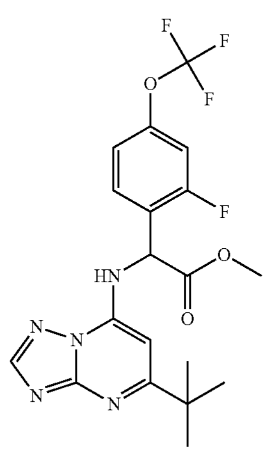 [SMILES: COC(=O)C(Nc1cc(C(C)(C)C)nc2ncnn12)c1ccc(OC(F)(F)F)cc1F] | Methyl 2-((5-tert-butyl-[1,2,4]triazolo[1,5-a]pyrimidin-7-yl)amino)-2-(2-fluoro-4-(trifluoromethoxy)phenyl)acetate | 442.1 | A |

TABLE P6-continued

| Preparatory Example # | Structure | IUPAC Name | Mass [M + H]+ | *Coupling method |
|---|---|---|---|---|
| 82 | 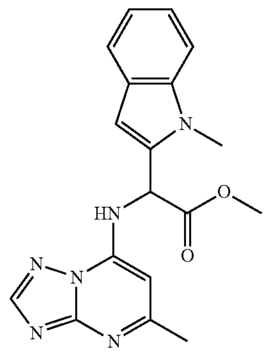 [SMILES: COC(=O)C(Nc1cc(C)nc2ncnn12)c1cc2ccccc2n1C] | Methyl 2-(1-methyl-1H-indol-2-yl)-2-(5-methyl-[1,2,4]triazolo[1,5-a]pyrimidin-7-ylamino)acetate | 351.1 | B |
| 83 | 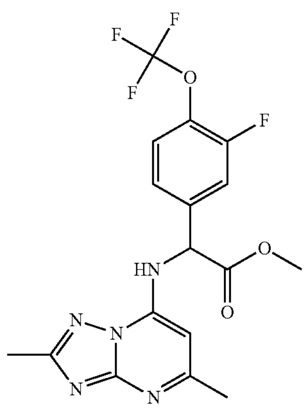 | Methyl 2-(2,5-dimethyl-[1,2,4]triazolo[1,5-a]pyrimidin-7-ylamino)-2-(3-fluoro-4-(trifluoromethoxy)phenyl)acetate | 414.1 | B |
| 84 | 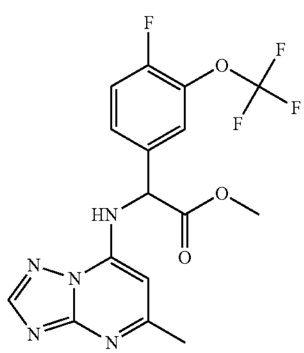 [SMILES: COC(=O)C(Nc1cc(C)nc2ncnn12)c1ccc(F)c(OC(F)(F)F)c1] | Methyl 2-(4-fluoro-3-(trifluoromethoxy)phenyl)-2-((5-methyl-[1,2,4]triazolo[1,5-a]pyrimidin-7-yl)amino)acetate | 400.2 | B |
| 85 | 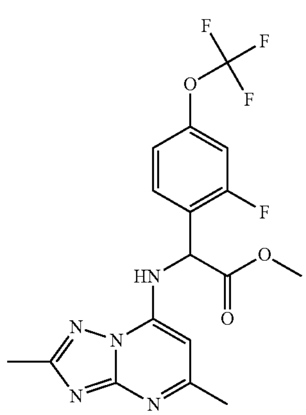 | Methyl 2-(2,5-dimethyl-[1,2,4]triazolo[1,5-a]pyrimidin-7-ylamino)-2-(2-fluoro-4-(trifluoromethoxy)phenyl)acetate | 414.3 | B |

TABLE P6-continued

| Preparatory Example # | Structure | IUPAC Name | Mass [M + H]+ | *Coupling method |
|---|---|---|---|---|
| 86 | 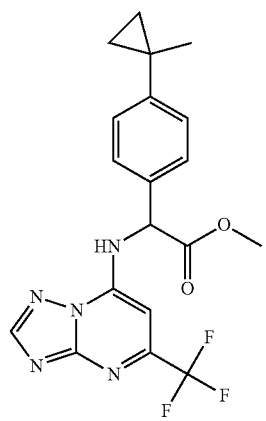 [SMILES: COC(=O)C(Nc1cc(C(F)(F)F)nc2ncnn12)c1ccc(C2(C)CC2)cc1] | Methyl 2-(4-(1-methylcyclopropyl)phenyl)-2-(5-(trifluoromethyl)-[1,2,4]triazolo[1,5-a]pyrimidin-7-ylamino)acetate | 406.1 | B |
| 87 | 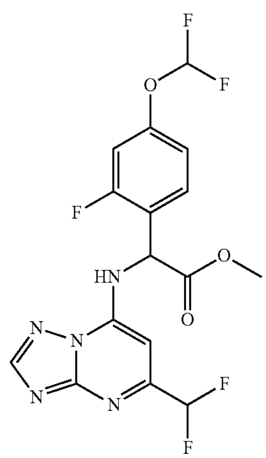 [SMILES: COC(=O)C(Nc1cc(C(F)F)nc2ncnn12)c1ccc(OC(F)F)cc1F] | Methyl 2-(4-(difluoromethoxy)-2-fluorophenyl)-2-(5-(difluoromethyl)-[1,2,4]triazolo[1,5-a]pyrimidin-7-ylamino)acetate | 417.9 | B |
| 88 | 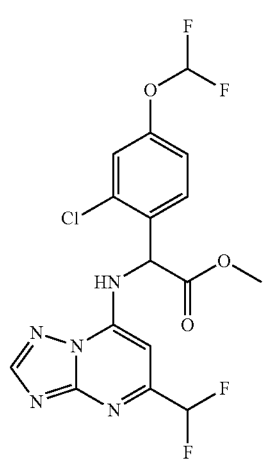 [SMILES: COC(=O)C(Nc1cc(C(F)F)nc2ncnn12)c1ccc(OC(F)F)cc1Cl] | Methyl 2-(2-chloro-4-(difluoromethoxy)phenyl)-2-((5-(difluoromethyl)-[1,2,4]triazolo[1,5-a]pyrimidin-7-yl)amino)acetate | 433.9; 435.9 (M + 2 + H) | B |

TABLE P6-continued

| Preparatory Example # | Structure | IUPAC Name | Mass [M + H]+ | *Coupling method |
|---|---|---|---|---|
| 89 | 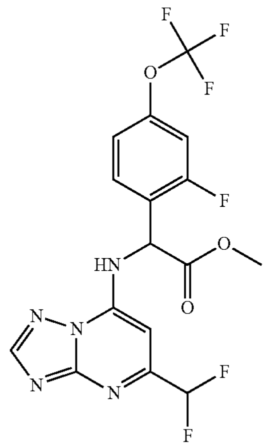 [SMILES: COC(=O)C(Nc1cc(C(F)F)nc2ncnn12)c1ccc(OC(F)(F)F)cc1F] | Methyl 2-(5-(difluoromethyl)-[1,2,4]triazolo[1,5-a]pyrimidin-7-ylamino)-2-(2-fluoro-4-(trifluoromethoxy)phenyl)acetate | 435.9 | A |
| 90 | 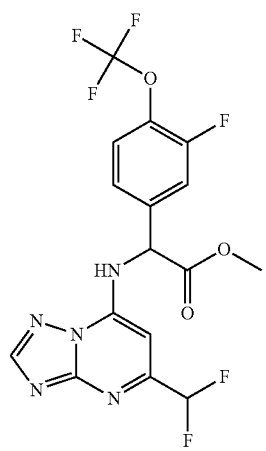 [SMILES: COC(=O)C(Nc1cc(C(F)F)nc2ncnn12)c1ccc(OC(F)(F)F)c(F)c1] | Methyl 2-(5-(difluoromethyl)-[1,2,4]triazolo[1,5-a]pyrimidin-7-ylamino)-2-(3-fluoro-4-(trifluoromethoxy)phenyl)acetate | 436.0 | B |
| 91 | 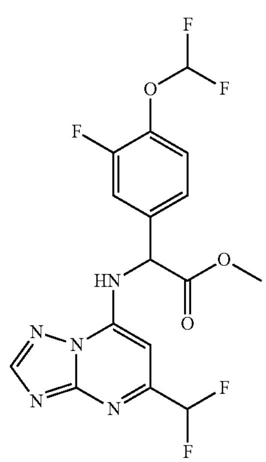 [SMILES: COC(=O)C(Nc1cc(C(F)F)nc2ncnn12)c1ccc(OC(F)F)c(F)c1] | Methyl 2-(4-(difluoromethoxy)-3-fluorophenyl)-2-(5-(difluoromethyl)-[1,2,4]triazolo[1,5-a]pyrimidin-7-ylamino)acetate | 418.0 | B |

*Coupling conditions: A. DIEA, NMP; B. DIEA, IPA

Preparatory Example 92

(5-Chloro-[1,2,4]triazolo[1,5-a]pyridin-7-yl)methanol

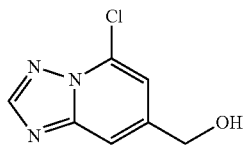 [SMILES: OCc1cc(Cl)n2ncnc2c1]

To a solution of [5-chloro-7-methyl-[1,2,4]triazolo[1,5-a]pyridine (5 g, 29.8 mmol) in CH₃CN (50 mL) was added benzoic peroxyanhydride (1.445 g, 5.97 mmol) and [1-chloropyrrolidine-2,5-dione (5.98 g, 44.8 mmol), followed by addition of acetic acid (0.102 mL, 1.790 mmol) and the resulting mixture refluxed for 2.5 hrs. Then, the mixture was poured into 50 mL water and extracted with EtOAc (100 mL×3), the organics dried over Na₂SO₄ and concentrated to afford crude intermediate as brown oil. The crude oil was suspended in 50 mL water and added potassium carbonate (6.18 g, 44.8 mmol). The suspension was then refluxed for 2.5 hrs. The resulting mixture was cooled to rt and extracted with EtOAc (100 mL×3). The organic layers were collected and combined, dried over Na₂SO₄, filtered, and concentrated to afford crude product. Purification with ISCO (40 g flash silica gel column, 0-100% EtOAc in Hexane (20 min), and 100% EtOAc:EtOH=3:1 (10 min)) afforded the title product as a solid. LC/MS (m/z): 184.1 (M+H)⁺.

Preparatory Example 93

5-Chloro-7-(difluoromethyl)-[1,2,4]triazolo[1,5-a]pyridine

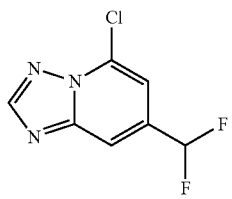 [SMILES: FC(F)c1cc(Cl)n2ncnc2c1]

Step 1: 5-Chloro-[1,2,4]triazolo[1,5-a]pyridine-7-carbaldehyde

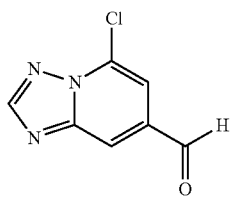 [SMILES: O=Cc1cc(Cl)n2ncnc2c1]

To (5-chloro-[1,2,4]triazolo[1,5-a]pyridin-7-yl)methanol (1 g, 5.45 mmol) in DCM (20 mL) was added Dess-Martin Periodinane (4.62 g, 10.89 mmol) and the resulting mixture stirred at room temperature for 2 h. The mixture was diluted with sat'd aqueous NaHCO₃ and extracted with DCM (100 mL×3). The organics were the combined, dried over sodium sulfate, filtered and the filtrate was concentrated under reduced pressure to afford crude product. Purification with ISCO (40 g flash silica gel column, 0-100% EtOAc in Hexane) gave the title compound as a solid. LC/MS (m/z): 182.0 (M+H)⁺.

Step 2: 5-Chloro-7-(difluoromethyl)-[1,2,4]triazolo[1,5-a]pyridine

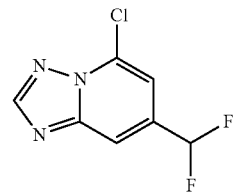 [SMILES: FC(F)c1cc(Cl)n2ncnc2c1]

To a solution of 5-chloro-[1,2,4]triazolo[1,5-a]pyridine-7-carbaldehyde (50 mg, 0.275 mmol) in DCM (1 mL) in plastic vial under N₂ was added DAST (0.073 ml, 0.551 mmol). The mixture was stirred at room temperature for 1 h. The mixture was then quenched with water, the organics were separated and then concentrated under reduced pressure to afford crude product as an oil. Purification with ISCO (12 g flash silica gel column, 0-100% EtOAc in Hexane) afforded the title compound as a solid. LC/MS (m/z): 204.0 (M+H)⁺.

EXAMPLES

Example 1

5-Methyl-N-{(1R)-1-[4-(trifluoromethyl)phenyl]ethyl}[1,2,4]triazolo[1,5-a]pyrimidin-7-amine

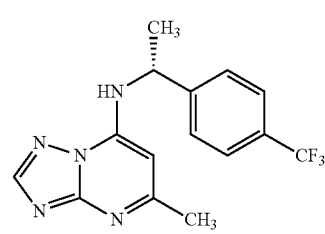

Step 1: 5-Methyl-N-{(1R)-1-[4-(trifluoromethyl)phenyl]ethyl}[1,2,4]triazolo[1,5-a]pyrimidin-7-amine

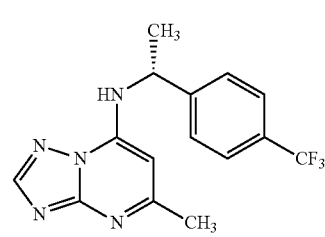 [SMILES: Cc1cc(N[C@H](C)c2ccc(C(F)(F)F)cc2)n2ncnc2n1]

To a solution of commercially available 7-chloro-5-methyl-[1,2,4]-triazolo[1,5-a]pyrimidine (25 mg, 0.148 mmol) and (R)-1-(4-(trifluoromethyl)phenyl)ethanamine hydrochloride (40.2 mg, 0.178 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool to RT and was quenched with 1 mL of sat'd. aqueous sodium bicarbonate soln. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness. The residue was taken up into 1.5 mL of acetonitrile/water (4:1) and purified by reverse phase HPLC (10-90% acetonitrile in water with 0.05% TFA) to afford the product as a solid. LC-MS (+ESI) m/z=322. $^1$H NMR (500 MHz, CD$_3$OD) δ: 8.48 (s, 1H), 7.72-7.66 (m, 4H), 6.36 (s, 1H), 5.18 (q, J=6.8 Hz, 1H), 2.48 (s, 3H), 1.77 (d, J=6.8 Hz, 3H).

Example 2

5-Methyl-N-{(1S)-1-[4-(trifluoromethyl)phenyl]ethyl}[1,2,4]triazolo[1,5-a]pyrimidin-7-amine

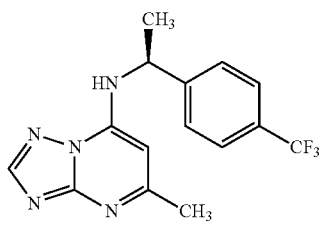

Step 1: 5-Methyl-N-{(1S)-1-[4-(trifluoromethyl)phenyl]ethyl}[1,2,4]triazolo[1,5-a]pyrimidin-7-amine

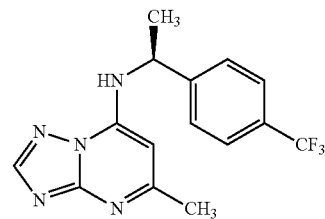 [SMILES: Cc1cc(N[C@@H](C)c2ccc(C(F)(F)F)cc2)n2ncnc2n1]

To a solution of commercially available 7-chloro-5-methyl-[1,2,4]-triazolo[1,5-a]pyrimidine (25 mg, 0.148 mmol) and (R)-1-(4-(trifluoromethyl)phenyl)ethanamine hydrochloride (40.2 mg, 0.178 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool and was quenched with 1 mL of sat'd. aqueous sodium bicarbonate soln. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness. Purification by reverse phase HPLC (10-90% acetonitrile in water with 0.05% TFA) afforded the product as a solid. LC-MS (+ESI) m/z=322. $^1$H NMR (500 MHz, CD$_3$OD) δ: 8.48 (s, 1H), 7.73-7.65 (m, 4H), 6.35 (s, 1H), 5.17 (q, J=6.8 Hz, 1H), 2.48 (s, 3H), 1.76 (d, J=6.8 Hz, 3H).

The following compounds in Table 1 were prepared using procedures similar to those described in Example 1 using appropriate starting materials.

TABLE 1

| Example No. | Structure | IUPAC Name | Observed Exact Mass [M + H]$^+$ |
|---|---|---|---|
| 3 | 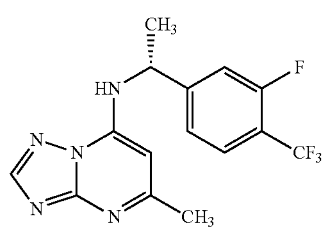 [SMILES: Cc1cc(N[C@H](C)c2ccc(C(F)(F)F)c(F)c2)n2ncnc2n1] | N-{(1R)-1-[3-Fluoro-4-(trifluoromethyl)phenyl]ethyl}-5-methyl[1,2,4]triazolo[1,5-a]pyrimidin-7-amine | 340.1 |
| 4 | 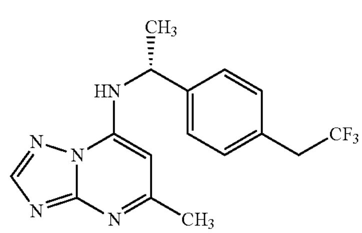 [SMILES: Cc1cc(N[C@H](C)c2ccc(CC(F)(F)F)cc2)n2ncnc2n1] | 5-Methyl-N-{(1R)-1-[4-(2,2,2-trifluoroethyl)phenyl]ethyl}[1,2,4]triazolo[1,5-a]pyrimidin-7-amine | 336.1 |

TABLE 1-continued

| Example No. | Structure | IUPAC Name | Observed Exact Mass [M + H]+ |
|---|---|---|---|
| 5 | 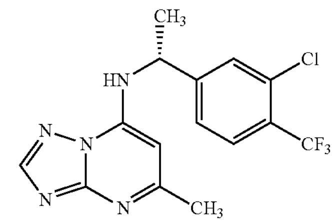 [SMILES: Cc1cc(N[C@H](C)c2ccc(C(F)(F)F)c(Cl)c2)n2ncnc2n1] | N-{(1R)-1-[3-Chloro-4-(trifluoromethyl)phenyl]ethyl}-5-methyl[1,2,4]triazolo[1,5-a]pyrimidin-7-amine | 356.0 358.1 (M + 2 + H) |
| 6 | 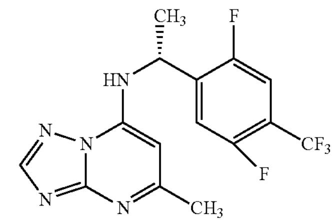 [SMILES: Cc1cc(N[C@H](C)c2cc(F)c(C(F)(F)F)cc2F)n2ncnc2n1] | N-{(1R)-1-[2,5-Difluoro-4-(trifluoromethyl)phenyl]ethyl}-5-methyl[1,2,4]triazolo[1,5-a]pyrimidin-7-amine | 358.2 |
| 7 | 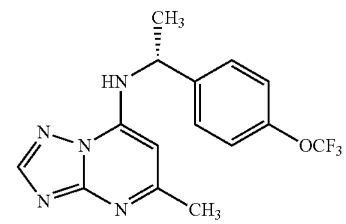 [SMILES: Cc1cc(N[C@H](C)c2ccc(OC(F)(F)F)cc2)n2ncnc2n1] | 5-Methyl-N-{(1R)-1-[4-(trifluoromethoxy)phenyl]ethyl}[1,2,4]triazolo[1,5-a]pyrimidin-7-amine | 338.0 |
| 8 | 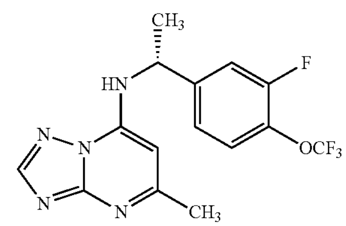 [SMILES: Cc1cc(N[C@H](C)c2ccc(OC(F)(F)F)c(F)c2)n2ncnc2n1] | N-{(1R)-1-[3-Fluoro-4-(trifluoromethoxy)phenyl]ethyl}-5-methyl[1,2,4]triazolo[1,5-a]pyrimidin-7-amine | 356.1 |
| 9 | 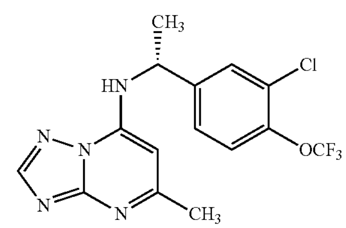 | N-{(1R)-1-[3-Chloro-4-(trifluoromethoxy)phenyl]ethyl}-5-methyl[1,2,4]triazolo[1,5-a]pyrimidin-7-amine | 371.9 374.0 (M + 2 + H) |
| 10 | 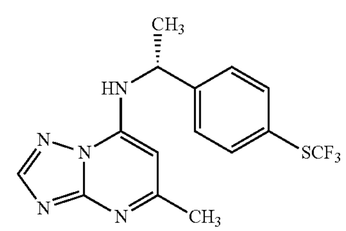 | 5-Methyl-N-[(1R)-1-{4-[(trifluoromethyl)sulfanyl]phenyl}ethyl][1,2,4]triazolo[1,5-a]pyrimidin-7-amine | 354.1 |
| 11 | 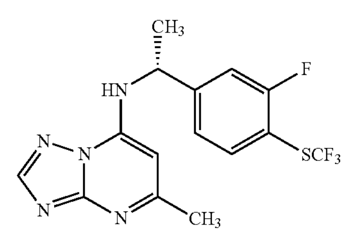 | N-[(1R)-1-{3-Fluoro-4-[(trifluoromethyl)sulfanyl]phenyl}ethyl]-5-methyl[1,2,4]triazolo[1,5-a]pyrimidin-7-amine | 372.0 |

TABLE 1-continued

| Example No. | Structure | IUPAC Name | Observed Exact Mass [M + H]+ |
|---|---|---|---|
| 12 | 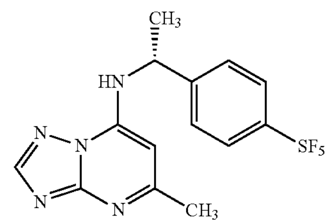 | 5-Methyl-N-{(1R)-1-[4-(pentafluoro-λ6-sulfanyl)phenyl]ethyl}[1,2,4]triazolo[1,5-a]pyrimidin-7-amine | 380.1 |
| 13 | 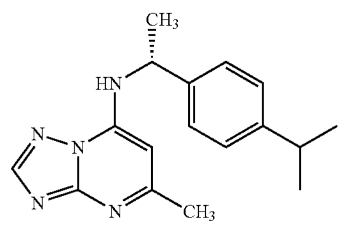 [SMILES: Cc1cc(N[C@H](C)c2ccc(C(C)C)cc2)n2ncnc2n1] | 5-Methyl-N-{(1R)-1-[4-(1-methylethyl)phenyl]ethyl}[1,2,4]triazolo[1,5-a]pyrimidin-7-amine | 296.2 |
| 14 | 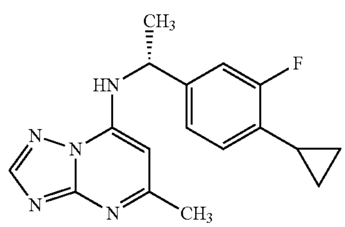 [SMILES: Cc1cc(N[C@H](C)c2ccc(C3CC3)c(F)c2)n2ncnc2n1] | N-[(1R)-1-(4-Cyclopropyl-3-fluorophenyl)ethyl]-5-methyl[1,2,4]triazolo[1,5-a]pyrimidin-7-amine | 312.1 |
| 15 | 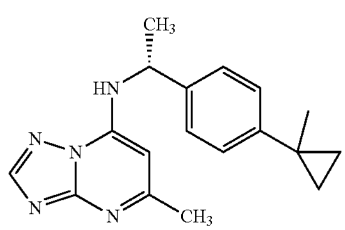 [SMILES: Cc1cc(N[C@H](C)c2ccc(C3(C)CC3)cc2)n2ncnc2n1] | 5-Methyl-N-{(1R)-1-[4-(1-methylcyclopropyl)phenyl]ethyl}[1,2,4]triazolo[1,5-a]pyrimidin-7-amine | 308.0 |
| 16 | 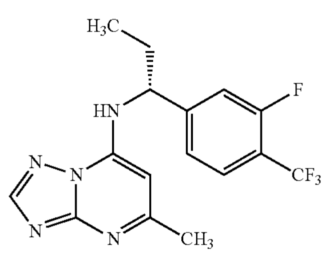 [SMILES: CC[C@@H](Nc1cc(C)nc2ncnn12)c1ccc(C(F)(F)F)c(F)c1] | N-{(1R)-1-[3-Fluoro-4-(trifluoromethyl)phenyl]propyl}-5-methyl[1,2,4]triazolo[1,5-a]pyrimidin-7-amine | 354.0 |
| 17 | 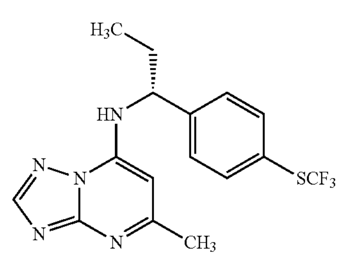 | 5-Methyl-N-[(1R)-1-{4-[(trifluoromethyl)sulfanyl]phenyl}propyl][1,2,4]triazolo[1,5-a]pyrimidin-7-amine | 368.1 |

TABLE 1-continued

| Example No. | Structure | IUPAC Name | Observed Exact Mass [M + H]+ |
|---|---|---|---|
| 18 | 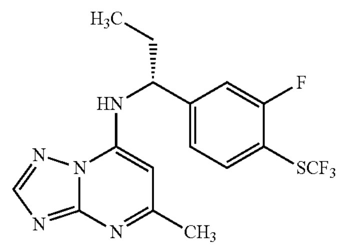 | N-[(1R)-1-{3-Fluoro-4-[(trifluoromethyl)sulfanyl]phenyl}propyl]-5-methyl[1,2,4]triazolo[1,5-a]pyrimidin-7-amine | 385.9 |
| 19 | 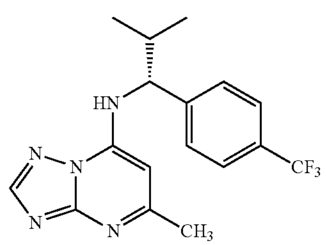 [SMILES: Cc1cc(N[C@@H](c2ccc(C(F)(F)F)cc2)C(C)C)n2ncnc2n1] | 5-Methyl-N-{(1R)-2-methyl-1-[4-(trifluoromethyl)phenyl]propyl}[1,2,4]triazolo[1,5-a]pyrimidin-7-amine | 350.1 |
| 20 | 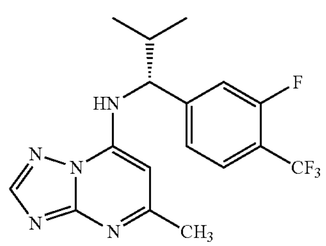 [SMILES: Cc1cc(N[C@@H](c2ccc(C(F)(F)F)c(F)c2)C(C)C)n2ncnc2n1] | N-{(1R)-1-[3-Fluoro-4-(trifluoromethyl)phenyl]-2-methylpropyl}-5-methyl[1,2,4]triazolo[1,5-a]pyrimidin-7-amine | 368.1 |
| 21 | 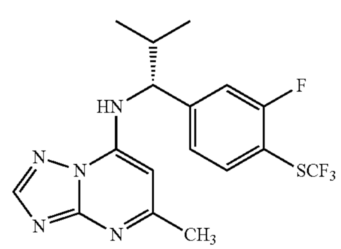 | N-[(1R)-1-{3-Fluoro-4-[(trifluoromethyl)sulfanyl]phenyl}-2-methylpropyl]-5-methyl[1,2,4]triazolo[1,5-a]pyrimidin-7-amine | 400.0 |
| 22 | 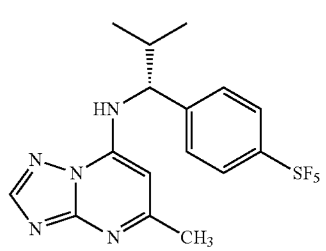 | 5-Methyl-N-{(1R)-2-methyl-1-[4-(pentafluoro-$\lambda^6$-sulfanyl)phenyl]propyl}[1,2,4]triazolo[1,5-a]pyrimidin-7-amine | 408.2 |
| 23 | 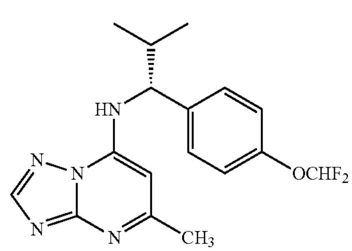 [SMILES: Cc1cc(N[C@@H](c2ccc(OC(F)F)cc2)C(C)C)n2ncnc2n1] | N-{(1R)-1-[4-(Difluoromethoxy)phenyl]-2-methylpropyl}-5-methyl[1,2,4]triazolo[1,5-a]pyrimidin-7-amine | 348.1 |

TABLE 1-continued

| Example No. | Structure | IUPAC Name | Observed Exact Mass [M + H]+ |
|---|---|---|---|
| 24 | 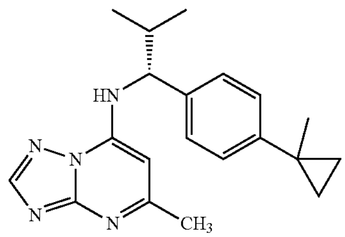 [SMILES: Cc1cc(N[C@@H](c2ccc(C3(C)CC3)cc2)C(C)C)n2ncnc2n1] | 5-Methyl-N-{(1R)-2-methyl-1-[4-(1-methyl-cyclopropyl)phenyl]propyl}[1,2,4]triazolo[1,5-a]pyrimidin-7-amine | 336.0 |
| 25 | 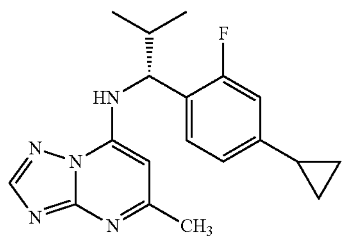 [SMILES: Cc1cc(N[C@@H](c2ccc(C3CC3)cc2F)C(C)C)n2ncnc2n1] | N-[(1R)-1-(4-Cyclopropyl-2-fluorophenyl)-2-methylpropyl]-5-methyl[1,2,4]triazolo[1,5-a]pyrimidin-7-amine | 340.1 |
| 26 | 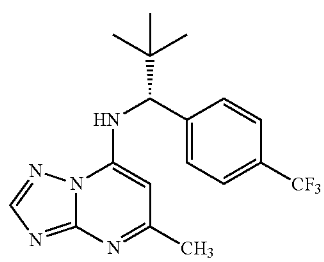 [SMILES: Cc1cc(N[C@@H](c2ccc(C(F)(F)F)cc2)C(C)(C)C)n2ncnc2n1] | N-{(1R)-2,2-Dimethyl-1-[4-(trifluoromethyl)phenyl]propyl}-5-methyl[1,2,4]triazolo[1,5-a]pyrimidin-7-amine | 364.1 |
| 27 | 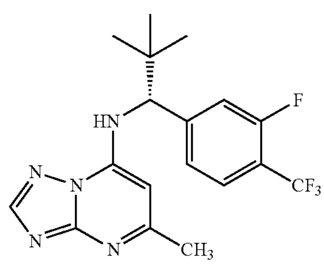 [SMILES: Cc1cc(N[C@@H](c2ccc(C(F)(F)F)c(F)c2)C(C)(C)C)n2ncnc2n1] | N-{(1R)-1-[3-Fluoro-4-(trifluoromethyl)phenyl]-2,2-dimethylpropyl}-5-methyl[1,2,4]triazolo[1,5-a]pyrimidin-7-amine | 382.1 |
| 28 | 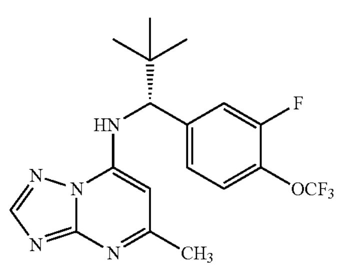 [SMILES: Cc1cc(N[C@@H](c2ccc(OC(F)(F)F)c(F)c2)C(C)(C)C)n2ncnc2n1] | N-{(1R)-1-[3-Fluoro-4-(trifluoromethoxy)phenyl]-2,2-dimethylpropyl}-5-methyl[1,2,4]triazolo[1,5-a]pyrimidin-7-amine | 398.0 |
| 29 | 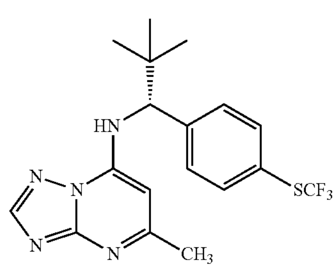 | N-[(1R)-2,2-Dimethyl-1-{4-[(trifluoromethyl)sulfanyl]phenyl}propyl]-5-methyl[1,2,4]triazolo[1,5-a]pyrimidin-7-amine | 396.0 |

TABLE 1-continued

| Example No. | Structure | IUPAC Name | Observed Exact Mass [M + H]+ |
|---|---|---|---|
| 30 | 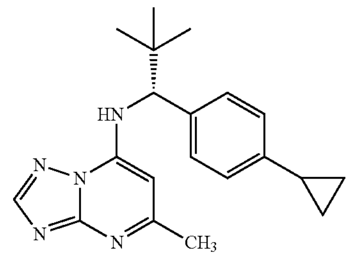 [SMILES: Cc1cc(N[C@@H](c2ccc(C3CC3)cc2)C(C)(C)C)n2ncnc2n1] | N-[(1R)-1-(4-Cyclopropyl-phenyl)-2,2-dimethylpropyl]-5-methyl[1,2,4]triazolo[1,5-a]pyrimidin-7-amine | 336.1 |
| 31 | 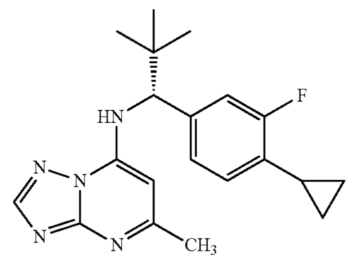 [SMILES: Cc1cc(N[C@@H](c2ccc(C3CC3)c(F)c2)C(C)(C)C)n2ncnc2n1] | N-[(1R)-1-(4-Cyclopropyl-3-fluorophenyl)-2,2-dimethylpropyl]-5-methyl[1,2,4]triazolo[1,5-a]pyrimidin-7-amine | 354.2 |
| 32 | 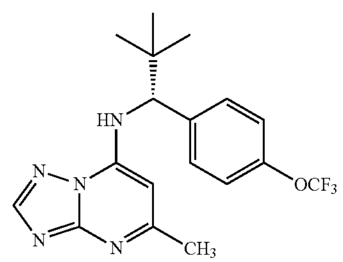 [SMILES: Cc1cc(N[C@@H](c2ccc(OC(F)(F)F)cc2)C(C)(C)C)n2ncnc2n1] | N-{(1R)-2,2-Dimethyl-1-[4-(trifluoromethoxy)phenyl]propyl}-5-methyl[1,2,4]triazolo[1,5-a]pyrimidin-7-amine | 380.0 |
| 33 | 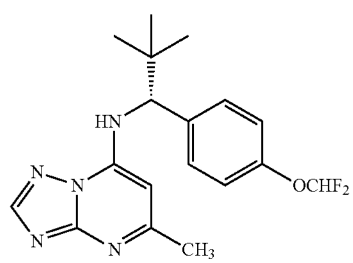 [SMILES: Cc1cc(N[C@@H](c2ccc(OC(F)F)cc2)C(C)(C)C)n2ncnc2n1] | N-{(1R)-1-[4-(Difluoromethoxy)phenyl]-2,2-dimethylpropyl}-5-methyl[1,2,4]triazolo[1,5-a]pyrimidin-7-amine | 362.1 |
| 34 | 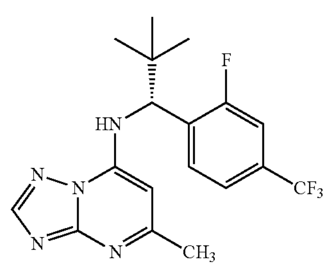 [SMILES: Cc1cc(N[C@@H](c2ccc(C(F)(F)F)cc2F)C(C)(C)C)n2ncnc2n1] | N-{(1R)-1-[2-Fluoro-4-(trifluoromethyl)phenyl]-2,2-dimethylpropyl}-5-methyl[1,2,4]triazolo[1,5-a]pyrimidin-7-amine | 382.1 |
| 35 | 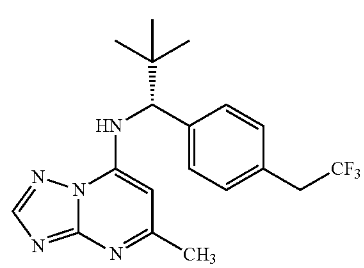 [SMILES: Cc1cc(N[C@@H](c2ccc(CC(F)(F)F)cc2)C(C)(C)C)n2ncnc2n1] | N-{(1R)-2,2-Dimethyl-1-[4-(2,2,2-trifluoroethyl)phenyl]propyl}-5-methyl[1,2,4]triazolo[1,5-a]pyrimidin-7-amine | 378.0 |

TABLE 1-continued

| Example No. | Structure | IUPAC Name | Observed Exact Mass [M + H]+ |
|---|---|---|---|
| 36 | 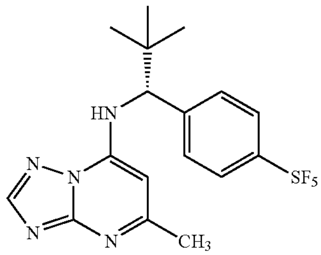 | N-{(1R)-2,2-Dimethyl-1-[4-(pentafluoro-λ⁶-sulfanyl)phenyl]propyl}-5-methyl[1,2,4]triazolo[1,5-a]pyrimidin-7-amine | 422.0 |
| 37 | 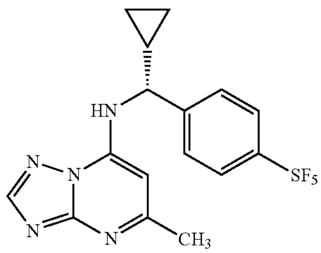 | N-{(1R)-Cyclopropyl[4-(pentafluoro-λ⁶-sulfanyl)phenyl]methyl}-5-methyl[1,2,4]triazolo[1,5-a]pyrimidin-7-amine | 406.2 |
| 38 | 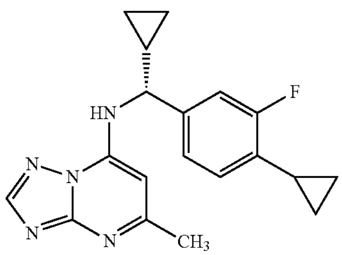 [SMILES: Cc1cc(N[C@@H](c2ccc(C3CC3)c(F)c2)C2CC2)n2ncnc2n1] | N-[(R)-Cyclopropyl(4-cyclopropyl-3-fluorophenyl)methyl]-5-methyl[1,2,4]triazolo[1,5-a]pyrimidin-7-amine | 338.1 |
| 39 | 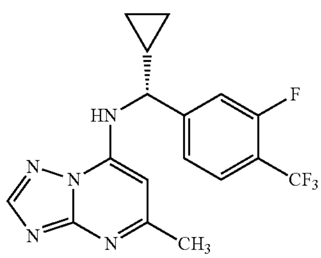 [SMILES: Cc1cc(N[C@@H](c2ccc(C(F)(F)F)c(F)c2)C2CC2)n2ncnc2n1] | N-{(R)-Cyclopropyl[3-fluoro-4-(trifluoromethyl)phenyl]methyl}-5-methyl[1,2,4]triazolo[1,5-a]pyrimidin-7-amine | 366.2 |
| 40 | 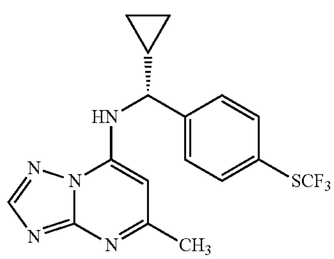 | N-[(R)-Cyclopropyl{4-[(trifluoromethyl)sulfanyl]phenyl}methyl]-5-methyl[1,2,4]triazolo[1,5-a]pyrimidin-7-amine | 380.1 |
| 41 | 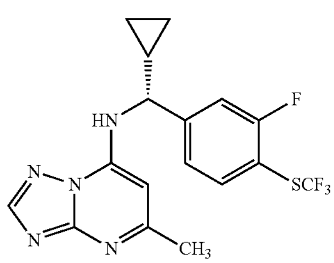 | N-[(R)-Cyclopropyl{3-fluoro-4-[(trifluoromethyl)sulfanyl]phenyl}methyl]-5-methyl[1,2,4]triazolo[1,5-a]pyrimidin-7-amine | 398.0 |

TABLE 1-continued

| Example No. | Structure | IUPAC Name | Observed Exact Mass [M + H]+ |
|---|---|---|---|
| 42 | 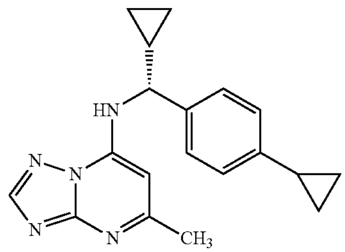 [SMILES: Cc1cc(N[C@@H](c2ccc(C3CC3)cc2)C2CC2)n2ncnc2n1] | N-[(R)-Cyclopropyl(4-cyclopropylphenyl)methyl]-5-methyl[1,2,4]triazolo[1,5-a]pyrimidin-7-amine | 320.0 |
| 43 | 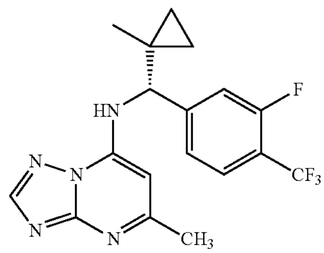 [SMILES: Cc1cc(N[C@@H](c2ccc(C(F)(F)F)c(F)c2)C2(C)CC2)n2ncnc2n1] | N-[(R)-[3-Fluoro-4-(trifluoromethyl)phenyl](1-methylcyclopropyl)methyl]-5-methyl[1,2,4]triazolo[1,5-a]pyrimidin-7-amine | 380.1 |
| 44 | 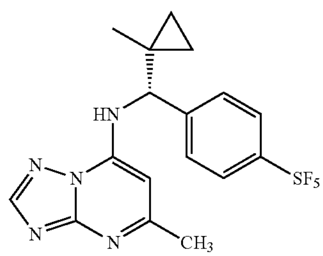 | 5-Methyl-N-{(R)-(1-methylcyclopropyl)[4-(pentafluoro-λ⁶-sulfanyl)phenyl]methyl}[1,2,4]triazolo[1,5-a]pyrimidin-7-amine | 419.9 |

Example 45

N-{1-[3-Fluoro-4-(trifluoromethoxy)phenyl]-1-methylethyl}-5-methyl[1,2,4]triazolo[1,5-a]pyrimidin-7-amine

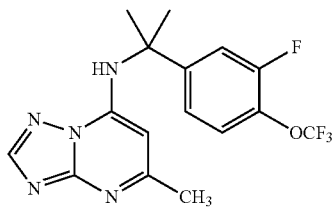

Step 1: N-{1-[3-Fluoro-4-(trifluoromethoxy)phenyl]-1-methylethyl}-5-methyl[1,2,4]triazolo [1,5-a]pyrimidin-7-amine

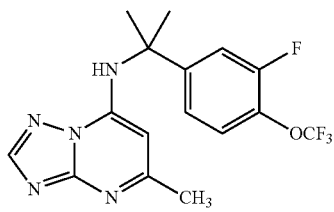 [SMILES: Cc1cc(NC(C)(C)c2ccc(OC(F)(F)F)c(F)c2)n2ncnc2n1]

To a solution of commercially available 7-chloro-5-methyl-[1,2,4]-triazolo[1,5-a]pyrimidine (25 mg, 0.148 mmol) and 2-[3-fluoro-4-(trifluoromethoxy)phenyl]propan-2-amine (52 mg, 0.22 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool and evaporated in Genvac to remove all volatiles. The residue was treated with 1 mL of DMSO, this mixture was filtered and then purified by reverse phase HPLC (10-90% acetonitrile in water with 0.05% TFA) to afford the product. LC-MS (+ESI) m/z=370. ¹H NMR (500 MHz, MNSO-d₆) δ: 8.42 (s, 1H), 7.81 (s, 1H), 7.52-7.63 (m, 2H), 7.38 (m, 1H), 5.43 (s, 1H), 2.22 (s, 3H), 1.78 (s, 6H).

The following compounds in Table 2 were prepared using procedures similar to those described in Example 45 using appropriate starting materials.

TABLE 2

| Example No. | Structure | IUPAC Name | Observed Exact Mass [M + H]+ |
|---|---|---|---|
| 46 | 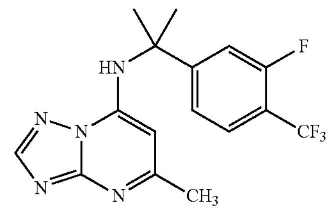 [SMILES: Cc1cc(NC(C)(C)c2ccc(C(F)(F)F)c(F)c2)n2ncnc2n1] | N-{1-[3-Fluoro-4-(trifluoromethyl)phenyl]-1-methylethyl}-5-methyl[1,2,4]triazolo[1,5-a]pyrimidin-7-amine | 354.0 |
| 47 | 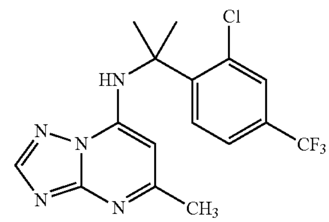 [SMILES: Cc1cc(NC(C)(C)c2ccc(C(F)(F)F)cc2Cl)n2ncnc2n1] | N-{1-[2-Chloro-4-(trifluoromethyl)phenyl]-1-methylethyl}-5-methyl[1,2,4]triazolo[1,5-a]pyrimidin-7-amine | 370.1 |
| 48 | 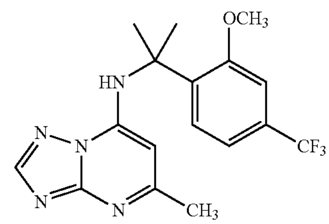 | N-{1-[2-Methoxy-4-(trifluoromethyl)phenyl]-1-methylethyl}-5-methyl[1,2,4]triazolo[1,5-a]pyrimidin-7-amine | 366.1 |
| 49 | 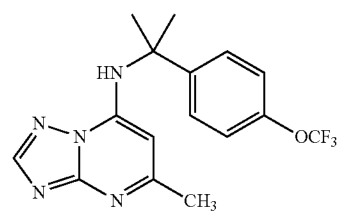 [SMILES: Cc1cc(NC(C)(C)c2ccc(OC(F)(F)F)cc2)n2ncnc2n1] | 5-Methyl-N-{1-methyl-1-[4-(trifluoromethoxy)phenyl]ethyl}[1,2,4]triazolo[1,5-a]pyrimidin-7-amine | 352.1 |
| 50 | 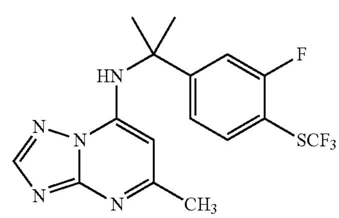 | N-(1-{3-Fluoro-4-[(trifluoromethyl)sulfanyl]phenyl}-1-methylethyl)-5-methyl[1,2,4]triazolo[1,5-a]pyrimidin-7-amine | 386.0 |
| 51 | 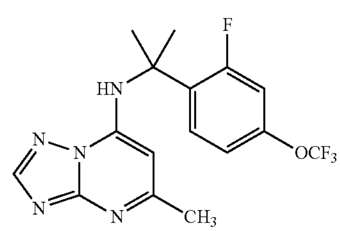 [SMILES: Cc1cc(NC(C)(C)c2ccc(OC(F)(F)F)cc2F)n2ncnc2n1] | N-{1-[2-Fluoro-4-(trifluoromethoxy)phenyl]-1-methylethyl}-5-methyl[1,2,4]triazolo[1,5-a]pyrimidin-7-amine | 370.2 |
| 52 | 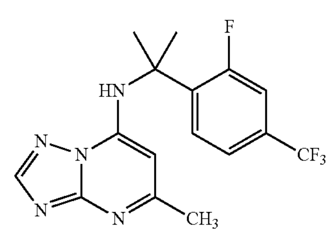 [SMILES: Cc1cc(NC(C)(C)c2ccc(C(F)(F)F)cc2F)n2ncnc2n1] | N-{1-[2-Fluoro-4-(trifluoromethyl)phenyl]-1-methylethyl}-5-methyl[1,2,4]triazolo[1,5-a]pyrimidin-7-amine | 354.0 |

TABLE 2-continued

| Example No. | Structure | IUPAC Name | Observed Exact Mass [M + H]+ |
|---|---|---|---|
| 53 | 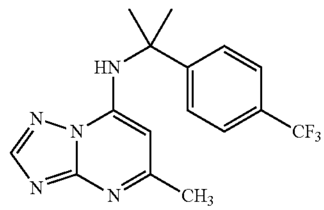 [SMILES: Cc1cc(NC(C)(C)c2ccc(C(F)(F)F)cc2)n2ncnc2n1] | 5-Methyl-N-{1-methyl-1-[4-(trifluoromethyl)phenyl]ethyl}[1,2,4]triazolo[1,5-a]pyrimidin-7-amine | 336.0 |
| 54 | 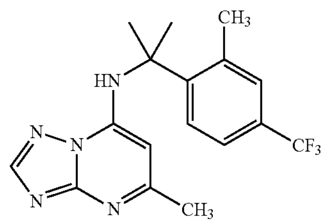 | 5-Methyl-N-{1-methyl-1-[2-methyl-4-(trifluoromethyl)phenyl]ethyl}[1,2,4]triazolo[1,5-a]pyrimidin-7-amine | 350.1 |
| 55 | 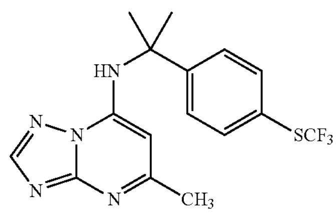 | 5-Methyl-N-(1-methyl-1-{4-[(trifluoromethyl)sulfanyl]phenyl}ethyl)[1,2,4]triazolo[1,5-a]pyrimidin-7-amine | 368.1 |

Example 56

5-Methyl-N-{1-[4-(trifluoromethyl)phenyl]cyclopropyl}[1,2,4]triazolo[1,5-a]pyrimidin-7-amine

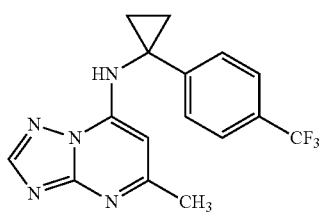 [SMILES: Cc1cc(NC2(c3ccc(C(F)(F)F)cc3)CC2)n2ncnc2n1]

Step 1: 5-Methyl-N-{-[4-(trifluoromethyl)phenyl]cyclopropyl}[1,2,4]triazolo[1,5-a]pyrimidin-7-amine

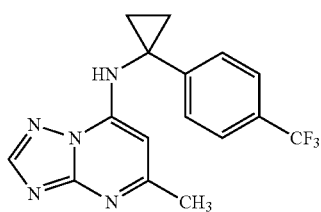 [SMILES: Cc1cc(NC2(c3ccc(C(F)(F)F)cc3)CC2)n2ncnc2n1]

To a solution of commercially available 7-chloro-5-methyl-[1,2,4]-triazolo[1,5-a]pyrimidine (25 mg, 0.148 mmol) and 1-[4-(trifluoromethyl)phenyl]cyclopropanamine hydrochloride (45.5 mg, 0.178 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool and was quenched with 1 mL of sat'd sodium bicarbonate soln. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness. The residue was purified by reverse phase HPLC (10-90% acetonitrile in water with 0.05% TFA) to afford the product as a white fluffy solid. LC-MS (+ESI) m/z=334. $^1$H NMR (500 MHz, CD$_3$OD) δ: 8.56 (s, 1H), 7.62 (d, J=8.6 Hz, 2H), 7.44 (d, J=8.6 Hz, 2H), 6.40 (s, 1H), 5.17 (q, J=6.8 Hz, 1H), 2.52 (s, 3H), 1.71-1.66 (m, 2H), 1.64-1.61 (m, 2H).

The following compounds in Table 3 were prepared using procedures similar to those described in Example 56 using appropriate starting materials.

TABLE 3

| Example No. | Structure | IUPAC Name | Observed Exact Mass [M + H]+ |
|---|---|---|---|
| 57 | 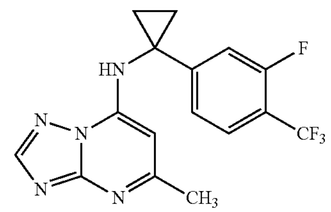 [SMILES: Cc1cc(NC2(c3ccc(C(F)(F)F)c(F)c3)CC2)n2ncnc2n1] | N-{1-[3-Fluoro-4-(trifluoromethyl)phenyl]cyclopropyl}-5-methyl[1,2,4]triazolo[1,5-a]pyrimidin-7-amine | 352.1 |
| 58 | 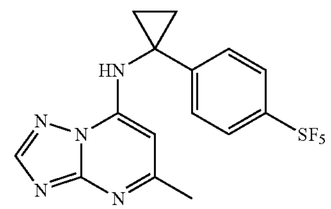 | 5-Methyl-N-{1-[4-(pentafluoro-λ$^6$-sulfanyl)phenyl]cyclopropyl}[1,2,4]triazolo[1,5-a]pyrimidin-7-amine | 391.9 |
| 59 | 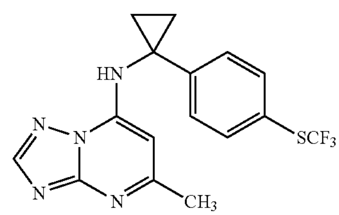 | 5-Methyl-N-(1-{4-[(trifluoromethyl)sulfanyl]phenyl}cyclopropyl)[1,2,4]triazolo[1,5-a]pyrimidin-7-amine | 366.2 |
| 60 | 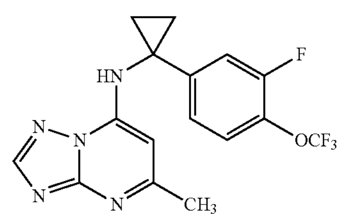 [SMILES: Cc1cc(NC2(c3ccc(OC(F)(F)F)c(F)c3)CC2)n2ncnc2n1] | N-{1-[3-Fluoro-4-(trifluoromethoxy)phenyl]cyclopropyl}5-methyl-[1,2,4]triazolo[1,5-a]pyrimidin-7-amine | 368.1 |
| 61 | 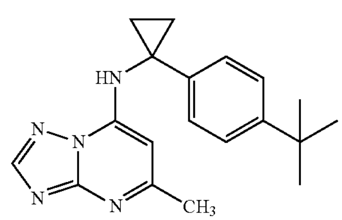 [SMILES: Cc1cc(NC2(c3ccc(C(C)(C)C)cc3)CC2)n2ncnc2n1] | N-{1-[4-(tert-Butyl)phenyl]cyclopropyl}5-methyl-[1,2,4]triazolo[1,5-a]pyrimidin-7-amine | 322.1 |
| 62 | 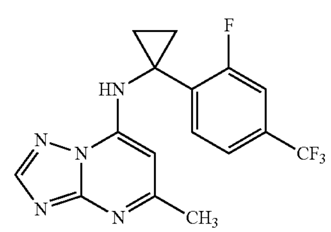 [SMILES: Cc1cc(NC2(c3ccc(C(F)(F)F)cc3F)CC2)n2ncnc2n1] | N-{1-[2-Fluoro-4-(trifluoromethyl)phenyl]cyclopropyl}5-methyl-[1,2,4]triazolo[1,5-a]pyrimidin-7-amine | 352.0 |
| 63 | 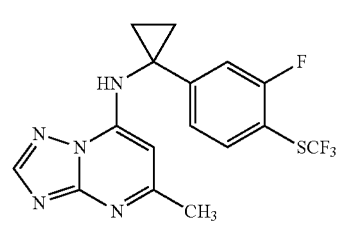 | N-(1-{3-Fluoro-4-[(trifluoromethyl)sulfanyl]phenyl}cyclopropyl)-5-methyl[1,2,4]triazolo[1,5-a]pyrimidin-7-amine | 384.0 |

TABLE 3-continued

| Example No. | Structure | IUPAC Name | Observed Exact Mass [M + H]+ |
|---|---|---|---|
| 64 | 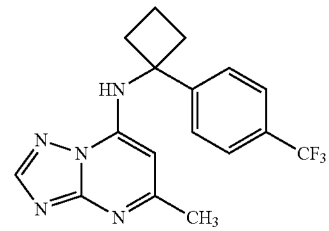 [SMILES: Cc1cc(NC2(c3ccc(C(F)(F)F)cc3)CCC2)n2ncnc2n1] | 5-Methyl-N-{1-[4-(trifluoromethyl)phenyl]cyclobutyl}[1,2,4]triazolo[1,5-a]pyrimidin-7-amine | 348.1 |
| 65 | 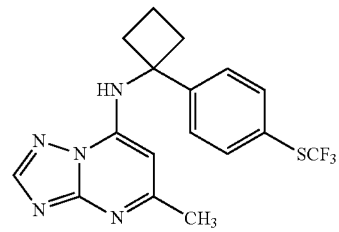 | 5-Methyl-N-(1-{4-[(trifluoromethyl)sulfanyl]phenyl}cyclobutyl)[1,2,4]triazolo[1,5-a]pyrimidin-7-amine | 380.0 |
| 66 | 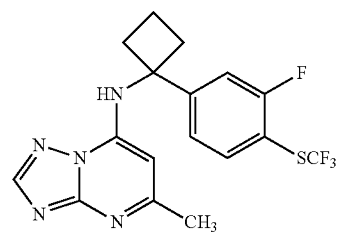 | N-(1-{3-Fluoro-4-[(trifluoromethyl)sulfanyl]phenyl}cyclobutyl)-5-methyl[1,2,4]triazolo[1,5-a]pyrimidin-7-amine | 398.1 |
| 67 | 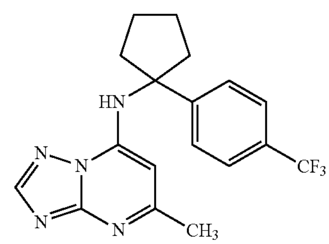 [SMILES: Cc1cc(NC2(c3ccc(C(F)(F)F)cc3)CCCC2)n2ncnc2n1] | 5-Methyl-N-{1-[4-(trifluoromethyl)phenyl]cyclopentyl}[1,2,4]triazolo[1,5-a]pyrimidin-7-amine | 362.1 |

Example 68

5-Ethyl-N-{1-[3-fluoro-4-(trifluoromethyl)phenyl]cyclopropyl}[1,2,4]triazolo[1,5-a]pyrimidin-7-amine

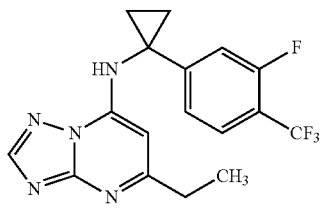 [SMILES: CCc1cc(NC2(c3ccc(C(F)(F)F)c(F)c3)CC2)n2ncnc2n1]

Step 1: 5-Ethyl-N-{1-[3-fluoro-4-(trifluoromethyl)phenyl]cyclopropyl}[1,2,4]triazolo[1,5-a]pyrimidin-7-amine To a solution of commercially available 7-chloro-5-ethyl-[1,2,4]-triazolo[1,5-a]pyrimidine (25 mg, 0.148 mmol) and 1-[3-fluoro-4-(trifluoromethyl)phenyl]cyclopropanamine hydrochloride (42 mg, 0.164 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool and was quenched with 1 mL of sat'd. aqueous sodium bicarbonate soln. The solution was diluted with 5 mL ethyl acetate. The organic layer was separated, the aqueous was re-extracted with 2.5 mL of ethyl acetate, and the organics then combined. The organics were washed with 1 mL water, dried over sodium sulfate, filtered and the filtrate concentrated to dryness. The residue was purified by reverse phase HPLC (10-90% acetonitrile in water with 0.05% TFA) to afford the product as a white fluffy solid. LC-MS (+ESI) m/z=366. $^1$H NMR (500 MHz, CD$_3$OD) δ: 8.60 (s, 1H), 7.64 (t, J=7.8 Hz, 2H), 7.27-7.22 (m, 2H), 6.38 (s, 1H), 2.80 (q, J=7.6 Hz, 2H), 1.74-1.64 (m, 4H), 1.27 (t, J=7.6 Hz, 3H).

The following compounds in Table 4 were prepared using procedures similar to those described in Example 68, however, using the appropriate starting materials and intermediates embodied in Table P1.

TABLE 4

| Example No. | Structure | IUPAC Name | Observed Exact Mass [M + H]+ |
|---|---|---|---|
| 69 | 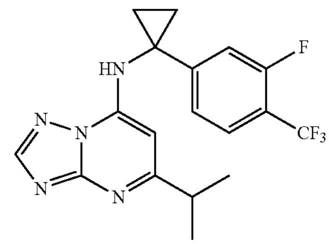 [SMILES: CC(C)c1cc(NC2(c3ccc(C(F)(F)F)c(F)c3)CC2)n2ncnc2n1] | 5-Propyl-N-{1-[3-fluoro-4-(trifluoromethyl)phenyl]cyclopropyl}[1,2,4]triazolo[1,5-a]pyrimidin-7-amine | 380.1 |
| 70 | 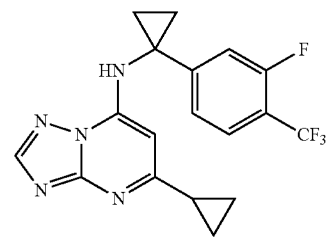 [SMILES: Fc1cc(C2(Nc3cc(C4CC4)nc4ncnn34)CC2)ccc1C(F)(F)F] | 5-Cyclopropyl-N-{1-[3-fluoro-4-(trifluoromethyl)phenyl]cyclopropyl}[1,2,4]triazolo[1,5-a]pyrimidin-7-amine | 378.1 |
| 71 | 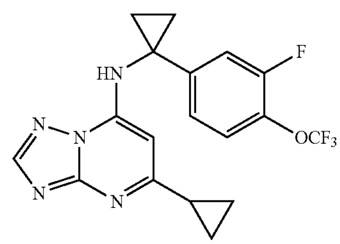 [SMILES: Fc1cc(C2(Nc3cc(C4CC4)nc4ncnn34)CC2)ccc1OC(F)(F)F] | 5-Cyclopropyl-N-{1-[3-fluoro-4-(trifluoromethoxy)phenyl]cyclopropyl}[1,2,4]triazolo[1,5-a]pyrimidin-7-amine | 394.0 |
| 72 | 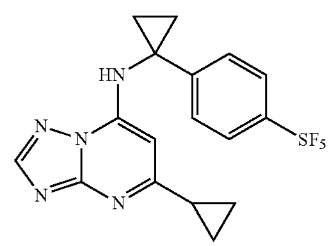 | 5-Cyclopropyl-N-{1-[4-(pentafluoro-$\lambda^6$-sulfanyl)phenyl]cyclopropyl}[1,2,4]triazolo[1,5-a]pyrimidin-7-amine | 418.1 |
| 73 | 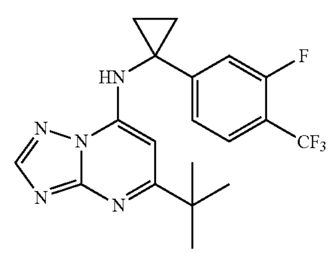 [SMILES: CC(C)(C)c1cc(NC2(c3ccc(C(F)(F)F)c(F)c3)CC2)n2ncnc2n1] | 5-tert-Butyl-N-{1-[3-fluoro-4-(trifluoromethoxy)phenyl]cyclopropyl}[1,2,4]triazolo[1,5-a]pyrimidin-7-amine | 394.2 |
| 74 | 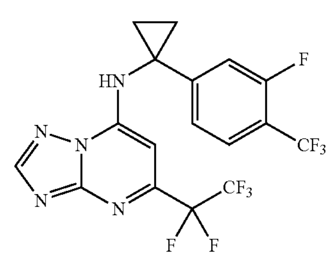 [SMILES: Fc1cc(C2(Nc3cc(C(F)(F)C(F)(F)F)nc4ncnn34)CC2)ccc1C(F)(F)F] | N-{1-[3-Fluoro-4-(trifluoromethyl)phenyl]cyclopropyl}-5-(pentafluoroethyl)[1,2,4]triazolo[1,5-a]pyrimidin-7-amine | 455.9 |

TABLE 4-continued

| Example No. | Structure | IUPAC Name | Observed Exact Mass [M + H]+ |
|---|---|---|---|
| 75 | 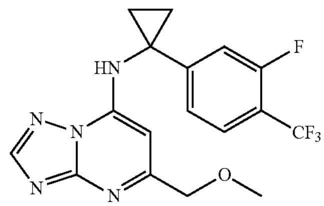 [SMILES: COCc1cc(NC2(c3ccc(C(F)(F)F)c(F)c3)CC2)n2ncnc2n1] | N-{1-[3-Fluoro-4-(trifluoromethyl)phenyl]cyclopropyl}-5-(methoxymethyl)[1,2,4]triazolo[1,5-a]pyrimidin-7-amine | 382.1 |
| 76 | 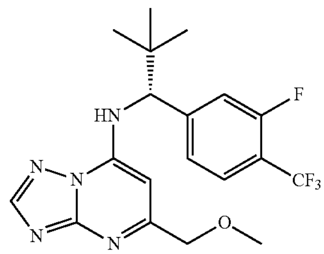 [SMILES: COCc1cc(N[C@@H](c2ccc(C(F)(F)F)c(F)c2)C(C)(C)C)n2ncnc2n1] | N-{(1R)-1-[3-Fluoro-4-(trifluoromethyl)phenyl]-2,2-dimethylpropyl}-5-(methoxymethyl)[1,2,4]triazolo[1,5-a]pyrimidin-7-amine | 412.2 |
| 77 | 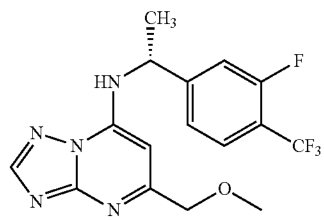 [SMILES: COCc1cc(N[C@H](C)c2ccc(C(F)(F)F)c(F)c2)n2ncnc2n1] | N-{(1R)-1-[3-Fluoro-4-(trifluoromethyl)phenyl]ethyl}-5-(methoxymethyl)[1,2,4]triazolo[1,5-a]pyrimidin-7-amine | 370.1 |

Example 78

[7-({1-[3-Fluoro-4-(trifluoromethyl)phenyl]cyclopropyl}amino)[1,2,4]triazolo[1,5-a]pyrimidin-5-yl]methanol

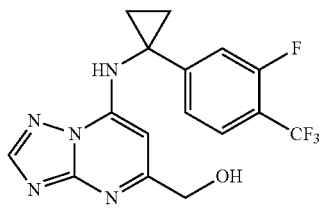 [SMILES: OCc1cc(NC2(c3ccc(C(F)(F)F)c(F)c3)CC2)n2ncnc2n1]

To a −78° C. solution of N-{1-[3-fluoro-4-(trifluoromethyl)phenyl]cyclopropyl}-5-(methoxymethyl) [1,2,4]triazolo[1,5-a]pyrimidin-7-amine (25 mg, 0.05 mmol) in 0.4 mL anhydrous DCM under nitrogen atmosphere was added via syringe a 1.0 M solution of BBr₃ in DCM (0.15 mL, 0.15 mmol) and the resulting solution stirred at −78° C. for 30 minutes. The mixture was then warmed to −15° C. by placing in an ice/salt water bath and then stirred overnight. The mixture was quenched with 1 mL of saturated aqueous sodium bicarbonate solution and the organic layer separated. The aqueous was washed with DCM (2 mL) and the organics were combined, dried over sodium sulfate, filtered, and concentrated under reduced pressure. The residue was purified by reverse phase HPLC (10-90% acetonitrile in water with 0.05% TFA) to afford the product as a solid. LC-MS (+ESI) m/z=368.0. ¹H NMR (500 MHz, CD₃OD) δ: 8.59 (s, 1H), 7.62 (t, J=7.8 Hz, 2H), 7.28-7.20 (m, 2H), 6.46 (s, 1H), 4.63 (s, 1H), 1.74-1.65 (m, 4H).

Example 79

[7-({(1R)-1-[3-Fluoro-4-(trifluoromethyl)phenyl]-2,2-dimethylpropyl}amino)[1,2,4]triazolo[1,5-a]pyrimidin-5-yl]methanol

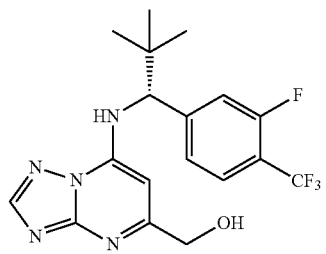

The following example was prepared using similar procedures as in Example 78 using N-{(1R)-1-[3-fluoro-4-(trifluoromethyl)phenyl]-2,2-dimethylpropyl}-5-(methoxymethyl) [1,2,4]triazolo[1,5-a]pyrimidin-7-amine (Example 76) as the appropriate starting material.

Example 80

[7-({(1R)-1-[3-Fluoro-4-(trifluoromethyl)phenyl]ethyl}amino)[1,2,4]triazolo[1,5-a]pyrimidin-5-yl]methanol

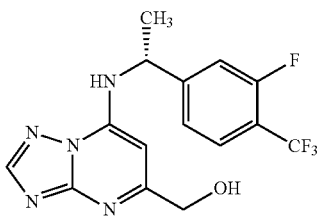 [SMILES: C[C@@H](Nc1cc(CO)nc2ncnn12)c1ccc(C(F)(F)F)c(F)c1]

The following example was prepared using similar procedures as in Example 78 using N-{(1R)-1-[3-fluoro-4-(trifluoromethyl)phenyl]ethyl}-5-(methoxymethyl)[1,2,4]triazolo[1,5-a]pyrimidin-7-amine (Example 77) as the appropriate starting material.

Example 81

5-(Fluoromethyl)-N-{1-[3-fluoro-4-(trifluoromethyl)phenyl]cyclopropyl}[1,2,4]triazolo[1,5-a]pyrimidin-7-amine

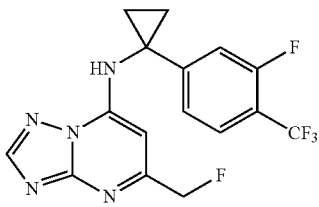 [SMILES: FCc1cc(NC2(c3ccc(C(F)(F)F)c(F)c3)CC2)n2ncnc2n1]

To a solution of [7-({1-[3-fluoro-4-(trifluoromethyl)phenyl]cyclopropyl}amino)[1,2,4]triazolo [1,5-a]pyrimidin-5-yl]methanol (10.5 mg, 0.029 mmol) in DCM (0.2 mL) was added DAST (two drops via syringe) under $N_2$ and the resulting mixture stirred for 2 h at room temperature. The reaction was quenched with a saturated aqueous solution of $NaHCO_3$ (1 mL) and the mixture diluted with DCM (2 mL). The organics were separated and the solvent removed under reduced pressure. The residue was purified by reverse phase HPLC (40-90% $CH_3CN/H_2O$ with 0.05% TFA). to afford the desired product as a powder. LC-MS (+ESI) m/z=370.1.

Example 82

N-{1-[3-Fluoro-4-(trifluoromethyl)phenyl]cyclopropyl}-5-(trifluoromethyl)-[1,2,4]triazolo[1,5-a]pyrimidin-7-amine

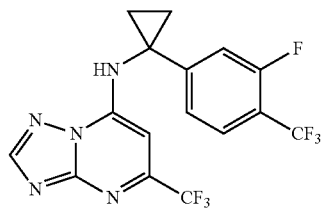

To a solution of 7-chloro-5-(trifluoromethyl)-[1,2,4]-triazolo[1,5-a]pyrimidine (25 mg, 0.112 mmol) and 1-[3-fluoro-4-(trifluoromethyl)phenyl]cyclopropanamine hydrochloride (34.5 mg, 0.135 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool and was quenched with 1 mL of sat'd. aqueous sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness. The residue was purified by reverse phase HPLC (10-90% acetonitrile in water with 0.05% TFA) to afford the product as a solid. LC-MS (+ESI) m/z=406.1. $^1$H NMR (500 MHz, $CD_3OD$) δ: 8.60 (s, 1H), 7.64 (t, J=8.0 Hz, 2H), 7.26 (d, J=10.1 Hz, 2H), 6.56 (s, 1H), 1.76-1.65 (m, 4H).

Example 83

N-{1-[4-(Trifluoromethyl)phenyl]ethyl}[1,2,4]triazolo[1,5-a]pyrimidin-7-amine

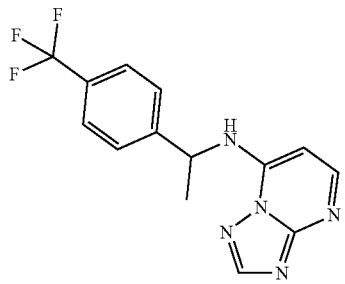 [SMILES: CC(Nc1ccnc2ncnn12)c1ccc(C(F)(F)F)cc1]

[1,2,4]Triazolo[1,5-a]pyrimidin-7-amine (25 mg, 0.185 mmol) and NaH (8.14 mg, 0.204 mmol) were stirred in DMF (1850 μl) under nitrogen at room temperature followed by addition of 1-(1-bromoethyl)-4-(trifluoromethyl)benzene (46.8 mg, 0.185 mmol). The resulting gray solution was then stirred at room temperature for 1 h. The solution was filtered through a 0.45 PTFE Gilman syringe filter and purified by reverse phase HPLC (10-90% MeCN in $H_2O$, 0.1% TFA), Peaks containing the desired mass were separately combined and concentrate to dryness under reduced pressure. The residues were taken up in 1 mL DCM and neutralized with saturated solution of aqueous sodium bicarbonate (2 mL) and then extracted into DCM (3×3 mL). The organics were combined, dried over magnesium sulfate, filtered, and the filtrate concentrated to dryness under reduced pressure to provide the title compound: LC-MS (+ESI) m/z=308.1. $^1$H NMR (500 MHz, CD$_3$OD) δ: 8.40 (s, 1H), 8.37 (d, J=6.1 Hz, 1H), 7.62 (d, J=8.0 Hz, 2H), 7.44 (d, J=8.0 Hz, 2H), 6.60-6.54 (m, 1H), 5.82 (d, J=6.1 Hz, 1H), 4.85 (q, J=6.8 Hz, 1H), 1.76 (d, J=6.8 Hz, 3H).

Example 84

N-{1-[4-(Trifluoromethoxy)phenyl]ethyl}[1,2,4]triazolo[1,5-a]pyrimidin-7-amine

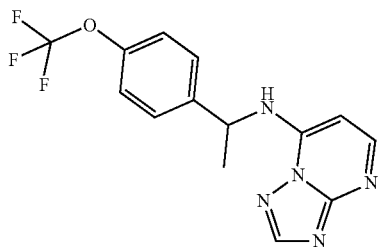 [SMILES: CC(Nc1ccnc2ncnn12)c1ccc(OC(F)(F)F)cc1]

The following example was prepared using similar procedures as in Example 83 using [1,2,4]triazolo[1,5-a]pyrimidin-7-amine and 1-(1-bromoethyl)-4-(trifluoromethoxy)benzene as starting materials. LC-MS (+ESI) m/z=324.1. $^1$H NMR (500 MHz, CD$_3$OD) δ: 8.40 (s, 1H), 8.28 (d, J=5.8 Hz, 1H), 7.58 (d, J=8.0 Hz, 2H), 7.25 (d, J=8.0 Hz, 2H), 6.22 (d, J=5.8 Hz, 1H), 5.02 (q, J=6.8 Hz, 1H), 1.74 (d, J=6.8 Hz, 3H).

Example 85

5,6-Dimethyl-N-{(1R)-1-[4-(trifluoromethyl)phenyl]ethyl}[1,2,4]triazolo[1,5-a]pyrimidin-7-amine

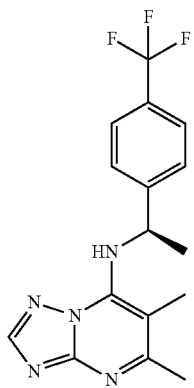 [SMILES: Cc1nc2ncnn2c(N[C@H](C)c2ccc(C(F)(F)F)cc2)c1C]

To a solution of commercially available 7-chloro-5,6-dimethyl-[1,2,4]triazolo[1,5-a]pyrimidine (27 mg, 0.148 mmol) and (R)-1-(4-(trifluoromethyl)phenyl)ethanamine hydrochloride (40.0 mg, 0.177 mmol) in anhydrous NMP (0.5 mL) in a 2-5 mL microwave vial was added dropwise via syringe DIEA (0.2 mL, 1.145 mmol) and the resulting solution heated via oil bath to 120° C. overnight. The reaction was allowed to cool and was quenched with 1 mL of sat'd. aqueous sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness under reduced pressure. The residue was purified by reverse phase HPLC (10-90% acetonitrile in water with 0.05% TFA) to afford the product as a solid. LC-MS (+ESI) m/z=336.1. $^1$H NMR (500 MHz, CD$_3$OD) δ: 8.44 (s, 1H), 7.66-7.62 (m, 4H), 6.58 (q, J=6.8 Hz, 1H), 2.58 (s, 3H), 2.31 (s, 3H), 1.74 (d, J=6.8 Hz, 3H).

Example 86

5,6-Dimethyl-N-{(1S)-1-[4-(trifluoromethyl)phenyl]ethyl}[1,2,4]triazolo[1,5-a]pyrimidin-7-amine

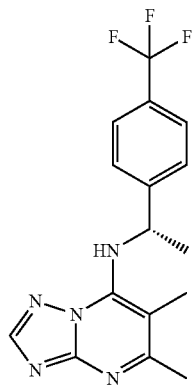 [SMILES: Cc1nc2ncnn2c(N[C@@H](C)c2ccc(C(F)(F)F)cc2)c1C]

The following example was prepared using similar procedures as in Example 85 using 7-chloro-5,6-dimethyl-[1,2,4]triazolo[1,5-a]pyrimidine and (S)-1-(4-(trifluoromethyl)phenyl)ethanamine hydrochloride as the appropriate starting materials. LC-MS (+ESI) m/z=336.1. $^1$H NMR (500 MHz, CD$_3$OD) δ: 8.44 (s, 1H), 7.66-7.60 (m, 4H), 6.57 (q, J=6.8 Hz, 1H), 2.58 (s, 3H), 2.32 (s, 3H), 1.74 (d, J=6.8 Hz, 3H).

Example 87

N-{1-[3-Fluoro-4-(trifluoromethyl)phenyl]cyclopropyl}-5,6-dimethyl[1,2,4]triazolo[1,5-a]pyrimidin-7-amine

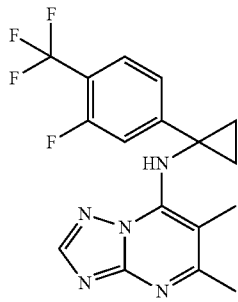 [SMILES: Cc1nc2ncnn2c(NC2(c3ccc(C(F)(F)F)c(F)c3)CC2)c1C]

The following example was prepared using similar procedures as in Example 85 using 7-chloro-5,6-dimethyl-[1, 2,4]triazolo[1,5-a]pyrimidine and 1-(3-fluoro-4-(trifluoromethyl)phenyl) cyclopropanamine hydrochloride as the appropriate starting materials. LC-MS (+ESI) m/z=366.1. ¹H NMR (500 MHz, CD₃OD) δ: 8.42 (s, 1H), 7.64 (t, J=8.0 Hz, 1H), 7.32-7.24 (m, 2H), 2.58 (s, 3H), 2.26 (s, 3H), 1.78-1.66 (m, 4H).

Example 88

2-[(5-Methyl[1,2,4]triazolo[1,5-a]pyrimidin-7-yl)amino]-2-[4-(trifluoromethyl)phenyl]ethanol

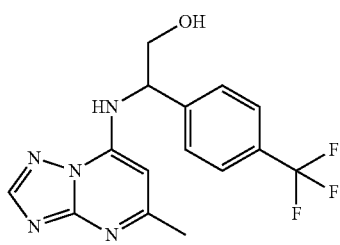 [SMILES: Cc1cc(NC(CO)c2ccc(C(F)(F)F)cc2)n2ncnc2n1]

To a solution of 7-chloro-5-(trifluoromethyl)-[1,2,4]-triazolo[1,5-a]pyrimidine (50 mg, 0.297 mmol) and 2-amino-2-[4-(trifluoromethyl)phenyl]ethanol hydrochloride (86 mg, 0.356 mmol) in anhydrous NMP (2.0 mL) in a 2-5 mL microwave vial was added dropwise via syringe DIEA (0.4 mL, 2.29 mmol) and the resulting solution heated via oil bath to 120° C. overnight. The reaction was allowed to cool and was quenched with 1 mL of sat'd. aqueous sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness under reduced pressure. The residue was purified by reverse phase HPLC (10-90% acetonitrile in water with 0.05% TFA) to afford the product as a solid. LC-MS (+ESI) m/z=338.1. ¹H NMR (500 MHz, CD₃OD) δ: 8.55 (s, 1H), 7.72-7.67 (m, 4H), 6.42 (s, 1H), 5.15 (t, J=5.8 Hz, 1H), 4.02 (dd, J=2.7, 5.8 Hz, 2H), 2.51 (s, 3H).

Example 89

(1S,2R)-1-[(5-Methyl[1,2,4]triazolo[1,5-a]pyrimidin-7-yl)amino]-1-[4-(trifluoromethyl)phenyl]propan-2-ol

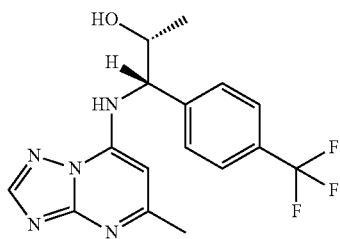 [SMILES: Cc1cc(N[C@@H](c2ccc(C(F)(F)F)cc2)[C@@H](C)O)n2ncnc2n1]

The following example was prepared using similar procedures as in Example 85 using 7-chloro-5,6-dimethyl-[1,2,4]triazolo[1,5-a]pyrimidine and (1S,2R)-1-amino-1-[4-(trifluoromethyl) phenyl]propan-2-ol hydrochloride as the appropriate starting materials. LC-MS (+ESI) m/z=352.1. ¹H NMR (500 MHz, CD₃OD) δ: 8.58 (s, 1H), 7.72-7.66 (m, 4H), 6.40 (s, 1H), 4.32-4.38 (m, 1H), 2.48 (s, 3H), 1.22 (d, J=6.8 Hz, 3H).

Example 90

(1S,2S)-1-[(5-Methyl[1,2,4]triazolo[1,5-a]pyrimidin-7-yl)amino]-1-[4-(trifluoromethyl)phenyl]propan-2-ol

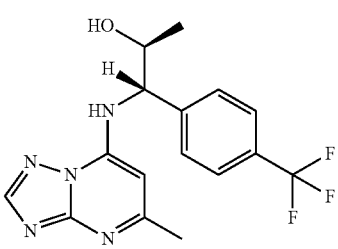 [SMILES: Cc1cc(N[C@@H](c2ccc(C(F)(F)F)cc2)[C@H](C)O)n2ncnc2n1]

The following example was prepared using similar procedures as in Example 85 using 7-chloro-5,6-dimethyl-[1,2,4]triazolo[1,5-a]pyrimidine and (1S,2S)-1-amino-1-[4-(trifluoromethyl) phenyl]propan-2-ol hydrochloride as the appropriate starting materials. LC-MS (+ESI) m/z=352.1. ¹H NMR (500 MHz, CD₃OD) δ: 8.58 (s, 1H), 7.72-7.66 (m, 4H), 6.40 (s, 1H), 4.32-4.38 (m, 1H), 2.48 (s, 3H), 1.22 (d, J=6.8 Hz, 3H).

Examples 91 and 92

(1R)-1-[3-Fluoro-4-(trifluoromethoxy)phenyl]-2-methyl-1-[(5-methyl[1,2,4]triazolo[1,5-a]pyrimidin-7-yl)amino]propan-2-ol and (1S)-1-[3-fluoro-4-(trifluoromethoxy)phenyl]-2-methyl-1-[(5-methyl[1,2,4]triazolo[1,5-a]pyrimidin-7-yl)amino]propan-2-ol

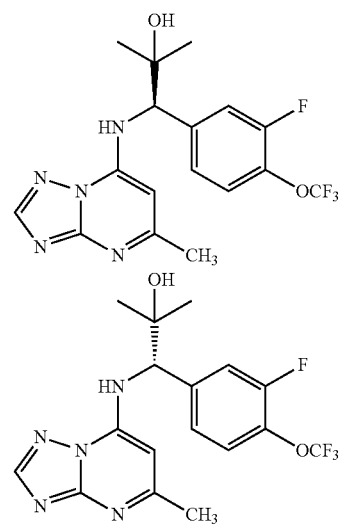

Step 1: (1R)-1-[3-Fluoro-4-(trifluoromethoxy)phenyl]-2-methyl-1-[(5-methyl[1,2,4]triazolo [1,5-a]pyrimidin-7-yl)amino]propan-2-ol and (1S)-1-[3-fluoro-4-(trifluoromethoxy)phenyl]-2-methyl-1-[(5-methyl[1,2,4]triazolo[1,5-a]pyrimidin-7-yl)amino]propan-2-ol

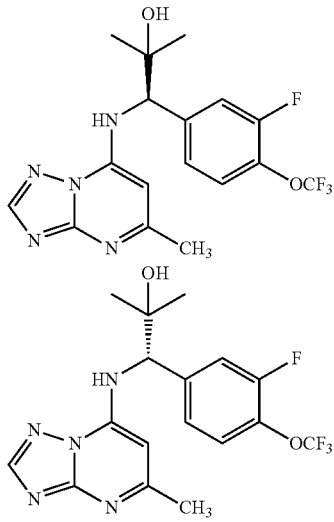

To a solution of commercially available 7-chloro-5-methyl-[1,2,4]-triazolo[1,5-a]pyrimidine (7.2 g, 42.7 mmol) in anhydrous NMP (136 mL) in a 500 mL round bottom flask was added (S)-1-amino-1-(3-fluoro-4-(trifluoromethyl)phenyl)-2-methylpropan-2-ol (12 g, 44.8 mmol) and the resulting solution heated via oil bath to 80° C. for 15 minutes. LC-MS exhibits about 30% complete reaction. To the solution was then added DIEA (7.5 mL, 42.7 mmol) and the resulting mixture continued heating at 80° C. for 1 h. The reaction was cooled to room temperature and was quenched with 70 mL of sat'd. aqueous sodium bicarbonate soln. The solution was diluted with 70 mL ethyl acetate. The organic layer was separated, the aqueous was re-extracted with 70 mL of ethyl acetate and the organics then combined. The organics were washed with 50 mL water, dried over sodium sulfate, filtered and the filtrate concentrated to dryness.

The residue was taken up into 10 mL of ethyl acetate and placed onto the Biotage using a 80 g silica gel GOLD column. Eluant as follows: 100% ethyl acetate was first used (~3 column volumes, CV), then 5% methanol in ethyl acetate (2 CV), followed by 10% methanol in ethyl acetate (2 CV), and finally 15% methanol in ethyl acetate (until end of run ~5 CV). The tubes containing the product were combined and the solvent removed under reduced pressure to afford the product as a solid. Chiral HPLC analysis indicated a 3:1 mixture of (S)- and (R)-isomers. The material was separated to afford the faster running (R)-isomer and second eluting desired (S)-isomer Chiral HPLC separation (OZ column using 20% MeOH/0.2% NH₄OH/CO₂ as eluant running at 2.1 mL/min at 100 Bar pressure at 40° C.) provided Example 91 (R)-isomer: LC-MS (+ESI) m/z=400.0. $^1$H NMR (500 MHz, CD$_3$OD) δ: 8.36 (s, 1H), 7.62 (dd, J=1.6 Hz, 10.4 Hz, 2H), 7.44-7.36 (m, 2H), 6.19 (s, 1H), 4.74 (s, 1H), 2.44 (s, 3H), 1.43 (s, 3H), 1.11 (s, 3H). The second eluting peak, Example 92 (S)-isomer, was isolated as a solid: LC-MS (+ESI) m/z=400.0. $^1$H NMR (500 MHz, CD$_3$OD) δ: 8.35 (s, 1H), 7.62 (dd, J=1.6 Hz, 10.4 Hz, 2H), 7.44-7.34 (m, 2H), 6.19 (s, 1H), 4.74 (s, 1H), 2.43 (s, 3H), 1.43 (s, 3H), 1.11 (s, 3H).

Example 93

(1S)-1-[2-Fluoro-4-(trifluoromethoxy)phenyl]-2-methyl-[(5-methyl-[1,2,4]triazolo[1,5-a]pyrimidin-7-yl)amino]propan-2-ol

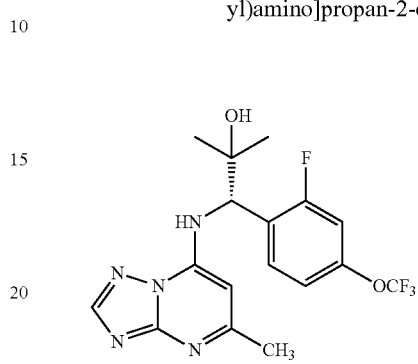

Step 1: (1S)-1-[(2-Fluoro-4-(trifluoromethoxy)phenyl]-2-methyl-[(5-methyl-[1,2,4]triazolo [1,5-a]pyrimidin-7-yl)amino]propan-ol

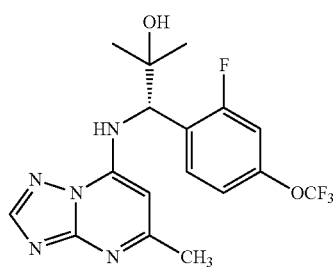 [SMILES: Cc1cc(N[C@@H](c2ccc(OC(F)(F)F)cc2F)C(C)(C)O)n2ncnc2n1]

To a solution of commercially available 7-chloro-5-methyl-[1,2,4]-triazolo[1,5-a]pyrimidine (5.2 g, 30.8 mmol) in anhydrous NMP (99 mL) in a 500 mL round bottom flask was added (S)-1-amino-1-(2-fluoro-4-(trifluoromethyl)phenyl)-2-methylpropan-2-ol (8.5 g, 31.8 mmol) and the resulting solution heated via oil bath to 80° C. for 15 minutes. LC-MS indicated about 15% conversion. To the solution was then added DIEA (5.4 mL, 30.8 mmol) and the resulting mixture continued heating at 80° C. for 1 h The reaction was cooled to room temperature and was quenched with 70 mL of sat'd. aqueous sodium bicarbonate soln. The solution was diluted with 70 mL ethyl acetate. The organic layer was separated, the aqueous was re-extracted with 70 mL of ethyl acetate and the organics then combined. The organics were washed with 50 mL water, dried over sodium sulfate, filtered and the filtrate concentrated to dryness. The residue was taken up into 10 mL of ethyl acetate and placed onto the Biotage using a 80 g silica gel GOLD column. Eluant as follows: 100% ethyl acetate was first used (~3 column volumes, CV), then 5% methanol in ethyl acetate (2 CV), followed by 10% methanol in ethyl acetate (2 CV), and finally 15% methanol in ethyl acetate (until end of run ~5 CV). The tubes containing the product were combined and the solvent removed under reduced pressure to afford the product as a solid. LC-MS (+ESI) m/z=400. $^1$H NMR (500 MHz, CD$_3$OD) δ: 8.38 (s, 1H), 7.64 (dd, J=8.6 Hz, 10.2 Hz, 2H), 7.15 (dd, J=8.6, 10.6 Hz, 2H), 6.10 (s, 1H), 5.02 (s, 1H), 2.45 (s, 3H), 1.46 (s, 3H), 1.15 (s, 3H).

The following compounds in Table 5 were prepared using procedures similar to those described in Example 89 and 90 using appropriate starting materials.

TABLE 5

| Example No. | Structure | IUPAC Name | Observed Exact Mass [M + H]$^+$ |
| --- | --- | --- | --- |
| 94 | 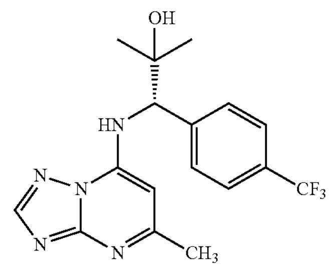 [SMILES: Cc1cc(N[C@@H](c2ccc(C(F)(F)F)cc2)C(C)(C)O)n2ncnc2n1] | (1S)-2-Methyl-1-[(5-methyl [1,2,4]triazolo[1,5-a]pyrimidin-7-yl)amino]-1-[4-(trifluoromethyl) phenyl]propan-2-ol | 366.1 |
| 95 | 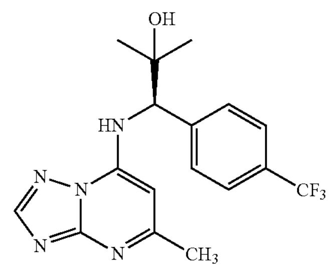 [SMILES: Cc1cc(N[C@H](c2ccc(C(F)(F)F)cc2)C(C)(C)O)n2ncnc2n1] | (1R)-2-Methyl-1-[(5-methyl [1,2,4]triazolo[1,5-a]pyrimidin-7-yl)amino]-1-[4-(trifluoromethyl) phenyl]propan-2-ol | 366.1 |
| 96 | 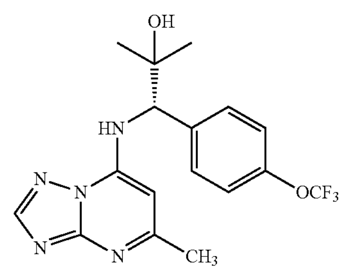 | (1S)-2-Methyl-1-[(5-methyl [1,2,4]triazolo[1,5-a]pyrimidin-7-yl)amino]-1-[4-(trifluoromethoxy) phenyl]propan-2-ol | 382.0 |
| 97 | 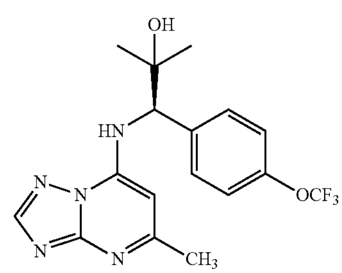 [SMILES: Cc1cc(N[C@H](c2ccc(OC(F)(F)F)cc2)C(C)(C)O)n2ncnc2n1] | (1R)-2-Methyl-1-[(5-methyl [1,2,4]triazolo[1,5-a]pyrimidin-7-yl)amino]-1-[4-(trifluoromethoxy) phenyl]propan-2-ol | 382.0 |
| 98 | 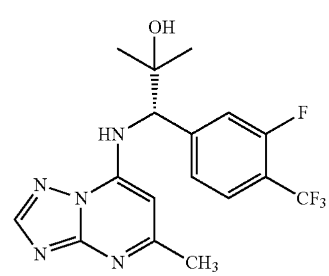 [SMILES: Cc1cc(N[C@@H](c2ccc(C(F)(F)F)c(F)c2)C(C)(C)O)n2ncnc2n1] | (1S)-1-[3-Fluoro-4-(trifluoromethyl)phenyl]-2-methyl-1-[(5-methyl [1,2,4]triazolo[1,5-a]pyrimidin-7-yl)amino]propan-2-ol | 384.1 |

TABLE 5-continued

| Example No. | Structure | IUPAC Name | Observed Exact Mass [M + H]+ |
|---|---|---|---|
| 99 | 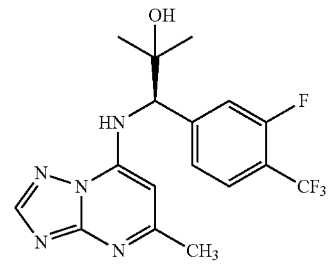 [SMILES: Cc1cc(N[C@H](c2ccc(C(F)(F)F)c(F)c2)C(C)(C)O)n2ncnc2n1] | (1R)-1-[3-Fluoro-4-(trifluoromethyl)phenyl]-2-methyl-1-[(5-methyl[1,2,4]triazolo[1,5-a]pyrimidin-7-yl)amino]propan-2-ol | 384.1 |
| 100 | 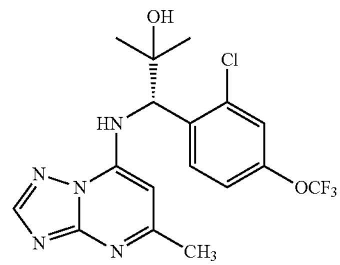 | (1S)-1-[2-Chloro-4-(trifluoromethoxy)phenyl]-2-methyl-1-[(5-methyl[1,2,4]triazolo[1,5-a]pyrimidin-7-yl)amino]propan-2-ol | |
| 101 | 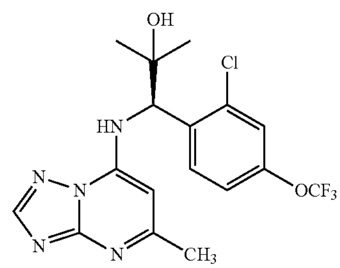 [SMILES: Cc1cc(N[C@H](c2ccc(OC(F)(F)F)cc2Cl)C(C)(C)O)n2ncnc2n1] | (1R)-1-[2-Chloro-4-(trifluoromethoxy)phenyl]-2-methyl-1-[(5-methyl[1,2,4]triazolo[1,5-a]pyrimidin-7-yl)amino]propan-2-ol | |
| 102 | 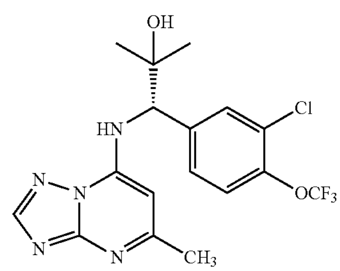 | (1S)-1-[3-Chloro-4-(trifluoromethoxy)phenyl]-2-methyl-1-[(5-methyl[1,2,4]triazolo[1,5-a]pyrimidin-7-yl)amino]propan-2-ol | |
| 103 | 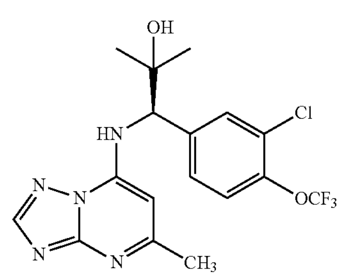 [SMILES: Cc1cc(N[C@H](c2ccc(OC(F)(F)F)c(Cl)c2)C(C)(C)O)n2ncnc2n1] | (1R)-1-[3-Chloro-4-(trifluoromethoxy)phenyl]-2-methyl-1-[(5-methyl[1,2,4]triazolo[1,5-a]pyrimidin-7-yl)amino]propan-2-ol | |

Examples 104 and 105

(1S or R)-1-[2-Chloro-4-(trifluoromethyl)phenyl]-2-methyl-1-[(5-methyl[1,2,4]triazolo[1,5-a]pyrimidin-7-yl)amino]propan-2-ol and (1R or S)-1-[2-Chloro-4-(trifluoromethyl)phenyl]-2-methyl-1-[(5-methyl[1,2,4]triazolo[1,5-a]pyrimidin-7-yl)amino]propan-2-ol

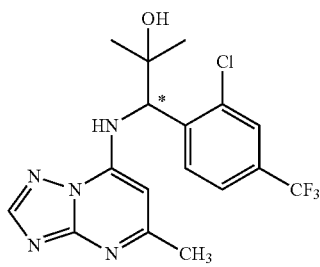

To a solution of methyl 2-(2-chloro-4-(trifluoromethyl)phenyl)-2-((5-methyl-[1,2,4]triazolo[1,5-a]pyrimidin-7-yl)amino)acetate (0.100 g, 0.250 mmol) in THF (2 mL) was added methylmagnesium bromide (1.0 M in THF, 2.5 mL, 2.5 mmol) at 0° C. under nitrogen atmosphere. The reaction mixture was stirred at 25° C. for 16 h. Then the resulting mixture was quenched with sat'd. aqueous NH$_4$Cl (10 mL) and extracted with ethyl acetate (3×35 mL). The combined organic layers was washed with water (3×10 mL), brine (3×10 mL), dried over anhydrous sodium sulfate and filtered. The filtrate was concentrated under reduced pressure to afford the title crude compound. The title crude compound was purified by Prep-HPLC with the following conditions: Instrument, GILSON (GX-281); Column: X Bridge RP$^{18}$, 19×150 mm, 5 um; Mobile Phase A: Water/0.05% NH$_4$HCO$_3$, Mobile Phase B: ACN; Flow rate: 20 mL/min; Gradient: 40% B to 45% B in 10 min; 254 nm. The fractions containing desired product were combined and concentrated to afford the title racemic compound. The title racemic compound was separated by Chiral-Prep-HPLC with the following conditions: Column: Phenomenex Lux 5 u Cellulose-4, AXIA Packed 250×21.2 mm, 5 um; Mobile Phase A: Hex-HPLC, Mobile Phase B: EtOH-HPLC; Flow rate: 20 mL/min; Gradient: isocratic 20% B in 13 min; 254/220 nm. The faster-eluting enantiomer of the title compound (Example 104) was obtained at 8.00 min as a solid. MS (+ESI) m/z=400.0, 402.1. $^1$H NMR (300 MHz, DMSO-d$_6$) δ: 8.48 (s, 1H), 7.98 (s, 1H), 7.88-7.69 (m, 3H), 5.95 (s, 1H), 5.67 (s, 1H), 5.15-5.02 (m, 1H), 2.38 (s, 3H), 1.43 (s, 3H), 1.03 (s, 3H); The slower-eluting enantiomer of the title compound (Example 105) was obtained at 11.00 min as a solid. MS (+ESI) m/z=400.1; 402.1. $^1$H NMR (300 MHz, DMSO-d$_6$) δ: 8.48 (s, 1H), 7.98 (s, 1H), 7.88-7.69 (m, 3H), 5.95 (s, 1H), 5.67 (s, 1H), 5.15-5.02 (m, 1H), 2.38 (s, 3H), 1.43 (s, 3H), 1.03 (s, 3H).

The following compounds in Table 6 were prepared using procedures similar to those described in Examples 104 and 105 using appropriate starting materials. Racemic products were separated using chiral columns specified in the table. For those pairs of enantiomers, the faster eluting isomer is always listed first in this table.

Coupling conditions: A. DIEA, NMP; B. DIEA, IPA

TABLE 6

| Example # | Structure | IUPAC Name | Mass [M + H]$^+$ | Coupling condition | Column |
|---|---|---|---|---|---|
| 106 | 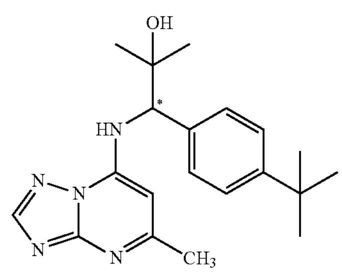 | (1S or R)-1-(4-tert-Butylphenyl)-2-methyl-1-{[5-(trifluoromethyl)[1,2,4]triazolo[1,5-a]pyrimidin-7-yl]amino}propan-2-ol | 354.3 | A | AXIA packed 250 × 21.2 mm 5 μM |
| 107 | 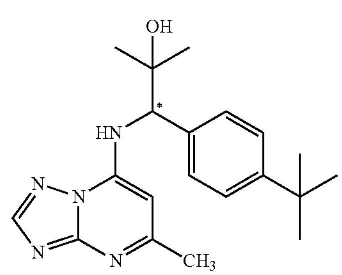 | (1R or S)-1-(4-tert-Butylphenyl)-2-methyl-1-{[5-(trifluoromethyl)[1,2,4]triazolo[1,5-a]pyrimidin-7-yl]amino}propan-2-ol | 354.4 | A | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 108 | 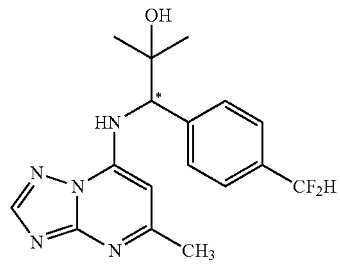 [SMILES: Cc1cc(NC(c2ccc(C(F)F)cc2)C(C)(C)O)n2ncnc2n1] | (1S or R)-1-[4-(Difluoromethyl)phenyl]-2-methyl-1-[(5-methyl[1,2,4]triazolo[1,5-a]pyrimidin-7-yl)amino]propan-2-ol | 348.2 | A | Chiral pak IA 2 × 25 cm, 5 μM |
| 109 | 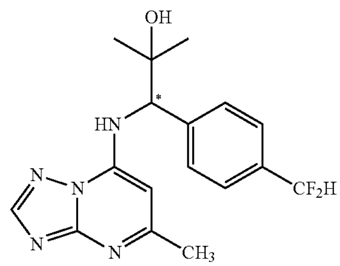 [SMILES: Cc1cc(NC(c2ccc(C(F)F)cc2)C(C)(C)O)n2ncnc2n1] | (1R or S)-1-[4-(Difluoromethyl)phenyl]-2-methyl-1-[(5-methyl[1,2,4]triazolo[1,5-a]pyrimidin-7-yl)amino]propan-2-ol | 348.2 | A | Chiral pak IA 2 × 25 cm, 5 μM |
| 110 | 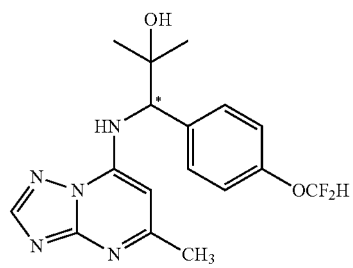 | (1S or R)-1-[4-(Difluoromethoxy)phenyl]-2-methyl-1-[(5-methyl[1,2,4]triazolo[1,5-a]pyrimidin-7-yl)amino]propan-2-ol | 364.2 | B | AXIA packed 250 × 21.2 mm 5 μM |
| 111 | 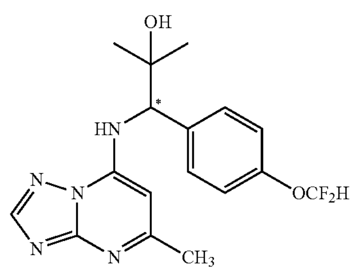 | (1R or S)-1-[4-(Difluoromethoxy)phenyl]-2-methyl-1-[(5-methyl[1,2,4]triazolo[1,5-a]pyrimidin-7-yl)amino]propan-2-ol | 364.2 | B | AXIA packed 250 × 21.2 mm 5 μM |
| 112 | 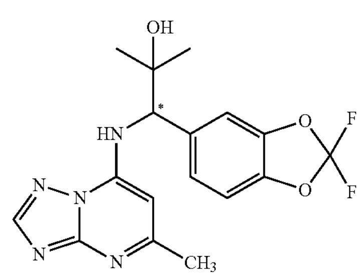 [SMILES: Cc1cc(NC(c2ccc3c(c2)OC(F)(F)O3)C(C)(C)O)n2ncnc2n1] | (1S or R)-1-(2,2-Difluoro-1,3-benzodioxol-5-yl)-2-methyl-1-[(5-methyl[1,2,4]triazolo[1,5-a]pyrimidin-7-yl)amino]propan-2-ol | 378.2 | A | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 113 | 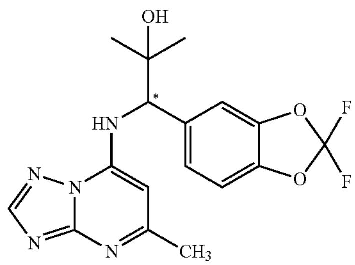 [SMILES: Cc1cc(NC(c2ccc3c(c2)OC(F)(F)O3)C(C)(C)O)n2ncnc2n1] | (1R or S)-1-(2,2-Difluoro-1,3-benzodioxol-5-yl)-2-methyl-1-[(5-methyl[1,2,4]triazolo[1,5-a]pyrimidin-7-yl)amino]propan-2-ol | 378.2 | A | AXIA packed 250 × 21.2 mm 5 μM |
| 114 | 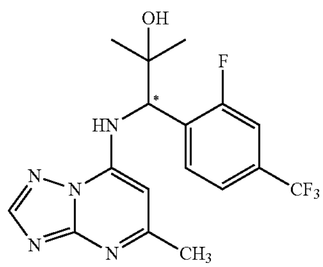 | (1S or R)-1-[2-Fluoro-4-(trifluoromethyl)phenyl]-2-methyl-1-[(5-methyl[1,2,4]triazolo[1,5-a]pyrimidin-7-yl)amino]propan-2-ol | 384.2 | A | AXIA packed 250 × 21.2 mm 5 μM |
| 115 | 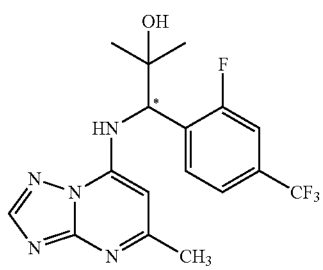 | (1R or S)-1-[2-Fluoro-4-(trifluoromethyl)phenyl]-2-methyl-1-[(5-methyl[1,2,4]triazolo[1,5-a]pyrimidin-7-yl)amino]propan-2-ol | 384.1 | A | AXIA packed 250 × 21.2 mm 5 μM |
| 116 | 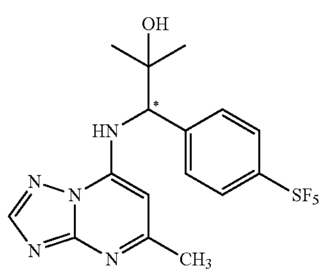 | (1S or R)-2-Methyl-1-[(5-methyl[1,2,4]triazolo[1,5-a]pyrimidin-7-yl)amino]-1-[4-(pentafluoro-λ$^6$-sulfanyl)phenyl]propan-2-ol | 424.0 | A | AXIA packed 250 × 21.2 mm 5 μM |
| 117 | 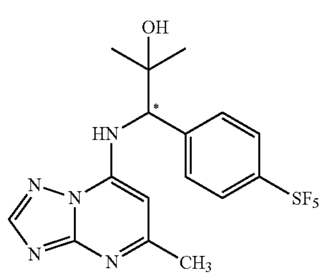 | (1R or S)-2-Methyl-1-[(5-methyl[1,2,4]triazolo[1,5-a]pyrimidin-7-yl)amino]-1-[4-(pentafluoro-λ$^6$-sulfanyl)phenyl]propan-2-ol | 424.0 | A | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 118 | 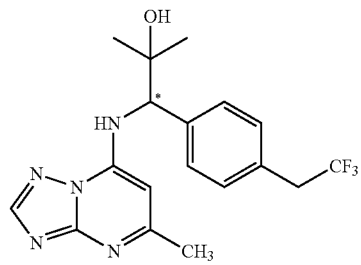 [SMILES: Cc1cc(NC(c2ccc(CC(F)(F)F)cc2)C(C)(C)O)n2ncnc2n1] | (1S or R)-2-Methyl-1-[(5-methyl [1,2,4]triazolo [1,5-a]pyrimidin-7-yl)amino]-1-[4-(2,2,2-trifluoroethyl) phenyl]propan-2-ol | 380.0 | B | AXIA packed 250 × 21.2 mm 5 µM |
| 119 | 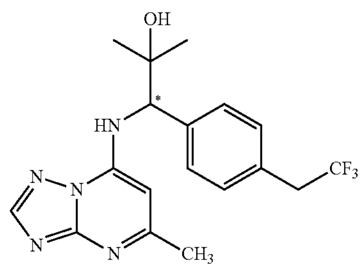 [SMILES: Cc1cc(NC(c2ccc(CC(F)(F)F)cc2)C(C)(C)O)n2ncnc2n1] | (1R or S)-2-Methyl-1-[(5-methyl [1,2,4]triazolo [1,5-a]pyrimidin-7-yl)amino]-1-[4-(2,2,2-trifluoroethyl) phenyl]propan-2-ol | 380.0 | B | AXIA packed 250 × 21.2 mm 5 µM |
| 120 | 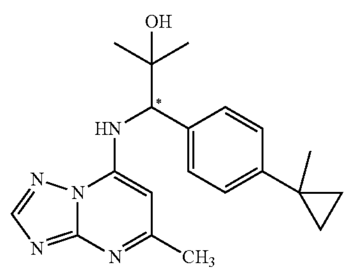 [SMILES: Cc1cc(NC(c2ccc(C3(C)CC3)cc2)C(C)(C)O)n2ncnc2n1] | (1S or R)-2-Methyl-1-[4-(1-methyl-cyclopropyl) phenyl]-1-[(5-methyl[1,2,4] triazolo[1,5-a] pyrimidin-7-yl)amino]propan-2-ol | 352.4 | B | AXIA packed 250 × 21.2 mm 5 µM |
| 121 | 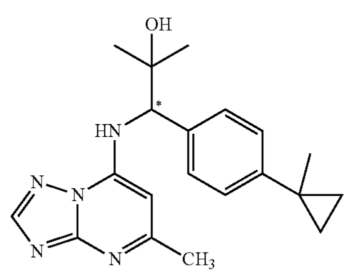 [SMILES: Cc1cc(NC(c2ccc(C3(C)CC3)cc2)C(C)(C)O)n2ncnc2n1] | (1R or S)-2-Methyl-1-[4-(1-methyl-cyclopropyl) phenyl]-1-[(5-methyl[1,2,4] triazolo[1,5-a] pyrimidin-7-yl)amino]propan-2-ol | 352.4 | B | AXIA packed 250 × 21.2 mm 5 µM |
| 122 | 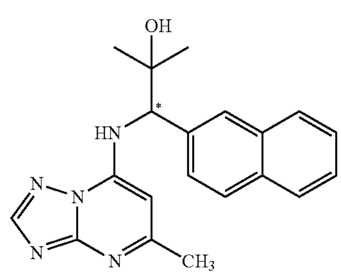 | (1S or R)-2-Methyl-1-[(5-methyl [1,2,4]triazolo [1,5-a]pyrimidin-7-yl)amino]-1-naphthalen-2-yl propan-2-ol | 348.1 | B | AXIA packed 250 × 21.2 mm 5 µM |

TABLE 6-continued

| Example # | Structure | IUPAC Name | Mass [M + H]+ | Coupling condition | Column |
|---|---|---|---|---|---|
| 123 | 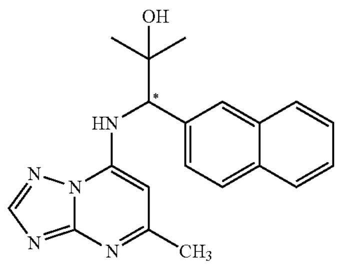 [SMILES: Cc1cc(NC(c2ccc3ccccc3c2)C(C)(C)O)n2ncnc2n1] | (1R or S)-2-Methyl-1-[(5-methyl [1,2,4]triazolo [1,5-a]pyrimidin-7-yl)amino]-1-naphthalen-2-yl propan-2-ol | 348.1 | B | AXIA packed 250 × 21.2 mm 5 μM |
| 124 | 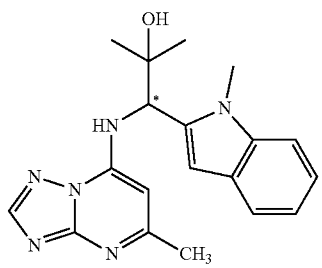 [SMILES: Cc1cc(NC(c2cc3ccccc3n2C)C(C)(C)O)n2ncnc2n1] | (1S or R)-2-Methyl-1-(1-methyl-1H-indol-2-yl)-1-[(5-methyl [1,2,4]triazolo [1,5-a]pyrimidin-7-yl)amino] propan-2-ol | 351.2 | B | (R,R) WHELK 01 5/100 Kromasil 25 cm × 21.1 mm SER# 50173 |
| 125 | 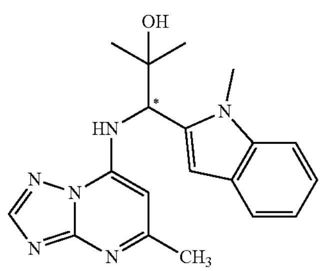 [SMILES: Cc1cc(NC(c2cc3ccccc3n2C)C(C)(C)O)n2ncnc2n1] | (1R or S)-2-Methyl-1-(1-methyl-1H-indol-2-yl)-1-[(5-methyl [1,2,4]triazolo [1,5-a]pyrimidin-7-yl)amino] propan-2-ol | 351.3 | B | (R,R) WHELK 01 5/100 Kromasil 25 cm × 21.1 mm SER# 50173 |
| 126 | 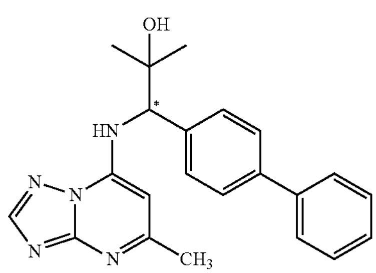 [SMILES: Cc1cc(NC(c2ccc(-c3ccccc3)cc2)C(C)(C)O)n2ncnc2n1] | (1S or R)-1-Biphenyl-4-yl-2-methyl-1-[(5-methyl[1,2,4] triazolo[1,5-a] pyrimidin-7-yl) amino]propan-2-ol | 374.1 | A | AXIA packed 250 × 21.2 mm 5 μM |
| 127 | 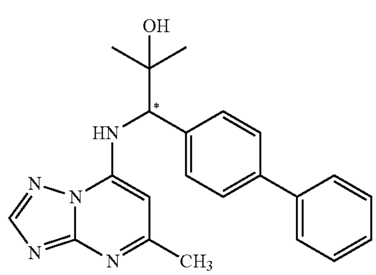 | (1R or S)-1-Biphenyl-4-yl-2-methyl-1-[(5-methyl[1,2,4] triazolo[1,5-a] pyrimidin-7-yl) amino]propan-2-ol | 374.1 | A | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 128 | 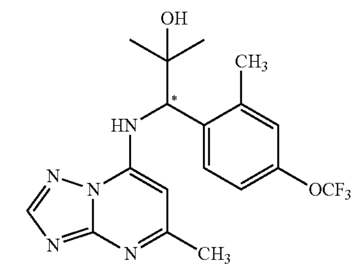 [SMILES: Cc1cc(NC(c2ccc(OC(F)(F)F)cc2C)C(C)(C)O)n2ncnc2n1] | (1S or R)-2-Methyl-1-[(5-methyl[1,2,4]triazolo[1,5-a]pyrimidin-7-yl)amino]-1-[2-methyl-4-(trifluoromethoxy)phenyl]propan-2-ol | 396.1 | B | AXIA packed 250 × 21.2 mm 5 μM |
| 129 | 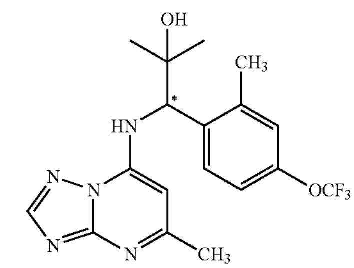 [SMILES: Cc1cc(NC(c2ccc(OC(F)(F)F)cc2C)C(C)(C)O)n2ncnc2n1] | (1R or S)-2-Methyl-1-[(5-methyl[1,2,4]triazolo[1,5-a]pyrimidin-7-yl)amino]-1-[2-methyl-4-(trifluoromethoxy)phenyl]propan-2-ol | 396.1 | B | AXIA packed 250 × 21.2 mm 5 μM |
| 130 | 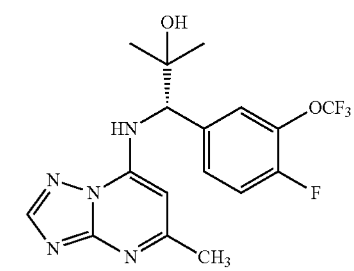 [SMILES: Cc1cc(N[C@@H](c2ccc(F)c(OC(F)(F)F)c2)C(C)(C)O)n2ncnc2n1] | (1S)-1-[4-Fluoro-3-(trifluoromethoxy)phenyl]-2-methyl-1-[(5-methyl[1,2,4]triazolo[1,5-a]pyrimidin-7-yl)amino]propan-2-ol | 400.2 | B | Chiral pak IA 2 × 25 cm, 5 μM |
| 131 | 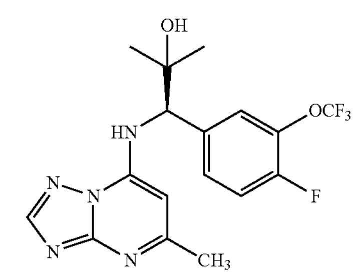 [SMILES: Cc1cc(N[C@H](c2ccc(F)c(OC(F)(F)F)c2)C(C)(C)O)n2ncnc2n1] | (1R)-1-[4-Fluoro-3-(trifluoromethoxy)phenyl]-2-methyl-1-[(5-methyl[1,2,4]triazolo[1,5-a]pyrimidin-7-yl)amino]propan-2-ol | 400.2 | B | Chiral pak IA 2 × 25 cm, 5 μM |
| 132 | 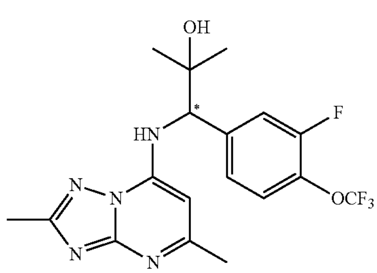 [SMILES: Cc1cc(NC(c2ccc(OC(F)(F)F)c(F)c2)C(C)(C)O)n2nc(C)nc2n1] | (1S or R)-1-[(2,5-Dimethyl[1,2,4]triazolo[1,5-a]pyrimidin-7-yl)amino]-1-[3-fluoro-4-(trifluoromethoxy)phenyl]-2-methylpropan-2-ol | 414.1 | B | Chiral pak IC 2 × 25 cm, 5 μM |

TABLE 6-continued

| Example # | Structure | IUPAC Name | Mass [M + H]+ | Coupling condition | Column |
|---|---|---|---|---|---|
| 133 | 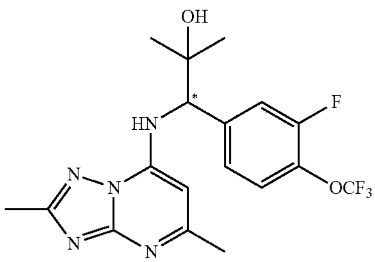 [SMILES: Cc1cc(NC(c2ccc(OC(F)(F)F)c(F)c2)C(C)(C)O)n2nc(C)nc2n1] | (1R or S)-1-[(2,5-Dimethyl[1,2,4]triazolo[1,5-a]pyrimidin-7-yl)amino]-1-[3-fluoro-4-(trifluoromethoxy)phenyl]-2-methylpropan-2-ol | 414.1 | B | Chiral pak IC 2 × 25 cm, 5 μM |
| 134 | 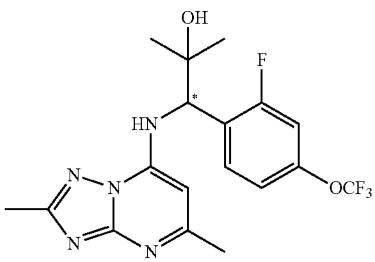 [SMILES: Cc1cc(NC(c2ccc(OC(F)(F)F)cc2F)C(C)(C)O)n2nc(C)nc2n1] | (1S or R)-1-[(2,5-Dimethyl[1,2,4]triazolo[1,5-a]pyrimidin-7-yl)amino]-1-[2-fluoro-4-(trifluoromethoxy)phenyl]-2-methylpropan-2-ol | 414.2 | B | AXIA packed 250 × 21.2 mm 5 μM |
| 135 | 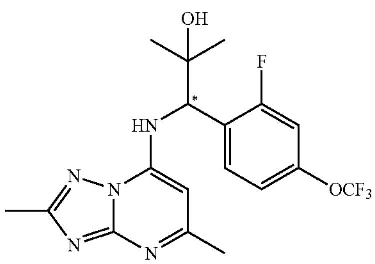 [SMILES: Cc1cc(NC(c2ccc(OC(F)(F)F)cc2F)C(C)(C)O)n2nc(C)nc2n1] | (1R or S)-1-[(2,5-Dimethyl[1,2,4]triazolo[1,5-a]pyrimidin-7-yl)amino]-1-[2-fluoro-4-(trifluoromethoxy)phenyl]-2-methylpropan-2-ol | 414.0 | B | AXIA packed 250 × 21.2 mm 5 μM |
| 136 | 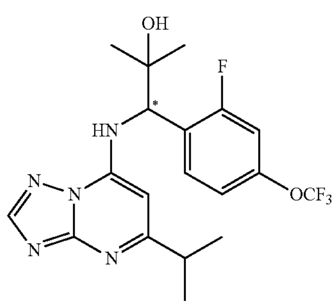 [SMILES: CC(C)c1cc(NC(c2ccc(OC(F)(F)F)cc2F)C(C)(C)O)n2ncnc2n1] | (1S or R)-1-[2-Fluoro-4-(trifluoromethoxy)phenyl]-2-methyl-1-{[5-(1-methylethyl)[1,2,4]triazolo[1,5-a]pyrimidin-7-yl]amino}propan-2-ol | 428.1 | A | AXIA packed 250 × 21.2 mm 5 μM |
| 137 | 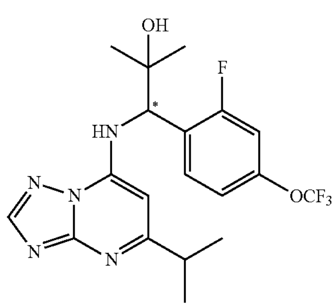 [SMILES: CC(C)c1cc(NC(c2ccc(OC(F)(F)F)cc2F)C(C)(C)O)n2ncnc2n1] | (1R or S)-1-[2-Fluoro-4-(trifluoromethoxy)phenyl]-2-methyl-1-{[5-(1-methylethyl)[1,2,4]triazolo[1,5-a]pyrimidin-7-yl]amino}propan-2-ol | 428.1 | A | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 138 | 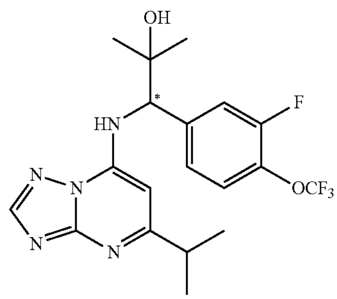 [SMILES: CC(C)c1cc(NC(c2ccc(OC(F)(F)F)c(F)c2)C(C)(C)O)n2ncnc2n1] | (1S or R)-1-[3-Fluoro-4-(trifluoromethoxy)phenyl]-2-methyl-1-{[5-(1-methylethyl)[1,2,4]triazolo[1,5-a]pyrimidin-7-yl]amino}propan-2-ol | 428.1 | B | Chiral pak IA 2 × 25 cm, 5 μM |
| 139 | 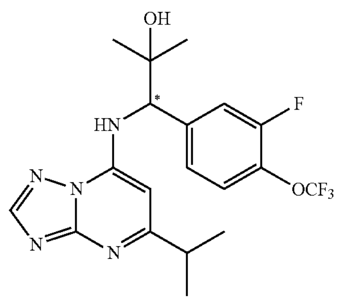 [SMILES: CC(C)c1cc(NC(c2ccc(OC(F)(F)F)c(F)c2)C(C)(C)O)n2ncnc2n1] | (1R or S)-1-[3-Fluoro-4-(trifluoromethoxy)phenyl]-2-methyl-1-{[5-(1-methylethyl)[1,2,4]triazolo[1,5-a]pyrimidin-7-yl]amino}propan-2-ol | 428.1 | B | Chiral pak IA 2 × 25 cm, 5 μM |
| 140 | 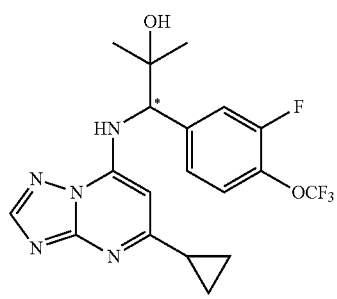 [SMILES: CC(C)(O)C(Nc1cc(C2CC2)nc2ncnn12)c1ccc(OC(F)(F)F)c(F)c1] | (1S or R)-1-[(5-Cyclopropyl[1,2,4]triazolo[1,5-a]pyrimidin-7-yl)amino]-1-[3-fluoro-4-(trifluoromethoxy)phenyl]-2-methylpropan-2-ol | 426.0 | A | AXIA packed 250 × 21.2 mm 5 μM |
| 141 | 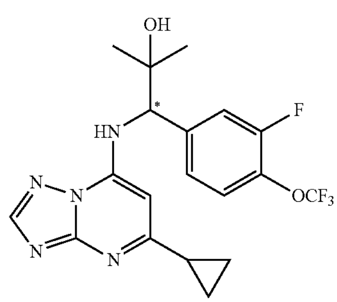 [SMILES: CC(C)(O)C(Nc1cc(C2CC2)nc2ncnn12)c1ccc(OC(F)(F)F)c(F)c1] | (1R or S)-1-[(5-Cyclopropyl[1,2,4]triazolo[1,5-a]pyrimidin-7-yl)amino]-1-[3-fluoro-4-(trifluoromethoxy)phenyl]-2-methylpropan-2-ol | 426.0 | A | AXIA packed 250 × 21.2 mm 5 μM |
| 142 | 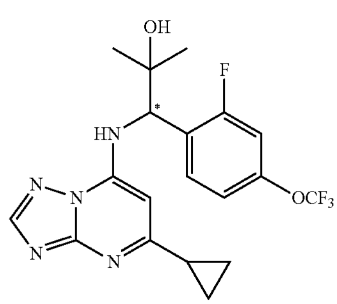 [SMILES: CC(C)(O)C(Nc1cc(C2CC2)nc2ncnn12)c1ccc(OC(F)(F)F)cc1F] | (1S or R)-1-[(5-Cyclopropyl[1,2,4]triazolo[1,5-a]pyrimidin-7-yl)amino]-1-[2-fluoro-4-(trifluoromethoxy)phenyl]-2-methylpropan-2-ol | 426.0 | A | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 143 | 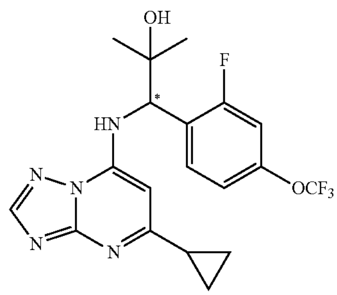 [SMILES: CC(C)(O)C(Nc1cc(C2CC2)nc2ncnn12)c1ccc(OC(F)(F)F)cc1F] | (1R or S)-1-[(5-Cyclopropyl[1,2,4]triazolo[1,5-a]pyrimidin-7-yl)amino)-1-[2-fluoro-4-(trifluoromethoxy)phenyl]-2-methylpropan-2-ol | 426.0 | A | AXIA packed 250 × 21.2 mm 5 μM |
| 144 | 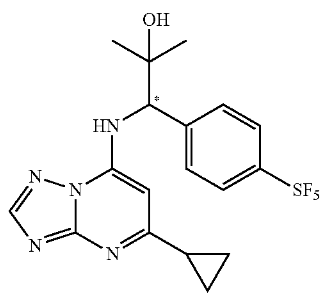 | (1S or R)-1-[(5-Cyclopropyl[1,2,4]triazolo[1,5-a]pyrimidin-7-yl)amino]-2-methyl-1-[4-(pentafluoro-$\lambda^6$-sulfanyl)phenyl]propan-2-ol | 449.9 | B | AXIA packed 250 × 21.2 mm 5 μM |
| 145 | 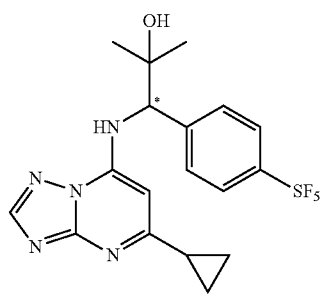 | (1R or S)-1-[(5-Cyclopropyl[1,2,4]triazolo[1,5-a]pyrimidin-7-yl)amino]-2-methyl-1-[4-(pentafluoro-$\lambda^6$-sulfanyl)phenyl]propan-2-ol | 450.0 | B | AXIA packed 250 × 21.2 mm 5 μM |
| 146 | 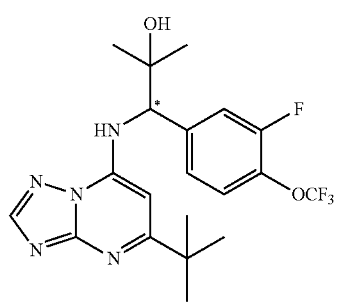 [SMILES: CC(C)(C)c1cc(NC(c2ccc(OC(F)(F)F)c(F)c2)C(C)(C)O)n2ncnc2n1] | (1S or R)-1-[(5-tert-Butyl[1,2,4]triazolo[1,5-a]pyrimidin-7-yl)amino]-1-[3-fluoro-4-(trifluoromethoxy)phenyl]-2-methylpropan-2-ol | 442.0 | B | AXIA packed 250 × 21.2 mm 5 μM |
| 147 | 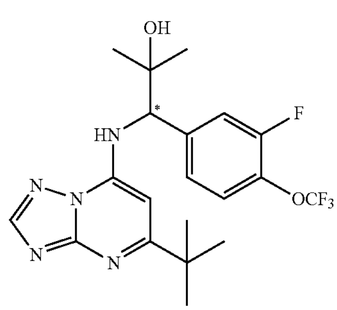 [SMILES: CC(C)(C)c1cc(NC(c2ccc(OC(F)(F)F)c(F)c2)C(C)(C)O)n2ncnc2n1] | (1R or S)-1-[(5-tert-Butyl[1,2,4]triazolo[1,5-a]pyrimidin-7-yl)amino]-1-[3-fluoro-4-(trifluoromethoxy)phenyl]-2-methylpropan-2-ol | 442.0 | B | AXIA packed 250 × 21.2 mm 5 μM |

TABLE 6-continued

| Example # | Structure | IUPAC Name | Mass [M + H]+ | Coupling condition | Column |
|---|---|---|---|---|---|
| 148 | 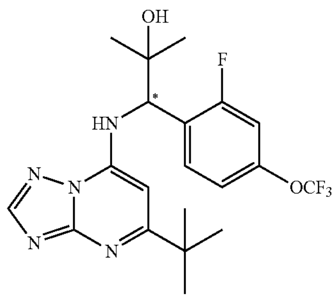 [SMILES: CC(C)(C)c1cc(NC(c2ccc(OC(F)(F)F)cc2F)C(C)(C)O)n2ncnc2n1] | (1S or R)-1-[(5-tert-butyl[1,2,4]triazolo[1,5-a]pyrimidin-7-yl)amino]-1-[2-fluoro-4-(trifluoromethoxy)phenyl]-2-methylpropan-2-ol | 442.1 | A | Chiral pak IA 2 × 25 cm, 5 μM |
| 149 | 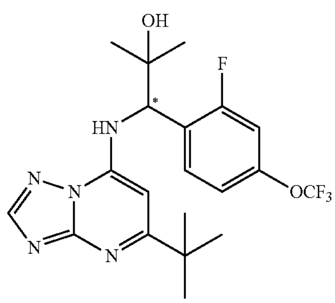 [SMILES: CC(C)(C)c1cc(NC(c2ccc(OC(F)(F)F)cc2F)C(C)(C)O)n2ncnc2n1] | (1R or S)-1-[(5-tert-butyl[1,2,4]triazolo[1,5-a]pyrimidin-7-yl)amino]-1-[2-fluoro-4-(trifluoromethoxy)phenyl]-2-methylpropan-2-ol | 442.1 | A | Chiral pak IA 2 × 25 cm, 5 μM |
| 150 | 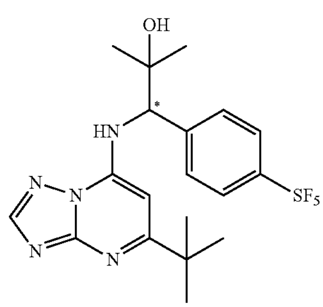 | (1S or R)-1-[(5-tert-Butyl[1,2,4]triazolo[1,5-a]pyrimidin-7-yl)amino]-2-methyl-1-[4-(pentafluoro-$\lambda^6$-sulfanyl)phenyl]propan-2-ol | 466.0 | B | AXIA packed 250 × 21.2 mm 5 μM |
| 151 | 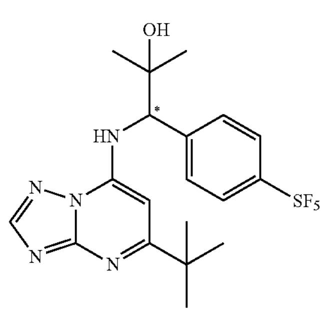 | (1R or S)-1-[(5-tert-Butyl[1,2,4]triazolo[1,5-a]pyrimidin-7-yl)amino]-2-methyl-1-[4-(pentafluoro-$\lambda^6$-sulfanyl)phenyl]propan-2-ol | 466.1 | B | AXIA packed 250 × 21.2 mm 5 μM |

Example 152

(4R)-4-[3-Fluoro-4-(trifluoromethyl)phenyl]-2-methyl-4-[(5-methyl[1,2,4]triazolo[1,5-a]pyrimidin-7-yl)amino]butan-2-ol

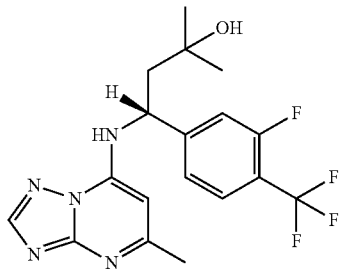 [SMILES: Cc1cc(N[C@H](CC(C)(C)O)c2ccc(C(F)(F)F)c(F)c2)n2ncnc2n1]

Step 1: Methyl (R)-3-[3-fluoro-4-(trifluoromethyl)phenyl]-3-[(5-methyl-[1,2,4]triazolo[1,5-a]pyrimidin-7-yl)amino]propanoate

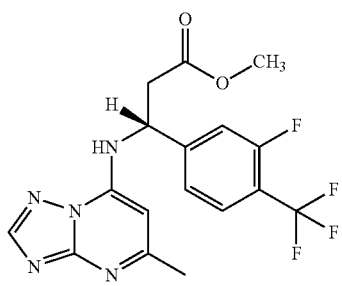 [SMILES: COC(=O)C[C@@H](Nc1cc(C)nc2ncnn12)c1ccc(C(F)(F)F)c(F)c1]

To a solution of commercially available 7-chloro-5-methyl-[1,2,4]triazolo[1,5-a]pyrimidine (140 mg, 0.830 mmol) and (R)-methyl 3-amino-3-[3-fluoro-4-(trifluoromethyl)phenyl)propanoate (200.0 mg, 0.754 mmol) in anhydrous NMP (3.0 mL) in a 2-5 mL microwave vial was added dropwise via syringe DIEA (0.16 mL, 0.905 mmol) and the resulting solution heated via oil bath to 80° C. for 2 h and then stirred at room temperature overnight. The reaction was quenched with 1 mL of sat'd. aqueous sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness under reduced pressure. This material was then used for the next reaction without further purification. LC-MS (+ESI) m/z=398.0.

Step 2: (4R)-4-[3-Fluoro-4-(trifluoromethyl)phenyl]-2-methyl-4-[(5-methyl[1,2,4]triazolo[1,5-a]pyrimidin-7-yl)amino]butan-2-ol

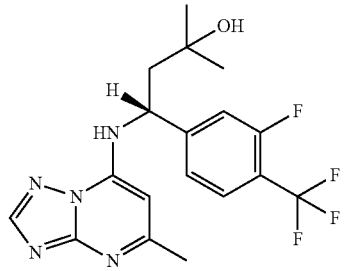 [SMILES: Cc1cc(N[C@H](CC(C)(C)O)c2ccc(C(F)(F)F)c(F)c2)n2ncnc2n1]

To the solution of methyl (R)-3-[3-fluoro-4-(trifluoromethyl)phenyl]-3-[(5-methyl-[1,2,4]triazolo[1,5-a]pyrimidin-7-yl)amino]propanoate (230 mg, 0.58 mmol) in 5 ml of anhydrous THF was added methylmagnesium bromide (3.0 M in diethyl ether, 0.8 ml, 2.32 mmol) at 0° C. and the resulting mixture stirred overnight allowing warming to room temperature. The reaction was then quenched with sat'd aqueous solution of NH$_4$Cl (50 mL), extracted with EtOAc (2×50 mL) and the organic layers combined. The organics were then washed with brine (50 mL), separated, dried over Na$_2$SO$_4$, filtered, and the filtrate concentrated in vacuo. The residue was purified by reverse phase HPLC (10-90% CH$_3$CN in water containing 0.05% TFA) to afford the title compound as a solid. LC-MS (+ESI) m/z=398.2. $^1$H NMR (500 MHz, CD$_3$OD) δ: 8.44 (s, 1H), 7.71 (t, J=7.8 Hz, 2H), 7.50-7.42 (m, 2H), 6.18 (s, 1H), 5.10-5.05 (m, 1H), 2.46 (s, 3H), 2.27 (dd, J=10.5, 15.0 Hz, 1H), 2.05 (dd, J=3.5, 15.0 Hz, 1H), 1.34 (s, 3H), 1.28 (s, 3H).

Example 153

(4S)-4-[3-Fluoro-4-(trifluoromethyl)phenyl]-2-methyl-4-[(5-methyl[1,2,4]triazolo[1,5-a]pyrimidin-7-yl)amino]butan-2-ol

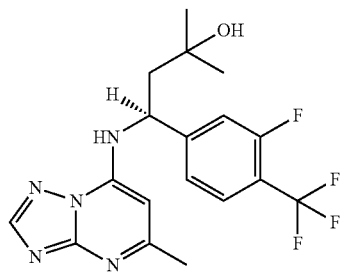 [SMILES: Cc1cc(N[C@@H](CC(C)(C)O)c2ccc(C(F)(F)F)c(F)c2)n2ncnc2n1]

The following example was prepared using similar procedures as in Example 130 using (S)-methyl 3-amino-3-[3-fluoro-4-(trifluoromethyl)phenyl)propanoate hydrochloride and other appropriate starting materials. LC-MS (+ESI) m/z=398.2. $^1$H NMR (500 MHz, CD$_3$OD) δ: 8.44 (s, 1H), 7.70 (t, J=7.8 Hz, 2H), 7.49-7.41 (m, 2H), 6.18 (s, 1H), 5.10-5.04 (m, 1H), 2.46 (s, 3H), 2.26 (dd, J=10.5, 15.0 Hz, 1H), 2.04 (dd, J=3.5, 15.0 Hz, 1H), 1.34 (s, 3H), 1.27 (s, 3H).

Example 154

(3R)-2-Methyl-3-[(5-methyl[1,2,4]triazolo[1,5-a]pyrimidin-7-yl)amino]-3-[4-(trifluoromethoxy)phenyl]butan-2-ol

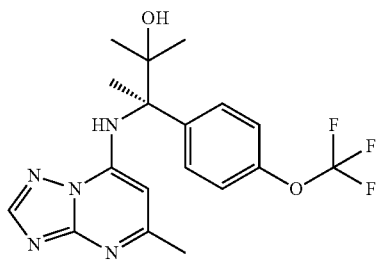 [SMILES: Cc1cc(N[C@](C)(c2ccc(OC(F)(F)F)cc2)C(C)(C)O)n2ncnc2n1]

The following example was prepared using similar procedures as in Example 130 using (R)-methyl 2-amino-2-[4-(trifluoromethoxy)phenyl]propanoate hydrochloride and other appropriate starting materials. LC-MS (+ESI) m/z=396.0. $^1$H NMR (500 MHz, CD$_3$OD) δ: 8.52 (s, 1H), 7.52 (d, J=8.1 Hz, 2H), 7.30 (d, J=8.1 Hz, 2H), 5.51 (s, 1H), 2.32 (s, 3H), 1.84 (s, 3H), 1.38 (s, 3H), 1.12 (s, 3H).

Example 155

(3S)-2-Methyl-3-[(5-methyl[1,2,4]triazolo[1,5-a]pyrimidin-7-yl)amino]-3-[4-(trifluoromethoxy)phenyl]butan-2-ol

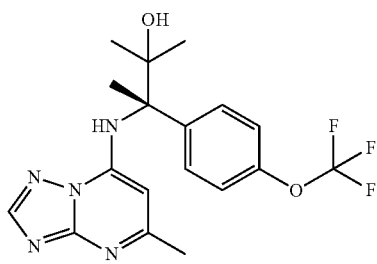 [SMILES: Cc1cc(N[C@@](C)(c2ccc(OC(F)(F)F)cc2)C(C)(C)O)n2ncnc2n1]

The following example was prepared using similar procedures as in Example 130 using (S)-methyl 2-amino-2-[4-(trifluoromethoxy)phenyl]propanoate hydrochloride and other appropriate starting materials. LC-MS (+ESI) m/z=396.0. $^1$H NMR (500 MHz, CD$_3$OD) δ: 8.50 (s, 1H), 7.58 (d, J=8.1 Hz, 2H), 7.30 (d, J=8.1 Hz, 2H), 5.52 (s, 1H), 2.32 (s, 3H), 1.85 (s, 3H), 1.38 (s, 3H), 1.12 (s, 3H).

Example 156

(1S)-2-Methyl-1-{[5-(1-methylethyl)[1,2,4]triazolo[1,5-a]pyrimidin-7-yl]amino}-1-[4-(trifluoromethyl)phenyl]propan-2-ol

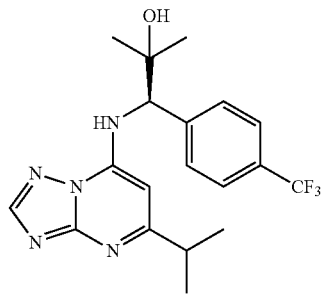 [SMILES: CC(C)c1cc(N[C@H](c2ccc(C(F)(F)F)cc2)C(C)(C)O)n2ncnc2n1]

A solution of 7-chloro-5-propyl-[1,2,4]triazolo[1,5-a]pyrimidine (60 mg, 0.3 mmol) and (S)-1-amino-2-methyl-1-[4-(trifluoromethyl)phenyl]propan-2-ol (123 mg, 0.46 mmol) in anhydrous NMP (1 mL) in a 2-5 mL microwave rxn vial was capped and heated via oil bath to 85° C. and stirred at that temperature for 4 h. The reaction was allowed to cool and was quenched with 10 mL of sat'd sodium bicarbonate aqueous solution, extracted with 25 mL ethyl acetate, separated and organic layer was washed by water (2×10 mL). The organic layer was then dried over sodium sulfate, filtered and the filtrate was concentrated to dryness in vacuo. The residue was purified by reverse phase HPLC (10-90% CH$_3$CN in water containing 0.05% TFA) to afford the desired product as a solid. LC-MS (+ESI) m/z=394.2. LC-MS (+ESI) m/z=408.1. H NMR (500 MHz, CD$_3$OD) δ: 8.61 (s, 1H), 7.72 (d, J=8.0 Hz, 2H), 7.67 (d, J=8.0, 2H), 6.31 (s, 1H), 4-90-4.85 (m, 1H; partially covered by CD$_3$OD peak), 2.98 (dq, J=7.0, 10.5 Hz, 1H), 1.48 (s, 3H), 1.22 (dd, J=7.0, 10.5 Hz, 6H), 1.13 (s, 3H).

Example 157

(1S)-1-[(5-Cyclopropyl[1,2,4]triazolo[1,5-a]pyrimidin-7-yl)amino]-2-methyl-1-[4-(trifluoromethyl)phenyl]propan-2-ol

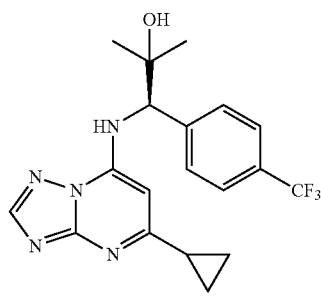 [SMILES: CC(C)(O)[C@H](Nc1cc(C2CC2)nc2ncnn12)c1ccc(C(F)(F)F)cc1]

A solution of 7-chloro-5-cyclopropyl-[1,2,4]triazolo[1,5-a]pyrimidine (60 mg, 0.3 mmol) and (S)-1-amino-2-methyl-1-[4-(trifluoromethyl)phenyl]propan-2-ol (123 mg, 0.46 mmol) in anhydrous NMP (1 mL) in a 2-5 mL microwave rxn vial was capped and heated via oil bath to 85° C. and stirred at that temperature for 4 hrs. The reaction was allowed to cool and was quenched with 10 mL of sat'd. aqueous sodium bicarbonate solution, extracted with 25 mL ethyl acetate, separated and organic layer was washed by water (2×10 mL). The organic layer was then dried over sodium sulfate, filtered and the filtrate was concentrated to dryness in vacuo. The residue was purified by reverse phase HPLC (10-90% $CH_3CN$ in water containing 0.05% TFA) to afford the desired product as a solid. LC-MS (+ESI) m/z=392.1.

Example 158

(1S)-1-[(5-tert-Butyl[1,2,4]triazolo[1,5-a]pyrimidin-7-yl)amino]-2-methyl-1-[4-(trifluoromethyl)phenyl]propan-2-ol

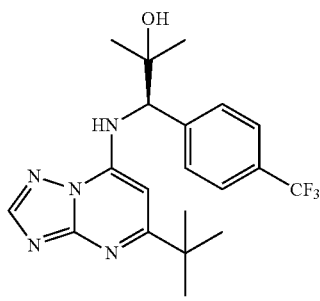 [SMILES: CC(C)(C)c1cc(N[C@H](c2ccc(C(F)(F)F)cc2)C(C)(C)O)n2ncnc2n1]

To a solution of 5-(tert-butyl)-7-chloro-[1,2,4]triazolo[1,5-a]pyrimidine (45 mg, 0.214 mmol) in anhydrous NMP (1.5 mL) in a 2-5 mL microwave vial was added (S)-1-amino-2-methyl-1-[4-(trifluoromethyl)phenyl]propan-2-ol (60 mg, 0.256 mmol) and the resulting solution heated via oil bath to 90° C. overnight. The reaction was allowed to cool and was quenched with 1 mL of sat'd. aqueous sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness. The residue was purified by reverse phase HPLC (10-90% acetonitrile in water with 0.05% TFA) to afford the desired product as a solid. LC-MS (+ESI) m/z=408.1. $^1$H NMR (500 MHz, $CD_3OD$) δ: 8.59 (s, 1H), 7.72 (d, J=8.0 Hz, 2H), 7.62 (d, J=8.0, 2H), 6.22 (s, 1H), 4-88-4.82 (m, 1H; partially covered by $CD_3OD$ peak), 1.48 (s, 3H), 1.25 (s, 9H), 1.14 (s, 3H).

Examples 159 and 160

(1S or R)-1-[2-Chloro-4-(trifluoromethyl)phenyl]-2-methyl-1-{[5-(trifluoromethyl)[1,2,4]triazolo[1,5-a]pyrimidin-7-yl]amino}propan-2-ol and (1R or S)-1-[2-chloro-4-(trifluoromethyl)phenyl]-2-methyl-1-{[5-(trifluoromethyl)[1,2,4]triazolo[1,5-a]pyrimidin-7-yl]amino}propan-2-ol

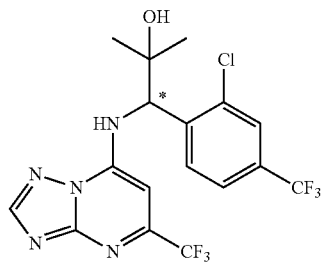 [SMILES: CC(C)(O)C(Nc1cc(C(F)(F)F)nc2ncnn12)c1ccc(C(F)(F)F)cc1Cl]

To a solution of methyl 2-(2-chloro-4-(trifluoromethyl)phenyl)-2-(5-(trifluoromethyl)-[1,2,4]triazolo[1,5-a]pyrimidin-7-ylamino)acetate from Preparatory Example 71 (0.100 g, 0.250 mmol) in THF (2 mL) was added methylmagnesium bromide (1.0 M in THF, 2.5 mL, 2.5 mmol) at 0° C. under nitrogen atmosphere. The reaction mixture was stirred at 25° C. for 16 h. Then the resulting mixture was quenched with sat'd. aqueous $NH_4Cl$ (10 mL) and extracted with ethyl acetate (3×35 mL). The combined organic layers was washed with water (3×10 mL), brine (3×10 mL), dried over anhydrous sodium sulfate and filtered. The filtrate was concentrated under reduced pressure to afford the title crude compound. The title crude compound was purified by Prep-HPLC with the following conditions: Instrument, GILSON (GX-281); Column: X Bridge RP[18], 19×150 mm, 5 um; Mobile Phase A: Water/0.05% $NH_4HCO_3$, Mobile Phase B: ACN; Flow rate: 20 mL/min; Gradient: 40% B to 45% B in 10 min; 254 nm. The fractions containing desired product were combined and concentrated to afford the title racemic compound. The title racemic compound was separated by Chiral-Prep-HPLC with the following conditions: Column: Phenomenex Lux 5 u Cellulose-4, AXIA Packed 250×21.2 mm, 5 um; Mobile Phase A: Hex-HPLC, Mobile Phase B: EtOH-HPLC; Flow rate: 20 mL/min; Gradient: isocratic 20% B in 13 min; 254/220 nm. The faster-eluting enantiomer of the title compound (Example 159) was obtained as a solid. MS (+ESI) m/z=454.2, 456.2 (M+2+H)$^+$. The slower-eluting enantiomer of the title compound (Example 160) was obtained as a solid. MS (+ESI) m/z=454.2, 456.2 (M+2+H)$^+$.

The following compounds in Table 7 were prepared using procedures similar to those described in Examples 159 and 160 using appropriate starting materials. Racemic products were separated using chiral columns specified in the table. For those pairs of enantiomers, the faster eluting isomer is always listed first in this table.

Coupling conditions: A. DIEA, NMP; B. DIEA, IPA

TABLE 7

| Example # | Structure | IUPAC Name | Mass [M + H]+ | Coupling condition | Column |
|---|---|---|---|---|---|
| 161 | 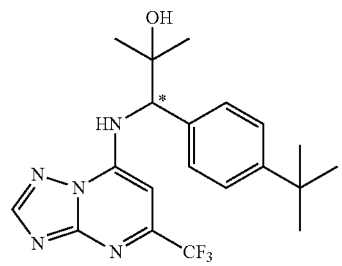 [SMILES: CC(C)(C)c1ccc(C(Nc2cc(C(F)(F)F)nc3ncnn23)C(C)(C)O)cc1] | (1S or S)-1-(4-tert-Butylphenyl)-2-methyl-1-{[5-(trifluoromethyl)[1,2,4]triazolo[1,5-a]pyrimidin-7-yl]amino}propan-2-ol | 408.3 | A | Chiral pak IA 2 × 25 cm, 5 μM |
| 162 | 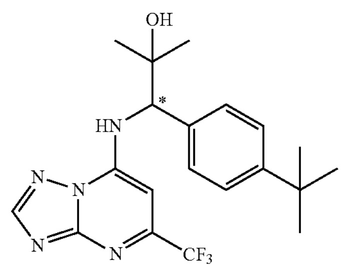 | (1R or S)-1-(4-tert-Butylphenyl)-2-methyl-1-{[5-(trifluoromethyl)[1,2,4]triazolo[1,5-a]pyrimidin-7-yl]amino}propan-2-ol | 408.3 | A | Chiral pak IA 2 × 25 cm, 5 μM |
| 163 | 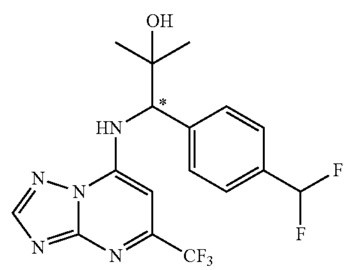 [SMILES: CC(C)(O)C(Nc1cc(C(F)(F)F)nc2ncnn12)c1ccc(C(F)F)cc1] | (1S or R)-1-[4-(Difluoromethyl)phenyl]-2-methyl-1-{[5-(trifluoromethyl)[1,2,4]triazolo[1,5-a]pyrimidin-7-yl]amino}propan-2-ol | 402.1 | B | Chiral pak IA 2 × 25 cm, 5 μM |
| 164 | 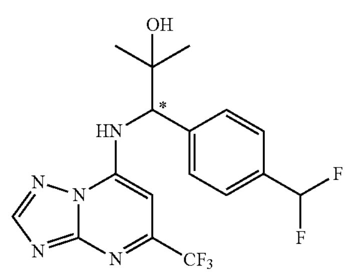 [SMILES: CC(C)(O)C(Nc1cc(C(F)(F)F)nc2ncnn12)c1ccc(C(F)F)cc1] | (1R or S)-1-[4-(Difluoromethyl)phenyl]-2-methyl-1-{[5-(trifluoromethyl)[1,2,4]triazolo[1,5-a]pyrimidin-7-yl]amino}propan-2-ol | 402.1 | B | Chiral pak IA 2 × 25 cm, 5 μM |
| 165 | 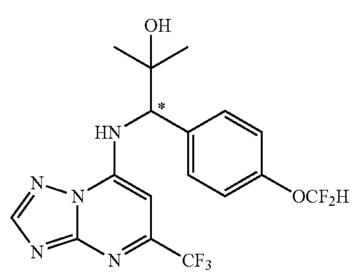 | (1S or R)-1-[4-(Difluoromethoxy)phenyl]-2-methyl-1-{[5-(trifluoromethyl)[1,2,4]triazolo[1,5-a]pyrimidin-7-yl]amino}propan-2-ol | 418.2 | B | Chiral pak IA 2 × 25 cm, 5 μM |

TABLE 7-continued

| Example # | Structure | IUPAC Name | Mass [M + H]+ | Coupling condition | Column |
|---|---|---|---|---|---|
| 166 | 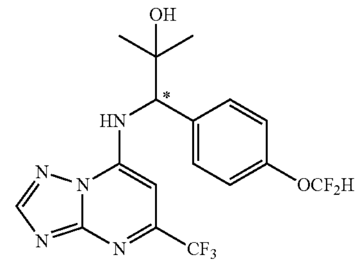 | (1R or S)-1-[4-(Difluoromethoxy)phenyl]-2-methyl-1-{[5-(trifluoromethyl)[1,2,4]triazolo[1,5-a]pyrimidin-7-yl]amino}propan-2-ol | 418.2 | B | Chiral pak IA 2 × 25 cm, 5 μM |
| 167 | 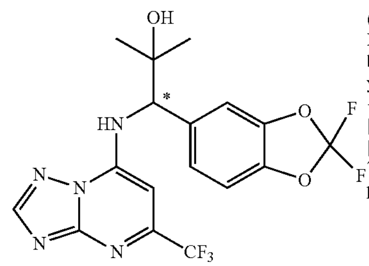 [SMILES: CC(C)(O)C(Nc1cc(C(F)(F)F)nc2ncnn12)c1ccc2c(c1)OC(F)(F)O2] | (1S or R)-1-(2,2-Difluoro-1,3-benzodioxol-5-yl)-2-methyl-1-{[5-(trifluoromethyl)[1,2,4]triazolo[1,5-a]pyrimidin-7-yl]amino}propan-2-ol | 432.1 | B | Chiral pak IA 2 × 25 cm, 5 μM |
| 168 | 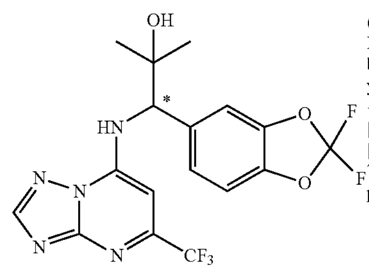 | (1R or S)-1-(2,2-Difluoro-1,3-benzodioxol-5-yl)-2-methyl-1-{[5-(trifluoromethyl)[1,2,4]triazolo[1,5-a]pyrimidin-7-yl]amino}propan-2-ol | 432.1 | B | Chiral pak IA 2 × 25 cm, 5 μM |
| 169 | 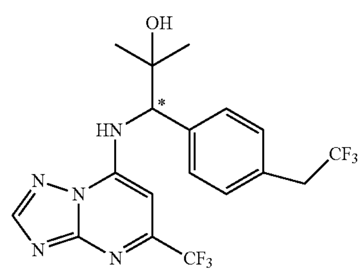 [SMILES: CC(C)(O)C(Nc1cc(C(F)(F)F)nc2ncnn12)c1ccc(CC(F)(F)F)cc1] | (1S or R)-2-Methyl-1-[4-(2,2,2-trifluoroethyl)phenyl]-1-{[5-(trifluoromethyl)[1,2,4]triazolo[1,5-a]pyrimidin-7-yl]amino}propan-2-ol | 434.0 | B | Chiral pak IA 2 × 25 cm, 5 μM |
| 170 | 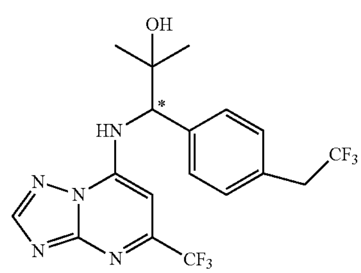 [SMILES: CC(C)(O)C(Nc1cc(C(F)(F)F)nc2ncnn12)c1ccc(CC(F)(F)F)cc1] | (1R or S)-2-Methyl-1-[4-(2,2,2-trifluoroethyl)phenyl]-1-{[5-(trifluoromethyl)[1,2,4]triazolo[1,5-a]pyrimidin-7-yl]amino}propan-2-ol | 434.0 | B | Chiral pak IA 2 × 25 cm, 5 μM |

TABLE 7-continued

| Example # | Structure | IUPAC Name | Mass [M + H]+ | Coupling condition | Column |
|---|---|---|---|---|---|
| 171 | 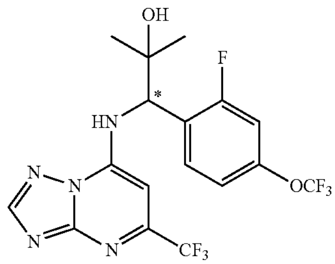 [SMILES: CC(C)(O)C(Nc1cc(C(F)(F)F)nc2ncnn12)c1ccc(OC(F)(F)F)cc1F] | (1S or R)-1-[2-Fluoro-4-(trifluoromethoxy)phenyl]-2-methyl-1-{[5-(trifluoromethyl)[1,2,4]triazolo[1,5-a]pyrimidin-7-yl]amino}propan-2-ol | 454.2 | B | AXIA packed 250 × 21.2 mm 5 µM |
| 172 | 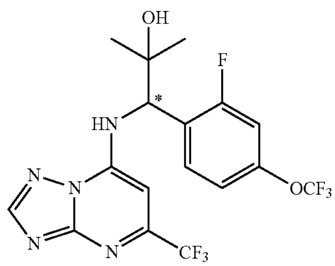 | (1R or S)-1-[2-Fluoro-4-(trifluoromethoxy)phenyl]-2-methyl-1-{[5-(trifluoromethyl)[1,2,4]triazolo[1,5-a]pyrimidin-7-yl]amino}propan-2-ol | 454.1 | B | AXIA packed 250 × 21.2 mm 5 µM |
| 173 | 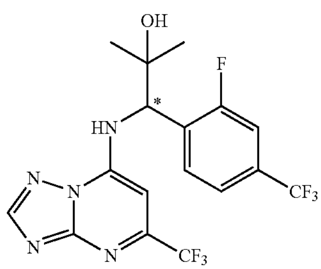 [SMILES: CC(C)(O)C(Nc1cc(C(F)(F)F)nc2ncnn12)c1ccc(C(F)(F)F)cc1F] | (1S or R)-1-[2-Fluoro-4-(trifluoromethyl)phenyl]-2-methyl-1-{[5-(trifluoromethyl)[1,2,4]triazolo[1,5-a]pyrimidin-7-yl]amino}propan-2-ol | 436.0 (M − 1) | B | AXIA packed 250 × 21.2 mm 5 µM |
| 174 | 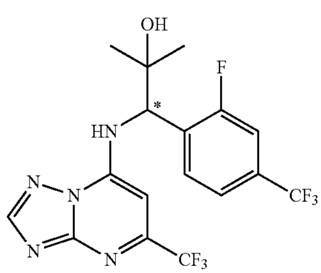 | (1R or S)-1-[2-Fluoro-4-(trifluoromethyl)phenyl]-2-methyl-1-{[5-(trifluoromethyl)[1,2,4]triazolo[1,5-a]pyrimidin-7-yl]amino}propan-2-ol | 436.0 (M − 1) | B | AXIA packed 250 × 21.2 mm 5 µM |
| 175 | 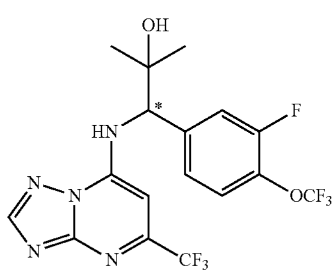 [SMILES: CC(C)(O)C(Nc1cc(C(F)(F)F)nc2ncnn12)c1ccc(OC(F)(F)F)c(F)c1] | (1S or R)-1-[3-Fluoro-4-(trifluoromethoxy)phenyl]-2-methyl-1-{[5-(trifluoromethyl)[1,2,4]triazolo[1,5-a]pyrimidin-7-yl]amino}propan-2-ol | 454.4 | B | Chiral pak IA 2 × 25 cm, 5 µM |

TABLE 7-continued

| Example # | Structure | IUPAC Name | Mass [M + H]+ | Coupling condition | Column |
|---|---|---|---|---|---|
| 176 | 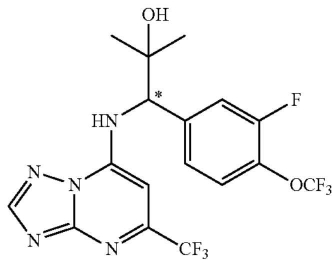 [SMILES: CC(C)(O)C(Nc1cc(C(F)(F)F)nc2ncnn12)c1ccc(OC(F)(F)F)c(F)c1] | (1R or S)-1-[3-Fluoro-4-(trifluoromethoxy)phenyl]-2-methyl-1-{[5-(trifluoromethyl)[1,2,4]triazolo[1,5-a]pyrimidin-7-yl]amino}propan-2-ol | 454.4 | B | Chiral pak IA 2 × 25 cm, 5 µM |
| 177 | 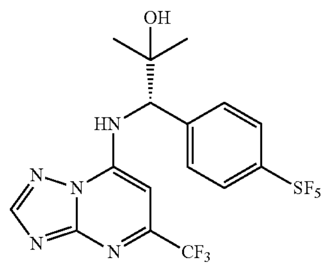 | (1S)-2-Methyl-1-[4-(pentafluoro-λ6-sulfanyl)phenyl]-1-{[5-(trifluoromethyl)[1,2,4]triazolo[1,5-a]pyrimidin-7-yl]amino}propan-2-ol | 478.0 | B | Chiral pak IA 2 × 25 cm, 5 µM |
| 178 | 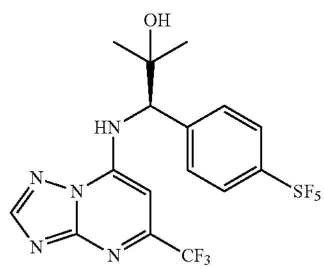 | (1R)-2-Methyl-1-[4-(pentafluoro-λ6-sulfanyl)phenyl]-1-{[5-(trifluoromethyl)[1,2,4]triazolo[1,5-a]pyrimidin-7-yl]amino}propan-2-ol | 478.0 | B | Chiral pak IA 2 × 25 cm, 5 µM |
| 179 | 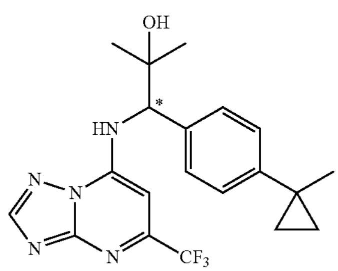 [SMILES: CC1(c2ccc(C(Nc3cc(C(F)(F)F)nc4ncnn34)C(C)(C)O)cc2)CC1] | (1S or R)-2-Methyl-1-[4-(1-methylcyclopropyl)phenyl]-1-{[5-(trifluoromethyl)[1,2,4]triazolo[1,5-a]pyrimidin-7-yl]amino}propan-2-ol | 406.0 | B | AXIA packed 250 × 21.2 mm 5 µM |
| 180 | 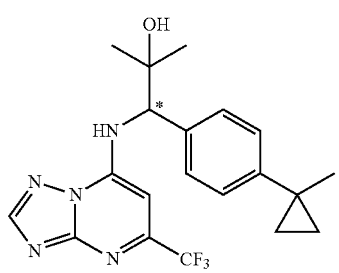 | (1R or S)-2-Methyl-1-[4-(1-methylcyclopropyl)phenyl]-1-{[5-(trifluoromethyl)[1,2,4]triazolo[1,5-a]pyrimidin-7-yl]amino}propan-2-ol | 406.0 | B | AXIA packed 250 × 21.2 mm 5 µM |

TABLE 7-continued

| Example # | Structure | IUPAC Name | Mass [M + H]+ | Coupling condition | Column |
|---|---|---|---|---|---|
| 181 | 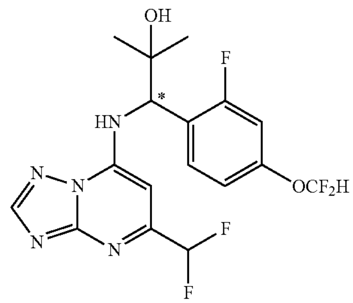 | (1S or R)-{[5-(Difluoromethyl)[1,2,4]triazolo[1,5-a]pyrimidin-7-yl]amino}-1-[3-fluoro-4-(trifluoromethoxy)phenyl]-2-methylpropan-2-ol | 418.0 | B | AXIA packed 250 x 21.2 mm 5 μM |
| 182 | 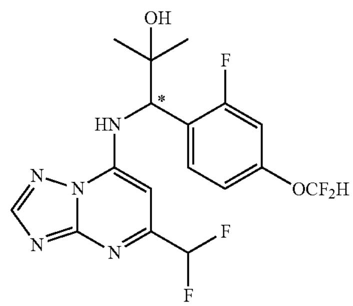 | (1R or S)-{[5-(Difluoromethyl)[1,2,4]triazolo[1,5-a]pyrimidin-7-yl]amino}-1-[3-fluoro-4-(trifluoromethoxy)phenyl]-2-methylpropan-2-ol | 418.0 | B | AXIA packed 250 x 21.2 mm 5 μM |
| 183 | 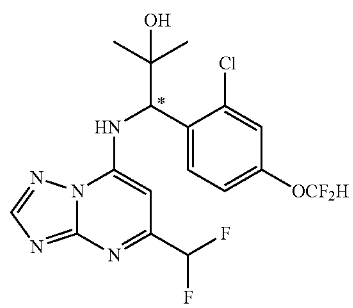 | (1S or R)-[2-Chloro-4-(difluoromethoxy)phenyl]-1-{[5-(difluoromethyl)[1,2,4]triazolo[1,5-a]pyrimidin-7-yl]amino}-2-methylpropan-2-ol | 434.0 436.0 (M + 2 + H) | B | AXIA packed 250 x 21.2 mm 5 μM |
| 184 | 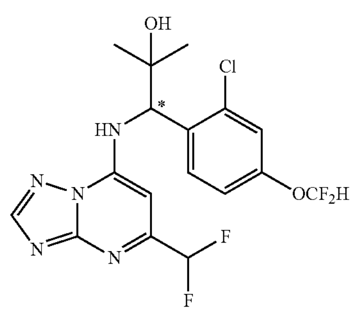 | (1R or S)-[2-Chloro-4-(difluoromethoxy)phenyl]-1-{[5-(difluoromethyl)[1,2,4]triazolo[1,5-a]pyrimidin-7-yl]amino}-2-methylpropan-2-ol | 434.0 436.0 (M + 2 + H) | B | AXIA packed 250 x 21.2 mm 5 μM |
| 185 | 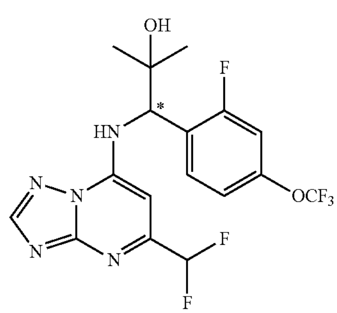 [SMILES: CC(C)(O)C(Nc1cc(C(F)F)nc2ncnn12)c1ccc(OC(F)(F)F)cc1F] | (1S or R)-{[5-(Difluoromethyl)[1,2,4]triazolo[1,5-a]pyrimidin-7-yl]amino}-1-[2-fluoro-4-(trifluoromethoxy)phenyl]-2-methylpropan-2-ol | 436.1 | A | AXIA packed 250 x 21.2 mm 5 μM |

TABLE 7-continued

| Example # | Structure | IUPAC Name | Mass [M + H]+ | Coupling condition | Column |
|---|---|---|---|---|---|
| 186 | 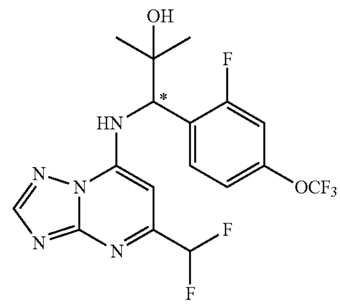 [SMILES: CC(C)(O)C(Nc1cc(C(F)F)nc2ncnn12)c1ccc(OC(F)(F)F)cc1F] | (1R or S)-{[5-(Difluoromethyl)[1,2,4]triazolo[1,5-a]pyrimidin-7-yl]amino}-1-[2-fluoro-4-(trifluoromethoxy)phenyl]-2-methylpropan-2-ol | 436.1 | A | AXIA packed 250 x 21.2 mm 5 μM |
| 187 | 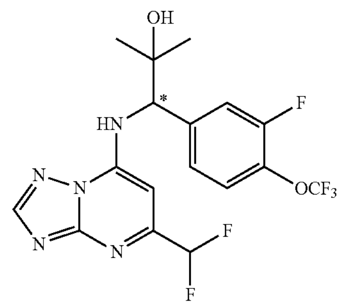 [SMILES: CC(C)(O)C(Nc1cc(C(F)F)nc2ncnn12)c1ccc(OC(F)(F)F)c(F)c1] | (1S or R)-{[5-(Difluoromethyl)[1,2,4]triazolo[1,5-a]pyrimidin-7-yl]amino}-1-[3-fluoro-4-(trifluoromethoxy)phenyl]-2-methylpropan-2-ol | 436.0 | B | AXIA packed 250 x 21.2 mm 5 μM |
| 188 | 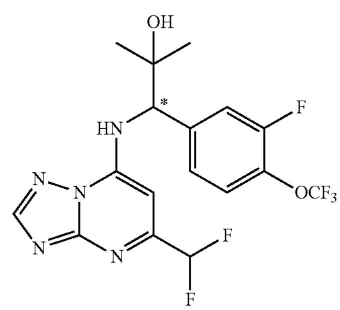 [SMILES: CC(C)(O)C(Nc1cc(C(F)F)nc2ncnn12)c1ccc(OC(F)(F)F)c(F)c1] | (1R or S)-{[5-(Difluoromethyl)[1,2,4]triazolo[1,5-a]pyrimidin-7-yl]amino}-1-[3-fluoro-4-(trifluoromethoxy)phenyl]-2-methylpropan-2-ol | 436.1 | B | AXIA packed 250 x 21.2 mm 5 μM |
| 189 | 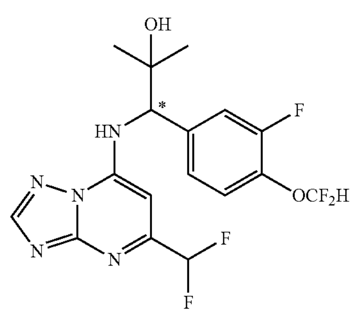 | (1S or R)-[4-(Difluoromethoxy)-3-fluorophenyl]-1-{[5-(difluoromethyl)[1,2,4]triazolo[1,5-a]pyrimidin-7-yl]amino}-2-methylpropan-2-ol | 418.1 | B | AXIA packed 250 x 21.2 mm 5 μM |
| 190 | 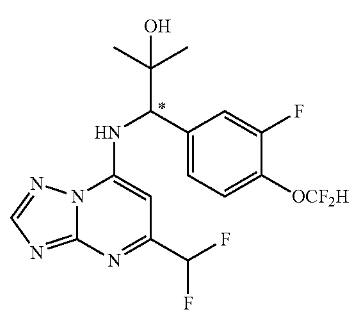 | (1R or S)-[4-(Difluoromethoxy)-3-fluorophenyl]-1-{[5-(difluoromethyl)[1,2,4]triazolo[1,5-a]pyrimidin-7-yl]amino}-2-methylpropan-2-ol | 418.2 | B | AXIA packed 250 x 21.2 mm 5 μM |

Example 191

2-(Fluoromethyl)-N-{(1R)-1-[3-fluoro-4-(trifluoromethyl)phenyl]-2,2-dimethylpropyl}-5-methyl[1,2,4]triazolo[1,5-a]pyrimidin-7-amine

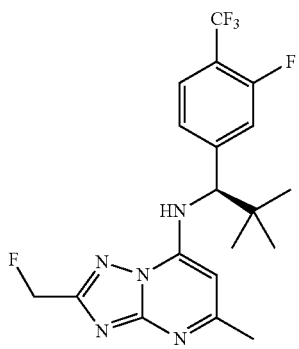 [SMILES: Cc1cc(N[C@@H](c2ccc(C(F)(F)F)c(F)c2)C(C)(C)C)n2nc(CF)nc2n1]

(R)-1-[3-Fluoro-4-(trifluoromethyl)phenyl]-2,2-dimethylpropan-1-amine hydrochloride (28.5 mg, 0.100 mmol) was added to a mixture of 7-chloro-2-(fluoromethyl)-5-methyl-[1,2,4]triazolo[1,5-a]pyrimidine (20.0 mg, 0.100 mmol) in NMP (1.5 mL). This was followed by the addition of DIEA (64.4 mg, 88 uL, 0.499 mmol). The reaction mixture was stirred at 80° C. for 16 h. The resulting mixture was cooled to room temperature, diluted with water (10 mL) and extracted with ethyl acetate (3×15 mL). The combined organic layers were washed with water (3×10 mL), brine (3×10 mL), dried over anhydrous sodium sulfate and filtered. The filtrate was concentrated under reduced pressure. The residue was purified by Prep-HPLC with the following conditions: Instrument, GILSON (GX-281); Column: X bridge RP[18], 5 um, 19×150 mm; mobile phase: water (0.05% $NH_4HCO_3$) and acetonitrile (40% acetonitrile up to 55% in 10 min, hold 100% for 2 min, down to 40% in 2 min); Detector, UV 220 and 254 nm. The title compound was obtained as a solid. MS (+ESI) m/z=414.3. $^1$H NMR (300 MHz, $CD_3OD$) δ: 7.69-7.64 (m, 1H), 7.52-7.44 (m, 2H), 6.22 (s, 1H), 5.64 (s, 1H), 5.49 (s, 1H), 4.76 (s, 1H), 2.42 (s, 3H), 1.08 (s, 9H).

The following compounds in Table 8 were prepared using procedures similar to those described in Example 191 using appropriate starting materials.

TABLE 8

| Example # | Structure | IUPAC Name | Mass [M + H]+ | Coupling method |
|---|---|---|---|---|
| 192 | 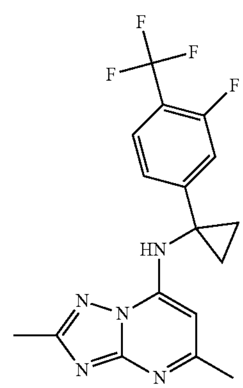 [SMILES: Cc1cc(NC2(c3ccc(C(F)(F)F)c(F)c3)CC2)n2nc(C)nc2n1] | N-(1-(3-Fluoro-4-(trifluoromethyl)phenyl)cyclopropyl)-2,5-dimethyl-[1,2,4]triazolo[1,5-a]pyrimidin-7-amine | 366.2 | A |
| 193 | 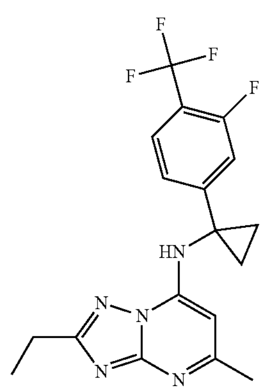 [SMILES: CCc1nc2nc(C)cc(NC3(c4ccc(C(F)(F)F)c(F)c4)CC3)n2n1] | 2-Ethyl-N-(1-(3-fluoro-4-(trifluoromethyl)phenyl)cyclopropyl)-5-methyl-[1,2,4]triazolo[1,5-a]pyrimidin-7-amine | 380.1 | A |

TABLE 8-continued

| Example # | Structure | IUPAC Name | Mass [M + H]+ | Coupling method |
|---|---|---|---|---|
| 194 | 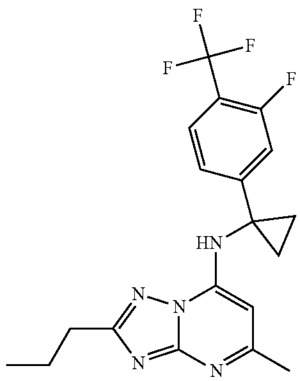 [SMILES: CCCc1nc2nc(C)cc(NC3(c4ccc(C(F)(F)F)c(F)c4)CC3)n2n1] | N-(1-(3-Fluoro-4-(trifluoromethyl)phenyl)cyclopropyl)-5-methyl-2-propyl-[1,2,4]triazolo[1,5-a]pyrimidin-7-amine | 394.0 | A |
| 195 | 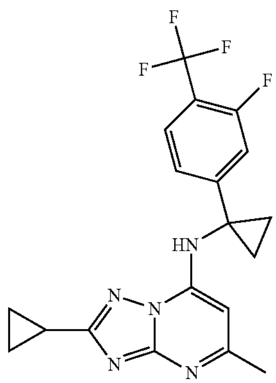 [SMILES: Cc1cc(NC2(c3ccc(C(F)(F)F)c(F)c3)CC2)n2nc(C3CC3)nc2n1] | 2-Cyclopropyl-N-(1-(3-fluoro-4-(trifluoromethyl)phenyl)cyclopropyl)-5-methyl-[1,2,4]triazolo[1,5-a]pyrimidin-7-amine | 392.1 | A |
| 196 | 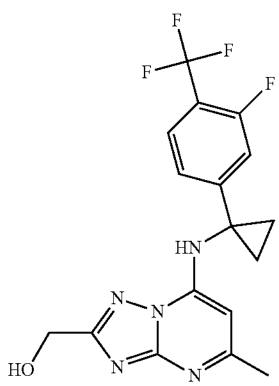 [SMILES: Cc1cc(NC2(c3ccc(C(F)(F)F)c(F)c3)CC2)n2nc(CO)nc2n1] | (7-(1-(3-Fluoro-4-(trifluoromethyl)phenyl)cyclopropylamino)-5-methyl-[1,2,4]triazolo[1,5-a]pyrimidin-2-yl)methanol | 382.2 | A |
| 197 | 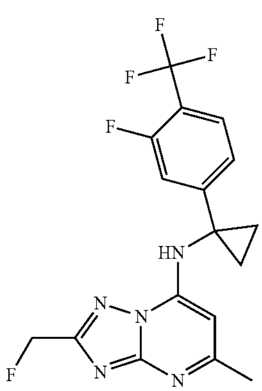 [SMILES: Cc1cc(NC2(c3ccc(C(F)(F)F)c(F)c3)CC2)n2nc(CF)nc2n1] | N-(1-(3-Fluoro-4-(trifluoromethyl)phenyl)cyclopropyl)-2-(fluoromethyl)-5-methyl-[1,2,4]triazolo[1,5-a]pyrimidin-7-amine | 384.2 | A |

TABLE 8-continued

| Example # | Structure | IUPAC Name | Mass [M + H]⁺ | Coupling method |
|---|---|---|---|---|
| 198 | 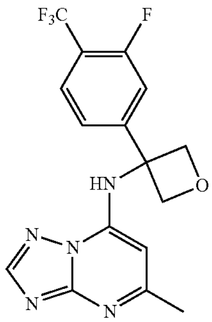 [SMILES: Cc1cc(NC2(c3ccc(C(F)(F)F)c(F)c3)COC2)n2ncnc2n1] | N-(3-(3-Fluoro-4-(trifluoromethyl)phenyl)oxetan-3-yl)-5-methyl-[1,2,4]triazolo[1,5-a]pyrimidin-7-amine | 368.2 | B |
| 199 | 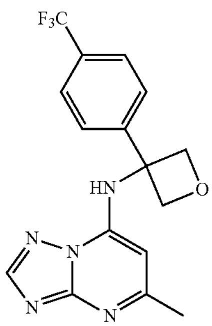 [SMILES: Cc1cc(NC2(c3ccc(C(F)(F)F)cc3)COC2)n2ncnc2n1] | 5-Methyl-N-(3-(4-(trifluoromethyl)phenyl)oxetan-3-yl)-[1,2,4]triazolo[1,5-a]pyrimidin-7-amine | 350.2 | B |
| 200 | 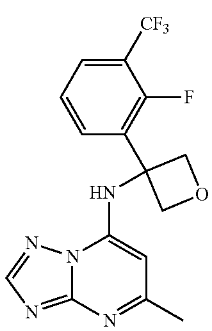 [SMILES: Cc1cc(NC2(c3cccc(C(F)(F)F)c3F)COC2)n2ncnc2n1] | N-(3-(2-Fluoro-3-(trifluoromethyl)phenyl)oxetan-3-yl)-5-methyl-[1,2,4]triazolo[1,5-a]pyrimidin-7-amine | 368.1 | B |
| 201 | 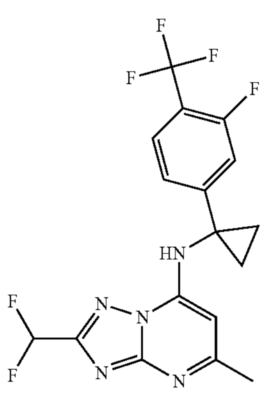 [SMILES: Cc1cc(NC2(c3ccc(C(F)(F)F)c(F)c3)CC2)n2nc(C(F)F)nc2n1] | 2-(Difluoromethyl)-N-(1-(3-fluoro-4-(trifluoromethyl)phenyl)cyclopropyl)-5-methyl-[1,2,4]triazolo[1,5-a]pyrimidin-7-amine | 402.2 | A |

TABLE 8-continued

| Example # | Structure | IUPAC Name | Mass [M + H]+ | Coupling method |
|---|---|---|---|---|
| 202 | 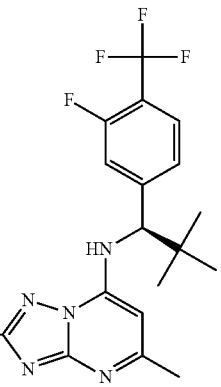 | (R)-N-(1-(3-Fluoro-4-(trifluoromethyl)phenyl)-2,2-dimethylpropyl)-2,5-dimethyl-[1,2,4]triazolo[1,5-a]pyrimidin-7-amine | 396.3 | A |
| 203 | 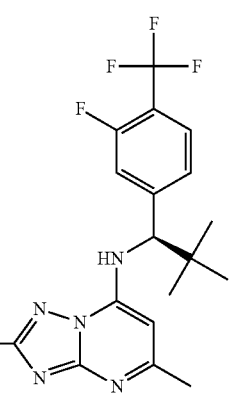 | (R)-2-Ethyl-N-(1-(3-fluoro-4-(trifluoromethyl)phenyl)-2,2-dimethylpropyl)-5-methyl-[1,2,4]triazolo[1,5-a]pyrimidin-7-amine | 410.1 | A |
| 204 | 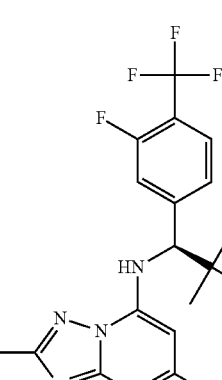 | (R)-N-(1-(3-Fluoro-4-(trifluoromethyl)phenyl)-2,2-dimethylpropyl)-5-methyl-2-propyl-[1,2,4]triazolo[1,5-a]pyrimidin-7-amine | 424.1 | A |
| 205 | 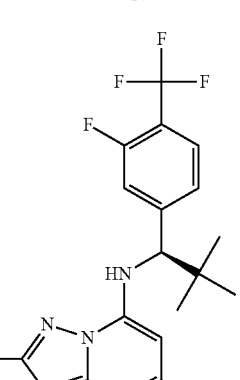 | (R)-2-Cyclopropyl-N-(1-(3-fluoro-4-(trifluoromethyl)phenyl)-2,2-dimethylpropyl)-5-methyl-[1,2,4]triazolo[1,5-a]pyrimidin-7-amine | 422.2 | A |

TABLE 8-continued

| Example # | Structure | IUPAC Name | Mass [M + H]+ | Coupling method |
|---|---|---|---|---|
| 206 | 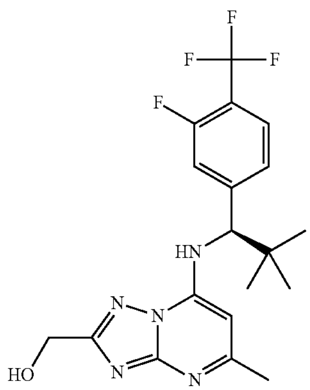 [SMILES: Cc1cc(N[C@@H](c2ccc(C(F)(F)F)c(F)c2)C(C)(C)C)n2nc(CO)nc2n1] | (R)-(7-(1-(3-Fluoro-4-(trifluoromethyl)phenyl)-2,2-dimethylpropylamino)-5-methyl-[1,2,4]triazolo[1,5-a]pyrimidin-2-yl)methanol | 411.9 | A |
| 207 | 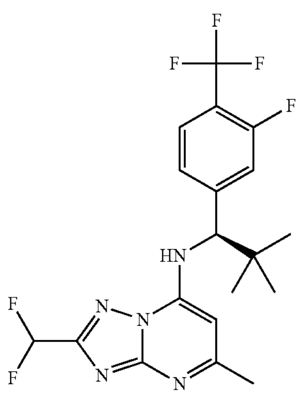 [SMILES: Cc1cc(N[C@@H](c2ccc(C(F)(F)F)c(F)c2)C(C)(C)C)n2nc(C(F)F)nc2n1] | (R)-2-(Difluoromethyl)-N-(1-(3-fluoro-4-(trifluoromethyl)phenyl)-2,2-dimethylpropyl)-5-methyl-[1,2,4]triazolo[1,5-a]pyrimidin-7-amine | 432.2 | A |
| 208 | 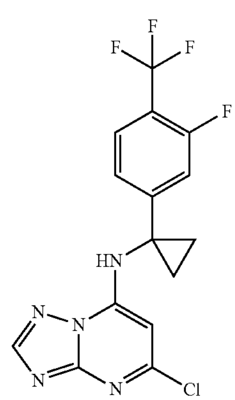 [SMILES: Fc1cc(C2(Nc3cc(Cl)nc4ncnn34)CC2)ccc1C(F)(F)F] | 5-Chloro-N-(1-(3-fluoro-4-(trifluoromethyl)phenyl)cyclopropyl)-[1,2,4]triazolo[1,5-a]pyrimidin-7-amine | 372.0; 374.0 (M + 2 + H) | C |

Coupling conditions: A. DIEA, NMP; B. DIEA, IPA; C. DIEA, EtOH

The following compounds in Table 9 were prepared using procedures similar to those described in Example 191 using appropriate starting materials. Racemic products were separated using chiral columns specified in the table. For those pairs of enantiomers, the faster eluting isomer is always listed first in this table.

TABLE 9

| Example # | Structure | IUPAC Name | Mass [M + H]+ | Coupling method | Chiral column |
|---|---|---|---|---|---|
| 209 | 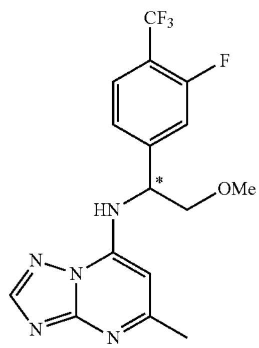 [SMILES: COCC(Nc1cc(C)nc2ncnn12)c1ccc(C(F)(F)F)c(F)c1] | (R)- or (S)-N-(1-(3-Fluoro-4-(trifluoromethyl)phenyl)-2-methoxyethyl)-5-methyl-[1,2,4]triazolo[1,5-a]pyrimidin-7-amine | 370.1 | B | AXIA Packed 250 × 21.2 mm, 5 μm |
| 210 | 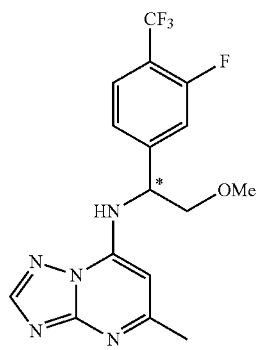 [SMILES: COCC(Nc1cc(C)nc2ncnn12)c1ccc(C(F)(F)F)c(F)c1] | (S)- or (R)-N-(1-(3-Fluoro-4-(trifluoromethyl)phenyl)-2-methoxyethyl)-5-methyl-[1,2,4]triazolo[1,5-a]pyrimidin-7-amine | 370.1 | B | AXIA Packed 250 × 21.2 mm, 5 μm |
| 211 | 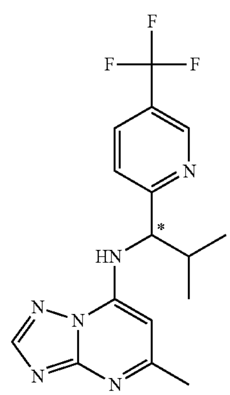 [SMILES: Cc1cc(NC(c2ccc(C(F)(F)F)cn2)C(C)C)n2ncnc2n1] | (R)- or (S)-5-Methyl-N-(2-methyl-1-(5-(trifluoromethyl)pyridin-2-yl)propyl)-[1,2,4]triazolo[1,5-a]pyrimidin-7-amine | 351.1 | A | Chiralpak AS-H 2 × 25 cm, 5 μm |
| 212 | 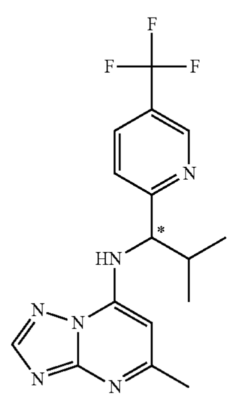 [SMILES: Cc1cc(NC(c2ccc(C(F)(F)F)cn2)C(C)C)n2ncnc2n1] | (S)- or (R)-5-Methyl-N-(2-methyl-1-(5-(trifluoromethyl)pyridin-2-yl)propyl)-[1,2,4]triazolo[1,5-a]pyrimidin-7-amine | 351.1 | A | Chiralpak AS-H 2 × 25 cm, 5 μm |

TABLE 9-continued

| Example # | Structure | IUPAC Name | Mass [M + H]+ | Coupling method | Chiral column |
|---|---|---|---|---|---|
| 213 | 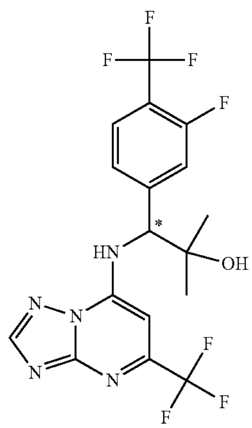 [SMILES: CC(C)(O)C(Nc1cc(C(F)(F)F)nc2ncnn12)c1ccc(C(F)(F)F)c(F)c1] | (S)- or (R)-1-(3-Fluoro-4-(trifluoromethyl)phenyl)-2-methyl-1-(5-(trifluoromethyl)-[1,2,4]triazolo[1,5-a]pyrimidin-7-ylamino)propan-2-ol | 438.0 | D | IA 21.2 × 150 mm, 5 μm |
| 214 | 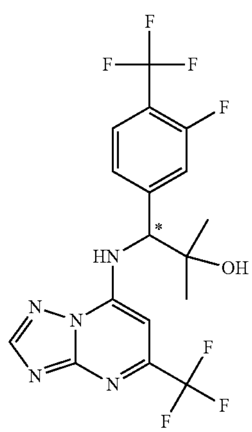 [SMILES: CC(C)(O)C(Nc1cc(C(F)(F)F)nc2ncnn12)c1ccc(C(F)(F)F)c(F)c1] | (S)- or (R)-1-(3-Fluoro-4-(trifluoromethyl)phenyl)-2-methyl-1-(5-(trifluoromethyl)-[1,2,4]triazolo[1,5-a]pyrimidin-7-ylamino)propan-2-ol | 438.0 | D | IA 21.2 × 150 mm, 5 μm |
| 215 | 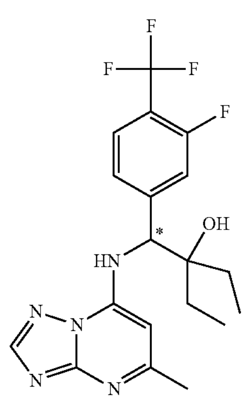 [SMILES: CCC(O)(CC)C(Nc1cc(C)nc2ncnn12)c1ccc(C(F)(F)F)c(F)c1] | (R)- or (S)-3-((3-Fluoro-4-(trifluoromethyl)phenyl)(5-methyl-[1,2,4]triazolo[1,5-a]pyrimidin-7-ylamino)methyl)pentan-3-ol | 412.2 | B | AXIA Packed 250 × 21.2 mm, 5 μm |

TABLE 9-continued

| Example # | Structure | IUPAC Name | Mass [M + H]+ | Coupling method | Chiral column |
|---|---|---|---|---|---|
| 216 | 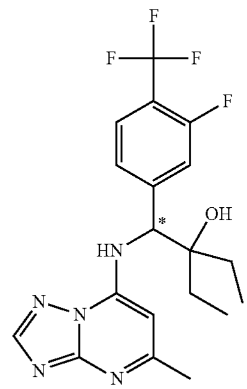 [SMILES: CCC(O)(CC)C(Nc1cc(C)nc2ncnn12)c1ccc(C(F)(F)F)c(F)c1] | (S)- or (R)-3-((3-Fluoro-4-(trifluoromethyl)phenyl)(5-methyl-[1,2,4]triazolo[1,5-a]pyrimidin-7-ylamino)methyl)pentan-3-ol | 412.3 | B | AXIA Packed 250 × 21.2 mm, 5 μm |
| 217 | 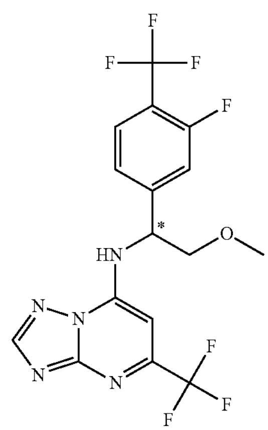 [SMILES: COCC(Nc1cc(C(F)(F)F)nc2ncnn12)c1ccc(C(F)(F)F)c(F)c1] | (R)- or (S)-N-(1-(3-Fluoro-4-(trifluoromethyl)phenyl)-2-methoxyethyl)-5-(trifluoromethyl)-[1,2,4]triazolo[1,5-a]pyrimidin-7-amine | 424.3 | B | AXIA Packed 250 × 21.2 mm, 5 μm |
| 218 | 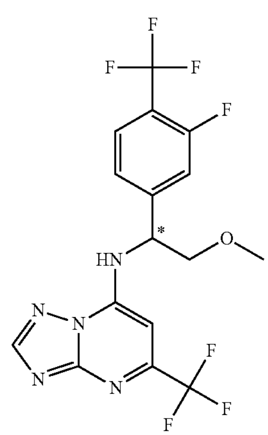 [SMILES: COCC(Nc1cc(C(F)(F)F)nc2ncnn12)c1ccc(C(F)(F)F)c(F)c1] | (S)- or (R)-N-(1-(3-Fluoro-4-(trifluoromethyl)phenyl)-2-methoxyethyl)-5-(trifluoromethyl)-[1,2,4]triazolo[1,5-a]pyrimidin-7-amine | 424.2 | B | AXIA Packed 250 × 21.2 mm, 5 μm |

TABLE 9-continued

| Example # | Structure | IUPAC Name | Mass [M + H]+ | Coupling method | Chiral column |
|---|---|---|---|---|---|
| 219 | 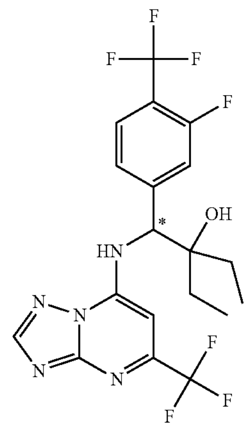 [SMILES: CCC(O)(CC)C(Nc1cc(C(F)(F)F)nc2ncnn12)c1ccc(C(F)(F)F)c(F)c1] | (R)- or (S)-3-((3-Fluoro-4-(trifluoromethyl)phenyl)(5-(trifluoromethyl)-[1,2,4]triazolo[1,5-a]pyrimidin-7-ylamino)methyl)pentan-3-ol | 466.3 | B | AXIA Packed 250 × 21.2 mm, 5 μm |
| 220 | 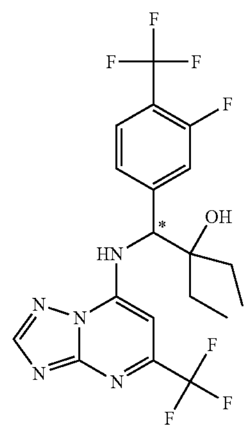 [SMILES: CCC(O)(CC)C(Nc1cc(C(F)(F)F)nc2ncnn12)c1ccc(C(F)(F)F)c(F)c1] | (S)- or (R)-3-((3-Fluoro-4-(trifluoromethyl)phenyl)(5-(trifluoromethyl)-[1,2,4]triazolo[1,5-a]pyrimidin-7-ylamino)methyl)pentan-3-ol | 466.3 | B | AXIA Packed 250 × 21.2 mm, 5 μm |
| 221 | 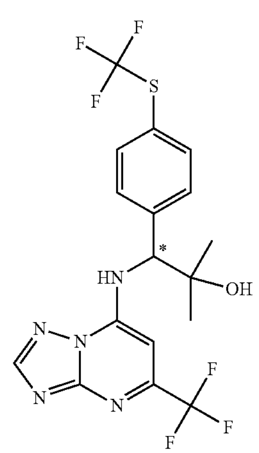 [SMILES: CC(C)(O)C(Nc1cc(C(F)(F)F)nc2ncnn12)c1ccc(SC(F)(F)F)cc1] | (R)- or (S)-2-Methyl-1-(5-(trifluoromethyl)-[1,2,4]triazolo[1,5-a]pyrimidin-7-ylamino)-1-(4-(trifluoromethylthio)phenyl)propan-2-ol | 452.0 | B | AXIA Packed 250 × 21.2 mm, 5 μm |

TABLE 9-continued

| Example # | Structure | IUPAC Name | Mass [M + H]+ | Coupling method | Chiral column |
|---|---|---|---|---|---|
| 222 | 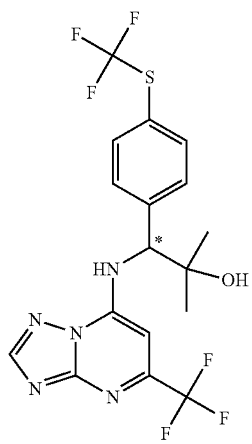 [SMILES: CC(C)(O)C(Nc1cc(C(F)(F)F)nc2ncnn12)c1ccc(SC(F)(F)F)cc1] | (S)- or (R)-2-Methyl-1-(5-(trifluoromethyl)-[1,2,4]triazolo[1,5-a]pyrimidin-7-ylamino)-1-(4-(trifluoromethylthio)phenyl)propan-2-ol | 452.0 | B | AXIA Packed 250 × 21.2 mm, 5 μm |
| 223 | 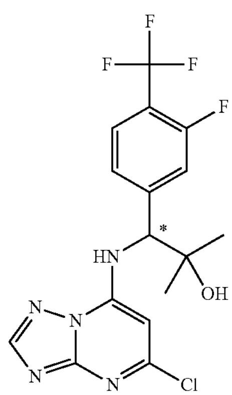 [SMILES: CC(C)(O)C(Nc1cc(Cl)nc2ncnn12)c1ccc(C(F)(F)F)c(F)c1] | (R)- or (S)-1-(5-Chloro-[1,2,4]triazolo[1,5-a]pyrimidin-7-ylamino)-1-(3-fluoro-4-(trifluoromethyl)phenyl)-2-methylpropan-2-ol | 404.0; 406.0 (M + 2 + H)+ | B | Chiralpak IA 2 × 25 cm, 5 μm |
| 224 | 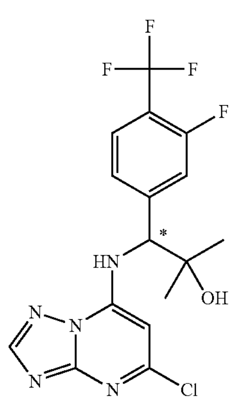 [SMILES: CC(C)(O)C(Nc1cc(Cl)nc2ncnn12)c1ccc(C(F)(F)F)c(F)c1] | (S)- or (R)-1-(5-Chloro-[1,2,4]triazolo[1,5-a]pyrimidin-7-ylamino)-1-(3-fluoro-4-(trifluoromethyl)phenyl)-2-methylpropan-2-ol | 404.0; 406.0 (M + 2 + H)+ | B | Chiralpak IA 2 × 25 cm, 5 μm |

TABLE 9-continued

| Example # | Structure | IUPAC Name | Mass [M + H]+ | Coupling method | Chiral column |
|---|---|---|---|---|---|
| 225 | 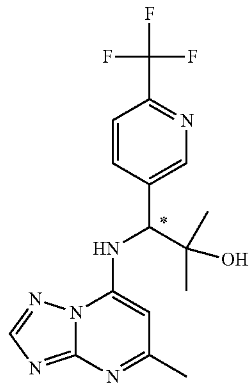 [SMILES: Cc1cc(NC(c2ccc(C(F)(F)F)nc2)C(C)(C)O)n2ncnc2n1] | (R)- or (S)-2-Methyl-1-(5-methyl-[1,2,4]triazolo[1,5-a]pyrimidin-7-ylamino)-1-(6-(trifluoromethyl)pyridin-3-yl)propan-2-ol | 367.1 | B | Chiralpak IA 2 × 25 cm, 5 μm |
| 226 | 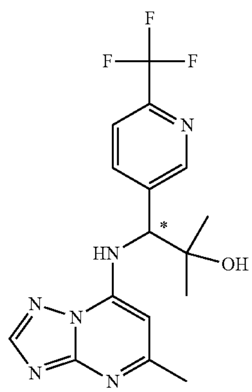 [SMILES: Cc1cc(NC(c2ccc(C(F)(F)F)nc2)C(C)(C)O)n2ncnc2n1] | (S)- or (R)-2-Methyl-1-(5-methyl-[1,2,4]triazolo[1,5-a]pyrimidin-7-ylamino)-1-(6-(trifluoromethyl)pyridin-3-yl)propan-2-ol | 367.0 | B | Chiralpak IA 2 × 25 cm, 5 μm |
| 227 | 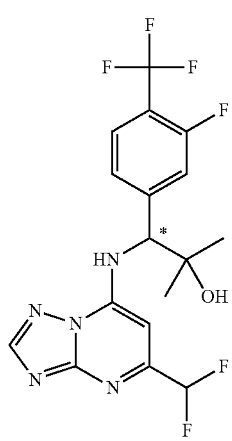 [SMILES: CC(C)(O)C(Nc1cc(C(F)F)nc2ncnn12)c1ccc(C(F)(F)F)c(F)c1] | (R)- or (S)-1-(5-(Difluoromethyl)-[1,2,4]triazolo[1,5-a]pyrimidin-7-ylamino)-1-(3-fluoro-4-(trifluoromethyl)phenyl)-2-methylpropan-2-ol | 420.0 | B | Chiralpak IA 2 × 25 cm, 5 μm |

TABLE 9-continued

| Example # | Structure | IUPAC Name | Mass [M + H]+ | Coupling method | Chiral column |
|---|---|---|---|---|---|
| 228 | 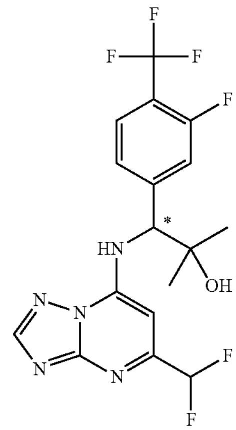 [SMILES: CC(C)(O)C(Nc1cc(C(F)F)nc2ncnn12)c1ccc(C(F)(F)F)c(F)c1] | (S)- or (R)-1-(5-(Difluoromethyl)-[1,2,4]triazolo[1,5-a]pyrimidin-7-ylamino)-1-(3-fluoro-4-(trifluoromethyl)phenyl)-2-methylpropan-2-ol | 420.0 | B | Chiralpak IA 2 × 25 cm, 5 μm |
| 229 | 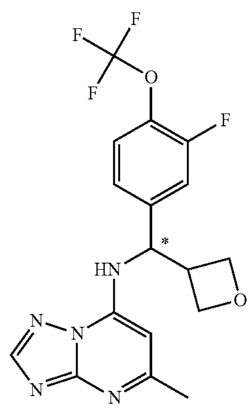 [SMILES: Cc1cc(NC(c2ccc(OC(F)(F)F)c(F)c2)C2COC2)n2ncnc2n1] | (R)- or (S)-N-((3-Fluoro-4-(trifluoromethoxy)phenyl)(oxetan-3-yl)methyl)-5-methyl-[1,2,4]triazolo[1,5-a]pyrimidin-7-amine | 398.0 | B | AXIA Packed 250 × 21.2 mm, 5 μm |
| 230 | 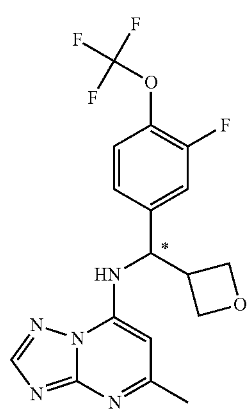 [SMILES: Cc1cc(NC(c2ccc(OC(F)(F)F)c(F)c2)C2COC2)n2ncnc2n1] | (S)- or (R)-N-((3-Fluoro-4-(trifluoromethoxy)phenyl)(oxetan-3-yl)methyl)-5-methyl-[1,2,4]triazolo[1,5-a]pyrimidin-7-amine | 398.0 | B | AXIA Packed 250 × 21.2 mm, 5 μm |

Coupling conditions: A. DIEA, NMP; B. DIEA, IPA; C. DIEA, EtOH; D. NMP, μW

Examples 231 and 232

(R or S)-2,2-Dimethyl-3-(3-methyl-4-(trifluoromethoxy)phenyl)-3-(5-methyl-[1,2,4]triazolo[1,5-a]pyrimidin-7-ylamino)propan-1-ol and (S or S)-3-(3-fluoro-4-(trifluoromethoxy)phenyl)-2,2-dimethyl-3-(5-methyl-[1,2,4]triazolo[1,5-a]pyrimidin-7-ylamino)propan-1-ol

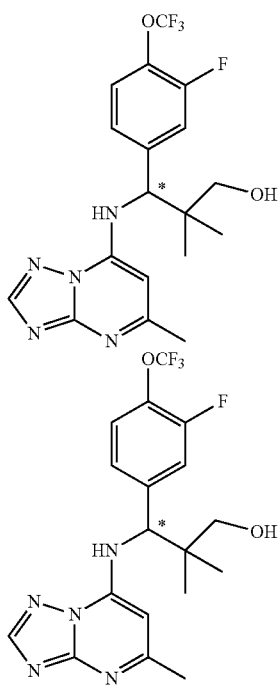

Step 1: 1-(3-Fluoro-4-(trifluoromethoxy)phenyl)-2-methylpropan-1-one

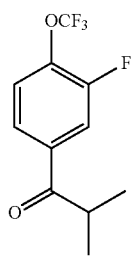 [SMILES: CC(C)C(=O)c1ccc(OC(F)(F)F)c(F)c1]

A mixture of magnesium (0.225 g, 9.27 mmol) and iodine (0.196 g, 0.772 mmol) in THF (40 mL) was purged with nitrogen for 3 times and stirred under nitrogen atmosphere at 25° C. This was followed by dropwise addition of 4-bromo-2-fluoro-1-(trifluoromethoxy)benzene (2.00 g, 7.72 mmol) in THF (40 mL) at 25° C. The reaction mixture was heated to reflux for 1 h under nitrogen atmosphere. The reaction mixture was cooled to 25° C. This was followed by the addition of N-methoxy-N-methylisobutyramide (0.709 g, 5.41 mmol) dropwise with stirring at room temperature for 2 h. The reaction mixture was quenched with sat'd. aqueous NH$_4$Cl (50 mL), extracted with ethyl acetate (3×50 mL). The combined organic layers were washed with water (2×50 mL) and brine (2×50 mL), dried over anhydrous Na$_2$SO$_4$ and filtered. The filtrate was concentrated under reduced pressure. The residue was purified by column chromatography over silica gel using gradient 0-10% of ethyl acetate in petroleum ether as eluent. The fractions containing desired product were combined and concentrated. The title compound was obtained as a liquid. $^1$H NMR (300 MHz, DMSO-d$_6$) δ: 8.09-8.04 (m, 1H), 7.95-7.91 (m, 1H), 7.77-7.71 (m, 1H), 3.72-3.63 (m, 1H), 1.84 (d, J=6.9 Hz, 6H).

Step 2: 1-(3-Fluoro-4-(trifluoromethoxy)phenyl)-2,2-dimethylpropane-1,3-diol

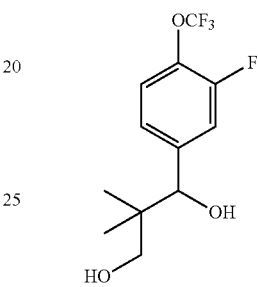

Formaldehyde (0.230 g, 7.67 mmol) was added to a solution of 1-(3-fluoro-4-(trifluoromethoxy)phenyl)-2-methylpropan-1-one (0.640 g, 2.56 mmol) and sodium hydroxide (0.307 g, 7.67 mmol) in ethanol (6 mL) at room temperature. The reaction mixture was stirred at 25° C. for 2 h. The reaction mixture was diluted with water (15 mL) and extracted with DCM (3×10 mL). The combined organic layers was washed with brine (3×20 mL), dried with anhydrous Na$_2$SO$_4$ and filtered. The filtrate was concentrated under reduced pressure. The residue was purified by column chromatography over silica gel using gradient 0-40% of ethyl acetate in petroleum ether as eluent. The title compound was obtained as a liquid. $^1$H NMR (400 MHz, DMSO-d$_6$) δ: 7.50-7.46 (m, 1H), 7.36-7.33 (m, 1H), 7.24-7.22 (m, 1H), 5.37 (d, J=4.4 Hz, 1H), 4.64 (t, J=5.2 Hz, 1H), 4.54 (d, J=4.0 Hz, 1H), 3.27-3.26 (m, 1H), 3.10-3.06 (m, 1H), 0.81 (s, 3H), 0.64 (s, 3H).

Step 3: 3-((tert-Butyldiphenylsilyl)oxy)-1-(3-fluoro-4-(trifluoromethoxy)phenyl)-2,2-dimethylpropan-1-ol

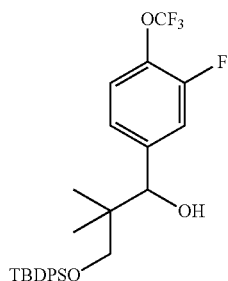

To a solution of 1-(3-fluoro-4-(trifluoromethoxy)phenyl)-2,2-dimethylpropane-1,3-diol (0.700 g, 2.48 mmol) and tert-butylchlorodiphenylsilane (0.818 g, 2.98 mmol) was added triethylamine (0.301 g, 2.98 mmol) and 4-dimethylaminopyridine (30.3 mg, 0.248 mmol) in anhydrous DCM (20 mL) at room temperature. The reaction mixture was stirred at 25° C. for 16 h. The reaction mixture was diluted with brine (30 mL), extracted with ethyl acetate (3×20 mL). The combined organic layers was washed with water (2×20 mL) and brine (2×20 mL), dried over anhydrous sodium sulfate and filtered. The filtrate was concentrated under reduced pressure. The residue was purified by column chromatography over silica gel using gradient 0-10% of ethyl acetate in petroleum ether as eluent. The title compound was obtained as a liquid. $^1$H NMR (400 MHz, DMSO-$d_6$) δ: 7.63-7.60 (m, 4H), 7.49-7.41 (m, 7H), 7.35-7.34 (m, 1H), 7.32-7.18 (m, 1H), 5.50 (d, J=4.0 Hz, 1H), 4.61 (d, J=4.0 Hz, 1H), 3.53-3.51 (m, 1H), 3.34-3.30 (m, 1H), 1.03 (s, 9H), 0.85 (s, 3H), 0.72 (s, 3H).

Step 4: 3-((tert-Butyldiphenylsilyl)oxy)-1-(3-fluoro-4-(trifluoromethoxy)phenyl)-2,2-dimethylpropan-1-one

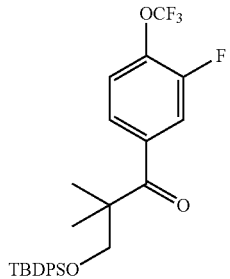

To a solution of 3-((tert-butyldiphenylsilyl)oxy)-1-(3-fluoro-4-(trifluoromethoxy)phenyl)-2,2-dimethylpropan-1-ol (0.350 g, 0.672 mmol) in DCM (15 mL) was added (1,1,1-triacetoxy)-1,1-dihydro-1,2-benziodoxol-3(1H)-one (0.428 g, 1.01 mmol) at room temperature. The reaction mixture was stirred at 25° C. for 2 h. The resulting mixture was filtered. The filter cake was washed with DCM (10.0 mL). The filtrate was concentrated under reduced pressure. The residue was purified by column chromatography over silica gel eluting with gradient 1-10% of ethyl acetate in petroleum ether. The title compound was obtained as a liquid. $^1$H NMR (400 MHz, DMSO-$d_6$) δ: 7.77-7.74 (m, 2H), 7.65-7.64 (m, 1H), 7.48-7.43 (m, 6H), 7.40-7.37 (m, 4H), 3.80 (s, 2H), 1.27 (s, 6H), 0.89 (s, 9H).

Step 5: 3-((tert-Butyldiphenylsilyl)oxy)-1-(3-fluoro-4-(trifluoromethoxy)phenyl)-2,2-dimethylpropan-1-amine

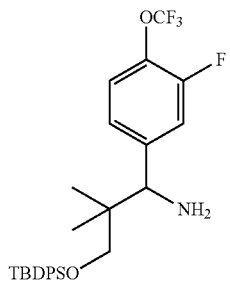

The title compound was prepared using procedures similar to those described in Step 3 of Preparatory Example 16 using 3-((tert-butyldiphenylsilyl)oxy)-1-(3-fluoro-4-(trifluoromethoxy)phenyl)-2,2-dimethylpropan-1-one to afford the title compound as a liquid which was used in the next step without further purification. MS (+ESI) m/z=520.1.

Step 6: N-(3-((tert-Butyldiphenylsilyl)oxy)-1-(3-fluoro-4-(trifluoromethoxy)phenyl)-2,2-dimethylpropyl)-5-methyl-[1,2,4]triazolo[1,5-a]pyrimidin-7-amine

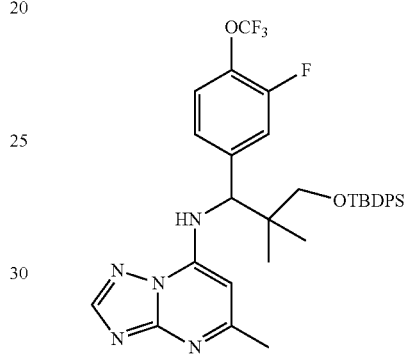

The title compound was prepared using procedures similar to those described in Step 1 of Preparatory Example 52 using 7-chloro-5-methyl-[1,2,4]triazolo[1,5-a]pyrimidine, 3-((tert-butyldiphenylsilyl)oxy)-1-(3-fluoro-4-(trifluoromethoxy)phenyl)-2,2-dimethylpropan-1-amine and N,N-diisopropylethylamine in anhydrous i-PrOH to afford the title compound as a liquid which was used in the next step without further purification. MS (+ESI) m/z=652.2.

Step 7: (R or S)- and (S or R)-3-(3-Fluoro-4-(trifluoromethoxy)phenyl)-2,2-dimethyl-3-((5-methyl-[1,2,4]triazolo[1,5-a]pyrimidin-7-yl)amino)propan-1-ol

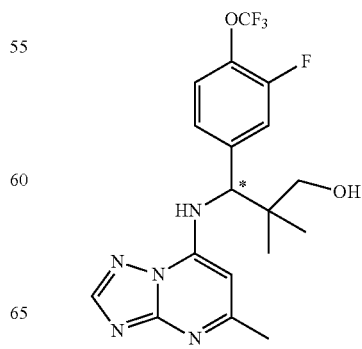

205
-continued

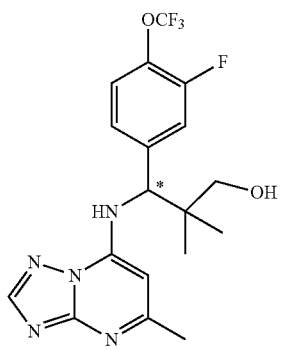

To a solution of N-(3-((tert-butyldiphenylsilyl)oxy)-1-(3-fluoro-4-(trifluoromethoxy)phenyl)-2,2-dimethylpropyl)-5-methyl-[1,2,4]triazolo[1,5-a]pyrimidin-7-amine (50.0 mg, 0.077 mmol) in THF (3 mL) was added tetrabutylammonium fluoride (1 M in THF, 0.384 mL, 0.384 mmol). The reaction mixture was stirred at 0° C. for 1 h. The reaction mixture was quenched with brine (15 mL) and extracted with ethyl acetate (3×15 mL). The combined organic layers were washed with water (2×15 mL), brine (2×15 mL), dried over anhydrous sodium sulfate and filtered. The filtrate was concentrated under reduced pressure. MS (+ESI) m/z=414.0. 3-(3-Fluoro-4-(trifluoromethoxy)phenyl)-2,2-dimethyl-3-((5-methyl-[1,2,4]triazolo[1,5-a]pyrimidin-7-yl) amino) propan-1-ol (21.0 mg, 0.051 mmol) was purified by Prep-HPLC with the following conditions: Column: X Union $C^{18}$, 20×150 mm, 5 um; Mobile Phase A: water/10 mM $NH_4HCO_3$; Mobile Phase B: ACN; Flow rate: 20 mL/min; Gradient: 20% B to 70% B in 10 min; 254 nm. The product was separated by Chiral-Prep-HPLC with the following conditions: Column: Chiralpak IC 2×25 cm, 5 um; Mobile Phase A: HPLC Hexane, Mobile Phase B: HPLC EtOH; Flow rate: 18 mL/min; Gradient: 15 B isocratic in 15 min; 254/220 nm. The faster-eluting enantiomer of the title compound (Example 231) was obtained at 11.57 min as a solid. MS (+ESI) m/z=414.0. $^1H$ NMR (300 MHz, MeOH-$d_4$) δ: 8.28 (s, 1H), 7.51-7.47 (m, 1H), 7.44-7.37 (m, 2H), 6.04 (s, 1H), 4.70 (s, 1H), 3.53 (d, J=11.1 Hz, 1H), 3.31 (d, J=11.4 Hz, 1H), 2.39 (s, 3H), 1.29 (s, 3H), 0.80 (s, 3H). The slower-eluting enantiomer of the title compound (Example 232) was obtained at 14.17 min as a solid. MS (+ESI) m/z=414.0. $^1H$ NMR (300 MHz, MeOH-$d_4$) δ: 8.28 (s, 1H), 7.50-7.47 (m, 1H), 7.44-7.39 (m, 2H), 6.04 (s, 1H), 4.78 (s, 1H), 3.53 (d, J=10.8 Hz, 1H), 3.31 (d, J=9.9 Hz, 1H), 2.39 (s, 3H), 1.29 (s, 3H), 0.80 (s, 3H).

Example 233

(R)—N-(1-(3-Fluoro-4-(trifluoromethyl)phenyl)-2,2-dimethylpropyl)-5-methoxy-[1,2,4]triazolo[1,5-a]pyrimidin-7-amine

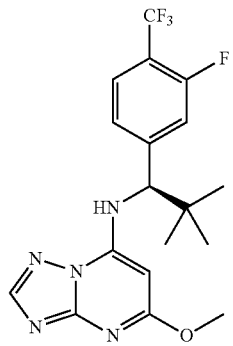 [SMILES: COc1cc(N[C@@H](c2ccc(C(F)(F)F)c(F)c2)C(C)(C)C)n2ncnc2n1]

Step 1: (R)-5-Chloro-N-(1-(3-fluoro-4-(trifluoromethyl)phenyl)-2,2-dimethylpropyl)-[1,2,4]triazolo[1,5-a]pyrimidin-7-amine

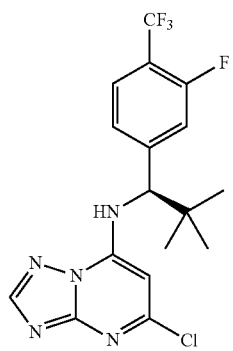 [SMILES: CC(C)(C)[C@@H](Nc1cc(Cl)nc2ncnn12)c1ccc(C(F)(F)F)c(F)c1]

The title compound was prepared using procedures similar to those described in Step 1 of Preparatory Example 52 using 5,7-dichloro-[1,2,4]triazolo[1,5-a]pyrimidine and (R)-1-(3-fluoro-4-(trifluoromethyl)phenyl)-2,2-dimethylpropan-1-amine hydrochloride in ethanol to afford the title compound as a solid. $^1H$ NMR (400 MHz, CDCl$_3$) δ: 8.37 (s, 1H), 7.67-7.63 (m, 1H), 7.22-7.15 (m, 2H), 6.81 (s, 1H), 5.82 (s, 1H), 4.33 (d, J=7.2 Hz, 1H), 1.12 (s, 9H).

Step 2: (R)—N-(1-(3-Fluoro-4-(trifluoromethyl)phenyl)-2,2-dimethylpropyl)-5-methoxy-[1,2,4]triazolo[1,5-a]pyrimidin-7-amine

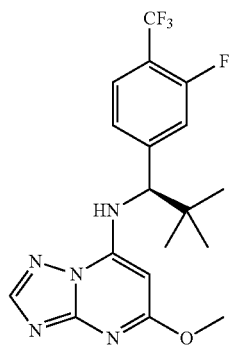 [SMILES: COc1cc(N[C@@H](c2ccc(C(F)(F)F)c(F)c2)C(C)(C)C)n2ncnc2n1]

To a solution of (R)-5-chloro-N-(1-(3-fluoro-4-(trifluoromethyl)phenyl)-2,2-dimethylpropyl)-[1,2,4]triazolo[1,5-a]pyrimidin-7-amine (50.0 mg, 0.1 mmol) in methanol (5 mL) was added sodium methanolate (30% in methanol, 0.1 mL, 0.6 mmol). The solution was stirred at 70° C. for 16 h. The mixture was cooled to room temperature and then diluted with ethyl acetate (40 mL). The mixture was washed with water (2×10 mL), brine (10 mL), dried with anhydrous sodium sulfate and filtered. The filtrate was concentrated under reduced pressure. The residue was purified with the following conditions: Column: X Bridge RP $C^{18}$, 19×150 mm, 5 um; Mobile Phase A: Water (0.05% TFA), Mobile Phase B: Acetonitrile; Flow rate: 20 mL/min; Gradient: isocratic 49% B in 14 min; Detector, UV 220 and 254 nm. The product was separated by Chiral-Prep-HPLC with the following conditions: Column: Phenomenex Lux 5u Cellulose-4, AXIA Packed 250×21.2 mm, 5 um; Mobile Phase A: Hexanes-HPLC, Mobile Phase B: IPA-HPLC; Flow rate: 20 mL/min; Gradient: isocratic 10% B in 25 min; Detector: 254/220 nm. The title compound was obtained as a solid. $^1$H NMR (400 MHz, DMSO-$d_6$) δ: 8.38 (s, 1H), 7.83-7.72 (m, 2H), 7.68-7.62 (m, 2H), 5.86 (s, 1H), 4.82 (d, J=6.8 Hz, 1H), 3.85 (s, 3H), 1.00 (s, 9H); MS (+ESI) m/z=398.2.

The following compounds in Table 10 were prepared using procedures similar to those described in Example 233 using appropriate starting materials.

TABLE 10

| Example # | Structure | IUPAC Name | Mass [M + H]$^+$ |
|---|---|---|---|
| 234 | 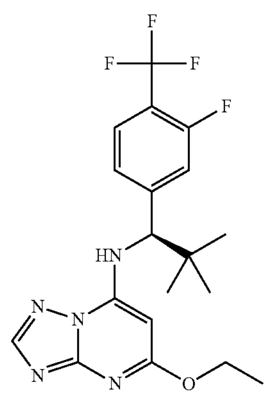 [SMILES: CCOc1cc(N[C@@H](c2ccc(C(F)(F)F)c(F)c2)C(C)(C)C)n2ncnc2n1] | (R)-5-Ethoxy-N-(1-(3-fluoro-4-(trifluoromethyl)phenyl)-2,2-dimethylpropyl)-[1,2,4]triazolo[1,5-a]pyrimidin-7-amine | 412.2 |
| 235 | 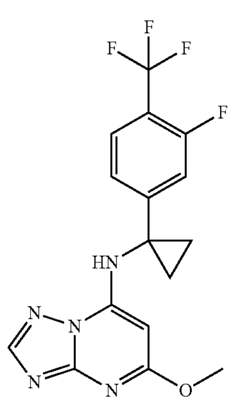 [SMILES: COc1cc(NC2(c3ccc(C(F)(F)F)c(F)c3)CC2)n2ncnc2n1] | N-(1-(3-Fluoro-4-(trifluoromethyl)phenyl)cyclopropyl)-5-methoxy-[1,2,4]triazolo[1,5-a]pyrimidin-7-amine | 368.0 |

Examples 236 and 237

(R)-1-(3-Fluoro-4-(trifluoromethyl)phenyl)-1-((5-methoxy-[1,2,4]triazolo[1,5-a]pyrimidin-7-yl)amino)-2-methylpropan-2-ol and (S)-1-(3-fluoro-4-(trifluoromethyl)phenyl)-1-((5-methoxy-[1,2,4]triazolo[1,5-a]pyrimidin-7-yl)amino)-2-methylpropan-2-ol

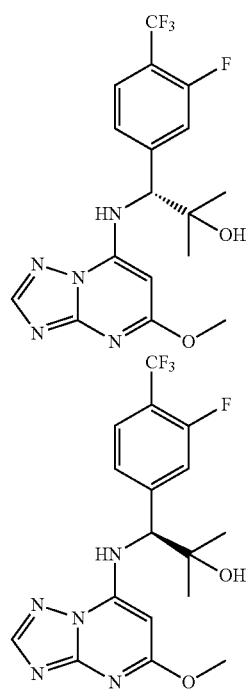

The title compound was prepared using procedures similar to those described in Step 2 of Example 233 using 1-((5-chloro-[1,2,4]triazolo[1,5-a]pyrimidin-7-yl)amino)-1-(3-fluoro-4-(trifluoromethyl) phenyl)-2-methylpropan-2-ol and sodium methanolate (30% in methanol) in 1,4-dioxane (1.5 mL) to afford the title compound as a liquid and was used in the next step without further purification. MS (+ESI) m/z=400.1. 1-(3-Fluoro-4-(trifluoromethyl)phenyl)-1-((5-methoxy-[1,2,4]triazolo[1,5-a]pyrimidin-7-yl)amino)-2-methylpropan-2-ol (40.0 mg, 0.100 mmol) was separated by Chiral prep-HPLC following the conditions: Column: Chiralpak IA 21.2×150 mm, 5 um; Mobile Phase A:Hex-HPLC, Mobile Phase B: EtOH-HPLC; Flow rate: 20 mL/min; Gradient: isocratic 10% B in 22 min; 254/220 nm. The faster-eluting enantiomer of the title compound (Example 236) was obtained at 9.43 min as a solid. MS (+ESI) m/z=400.0. $^1$H NMR (400 MHz, MeOH-$d_4$) δ: 8.25 (s, 1H), 7.69-7.65 (m, 1H), 7.49-7.46 (m, 2H), 5.59 (s, 1H), 4.67 (s, 1H), 3.91 (s, 3H), 1.45 (s, 3H), 1.10 (s, 3H). The slower-eluting enantiomer of the title compound (Example 237) was obtained at 19.7 min as a solid. MS (+ESI) m/z=400.0. $^1$H NMR (400 MHz, MeOH-$d_4$) δ: 8.25 (s, 1H), 7.69-7.65 (m, 1H), 7.49-7.46 (m, 2H), 5.59 (s, 1H), 4.67 (s, 1H), 3.91 (s, 3H), 1.45 (s, 3H), 1.10 (s, 3H).

Example 238

(R)-7-(1-(3-Fluoro-4-(trifluoromethyl)phenyl)-2,2-dimethylpropylamino)-[1,2,4]triazolo[1,5-a]pyrimidin-5-ol

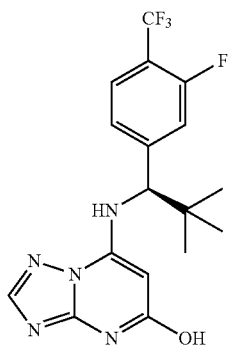 [SMILES: CC(C)(C)[C@@H](Nc1cc(O)nc2ncnn12)c1ccc(C(F)(F)F)c(F)c1]

To a solution of (R)—N-(1-(3-fluoro-4-(trifluoromethyl)phenyl)-2,2-dimethyl propyl)-5-methoxy-[1,2,4]triazolo[1,5-a]pyrimidin-7-amine (40.0 mg, 0.101 mmol) in MeCN (3 mL) were added trimethylchlorosilane (0.064 mL, 0.503 mmol) and sodium iodide (75.0 mg, 0.503 mmol) at room temperature. The resulted mixture was warmed to 70° C. and stirred for 4 h. The reaction mixture was cooled down to room temperature, diluted with water (30 mL) and extracted with ethyl acetate (3×30 mL). The combined organic layers was washed with brine (3×50 mL), dried over anhydrous sodium sulfate and filtered. The filtrate was concentrated under reduced pressure. The residue was purified by Prep-HPLC with the following conditions: Column: X select, 19×150 mm, 5 um; Mobile Phase A: Water/0.05% NH$_4$HCO$_3$, Mobile Phase B: ACN; Flow rate: 20 mL/min; Gradient: 20-70% B in 8 min; 254 nm. The collected fractions were combined and concentrated under vacuum. The residue was purified by Chiral-Prep-HPLC with the following conditions: Column: Chiralpak IC 2×25 cm, 5 um; Mobile Phase A: Hex-HPLC, Mobile Phase B: IPA-HPLC; Flow rate: 18 mL/min; Gradient: isocratic 25% B in 15.5 min; 254/220 nm. The title compound was obtained at 12.8 min as a solid. MS (+ESI) m/z=384.1. $^1$H NMR (400 MHz, CD$_3$OD) δ: 8.09 (s, 1H), 7.70-7.68 (m, 1H), 7.48-7.41 (m, 2H), 4.87 (s, 1H), 4.54 (s, 1H), 1.08 (s, 9H).

Example 239

N$^7$-(1-(3-Fluoro-4-(trifluoromethyl)phenyl)cyclopropyl)-N,N-dimethyl-[1,2,4]triazolo[1,5-a]pyrimidine-5,7-diamine

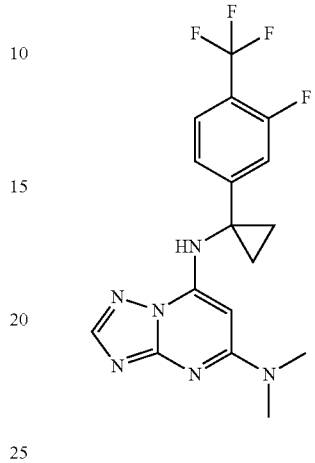

To a solution of 5-chloro-N-(1-(3-fluoro-4-(trifluoromethyl)phenyl)cyclopropyl)-[1,2,4]triazolo[1,5-a]pyrimidin-7-amine (40.0 mg, 0.1 mmol) in EtOH (3 mL) were added dimethylamine (14.6 mg, 0.3 mmol) and DIEA (0.113 mL, 0.6 mmol) at room temperature. The resulted mixture was heated to 90° C. and stirred for 16 h. The reaction mixture was cooled down to room temperature, diluted with water (30 mL) and extracted with ethyl acetate (3×30 mL). The combined organic layers were washed with brine (3×50 mL), dried over anhydrous sodium sulfate and filtered. The filtrate was concentrated under reduced pressure. The residue was purified by Prep-HPLC with the following conditions: Column: X Select CSH Prep C$^{18}$ OBD Column 19×150 mm 5 um; Mobile Phase A: Water (10 mmol NH$_4$HCO$_3$), Mobile Phase B: Acetonitrile; Flow rate: 20 mL/min; Gradient: 15-95% B in 8 min; 254 nm. The collected fractions were combined and concentrated under reduced pressure. The title compound was obtained as a solid. $^1$H NMR (400 MHz, DMSO-d$_6$) δ: 8.83 (s, 1H), 8.13 (s, 1H), 7.71-7.59 (m, 1H), 7.30 (d, J=12.8 Hz, 1H), 7.27 (d, J=8.4 Hz, 1H), 5.28 (s, 1H), 2.97 (s, 6H), 1.59-1.52 (m, 4H); MS (+ESI) m/z=381.1.

The following compounds in Table 11 were prepared using procedures similar to those described in Example 239 using appropriate starting materials.

TABLE 11

| Example # | Structure | IUPAC Name | Mass [M + H]$^+$ |
|---|---|---|---|
| 240 | 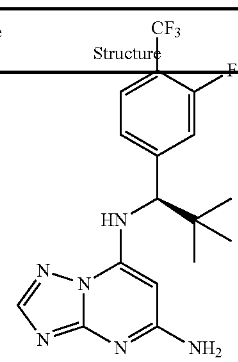 | (R)-N$^7$-(1-(3-Fluoro-4-(trifluoromethyl)phenyl)-2,2-dimethylpropyl)-[1,2,4]triazolo[1,5-a]pyrimidine-5,7-diamine | 383.1 |

TABLE 11-continued

| Example # | Structure | IUPAC Name | Mass [M + H]+ |
|---|---|---|---|
| 241 | 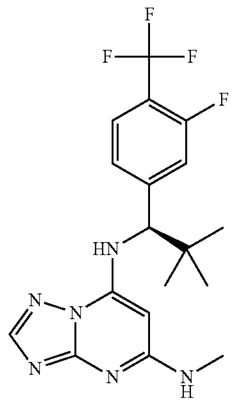 [SMILES: CNc1cc(N[C@@H](c2ccc(C(F)(F)F)c(F)c2)C(C)(C)C)n2ncnc2n1] | (R)-N7-(1-(3-Fluoro-4-(trifluoromethyl)phenyl)-2,2-dimethylpropyl)-N5-methyl-[1,2,4]triazolo[1,5-a]pyrimidine-5,7-diamine | 397.2 |
| 242 | 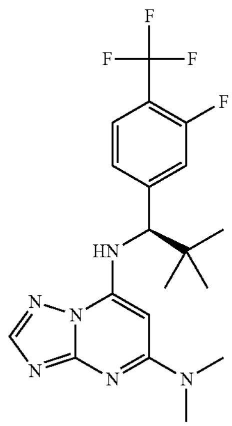 [SMILES: CN(C)c1cc(N[C@@H](c2ccc(C(F)(F)F)c(F)c2)C(C)(C)C)n2ncnc2n1] | (R)-N7-(1-(3-Fluoro-4-(trifluoromethyl)phenyl)-2,2-dimethylpropyl)-N5,N5-dimethyl-[1,2,4]triazolo[1,5-a]pyrimidine-5,7-diamine | 411.2 |

Examples 243 and 244

(R)-1-(5-(Dimethylamino)-[1,2,4]triazolo[1,5-a]pyrimidin-7-ylamino)-1-(3-fluoro-4-(trifluoromethyl)phenyl)-2-methylpropan-2-ol and (S)-1-(5-(Dimethylamino)-[1,2,4]triazolo[1,5-a]pyrimidin-7-ylamino)-1-(3-fluoro-4-(trifluoromethyl)phenyl)-2-methylpropan-2-ol

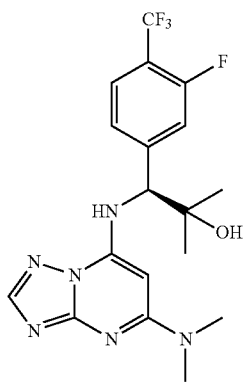

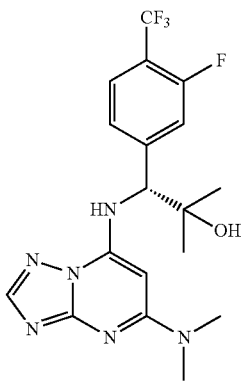

The title compounds were prepared using procedures similar to those described in Step 1 of Example 239 using 1-((5-chloro-[1,2,4]triazolo[1,5-a]pyrimidin-7-yl)amino)-1-(3-fluoro-4-(trifluoromethyl) phenyl)-2-methylpropan-2-ol, dimethylamine hydrochloride and DIEA in 1,4-dioxane to afford the title compound as a liquid. MS (+ESI) m/z=413.3. 1-((5-(Dimethylamino)-[1,2,4]triazolo[1,5-a]pyrimidin-7-yl)amino)-1-(3-fluoro-4-(trifluoromethyl) phenyl)-2-methylpropan-2-ol (50.0 mg, 0.121 mmol) was separated by Chiral prep-HPLC following the conditions: Column: Phenomenex Lux 5u Cellulose-4, AXIA Packed 250×21.2 mm, 5 um; Mobile Phase A:Hex-HPLC, Mobile Phase B: EtOH-HPLC; Flow rate: 20 mL/min; Gradient: isocratic 30% B in 10 min; 254/220 nm. The faster-eluting enantiomer of the title compound (Example 243) was obtained at 25.70 min as a solid. MS (+ESI) m/z=413.1. $^1$H NMR (400 MHz, MeOH-$d_4$) δ: 8.06 (s, 1H), 7.69-7.65 (m, 1H), 7.50-7.48 (m, 2H), 5.28 (s, 1H), 4.69 (s, 1H), 3.04 (s, 6H), 1.46 (s, 3H), 1.12 (s, 3H). The slower-eluting enantiomer of the title compound (Example 244) was obtained at 39.92 min as a solid. MS (+ESI) m/z=413.1. $^1$H NMR (400 MHz, MeOH-$d_4$) δ: 8.06 (s, 1H), 7.69-7.65 (m, 1H), 7.50-7.48 (m, 2H), 5.28 (s, 1H), 4.69 (s, 1H), 3.04 (s, 6H), 1.46 (s, 3H), 1.12 (s, 3H).

Example 245

3-(7-((1-(3-Fluoro-4-(trifluoromethyl)phenyl)cyclopropyl)amino)-[1,2,4]triazo[1,5-a]pyrimidin-5-yl)propan-1-ol

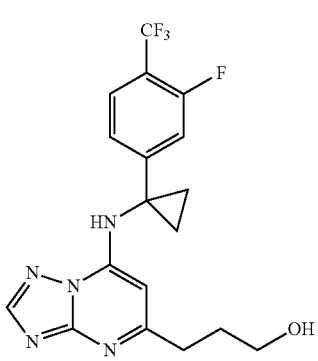 [SMILES: OCCCc1cc(NC2(c3ccc(C(F)(F)F)c(F)c3)CC2)n2ncnc2n1]

Step 1: (E)-5-(3-((tert-Butyldimethylsilyl)oxy)prop-1-en-1-yl)-N-(1-(3-fluoro-4-(trifluoromethyl)phenyl)cyclopropyl)-[1,2,4]triazolo[1,5-a]pyrimidin-7-amine

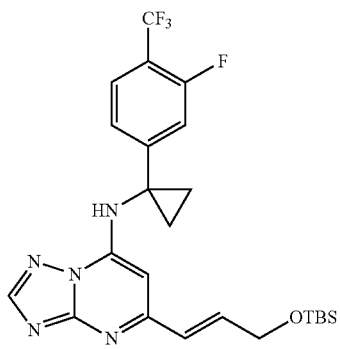 [SMILES: CC(C)(C)[Si](C)(C)OC/C=C/c1cc(NC2(c3ccc(C(F)(F)F)c(F)c3)CC2)n2ncnc2n1]

To a mixture of 5-chloro-N-(1-(3-fluoro-4-(trifluoromethyl)phenyl)cyclopropyl)-[1,2,4]triazolo[1,5-a]pyrimidin-7-amine (0.200 g, 0.538 mmol) in 1,4-dioxane (1 mL) and water (0.4 mL) were added (E)-tert-butyldimethyl((3-(4,4,5,5-tetramethyl-1,3,2-dioxaborolan-2-yl)allyl)oxy)silane (0.321 g, 1.08 mmol) and NaHCO$_3$ (0.136 g, 1.61 mmol). The reaction mixture was purged with nitrogen 3 times, then to the mixture was added Pd(dppf)Cl$_2$ (79.0 mg, 0.108 mmol). The reaction mixture was purged with nitrogen 3 times again and stirred under nitrogen atmosphere at 80° C. for 6 h. Then the reaction mixture was cooled, diluted with saturated aqueous NH$_4$Cl solution (100 mL) and extracted with ethyl acetate (3×20 mL). The combined organic layers was washed with brine (3×20 mL), dried over anhydrous sodium sulfate and filtered. The filtrate was concentrated under reduced pressure. The residue was purified by column chromatography over silica gel using gradient 0-50% of ethyl acetate in petroleum ether as eluent. The title compound was obtained as a solid. MS (+ESI) m/z=508.3.

Step 2: 5-(3-((tert-Butyldimethylsilyl)oxy)propyl)-N-(1-(3-fluoro-4-(trifluoromethyl)phenyl) cyclopropyl)-[1,2,4]triazolo[1,5-a]pyrimidin-7-amine

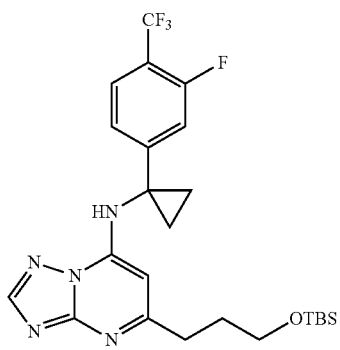 [SMILES: CC(C)(C)[Si](C)(C)OCCCc1cc(NC2(c3ccc(C(F)(F)F)c(F)c3)CC2)n2ncnc2n1]

To a solution of (E)-5-(3-((tert-butyldimethylsilyl)oxy)prop-1-en-1-yl)-N-(1-(3-fluoro-4-(trifluoromethyl)phenyl)cyclopropyl)-[1,2,4]triazolo[1,5-a]pyrimidin-7-amine (0.140 g, 0.276 mmol) in EtOAc (7 mL) was added Pd—C (73.4 mg, 0.069 mmol). The reaction mixture was purged with H$_2$ for 3 times and stirred under H$_2$ atmosphere at 25° C. for 16 h. The resulting mixture was filtered and the filtrate was concentrated under reduced pressure. The title compound was obtained as a solid which was used in the next step without further purification. MS (+ESI) m/z=510.3.

Step 3: 3-(7-((1-(3-Fluoro-4-(trifluoromethyl)phenyl)cyclopropyl)amino)-[1,2,4]triazolo[1,5-a]pyrimidin-5-yl)propan-1-ol

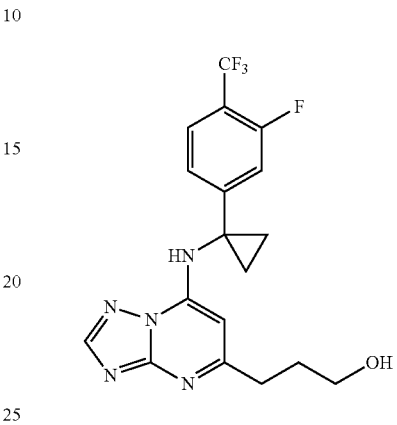

To a solution of 5-(3-((tert-butyldimethylsilyl)oxy)propyl)-N-(1-(3-fluoro-4-(trifluoromethyl)phenyl) cyclopropyl)-[1,2,4]triazolo[1,5-a]pyrimidin-7-amine (0.100 g, 0.196 mmol) in THF (2.5 mL) was added TBAF (1.0 M in THF, 0.196 mL, 0.196 mmol) at 0° C. The resulting solution was stirred for 16 h at room temperature. Then the reaction mixture was diluted with brine (50 mL) and extracted with ethyl acetate (3×50 mL). The combined organic layers was washed with brine (3×100 mL), dried over anhydrous sodium sulfate and filtered. The filtrate was concentrated under reduced pressure. The residue was purified by Prep-HPLC with the following conditions: Column: X Bridge C$^{18}$, 19×150 mm, 5 um; Mobile Phase A: Water/0.2 mM NH$_4$HCO$_3$, Mobile Phase B: ACN; Flow rate: 20 mL/min; Gradient: 3% B to 45% B in 10 min; 254 nm. The title compound was obtained as a solid. MS (+ESI) m/z=396.2. $^1$H NMR (400 MHz, MeOH-d$_4$) δ: ppm 8.32 (s, 1H), 7.61-7.56 (m, 1H), 7.21-7.15 (m, 2H), 6.19 (s, 1H), 3.64 (t, J=6.0 Hz, 2H), 2.83 (t, J=7.5 Hz, 2H), 1.91-1.83 (m, 2H), 1.70-1.60 (m, 4H).

Example 246

(N-(1-(3-Fluoro-4-(trifluoromethyl)phenyl)cyclopropyl)-N,5-dimethyl-[1,2,4]triazolo[1,5-a]pyrimidin-7-amine

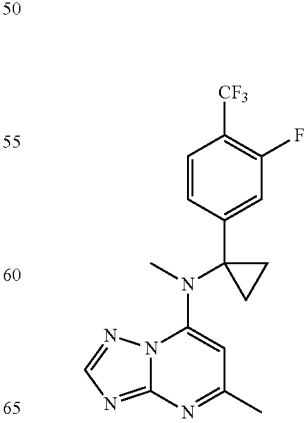

Step 1: N-(1-(3-Fluoro-4-(trifluoromethyl)phenyl)cyclopropyl)-5-methyl-[1,2,4]triazolo[1,5-a]pyrimidin-7-amine

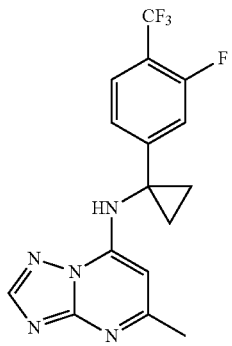 [SMILES: Cc1cc(NC2(c3ccc(C(F)(F)F)c(F)c3)CC2)n2ncnc2n1]

The title compound was prepared using procedures similar to those described in Step 1 of Example 191 using 7-chloro-5-methyl-[1,2,4]triazolo[1,5-a]pyrimidine and 1-(3-fluoro-4-(trifluoromethyl) phenyl)cyclopropanamine hydrochloride to afford the title compound as a solid. MS (+ESI) m/z=352.1.

Step 2: (N-(1-(3-Fluoro-4-(trifluoromethyl)phenyl)cyclopropyl)-N,5-dimethyl-[1,2,4]triazolo[1,5-a]pyrimidin-7-amine

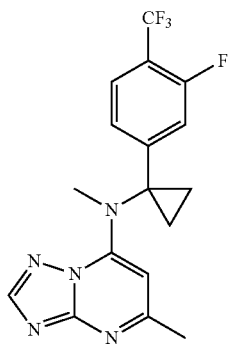 [SMILES: Cc1cc(N(C)C2(c3ccc(C(F)(F)F)c(F)c3)CC2)n2ncnc2n1]

To the mixture of N-(1-(3-fluoro-4-(trifluoromethyl)phenyl)cyclopropyl)-5-methyl-[1,2,4]triazolo [1,5-a]pyrimidin-7-amine (50.0 mg, 0.1 mmol) in THF (2 mL) was added potassium 2-methylpropan-2-olate (14.4 mg, 0.1 mmol). The final reaction mixture was stirred for 10 min at 25° C. This was followed by the addition of iodomethane (22.2 mg, 0.2 mmol). The reaction mixture was stirred at 25° C. for 24 h. The resulting mixture was diluted with water (10 mL) and extracted with ethyl acetate (3×10 mL). The combined organic layers was washed with water (3×10 mL), brine (3×10 mL), dried over anhydrous sodium sulfate and filtered. The filtrate was concentrated under reduced pressure. The crude product was purified by Prep-HPLC with the following conditions: Column: X Bridge $C^{18}$, 19×150 mm, 5 um; Mobile Phase A: Water (0.05% ammonium bicarbonate), Mobile Phase B: acetonitrile; Flow rate: 20 mL/min; Gradient: 37-52% B in 14 min; 254 nm. The collected fractions were combined and concentrated under reduced pressure. The title compound was obtained as a solid. $^1$H NMR (300 MHz, $CD_3OD$) δ: 8.18 (s, 1H), 7.66-7.51 (m, 1H), 7.14-7.09 (m, 2H), 6.19 (s, 1H), 3.68 (s, 3H), 2.42 (s, 3H), 1.70-1.58 (m, 4H); MS (+ESI) m/z=366.3.

The following compounds in Table 12 were prepared using procedures similar to those described in Example 246 using appropriate starting materials. Racemic products were separated using chiral columns specified in the table. For those pairs of enantiomers, the faster eluting isomer is always listed first in this table.

TABLE 12

| Example # | Structure | IUPAC Name | Mass [M + H]⁺ | Chiral column |
|---|---|---|---|---|
| 247 | 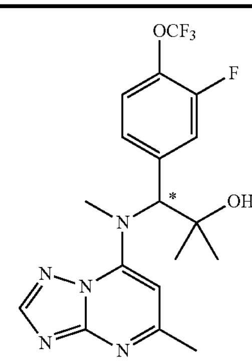 | (R)- or (S)-1-(3-Fluoro-4-(trifluoromethoxy)phenyl)-2-methyl-1-(methyl(5-methyl-[1,2,4]triazolo[1,5-a]pyrimidine-7-yl)amino)propan-2-ol | 414.0 | Chiralpak IC 2 × 25 cm, 5 um |

TABLE 12-continued

| Example # | Structure | IUPAC Name | Mass [M + H]+ | Chiral column |
|---|---|---|---|---|
| 248 | (structure shown) | (S)- or (R)-1-(3-Fluoro-4-(trifluoromethoxy)phenyl)-2-methyl-1-(methyl(5-methyl-[1,2,4]triazolo[1,5-a]pyrimidine-7-yl)amino)propan-2-ol | 414.0 | Chiralpak IC 2 × 25 cm, 5 um |

Example 249

(R)-3-(7-(1-(3-Fluoro-4-(trifluoromethyl)phenyl)-2,2-dimethylpropylamino)-5-methyl-[1,2,4]triazolo[1,5-a]pyrimidin-2-yl)propan-1-ol

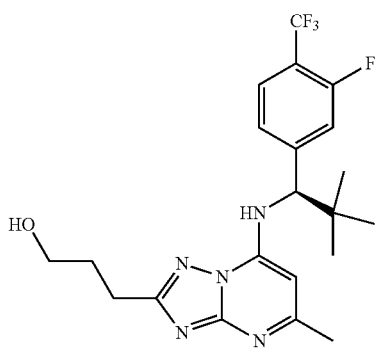 [SMILES: Cc1cc(N[C@@H](c2ccc(C(F)(F)F)c(F)c2)C(C)(C)C)n2nc(CCCO)nc2n1]

Step 1: Ethyl 3-(7-hydroxy-5-methyl-[1,2,4]triazolo[1,5-a]pyrimidin-2-yl)propanoate

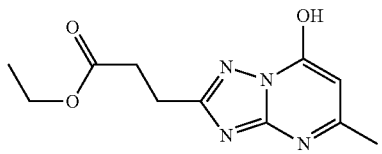 [SMILES: CCOC(=O)CCc1nc2nc(C)cc(Cl)n2n1]

To a mixture of 2,3-diamino-6-methylpyrimidin-4(3H)-one (0.200 g, 1.4 mmol) in dioxane (2 mL) and DMF (0.5 mL) was added ethyl 4-chloro-4-oxobutanoate (0.352 g, 2.1 mmol). The reaction mixture was stirred at 100° C. for 16 h and then cooled to room temperature. The mixture was concentrated under reduced pressure. The residue was purified by column chromatography over silica gel eluting with isocratic 12% methanol in dichloromethane. The fractions containing desired product were combined and concentrated. The title compound was obtained as a solid. MS (+ESI) m/z=251.1.

Step 2: Ethyl 3-(7-chloro-5-methyl-[1,2,4]triazolo[1,5-a]pyrimidin-2-yl)propanoate

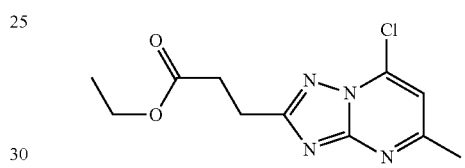

The title compound was prepared using procedures similar to those described in Step 2 of Preparatory Example 7 using ethyl 3-(7-hydroxy-5-methyl-[1,2,4]triazolo[1,5-a]pyrimidin-2-yl) propanoate and phosphoryl trichloride to afford the title compound as a solid which was used in the next step without further purification. MS (+ESI) m/z=269.1; 271.1.

Step 3: (R)-Ethyl 3-(7-(1-(3-fluoro-4-(trifluoromethyl)phenyl)-2,2-dimethylpropylamino)-5-methyl[1,2,4]triazolo[1,5-a]pyrimidin-2-yl)propanoate

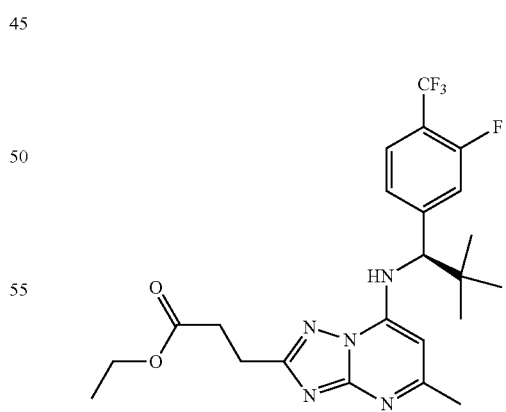

The title compound was prepared using procedures similar to those described in Step 1 of Example 191 using ethyl 3-(7-chloro-5-methyl-[1,2,4]triazolo[1,5-a]pyrimidin-2-yl) propanoate and (R)-1-(3-fluoro-4-(trifluoromethyl)phenyl)-2,2-dimethylpropan-1-amine hydrochloride to afford the title compound as a liquid. MS (+ESI) m/z=482.3.

Step 4: (R)-3-(7-(1-(3-Fluoro-4-(trifluoromethyl) phenyl)-2,2-dimethylpropylamino)-5-methyl-[1,2,4]triazolo[1,5-a]pyrimidin-2-yl)propan-1-ol

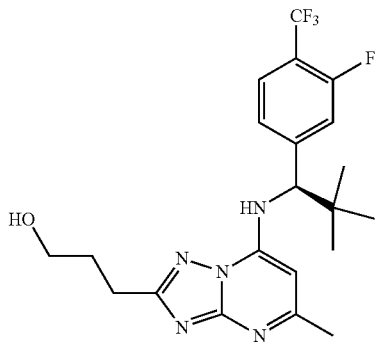 [SMILES: Cc1cc(N[C@@H](c2ccc(C(F)(F)F)c(F)c2)C(C)(C)C)n2nc(CCCO)nc2n1]

To a mixture of (R)-ethyl 3-(7-((1-(3-fluoro-4-(trifluoromethyl)phenyl)-2,2-dimethylpropyl)amino)-5-methyl-[1,2,4]triazolo[1,5-a]pyrimidin-2-yl)propanoate (50.0 mg, 0.104 mmol) in methanol (2 mL) was added NaBH$_4$ (79.0 mg, 2.08 mmol). The reaction mixture was stirred at 25° C. for 2 h. The resulting mixture was quenched by water (10 mL) and extracted with ethyl acetate (3×10 mL). The combined organic layers were washed with brine (10 mL), dried over anhydrous sodium sulfate and filtered. The filtrate was concentrated under reduced pressure. The crude product was purified by Prep-HPLC with the following conditions: Instrument, GILSON (GX-281); Column: Xbridge RP[18], 5 um, 19×150 mm; mobile phase: water (0.05% NH$_4$HCO$_3$) and acetonitrile (30% acetonitrile up to 62% in 10 min, hold 100% for 2 min, down to 30% in 2 min); Detector, UV 220 and 254 nm. The fractions containing desired product were combined and concentrated. The title compound was obtained as a solid. $^1$H NMR (400 MHz, CD$_3$OD) δ: 7.73-7.69 (m, 1H), 7.55-7.48 (m, 2H), 6.17 (s, 1H), 4.78 (s, 1H), 3.70 (t, J=6.4 Hz, 2H), 3.00 (t, J=7.6 Hz, 2H), 2.45 (s, 3H), 2.13-2.06 (m, 2H), 1.14 (s, 9H); MS (+ESI) m/z=440.2.

Example 250

(R)-2-(7-(1-(3-Fluoro-4-(trifluoromethyl)phenyl)-2,2-dimethylpropylamino)-5-methyl-[1.2.4]triazolo[1,5-a]pyrimidin-2-yl)ethanol

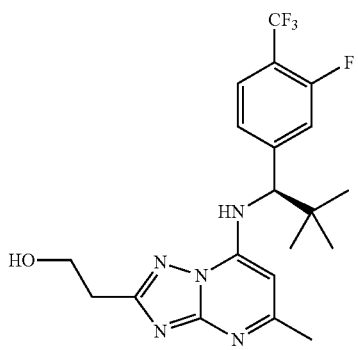 [SMILES: Cc1cc(N[C@@H](c2ccc(C(F)(F)F)c(F)c2)C(C)(C)C)n2nc(CCO)nc2n1]

The following example was prepared using similar procedures as in Example 260 using ethyl 2-(7-chloro-5-methyl-[1,2,4]triazolo[1,5-a]pyrimidin-2-yl)acetate and the appropriate starting materials. LC-MS (+ESI) m/z=426.2.

Example 251

2-(7-(1-(3-Fluoro-4-(trifluoromethyl)phenyl)cyclopropylamino)-[1,2,4]triazolo[1,5-a]pyrimidin-5-yl)ethanol

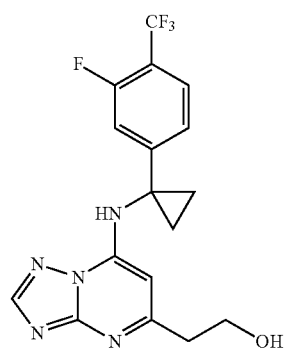 [SMILES: OCCc1cc(NC2(c3ccc(C(F)(F)F)c(F)c3)CC2)n2ncnc2n1]

Step 1: Methyl 2-(7-hydroxy-[1,2,4]triazolo[1,5-a]pyrimidin-5-yl)acetate

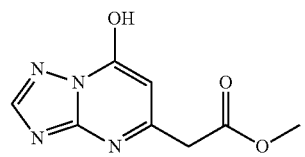

The title compound was prepared using procedures similar to those described in Step 1 of Preparatory Example 7 using 2H-1,2,4-triazol-3-amine and dimethyl 3-oxopentanedioate to afford the title compound as a solid. MS (+ESI) m/z=209.1.

Step 2: Methyl 2-(7-chloro-[1,2,4]triazolo[1,5-a]pyrimidin-5-yl)acetate

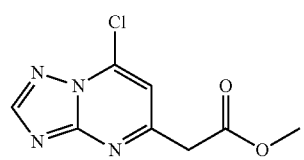

The title compound was prepared using procedures similar to those described in Step 2 of Preparatory Example 7 using methyl 2-(7-hydroxy-[1,2,4]triazolo[1,5-a]pyrimidin-5-yl)acetate to afford the title compound as a liquid. MS (+ESI) m/z=227.1; 229.1 (M+2+H)$^+$.

221

Step 3: Methyl 2-(7-(1-(3-fluoro-4-(trifluoromethyl)phenyl)cyclopropylamino)-[1,2,4]triazolo[1,5-a]pyrimidin-5-yl)acetate

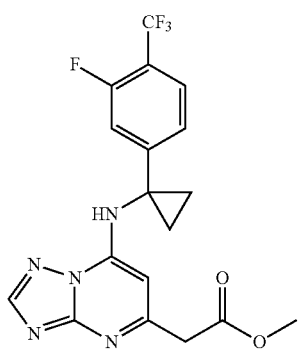 [SMILES: COC(=O)Cc1cc(NC2(c3ccc(C(F)(F)F)c(F)c3)CC2)n2ncnc2n1]

The title compound was prepared using procedures similar to those described in Step 1 of Example 191 using methyl 2-(7-chloro-[1,2,4]triazolo[1,5-a]pyrimidin-5-yl)acetate and 1-(3-fluoro-4-(trifluoromethyl)phenyl)cyclopropanamine hydrochloride to afford the title compound as a liquid. MS (+ESI) m/z=410.3.

Step 4: 2-(7-(1-(3-Fluoro-4-(trifluoromethyl)phenyl)cyclopropylamino)-[1,2,4]triazolo[1,5-a]pyrimidin-5-yl)ethanol

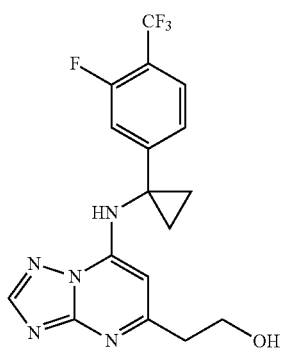 [SMILES: OCCc1cc(NC2(c3ccc(C(F)(F)F)c(F)c3)CC2)n2ncnc2n1]

The title compound was prepared using procedures similar to those described in Step 4 of Example 249 using methyl 2-(7-(1-(3-fluoro-4-(trifluoromethyl)phenyl)cyclopropylamino)-[1,2,4]triazolo[1,5-a]pyrimidin-5-yl)acetate to afford the title compound as a liquid. $^1$H NMR (400 MHz, CD$_3$OD-d$_4$) δ: 8.38 (s, 1H), 7.66-7.56 (m, 1H), 7.25-7.21 (m, 2H), 6.29 (s, 1H), 3.91 (t, J=6.2 Hz, 2H), 2.92 (t, J=6.4 Hz, 2H), 1.70-1.63 (m, 4H); MS (+ESI) m/z=382.2.

Example 252

1-(3-Fluoro-4-(trifluoromethyl)phenyl)-2-methyl-N-(5-methyl-[1,2,4]triazolo[1,5-a]pyrimidin-7-yl)propane-1,2-diamine

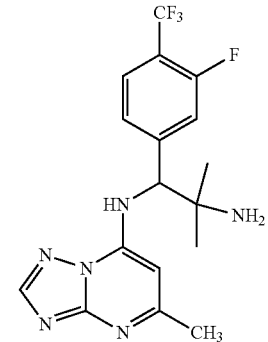 [SMILES: Cc1cc(NC(c2ccc(C(F)(F)F)c(F)c2)C(C)(C)N)n2ncnc2n1]

Step 1: 1-(3-Fluoro-4-(trifluoromethyl)phenyl)-2-methyl-2-nitropropan-1-ol

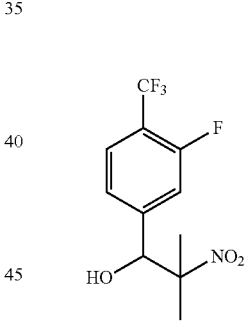

To a mixture of 3-fluoro-4-(trifluoromethyl)benzaldehyde (1.00 g, 5.2 mmol) in toluene (4 mL) was added 2-nitropropane (1.86 g, 20.8 mmol). This was followed by the addition of TEA (1.58 g, 15.6 mmol). The reaction solution was stirred at 40° C. for 3 h. The reaction mixture was cooled, diluted with water (10 mL) and extracted with ethyl acetate (3×10 mL). The combined organic layers was washed with brine (10 mL), dried over anhydrous sodium sulfate and filtered. The filtrate was concentrated under reduced pressure. The residue was purified by column chromatography over silica gel eluting with isocratic 20% ethyl acetate in petroleum ether. The fractions containing desired product were combined and concentrated. The title compound was obtained as a solid. $^1$H NMR (300 MHz, DMSO-d$_6$) δ: 7.85-7.73 (m, 1H), 7.51-7.42 (m, 2H), 6.44 (d, J=4.8 Hz, 1H), 5.23 (d, J=4.8 Hz, 1H), 1.41 (d, J=3.9 Hz, 6H).

Step 2: 2-Amino-1-(3-fluoro-4-(trifluoromethyl) phenyl)-2-methylpropan-1-ol

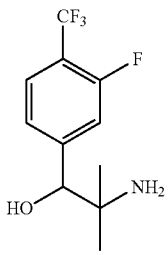

To a mixture of 1-(3-fluoro-4-(trifluoromethyl)phenyl)-2-methyl-2-nitropropan-1-ol (0.500 g, 1.8 mmol) in AcOH (3 mL) was added Zn (1.16 g, 17.8 mmol). The reaction mixture was stirred at room temperature for 3 h. The reaction mixture was diluted with water (10 mL) and extracted with ethyl acetate (3×10 mL). The combined organic layers were washed with brine (10 mL), dried over anhydrous sodium sulfate and filtered. The filtrate was concentrated under reduced pressure. The title compound was obtained as a solid which was used in the next step without further purification. MS (+ESI) m/z=252.0.

Step 3: tert-Butyl 1-(3-fluoro-4-(trifluoromethyl) phenyl)-1-hydroxy-2-methylpropan-2-ylcarbamate

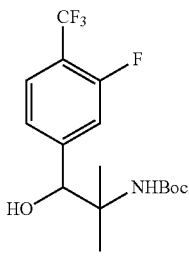

To a mixture of 2-amino-1-(3-fluoro-4-(trifluoromethyl) phenyl)-2-methylpropan-1-ol (0.4 g, 1.6 mmol) and di-tert-butyl dicarbonate (0.382 g, 1.8 mmol) in DCM (5 mL) was added triethylamine (0.322 g, 3.2 mmol). The reaction was stirred at room temperature for 3 h. The reaction mixture was diluted with water (10 mL) and extracted with ethyl acetate (3×10 mL). The combined organic layers were washed with brine (10 mL), dried over anhydrous sodium sulfate and filtered. The filtrate was concentrated under reduced pressure. The residue was purified by column chromatography over silica gel eluting with isocratic 20% ethyl acetate in petroleum ether. The fractions containing desired product were combined and concentrated. The title compound was obtained as a solid. $^1$H NMR (300 MHz, DMSO-$d_6$) δ: 7.78-7.66 (m, 1H), 7.35-7.17 (m, 2H), 6.44-6.26 (br, 1H), 5.80 (d, J=5.1 Hz, 1H), 5.15-5.01 (br, 1H), 1.41 (s, 9H), 1.34 (s, 3H), 0.95 (s, 3H).

Step 4: tert-Butyl (1-(3-fluoro-4-(trifluoromethyl) phenyl)-2-methyl-1-oxopropan-2-yl)carbamate

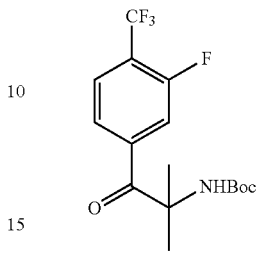

To a solution of tert-butyl (1-(3-fluoro-4-(trifluoromethyl) phenyl)-1-hydroxy-2-methylpropan-2-yl)carbamate (0.300 g, 0.9 mmol) in DCM (5 mL) was added (1,1,1-triacetoxy)-1,1-dihydro-1,2-benziodoxol-3(1H)-one (1.81 g, 4.3 mmol). The reaction solution was stirred at 25° C. for 16 h. The reaction mixture was diluted with water (10 mL) and extracted with ethyl acetate (3×10 mL). The combined organic layers was washed with brine (10 mL), dried over anhydrous sodium sulfate and filtered. The filtrate was concentrated under reduced pressure. The residue was purified by column chromatography over silica gel eluting with isocratic 20% ethyl acetate in petroleum ether. The fractions containing desired product were combined and concentrated. The title compound was obtained as a solid. $^1$H NMR (300 MHz, DMSO-$d_6$) δ: 8.02-7.80 (m, 3H), 1.45 (s, 6H), 1.11 (s, 9H).

Step 5: tert-Butyl (1-amino-1-(3-fluoro-4-(trifluoromethyl)phenyl)-2-methylpropan-2-yl)carbamate

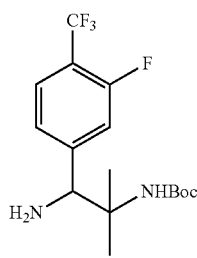 [SMILES: CC(C)(C)OC(=O)NC(C)(C)C(N)c1ccc(C(F)(F)F)c(F)c1]

To a mixture of tert-butyl (1-(3-fluoro-4-(trifluoromethyl)phenyl)-2-methyl-1-oxopropan-2-yl) carbamate (0.100 g, 0.3 mmol) in NH₃ (2 M in MeOH, 2 mL) was added titanium(IV) isopropoxide (0.163 g, 0.6 mmol). The reaction solution was stirred at 60° C. for 16 h. The reaction mixture was cooled, diluted with water (10 mL) and extracted with ethyl acetate (3×10 mL). The combined organic layers were washed with brine (10 mL), dried over anhydrous sodium sulfate and filtered. The filtrate was concentrated under reduced pressure. The tert-butyl (1-(3-fluoro-4-(trifluoromethyl)phenyl)-1-imino-2-methylpropan-2-yl)carbamate was obtained as a solid which was used in the next step without further purification. To a mixture of tert-butyl (1-(3-fluoro-4-(trifluoromethyl)phenyl)-1-imino-2-methylpropan-2-yl)carbamate (70.0 mg, 0.2 mmol) in MeOH (2 mL) was added NaBH₄ (38.0 mg, 1.0 mmol). The reaction mixture was stirred at 50° C. for 16 h. The reaction mixture was cooled, diluted with water (10 mL) and extracted with ethyl acetate (3×10 mL). The combined organic layers was washed with brine (10 mL), dried over anhydrous sodium sulfate and filtered. The filtrate was concentrated under reduced pressure. The title compound was obtained as a solid which was used in the next step without further purification. MS (+ESI) m/z=351.0.

Step 6: tert-Butyl (1-(3-fluoro-4-(trifluoromethyl)phenyl)-2-methyl-1-((5-methyl-[1,2,4]triazolo [1,5-a]pyrimidin-7-yl)amino)propan-2-yl)carbamate

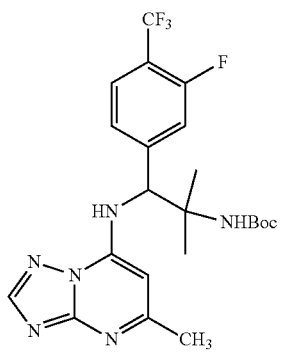 [SMILES: Cc1cc(NC(c2ccc(C(F)(F)F)c(F)c2)C(C)(C)NC(=O)OC(C)(C)C)n2ncnc2n1]

The title compound was prepared using procedures similar to those described in Step 1 of Example 191 using 7-chloro-5-methyl-[1,2,4]triazolo[1,5-a]pyrimidine and tert-butyl 1-amino-1-(3-fluoro-4-(trifluoromethyl)phenyl)-2-methylpropan-2-ylcarbamate to afford the title compound as a solid. MS (+ESI) m/z=483.1.

Step 7: 1-(3-Fluoro-4-(trifluoromethyl)phenyl)-2-methyl-N-(5-methyl-[1,2,4]triazolo[1,5-a]pyrimidin-7-yl)propane-1,2-diamine

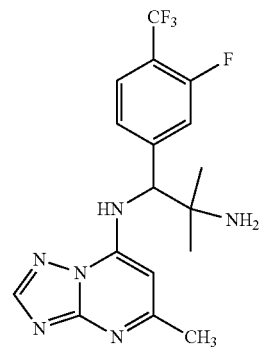 [SMILES: Cc1cc(NC(c2ccc(C(F)(F)F)c(F)c2)C(C)(C)N)n2ncnc2n1]

To HCl (3 M in ethyl acetate, 2 mL) was added tert-butyl (1-(3-fluoro-4-(trifluoromethyl)phenyl)-2-methyl-1-((5-methyl-[1,2,4]triazolo[1,5-a]pyrimidin-7-yl)amino)propan-2-yl)carbamate (15.0 mg, 0.03 mmol). The reaction solution was stirred at 25° C. for 6 h. The reaction solution was cooled to 0° C. and then quenched with water (10 mL). The pH value of the mixture was adjusted to 9 with aqueous sodium carbonate (1 M). The solution was extracted with ethyl acetate (3×10 mL). The combined organic layers was washed with brine (10 mL), dried over anhydrous sodium sulfate and filtered. The filtrate was concentrated under reduced pressure. The residue was purified by Prep-HPLC with the following conditions: Column: X Sunfire C¹⁸, 19×150 mm, 5 um; Mobile Phase A: Water (0.05% ammonium bicarbonate), Mobile Phase B: Acetonitrile; Flow rate: 20 mL/min; Gradient: 30-65% B in 9 min; Detector, UV 254 nm. The fractions containing desired product were combined and concentrated. The title compound was obtained as a solid. ¹H NMR (300 MHz, DMSO-d₆) δ: 8.44 (s, 1H), 7.82-7.74 (m, 1H), 7.64-7.45 (m, 2H), 6.16 (s, 1H), 4.78 (s, 1H), 2.36 (s, 3H), 1.2 (s, 3H), 0.97 (s, 3H); MS (+ESI) m/z=383.0.

The following compounds in Table 13 were prepared using procedures similar to those described in Example 252 using appropriate starting materials. Racemic products were separated using chiral columns specified in the table. For those pairs of enantiomers, the faster eluting isomer is always listed first in this table.

TABLE 13

| Example # | Structure | IUPAC Name | Mass [M + H]+ | Chiral column |
|---|---|---|---|---|
| 253 | 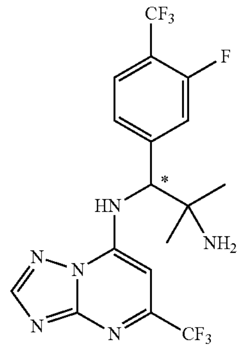 [SMILES: CC(C)(N)C(Nc1cc(C(F)(F)F)nc2ncnn12)c1ccc(C(F)(F)F)c(F)c1] | (R)- or (S)-1-(3-Fluoro-4-(trifluoromethyl)phenyl)-2-methyl-N¹-(5-(trifluoromethyl)-[1,2,4]triazolo[1,5-a]pyrimidin-7-yl)propane-1,2-diamine | 437.0 | (R,R) WHELK-015/100 Kromasil 25 cm × 21.1 mm |
| 254 | 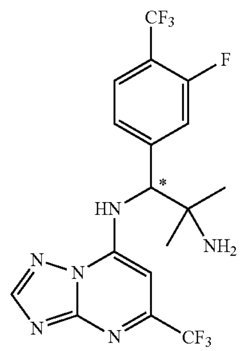 [SMILES: CC(C)(N)C(Nc1cc(C(F)(F)F)nc2ncnn12)c1ccc(C(F)(F)F)c(F)c1] | (S)- or (R)-1-(3-Fluoro-4-(trifluoromethyl)phenyl)-2-methyl-N¹-(5-(trifluoromethyl)-[1,2,4]triazolo[1,5-a]pyrimidin-7-yl)propane-1,2-diamine | 437.0 | (R,R) WHELK-015/100 Kromasil 25 cm × 21.1 mm |

Example 255

N⁷-{1-[3-Fluoro-4-(trifluoromethyl)phenyl]cyclopropyl}-5-methyl[1,2,4]triazolo[1,5-a]pyrimidine-2,7-diamine

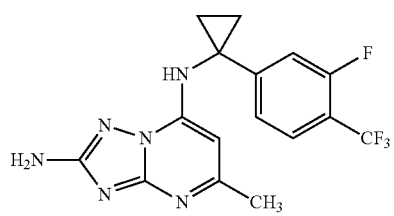 [SMILES: Cc1cc(NC2(c3ccc(C(F)(F)F)c(F)c3)CC2)n2nc(N)nc2n1]

Step 1: 2-Amino-5-methyl-[1,2,4]triazolo[1,5-a]pyrimidin-7-ol

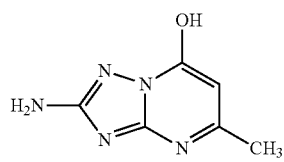

To a solution of 1H-[1,2,4]-triazole-3,5-diamine (500 mg, 5.05 mmol) in 10 mL of acetic acid was added methyl 3-oxobutanoate (0.5 mL, 4.31 mmol) via syringe and the resulting solution was heated to 90° C. by oil bath for 30 minutes. The mixture was cooled to room temperature and the acetic acid was removed under reduced pressure to afford a solid. The solid was triturated with 15 mL of methanol, then the solid was filtered off and washed with 10 mL of methanol. The solid was allowed to air dry for 15 minutes to afford the desired product as a light brown colored solid. LCMS (+ESI) m/z=166.0. ¹H NMR (500 MHz, DMSO-$d_6$) δ: 5.60 (s, 1H), 2.22 (s, 3H).

Step 2: 7-Chloro-5-methyl-[1,2,4]triazolo[1,5-a]pyrimidin-2-amine

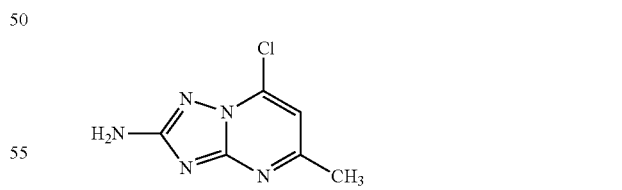

2-Amino-5-methyl-[1,2,4]triazolo[1,5-a]pyrimidin-7-ol (220 mg, 1.33 mmol) was treated with 3 mL of POCl₃ (4.93 g, 32.2 mmol) at 115° C. for 1.5 h. The POCl₃ was then removed in vacuo and the residue triturated with 50 mL of ethyl acetate and 20 mL of water. The organic layer was separated, dried over sodium sulfate, filtered, and the filtrate concentrated to dryness under reduced pressure to afford the crude desired product. LCMS (+ESI) m/z=183.9 and 185.9 (M+2+H)⁺.

Step 3: N⁷-{1-[3-Fluoro-4-(trifluoromethyl)phenyl]cyclopropyl}-5-methyl[1,2,4]triazolo[1,5-a]pyrimidine-2,7-diamine

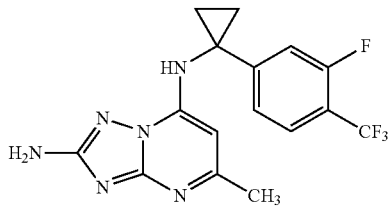 [SMILES: Cc1cc(NC2(c3ccc(C(F)(F)F)c(F)c3)CC2)n2nc(N)nc2n1]

To a mixture of 1-[3-fluoro-4-(trifluoromethyl)phenyl]cyclopropanamine (70 mg, 0.32 mmol) and 7-chloro-5-methyl-[1,2,4]triazolo[1,5-a]pyrimidin-2-amine (crude, 50 mg, 0.27 mmol) in 1.5 mL of NMP was added Hunig's base (0.05 mL, 0.27 mmol) and the resulting mixture was then heated to 120° C. via oil bath for 24 h. The reaction mixture was allowed to cool to room temperature and then was diluted with 10 mL of ethyl acetate. The mixture was washed with brine (2×5 mL), separated organic layer and removed the ethyl acetate under reduced pressure. The residue was purified by reverse phase HPLC (10-90% gradient of acetonitile in water with 0.05% TFA) to afford the title compound as a solid. LCMS (+ESI) m/z=367.0. $^1$H NMR (500 MHz, DMSO-d₆) δ: 7.64 (t, J=8.0 Hz, 1H), 7.32-7.22 (m, 2H), 6.38 (s, 1H), 2.44 (s, 3H), 1.77-1.62 (m, 4H).

Example 256

N⁷-{1-[3-Fluoro-4-(trifluoromethyl)phenyl]cyclopropyl}-N²,N²,5-trimethyl[1,2,4]triazolo[1,5-a]pyrimidine-2,7-diamine

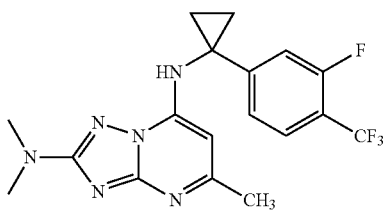

Step 1: 2-(Dimethylamino)-5-methyl-[1,2,4]triazolo[1,5-a]pyrimidin-7-ol

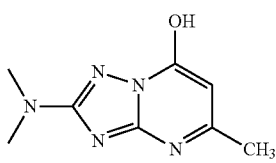

2-Amino-5-methyl-[1,2,4]triazolo[1,5-a]pyrimidin-7-ol, (220 mg, 1.33 mmol) was suspended in a mixed solvent of 5 ml MeOH and 5 ml DCM and then formaldehyde (37% in water, 0.5 mL, 6.66 mmol) was added followed by sodium cyanoborohydride (251 mg, 4.0 mmol). To this resulting mixture was then added drops of acetic acid and the mixture left to stir for 2 days at room temperature. The volitiles were removed in vacuo, and the residue was then partitioned between water (10 ml) and ethyl acetate (50 ml). The ethyl acetate layer was then dried on sodium sulfate, filtered and the filtrate concentrated in vacuo. This residue was used for next reaction without further purification. LCMS (+ESI) m/z=194.0.

Step 2: 7-Chloro-N,N,5-trimethyl-[1,2,4]triazolo[1,5-a]pyrimidin-2-amine

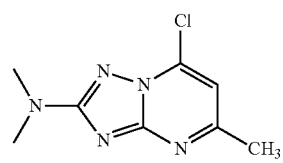

To a flask charged with crude 2-(dimethylamino)-5-methyl-[1,2,4]triazolo[1,5-a]pyrimidin-7-ol (200 mg, 1.04 mmol) was added 1 ml of POCl₃ and the resulting mixture was then warmed to 115° C. via oil bath, and stirred at that temperature for 1.5 h. The excess POCl3 was removed in vacuo and the residue was then partitioned between ethyl acetate and water. The ethyl acetate layer was then separated, dried over sodium sulfate, filtered and the filtrate concentrated in vacuo to give the crude desired product. LCMS (+ESI) m/z=212.0 and 214.0 (M+2+H)⁺.

Step 3: N⁷-{1-[3-Fluoro-4-(trifluoromethyl)phenyl]cyclopropyl}-N²,N²,5-trimethyl[1,2,4]triazolo [1,5-a]pyrimidine-2,7-diamine

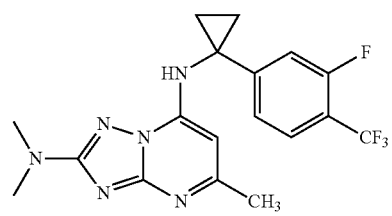 [SMILES: Cc1cc(NC2(c3ccc(C(F)(F)F)c(F)c3)CC2)n2nc(N(C)C)nc2n1]

To a solution of crude 7-chloro-N,N,5-trimethyl-[1,2,4]triazolo[1,5-a]pyrimidin-2-amine (7 mg, 0.03 mmol) and 1-(3-fluoro-4-(trifluoromethyl)phenyl)cyclopropanamine (18 mg, 0.083 mmol) in 1.5 ml of NMP was added Hunig's base (0.03 ml, 0.16 mmol) and the resulting mixture was then heated to 130° C. and stirred at that temperature overnight. The mixture was then cooled to 80° C. and stirred for 20 hrs at that temperature. The mixture was then cooled and diluted with 10 mL ethyl acetate, washed with brine (2×5 mL), separated, and ethyl acetate layer was concentrated in vacuo. The residue was purified by reverse phase HPLC (10-90% CH₃CN in water contain 0.05% TFA) to give the desired product. LCMS (+ESI) m/z=395.1; $^1$H NMR (500 MHz, DMSO-d₆) δ: 7.66 (t, J=8.0 Hz, 1H), 7.32-7.20 (m, 2H), 6.36 (s, 1H), 3.21 (s, 6H), 2.43 (s, 3H), 1.76-1.62 (m, 4H).

Example 257

N[7]-{1-[3-Fluoro-4-(trifluoromethyl)phenyl]cyclopropyl}-N[2],5-dimethyl[1,2,4]triazolo[1,5-a]pyrimidine-2,7-diamine

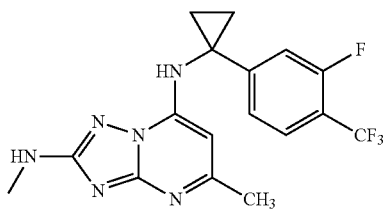

Step 1: 7-Chloro-N,5-dimethyl-[1,2,4]triazolo[1,5-a]pyrimidin-2-amine

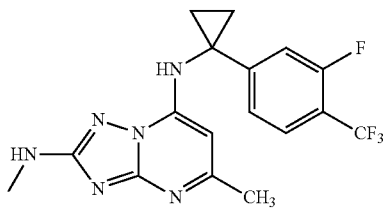 [SMILES: CNc1nc2nc(C)cc(NC3(c4ccc(C(F)(F)F)c(F)c4)CC3)n2n1]

7-Chloro-5-methyl-[1,2,4]triazolo[1,5-a]pyrimidin-2-amine (150 mg, 0.82 mmol) was taken up into 7 mL of DCM and 3 mL of MeOH (not completely soluble), then formaldehyde (0.6 ml of 37% aq soln, 8.2 mmol) was added. After stirring for 5 minutes, sodium cyanoborohydride (3.27 mL of 1M soln in THF) was added and the resulting mixture was stirred overnight at room temperature. The volatiles were removed in vacuo and the residue was triturated with ethyl acetate. The precipitated solid was filtered, and the filtrate was concentrated in vacuo. The residue was partitioned between water (3 mL) and ethyl acetate (7 mL). The organic layer was then separated, dried over sodium sulfate, filtered, and the filtrate concentrated in vacuo. The residue was purified by ISCO 24 g silica gel column using 700 mL of a gradient eluant of 0-70% ethyl acetate with 25% EtOH in hexane. A mixture of both di-methyl and mono-methyl products was isolated, which was used in next reaction without further purification. LCMS (+ESI) m/z=198.0 and 200.0 (M+2H)[+] major desired product; and minor product 212.0 and 214.0 (M+2H)[+].

Step 2: N[7]-{1-[3-Fluoro-4-(trifluoromethyl)phenyl]cyclopropyl}-N[2],5-dimethyl [1,2,4]triazolo[1,5-a]pyrimidine-2,7-diamine

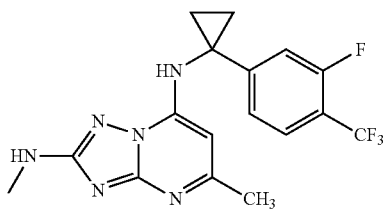 [SMILES: CNc1nc2nc(C)cc(NC3(c4ccc(C(F)(F)F)c(F)c4)CC3)n2n1]

7-Chloro-N,5-dimethyl-[1,2,4]triazolo[1,5-a]pyrimidin-2-amine, (13 mg, 0.066 mmol) was placed in 10 mL round bottom flask and 1.5 mL of NMP was added followed by 1-(3-fluoro-4-(trifluoromethyl)phenyl)cyclopropanamine (70 mg, 0.32 mmol) and Hunig's base (46 uL, 0.26 mmol). The resulting mixture was then heated to 120° C. and stirred at that temperature for 24 hrs. The mixture was allowed to cool to room temperature and then diluted with 10 ml of EtOAc, washed with brine (2×5 mL), separated and the EtOAc layer was concentrated in vacuo. The residue was purified by reverse phase HPLC (10-90% $CH_3CN$ in water containing 0.05% TFA) to give desired product. LCMS (+ESI) m/z=381.2; $^1$H NMR (500 MHz, DMSO-$d_6$) δ: 7.66 (t, J=8.0 Hz, 1H), 7.32-7.20 (m, 2H), 6.36 (s, 1H), 3.20 (s, 3H), 2.46 (s, 3H), 1.76-1.64 (m, 4H).

Example 258

(1S)-1-[(2-Amino-5-methyl[1,2,4]triazolo[1,5-a]pyrimidin-7-yl)amino]-1-[2-fluoro-4-(trifluoromethoxy)phenyl]-2-methylpropan-2-ol

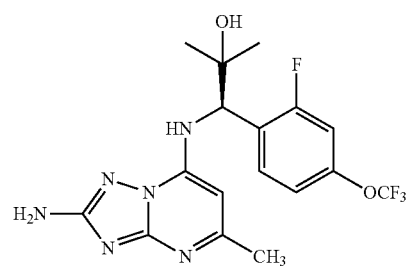

Step 1: Methyl (R)-2-[(2-amino-5-methyl-[1,2,4]triazolo[1,5-a]pyrimidin-7-yl)amino]-2-[3-fluoro-4-(trifluoromethyl)phenyl]acetate

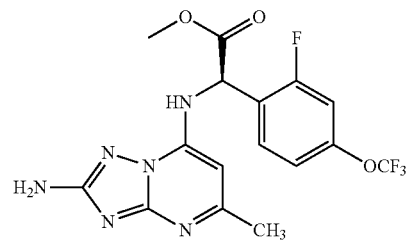 [SMILES: COC(=O)[C@H](Nc1cc(C)nc2nc(N)nn12)c1ccc(OC(F)(F)F)cc1F]

To a mixture of (S)-methyl 3-amino-3-[3-fluoro-4-(trifluoromethyl)phenyl]propanoate (200 mg, 0.83 mmol) and 7-chloro-5-methyl-[1,2,4]triazolo[1,5-a]pyrimidin-2-amine (crude, 140 mg, 0.83 mmol) in 3 mL of NMP was added Hunig's base (0.05 mL, 0.27 mmol) and the resulting mixture was then heated to 80° C. via oil bath for 2 h. The reaction mixture was allowed to cool to room temperature overnight and then was diluted with 10 mL of ethyl acetate. The mixture was washed with brine (2×5 mL), the organic layer separated, dried over sodium sulfate, filtered and the filtrate concentrated to dryness under reduced pressure. The residue was purified by reverse phase HPLC (10-90% gradient of acetonitrile in water with 0.05% TFA) to afford the title compound as a solid. LCMS (+ESI) m/z=401.2.

Step 2: (1S)-1-[(2-Amino-5-methyl[1,2,4]triazolo[1,5-a]pyrimidin-7-yl)amino]-1-[2-fluoro-4-(trifluoromethoxy)phenyl]-2-methylpropan-2-ol

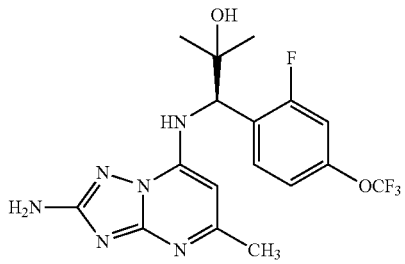 [SMILES: Cc1cc(N[C@H](c2ccc(OC(F)(F)F)cc2F)C(C)(C)O)n2nc(N)nc2n1]

To a solution of methyl (R)-2-[(2-amino-5-methyl-[1,2,4]triazolo[1,5-a]pyrimidin-7-yl)amino]-2-[3-fluoro-4-(trifluoromethyl)phenyl]acetate (200 mg, 0.5 mmol) in 5 mL of anhydrous THF cooled to 0° C. via ice/water bath was added methylmagnesium bromide (0.67 mL of a 3.0 M soln in ether, 2.0 mmol) and the resulting solution stirred overnight allowing to warm to room temperature. The mixture was quenched with aqueous saturated solution of ammonium chloride and extracted with ethyl acetate (2×50 mL). The organics were combined, dried over sodium sulfate, filtered, and the filtrate concentrated under reduced pressure. The residue was purified by reverse phase HPLC (10-90% gradient of acetonitile in water with 0.05% TFA) to afford the title compound as a solid. LCMS (+ESI) m/z=415.2; $^1$H NMR (500 MHz, CD$_3$OD) δ: 7.66 (t, J=8.5 Hz, 1H), 7.22 (d, J=10 Hz, 1H), 7.16 (d, J=8.5 Hz, 1H), 6.28 (s, 1H), 5.08 (br. s, 1H), 2.44 (s, 3H), 1.42 (s, 3H), 1.08 (s, 3H).

Example 259

(R)—N-{1-[4-(Pentafluoro-λ$^6$-sulfanyl)phenyl]ethyl}-[1,2,4]triazolo[5,1-a][1,2,4]trizain-4-amine

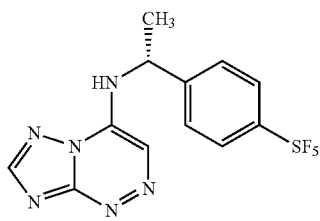

Step 1: 5-[2-(1H-1,2,4-Triazol-5-yl)hydrazono]-2,2-dimethyl-1,3-diozane-4,6-dione

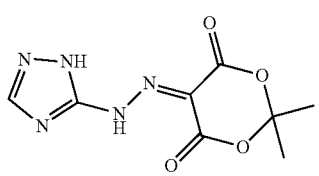 [SMILES: CC1(C)OC(=O)C(=NNc2ncn[nH]2)C(=O)O1]

2.5 ml of concentrated HCl (37%) was added to solid 1H-1,2,4-triazol-5-amine (1.2 g, 14.27 mmol) in a 50 mL round bottom flask and the resulting solution was then cooled to −10° C. via acetone/dry ice. To this solution was added NaNO$_2$ (985 mg, 14.27 mmol), dissolved in 2.5 mL of water, slowly over 30 seconds (brown color gas was observed during addition) and the resulting mixture was stirred at −10° C. to −5° C. for 15 minutes. The mixture became a paste (semi-solid), therefore, 5 ml of water was added. This diazonium salt solution was then added (slowly via pipet over 1 min) to a pre-made solution of 2,2-dimethyl-1,3-dioxane-4,6-dione (2.06 g, 14.27 mmol) and sodium acetate (2.58 g, 31.4 mmol) in 15 mL of ethanol and 11 mL water cooled to 0° C. via ice/water bath. The resulting mixture was then stirred at 5° C. for 1 h, and then for an additional 2 h at room temperature. The reaction mixture was filtered to remove the yellow solid, which was washed by water (2×10 mL) and then dried by air, to afford the title compound. LCMS (+ESI) m/z=240.0; $^1$H NMR (500 MHz, DMSO-d$_6$) δ: 8.60 (s, 1H), 1.76 (s, 6H).

Step 2: [1,2,4]Triazolo[5,1-a][1,2,4]-triazin-4(1H)-one

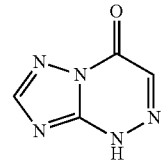

5-[2-(1H-1,2,4-Triazol-5-yl)hydrazono]-2,2-dimethyl-1,3-diozane-4,6-dione (780 mg, 3.26 mmol) was suspended in 40 mL of AcOH and heated via oil bath to 120° C. for 24 hours. The reaction mixture turned to a clear homogenous solution after overnight heating. The AcOH was removed in vacuo and the residue was triturated with 5 mL of water and 2.5 mL of EtOH. The material was filtered and the filtrate concentrated in vacuo to afford the title compound. LCMS (+ESI) m/z=138.0; $^1$H NMR (500 MHz, DMSO-d$_6$) δ: 8.39 (s, 1H), 7.31 (s, 1H).

Step 3: 4-Chloro-[1,2,4]triazolo[5,1-a][1,2,4]triazine

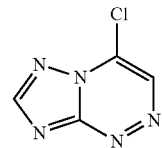

[1,2,4]Triazolo[5,1-a][1,2,4]-triazin-4(1H)-one (50 mg, 0.365 mmol) was placed in a microwave reaction tube and POCl$_3$ (1 mL) was added to it slowly, followed by DIEA (0.1 mL, 0.573 mmol). The mixture gradually became a homogenous solution. The tube was then sealed and stirred at 125° C. overnight. The mixture was cooled to room temperature and then diluted with 2 mL of DCM. The mixture was then concentrated to dryness in vacuo and used for next reaction without further purification (quantitative). LCMS (+ESI) m/z=155.9 and 157.9 (M+2+H)$^+$.

Step 4: (R)—N-{1-[4-(Pentafluoro-λ⁶-sulfanyl)phenyl]ethyl}-[1,2,4]triazolo[5,1-a][1,2,4]trizain-4-amine

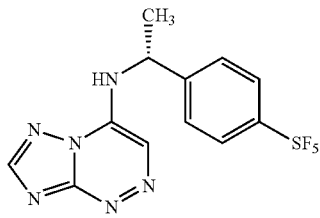

A solution of 4-chloro-[1,2,4]triazolo[5,1-a][1,2,4]triazine (55 mg, 0.354 mmol) and (R)-1-[4-(pentafluoro-λ⁶-sulfanyl)phenyl]ethan-1-amine (60 mg, 0.243 mmol) in anhydrous NMP (1.5 mL) in a 2-5 mL microwave rxn vial was capped and heated via oil bath to 120° C. and stirred at that temperature for 1 h. The reaction was allowed to cool and was quenched with 5 mL of sat'd. aqueous sodium bicarbonate aqueous solution, extracted with 10 mL ethyl acetate, separated and organic layer was washed by water (2×5 mL). The organic layer was then dried over sodium sulfate, filtered and the filtrate was concentrated to dryness in vacuo. The residue was purified by reverse phase HPLC (10-85% CH₃CN in water containing 0.05% TFA) to afford the desired product as a solid. LC-MS (+ESI) m/z=367.0. ¹H NMR (500 MHz, CD₃OD) δ: 8.62 (s, 1H), 8.53 (br. s, 1H), 7.85 (d, J=8.1 Hz, 2H), 7.66 (d, J=8.1 Hz, 2H), 5.42 (br. s, 1H), 1.80 (d, J=6.8 Hz, 3H).

Examples 260 and 261

(R)-7-{2,2-Dimethyl-1-[4-(trifluoromethyl)phenyl]propoxy}-5-methyl[1,2,4]triazolo[1,5-a]pyrimidine and (S)-7-{2,2-Dimethyl-1-[4-(trifluoromethyl)phenyl]propoxy}-5-methyl[1,2,4]triazolo[1,5-a]pyrimidine

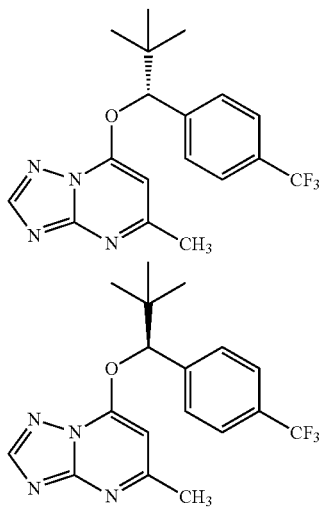

Step 1: 2,2-dimethyl-1[4-(trifluoromethyl)phenyl]propan-1-ol

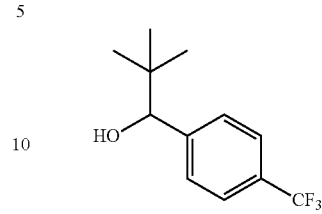

To a solution of 4-(trifluoromethyl)benzaldehyde (1000 mg, 5.74 mmol) in 5 mL of anhydrous THF was added tert-butylmagnesium chloride (5.74 mL of 1 M soln, 5.74 mmol) at −78° C. and the resulting mixture was stirred for 30 min at −78° C. Then the cooling bath was removed and the mixture was stirred for 1 hr, followed by quench with sat'd. aqueous NH₄Cl soln. The solution was extracted with EtOAc, separated and the organic layer was concentrated in vacuo. The residue was purified by silica gel column chromatography, to give the title compound. LCMS (+ESI) m/z=215.1 (M-OH)⁺ and 255.2 (M+Na)⁺.

Step 2: (R)-7-{2,2-Dimethyl-1-[4-(trifluoromethyl)phenyl]propoxy}-5-methyl[1,2,4]triazolo[1,5-a]pyrimidine and (S)-7-{2,2-Dimethyl-1-[4-(trifluoromethyl)phenyl]propoxy}-5-methyl[1,2,4]triazolo[1,5-a]pyrimidine

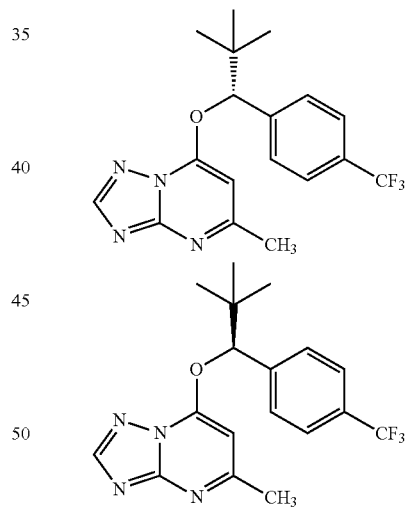

To a solution of 2,2-dimethyl-1-[4-(trifluoromethyl)phenyl]propan-1-ol (207 mg, 0.89 mmol) in 3 mL of 1,4-dioxane was added potassium tert-butoxide (100 mg, 0.89 mmol) at room temperature and the resulting mixture was stirred for 2 minutes. Then, 7-chloro-5-methyl-[1,2,4]triazolo[1,5-a]pyrimidine (100 mg, 0.59 mmol) was added and the resulting mixture was stirred 30 min at room temperature. The reaction was quenched by 5 mL of saturated aqueous NH₄Cl solution, extracted with 15 mL of EtOAC, separated and the organic layer concentrated in vacuo. The residue was purified by reverse phase HPLC (10-90% CH₃CN in water containing 0.05% TFA) to give the desired product. Purification by chiral HPLC (insert details here)

provided the faster-eluting enantiomer of the title compound (Example 260) as a solid. MS (+ESI) m/z=365.1. $^1$H NMR (500 MHz, MeOH-d$_4$) δ: 8.60 (s, 1H), 7.76-7.62 (m, 4H), 6.56 (s, 1H), 5.71 (s, 1H), 2.50 (s, 3H), 1.08 (s, 9H). The slower-eluting enantiomer of the title compound (Example 261) was as a solid. MS (+ESI) m/z=365.1. $^1$H NMR (500 MHz, MeOH-d$_4$) δ: 8.61 (s, 1H), 7.75-7.62 (m, 4H), 6.56 (s, 1H), 5.70 (s, 1H), 2.49 (s, 3H), 1.08 (s, 9H).

Example 262

5-Methyl-7-({1-[4-(trifluoromethyl)phenyl] cyclopropyl}oxy)[1,2,4]triazolo[1,5-a]pyrimidine

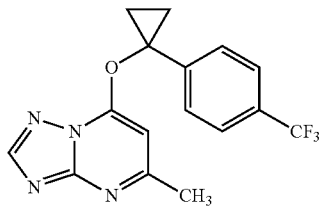 [SMILES: Cc1cc(OC2(c3ccc(C(F)(F)F)cc3)CC2)n2ncnc2n1]

To a solution of 7-chloro-5-methyl-[1,2,4]-triazolo[1,5-a] pyrimidine (25 mg, 0.148 mmol) and 1-[4-(trifluoromethyl) phenyl]cyclopropanol (42.5 mg, 0.178 mmol) in anhydrous DMSO (0.5 mL) in a 2-5 mL microwave vial was added dropwise via syringe DIEA (0.2 mL, 1.1 mmol) and the resulting solution heated via oil bath to 120° C. overnight. The reaction was allowed to cool and was quenched with 1 mL of sat'd. aqueous sodium bicarbonate solution. The solution was diluted with 5 mL ethyl acetate. The organic layer was separated, the aqueous was re-extracted with 2.5 mL of ethyl acetate and the organics then combined. The organics were washed with 1 mL water, dried over sodium sulfate, filtered and the filtrate concentrated to dryness under reduced pressure. The residue was purified by reverse phase HPLC (10-90% acetonitrile in water with 0.05% TFA) to afford the product as a solid. LC-MS (+ESI) m/z=335.0. $^1$H NMR (500 MHz, CD$_3$OD) δ: 8.51 (s, 1H), 7.68 (d, J=8.6 Hz, 2H), 7.52 (d, J=8.6 Hz, 2H), 6.62 (s, 1H), 2.54 (s, 3H), 1.85-1.78 (m, 2H), 1.72-1.66 (m, 2H).

Example 263

N-(1-(3-Fluoro-4-(trifluoromethyl)phenyl)cyclopropyl)-7-methyl-[1,2,4]triazolo[1,5-a]pyridin-5-amine

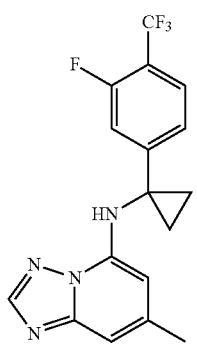 [SMILES: Cc1cc(NC2(c3ccc(C(F)(F)F)c(F)c3)CC2)n2ncnc2c1]

Step 1: N-(1-(3-Fluoro-4-(trifluoromethyl)phenyl) cyclopropyl)-7-methyl-[1,2,4]triazolo[1,5-a]pyridin-5-amine To a solution of 5-chloro-7-methyl-[1,2,4]triazolo[1,5-a] pyridine (100 mg, 0.597 mmol) in anhydrous toluene (2 mL) was added 1-(3-fluoro-4-(trifluoromethyl)phenyl) cyclopropanamine hydrochloride (168 mg, 0.656 mmol), Pd(OAc)$_2$ (6.70 mg, 0.030 mmol), sodium tert-butoxide (287 mg, 2.98 mmol), and BINAP (18.58 mg, 0.030 mmol) under N$_2$. The mixture was then stirred at 110° C. for 24 h. The mixture was diluted with EtOAc (50 mL) and washed with sat. NH$_4$Cl (10 mL×2) and brine. The organics were dried over Na$_2$SO$_4$, filtered, and the filtrate concentrated under reduced pressure to afford the crude product. Purification with reverse phase HPLC (30-90% CH$_3$CN/H$_2$O with 0.05% TFA) afforded the title compound as a powder. LC-MS (+ESI) m/z=351.1; $^1$H NMR (CDCl$_3$, 500 MHz) δ: 9.81 (brs, 1H), 7.59 (m, 1H), 7.29 (m, 1H), 7.01 (m, 2H), 6.78 (s, 1H), 6.19 (s, 1H), 2.43 (s, 3H), 1.62 (m, 4H). LC/MS (m/z): 351.1 (M+H)$^+$.

Example 264

(R)—N-{1-[3-Fluoro-4-(trifluoromethyl)phenyl]-2,2-dimethylpropyl}-7-methyl-[1,2,4]triazolo[1,5-a] pyridin-5-amine

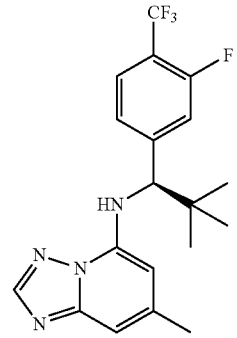 [SMILES: Cc1cc(N[C@@H](c2ccc(C(F)(F)F)c(F)c2)C(C)(C)C)n2ncnc2c1]

The following example was prepared using similar procedures as in Example 263 using the appropriate starting materials. LC-MS (+ESI) m/z=381.1.

Example 265

(1S)-2-Methyl-1-[(7-methyl[1,2,4]triazolo[1,5-a] pyridin-5-yl)amino]-1-[4-(trifluoromethyl)phenyl] propan-2-ol

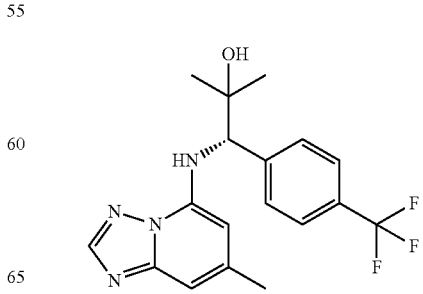

The following example was prepared using similar procedures as in Example 263 using the appropriate starting materials. LC-MS (+ESI) m/z=365.1.

Example 266a (5-((1-(3-Fluoro-4-(trifluoromethyl)phenyyl)cyclopropyyl)amino)-[1,2,4]triazolo[1,5-a]pyridin-7-yl)methanol

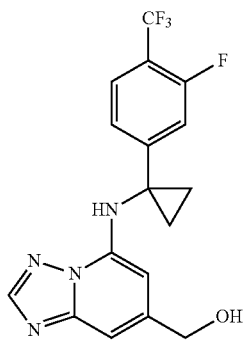 [SMILES: OCc1cc(NC2(c3ccc(C(F)(F)F)c(F)c3)CC2)n2ncnc2c1]

Step 1: (5-((1-(3-Fluoro-4-(trifluoromethyl)phenyl)cyclopropyl)amino)-[1,2,4]triazolo[1,5-a]pyridin7-yl)methanol To a solution of (5-chloro-[1,2,4]triazolo[1,5-a]pyridin-7-yl)methanol (Preparatory Example 92, 100 mg, 0.545 mmol) in dioxane (2 mL) was added 1-(3-fluoro-4-(trifluoromethyl)phenyl) cyclopropanamine hydrochloride (153 mg, 0.599 mmol), MorDalPhos G3 biaryl precatalyst (90 mg, 0.108 mmol), and $Cs_2CO_3$ (710 mg, 2.179 mmol) under $N_2$ and the resulting mixture stirred at 100° C. for 18 h. The mixture was filtered and concentrated to afford crude product. Purification with reverse phase HPLC (30-90% $CH_3CN$/ $H_2O$ with 0.05% TFA) afforded the title compound as a solid. $^1H$ NMR ($CDCl_3$, 500 MHz) δ: 8.59 (s, 1H), 7.59 (m, 1H), 7.40 (s, 1H), 7.01 (m, 2H), 6.72 (s, 1H), 6.18 (s, 1H), 4.78 (s, 2H), 1.61 (m, 4H). LC/MS (m/z): 367.1 $(M+H)^+$.

Example 266b (5-((1-(3-Fluoro-4-(trifluoromethyl)phenyl)cyclopropyl)amino)-[1,2,4]triazolo[1,5-a]pyridin-7-yl)methanol

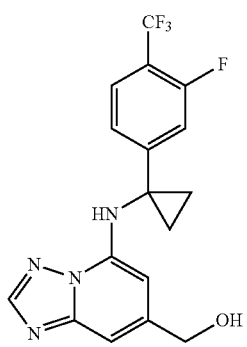 [SMILES: OCc1cc(NC2(c3ccc(C(F)(F)F)c(F)c3)CC2)n2ncnc2c1]

Step 1: 7-(((tert-Butyldimethylsilyl)oxy)methyl)-5-chloro-[1,2,4]triazolo[1,5-a]pyridine

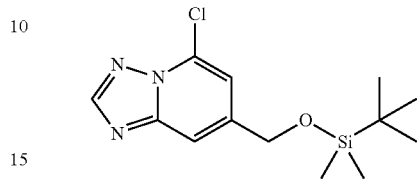

To a solution of (5-chloro-[1,2,4]triazolo[1,5-a]pyridin-7-yl)methanol (Preparatory Example 92, 50 mg, 0.272 mmol) in DCM (1 ml) added TBDMS-Cl (82 mg, 0.545 mmol) and DMAP (33.3 mg, 0.272 mmol), followed with TEA (0.038 mL, 0.272 mmol). The mixture was stirred at rt for 3 h. LCMS indicated the reaction complete. The solvent was removed and the crude product was directly purified with ISCO (biotage 10 g column, 0-100% EtOAc in Hexane) to afford the title compound as a solid. LC/MS (m/z): 298.0 $(M+H)^+$.

Step 2: 7-(((tert-Butyldimethylsilyl)oxy)methyl)-N-(1-(3-fluoro-4-(trifluoromethyl)phenyl) cyclopropyl)-[1,2,4]triazolo[1,5-a]pyridin-5-amine

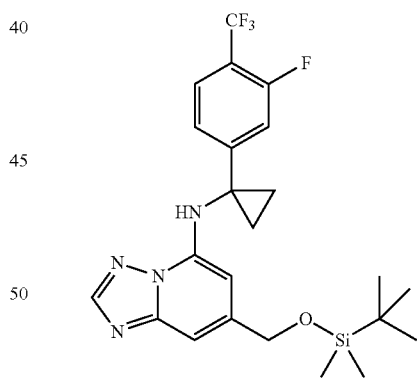

To a solution of 7-(((tert-butyldimethylsilyl)oxy)methyl)-5-chloro-[1,2,4]triazolo[1,5-a]pyridine (50 mg, 0.168 mmol) in Toluene (2 mL) was added 1-(3-fluoro-4-(trifluoromethyl) phenyl) cyclopropanamine hydrochloride (47.2 mg, 0.185 mmol), $Pd(OAc)_2$ (18.84 mg, 0.084 mmol), sodium tert-butoxide (81 mg, 0.839 mmol), and BINAP (52.3 mg, 0.084 mmol) under $N_2$ and the resulting mixture stirred at 110° C. for 24 h. The mixture was filtered and concentrated under reduced pressure to afford crude product. Purification with ISCO (12 g biotage column, 0-100% EtOAc in Hexane) afforded the title compound. LC/MS (m/z): 481.1 $(M+H)^+$.

Step 3: (5-((1-(3-Fluoro-4-(trifluoromethyl)phenyl)cyclopropyl)amino)-[1,2,4]triazolo[1,5-a]pyridin-7-yl)methanol

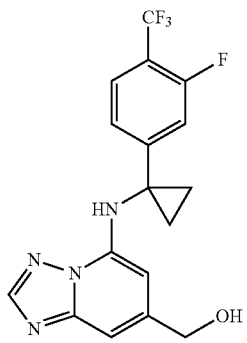 [SMILES: OCc1cc(NC2(c3ccc(C(F)(F)F)c(F)c3)CC2)n2ncnc2c1]

To a solution of 7-(((tert-butyldimethylsilyl)oxy)methyl)-N-(1-(3-fluoro-4-(trifluoromethyl)phenyl) cyclopropyl)-[1,2,4]triazolo[1,5-a]pyridin-5-amine (80 mg, 0.166 mmol) in DCM (2 mL) was added TFA (1.283 ml, 16.65 mmol) under $N_2$ and the resulting mixture stirred at rt for 5 h. The solvent was then removed under reduced pressure to afford crude product. Purification with reverse phase HPLC (30-90% $CH_3CN/H_2O$ with 0.05% TFA) afforded the title compound. $^1$H NMR (CDCl$_3$, 500 MHz) δ: 8.58 (s, 1H), 7.60 (m, 1H), 7.42 (s, 1H), 7.01 (m, 2H), 6.70 (s, 1H), 6.18 (s, 1H), 4.80 (s, 2H), 1.61 (m, 4H). LC/MS (m/z): 367.0 (M+H)$^+$.

The following compounds in Table 14 were prepared using procedures similar to those described in Example 266a using and the appropriate starting materials.

TABLE 14

| Example No. | Structure | IUPAC Name | Observed Exact Mass [M + H]$^+$ |
|---|---|---|---|
| 267 | 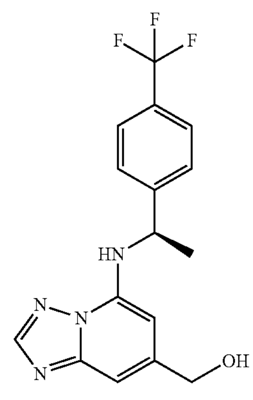 [SMILES: C[C@@H](Nc1cc(CO)cc2ncnn12)c1ccc(C(F)(F)F)cc1] | [5-({(1R)-1-[4-(Trifluoromethyl)phenyl]ethyl}amino)[1,2,4]triazolo[1,5-a]pyridin-7-yl]methanol | 337.1 |
| 268 | 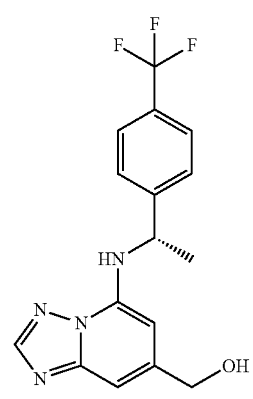 [SMILES: C[C@H](Nc1cc(CO)cc2ncnn12)c1ccc(C(F)(F)F)cc1] | [5-({(1S)-1-[4-(Trifluoromethyl)phenyl]ethyl}amino)[1,2,4]triazolo[1,5-a]pyridin-7-yl]methanol | 337.1 |

TABLE 14-continued

| Example No. | Structure | IUPAC Name | Observed Exact Mass [M + H]+ |
|---|---|---|---|
| 269 | 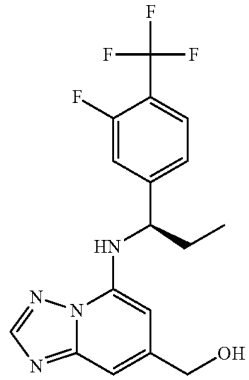 [SMILES: CC[C@@H](Nc1cc(CO)cc2ncnn12)c1ccc(C(F)(F)F)c(F)c1] | [5-({(1R)-1-[3-Fluoro-4-(trifluoromethyl)phenyl]propyl}amino)[1,2,4]triazolo[1,5-a]pyridin-7-yl]methanol | 369.0 |
| 270 | 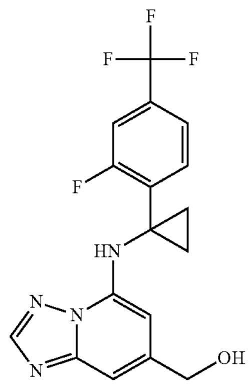 [SMILES: OCc1cc(NC2(c3ccc(C(F)(F)F)cc3F)CC2)n2ncnc2c1] | [5-({1-[2-Fluoro-4-(trifluoromethyl)phenyl]cyclopropyl}amino)[1,2,4]triazolo[1,5-a]pyridin-7-yl]methanol | 367.1 |
| 271 | 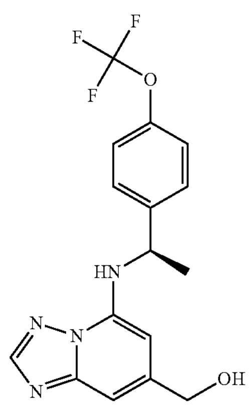 [SMILES: C[C@@H](Nc1cc(CO)cc2ncnn12)c1ccc(OC(F)(F)F)cc1] | [5-({(1R)-1-[4-(Trifluoromethoxy)phenyl]ethyl}amino)[1,2,4]triazolo[1,5-a]pyridin-7-yl]methanol | 353.0 |
| 272 | 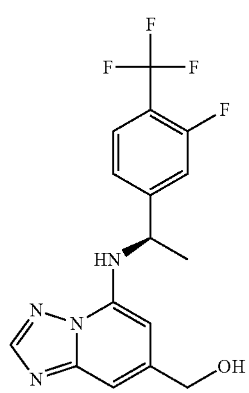 [SMILES: C[C@@H](Nc1cc(CO)cc2ncnn12)c1ccc(C(F)(F)F)c(F)c1] | [5-({(1R)-1-[3-Fluoro4-(trifluoromethyl)phenyl]ethyl}amino)[1,2,4]triazolo[1,5-a]pyridin-7-yl]methanol | 355.1 |

TABLE 14-continued

| Example No. | Structure | IUPAC Name | Observed Exact Mass [M + H]+ |
|---|---|---|---|
| 273 | 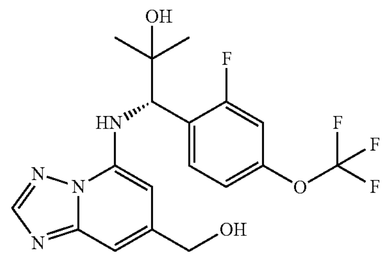 [SMILES: CC(C)(O)[C@@H](Nc1cc(CO)cc2ncnn12)c1ccc(OC(F)(F)F)cc1F] | (1S)-1-[2-Fluoro-4-(trifluoromethoxy)phenyl]-1-{[7-(hydroxymethyl)[1,2,4]triazolo[1,5-a]pyridin-5-yl]amino}-2-methylpropan-2-ol | 415.1 |

Example 274

7-(Difluoromethyl)-N-(1-(3-fluoro-4-(trifluoromethy)phenyl)cyclopropyl)-[1,2,4]triazol-[1,5-a]pyridin-5-amine

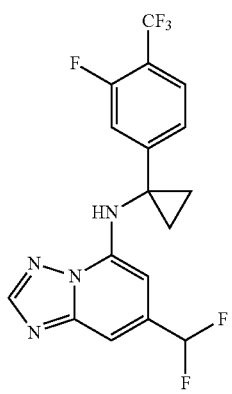 [SMILES: Fc1cc(C2(Nc3cc(C(F)F)cc4ncnn34)CC2)ccc1C(F)(F)F]

Step 1: 7-(Difluoromethyl)-N-(1-(3-fluoro-4-(trifluoromethyl)phenyl)cyclopropyl)-[1,2,4]triazol [1,5-a]pyridin-5-amine To a solution of 5-chloro-7-(difluoromethyl)-[1,2,4]triazolo[1,5-a]pyridine (Preparatory Example 93, 12 mg, 0.059 mmol) in toluene (2 mL) was added 1-(3-fluoro-4-(trifluoromethyl)phenyl) cyclopropanamine hydrochloride (16.58 mg, 0.065 mmol), Pd(OAc)$_2$ (6.62 mg, 0.029 mmol), sodium tert-butoxide (28.3 mg, 0.295 mmol) and BINAP (14.68 mg, 0.024 mmol) under N$_2$ and the resulting mixture was stirred at 110° C. for 24 h. The mixture was filtered and solvent removed under reduced pressure. Purification by reverse phase HPLC (30-90% CH$_3$CN/H$_2$O with 0.05% TFA) afforded the title compound as a solid. $^1$H NMR (CDCl$_3$, 500 MHz) δ: 8.46 (s, 1H), 7.60 (m, 1H), 7.48 (s, 1H), 7.01 (m, 2H), 6.82 (s, 1H), 6.63 (m, 1H), 6.34 (s, 1H), 1.61 (m, 4H). LC/MS (m/z): 387.1 (M+H)+.

Example 275

1-(5-((1-(3-Fluoro-4-(trifluoromethyl)phenyl)cyclopropyl)amino)-[1,2,4]triazolo[1,5-a]pyridin-7-yl)ethanol

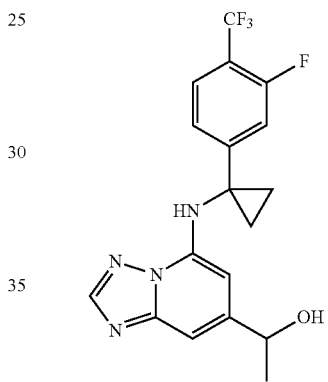

Step 1: 1-(5-Chloro-[1,2,4]triazolo[1,5-a]pyridin-7-yl)ethanol

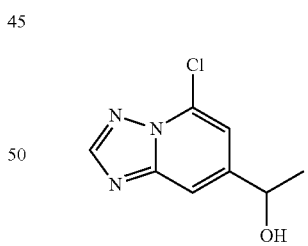

To a solution of 5-chloro-[1,2,4]triazolo[1,5-a]pyridine-7-carbaldehyde (50 mg, 0.275 mmol) in anhydrous THF (2 mL) was added 3.0 M methylmagnesium bromide (0.119 mL, 0.358 mmol) at 0° C. The mixture was stirred at 0° C. for 1 h and then was allowed to warm to room temperature over 1-2 hr. The mixture was then diluted with saturated aqueous NH$_4$Cl, extracted with EtOAc (30 mL×3), and the organic layer was collected. The organics were dried over Na$_2$SO$_4$, filtered and concentrated to afford crude product. Purification with ISCO (12 g biotage silica gel column, 0-100% EtOAc in Hexane) afforded the title compound. LC/MS (m/z): 198.0 (M+H)+.

Step 2: 7-(1-((tert-Butyldimethylsilyl)oxy)ethyl)-5-chloro-[1,2,4]triazolo[1,5-a]pyridine

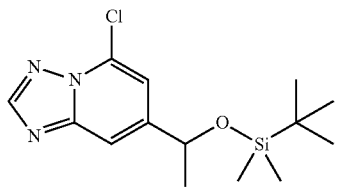 [SMILES: CC(O[Si](C)(C)C(C)(C)C)c1cc(Cl)n2ncnc2c1]

To a solution of 1-(5-chloro-[1,2,4]triazolo[1,5-a]pyridin-7-yl)ethanol (45 mg, 0.228 mmol) in DCM (1 ml) was added TBDMS-Cl (68.6 mg, 0.455 mmol) and DMAP (41.7 mg, 0.342 mmol), followed by TEA (0.032 ml, 0.228 mmol) and the resulting mixture was stirred at room temperature overnight. The solvent was removed under vacuo. Purification with ISCO (10 g biotage silica gel column, 0-100% EtOAc in Hexane) afforded the title as a liquid. LC/MS (m/z): 312.1 (M+H)$^+$.

Step 3: 7-(1-((tert-Butyldimethylsilyl)oxy)ethyl)-N-(1-(3-fluoro-4-(trifluoromethyl)phenyl) cyclopropyl)-[1,2,4]triazolo[1,5-a]pyridin-5-amine

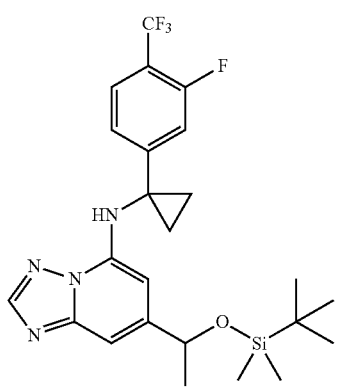 [SMILES: CC(O[Si](C)(C)C(C)(C)C)c1cc(NC2(c3ccc(C(F)(F)F)c(F)c3)CC2)n2ncnc2c1]

To a solution of 7-(1-((tert-butyldimethylsilyl)oxy)ethyl)-5-chloro-[1,2,4]triazolo[1,5-a]pyridine (60 mg, 0.192 mmol) in toluene (2 mL) was added 1-(3-fluoro-4-(trifluoromethyl) phenyl)cyclopropanamine hydrochloride (54.1 mg, 0.212 mmol), Pd(OAc)$_2$ (12.96 mg, 0.058 mmol), sodium tert-butoxide (74.0 mg, 0.770 mmol) and BINAP (35.9 mg, 0.058 mmol) under N$_2$. The mixture was stirred at 110° C. for 24 h. The mixture was then filtered and solvent removed under reduced pressure to afford crude product. Purification with ISCO (10 g biotage silica gel column, 0-100% EtOAc in Hexane) afforded the title compound. LC/MS (m/z): 495.1 (M+H)$^+$.

Step 4: 1-(5-((1-(3-Fluoro-4-(trifluoromethyl)phenyl)cyclopropyl)amino)-[1,2,4]triazolo[1,5-a]pyridin-7-yl)ethanol

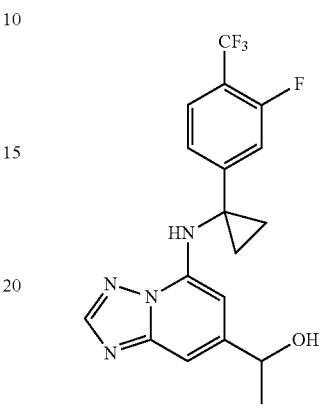

To a solution of 7-(1-((tert-butyldimethylsilyl)oxy)ethyl)-N-(1-(3-fluoro-4-(trifluoromethyl) phenyl)cyclopropyl)-[1,2,4]triazolo[1,5-a]pyridin-5-amine (66 mg, 0.133 mmol) in DCM (1 mL) and water (1 mL) was added TFA (0.3 mL, 3.89 mmol) and the resulting mixture stirred at room temperature overnight. The solvent was removed under vacuo and the residue purified by reverse phase HPLC (30-90% CH$_3$CN/H$_2$O with 0.05% TFA) to afford the title compound as a solid. $^1$H NMR (CDCl$_3$, 500 MHz) δ: 8.58 (s, 1H), 7.59 (m, 1H), 7.40 (s, 1H), 7.01 (m, 2H), 6.71 (s, 1H), 6.40 (s, 1H), 4.98 (m, 1H), 1.61 (m, 4H), 1.43 (m, 3H). LC/MS (m/z): 381.1 (M+H)$^+$.

Example 276

N-(1-(3-fluoro-4-(trifluoromethyl)phenyl)cyclopropyl)-7-(trifluoromethyl)-[1,2,4]triazolo[1,5-a]pyridin-5-amine

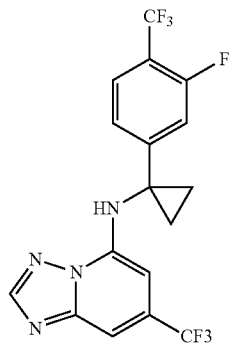 [SMILES: Fc1cc(C2(Nc3cc(C(F)(F)F)cc4ncnn34)CC2)ccc1C(F)(F)F]

249

Step 1: N-(1-(3-fluoro-4-(trifluoromethyl)phenyl) cyclopropyl)-7-(trifluoromethyl)-[1,2,4]triazolo [1,5-a]pyridin-5-amine To a solution of 5-chloro-7-(trifluoromethyl)-[1,2,4]triazolo[1,5-a]pyridine (50 mg, 0.226 mmol) from WO 2011090127A1 in toluene (2 mL) was added 1-(3-fluoro-4-(trifluoromethyl)phenyl) cyclopropanamine hydrochloride (63.5 mg, 0.248 mmol), Pd(OAc)$_2$ (25.3 mg, 0.113 mmol), sodium tert-butoxide (87 mg, 0.903 mmol) and BINAP (56.2 mg, 0.090 mmol) under N$_2$ and the resulting mixture was stirred at 110° C. for 24 h. The mixture was then filtered and the solvent removed under reduced pressure to afford crude product. Purification by reverse phase HPLC (30-90% CH$_3$CN/H$_2$O with 0.05% TFA) afforded the title compound, with a little impurity, as a yellow solid. The compound was re-purified with basic conditions (Xbridge column 19*100, AcCN/Water with Ammonium hydroxide; gradient 20 to 65% AcCN) to afford the title compound. $^1$H NMR (CDCl$_3$, 500 MHz) δ: 7.59 (m, 1H), 7.50 (br s, 1H), 7.01 (m, 2H), 6.80 (s, 1H), 6.22 (s, 1H), 4.98 (m, 1H), 1.61 (m, 4H), LC/MS (m/z): 405.0 (M+H)$^+$.

The following compounds in Table 15 were prepared using procedures similar to those described in Example 276 using and the appropriate starting materials.

250

Example 279

(S)-1-((7-(Difluoromethyl)-[1,2,4]triazolo[1,5-a]pyridin-5-yl)amino)-1-(3-fluoro-4-(trifluoromethoxy)phenyl)-2-methylpropan-2-ol

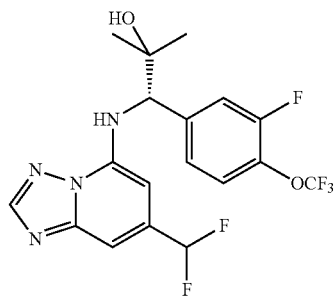 [SMILES: CC(C)(O)[C@@H](Nc1cc(C(F)F)cc2ncnn12)c1ccc(OC(F)(F)F)c(F)c1]

To a solution of 5-chloro-7-(difluoromethyl)-[1,2,4]triazolo[1,5-a]pyridine (100 mg, 0.491 mmol) in toluene (4 mL) was added (S)-1-amino-1-(3-fluoro-4-(trifluoromethoxy) phenyl)-2-methylpropan-2-ol (197 mg, 0.737 mmol), Pd(OAc)$_2$ (22.06 mg, 0.098 mmol), sodium tert-butoxide (94 mg, 0.982 mmol) and BINAP (61.2 mg, 0.098 mmol) under N$_2$ and the resulting mixture was stirred at 100° C. for 3 h. The mixture was then filtered and solvent removed under reduced pressure. The residue was purified by reverse phase HPLC (30-90% CH$_3$CN/H$_2$O with 0.05% TFA) to elute the desired product with a little impurity. The compound was re-purified under basic conditions (Xbridge

TABLE 15

| Example No. | Structure | IUPAC Name | Observed Exact Mass [M + H]$^+$ |
|---|---|---|---|
| 277 | 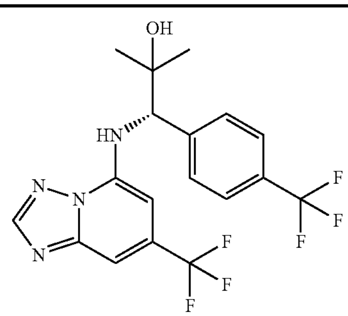 | (1S)-2-Methyl-1-[4-(trifluoromethyl)phenyl]-1-{[7-(trifluoromethyl)[1,2,4]triazolo[1,5-a]pyridin-5-yl]amino}propan-2-ol | 419.1 |
| 278 | | (1S)-1-[2-Fluoro-4-(trifluoromethoxy)phenyl]-2-methyl-1-{[7-(trifluoromethyl)[1,2,4]triazolo[1,5α]pyridin-5-yl]amino}propan-2-ol | 453.2 | column 19*100, AcCN/Water with Ammonium hydroxide; gradient 20 to 65% AcCN) to afford the pure title compound as a solid. LC/MS (m/z): 435.1 (M+H)+. ¹H NMR (CDCl₃, 500 MHz) δ: 8.40 (s, 1H), 7.39 (m, 2H), 7.26 (m, 2H), 7.08 (m, 1H), 6.80 (m, 1H), 5.85 (s, 1H), 4.42 (m, 1H), 1.59 (s, 3H), 1.23 (s, 3H). LC/MS (m/z): 434.8 (M+H)+.

The following compounds in Table 16 were prepared using procedures similar to those described in Example 279 using and the appropriate starting materials.

TABLE 16

| Example No. | Structure | IUPAC Name | Observed Exact Mass [M + H]+ |
| --- | --- | --- | --- |
| 280 | 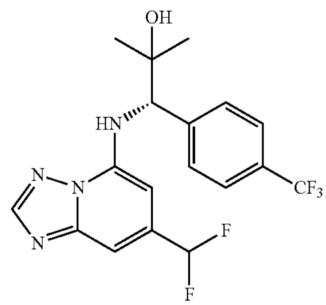 [SMILES: CC(C)(O)[C@@H](Nc1cc(C(F)F)cc2ncnn12)c1ccc(C(F)(F)F)cc1] | (1S)-1-{[7-(Difluoromethyl)[1,2,4]triazolo[1,5-a]pyridin-5-yl]amino}-1-[4-(trifluoromethyl)phenyl]-2-methylpropan-2-ol | 401.2 |
| 281 | 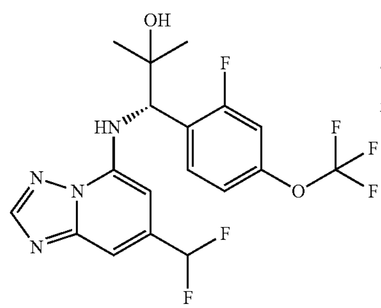 [SMILES: CC(C)(O)[C@@H](Nc1cc(C(F)F)cc2ncnn12)c1ccc(OC(F)(F)F)cc1F] | (1S)-1-{[7-(Difluoromethyl)[1,2,4]triazolo[1,5-a]pyridin-5-yl]amino}-1-[2-fluoro-4-(trifluoromethoxy)phenyl]-2-methylpropan-2-ol | 435.1 |
| 282 | 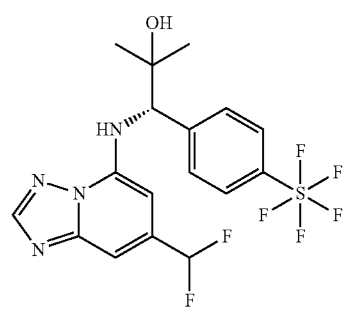 [SMILES: CC(C)(O)[C@@H](Nc1cc(C(F)F)cc2ncnn12)c1ccc(S(F)(F)(F)(F)F)cc1] | (1S)-1-{[7-(Difluoromethyl)[1,2,4]triazolo[1,5-a]pyridin-5-yl]amino}-2-methyl-1-[4-(pentafluoro-λ⁶-sulfanyl)phenyl]propan-2-ol | 459.1 |
| 283 | 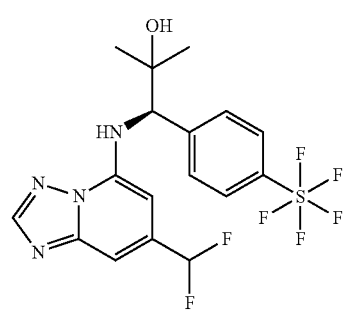 [SMILES: CC(C)(O)[C@H](Nc1cc(C(F)F)cc2ncnn12)c1ccc(S(F)(F)(F)(F)F)cc1] | (1R)-1-{[7-(Difluoromethyl)[1,2,4]triazolo[1,5-a]pyridin-5-yl]amino}-2-methyl-1-[4-(pentafluoro-λ⁶-sulfanyl)phenyl]propan-2-ol | 459.1 |

Example 284

((R)—N-(1-(3-Fluoro-4-(trifluoromethyl)phenyl)-2,2-dimethylpropyl)-[1,2,4]triazolo[1,5-a]pyrazin-5-amine

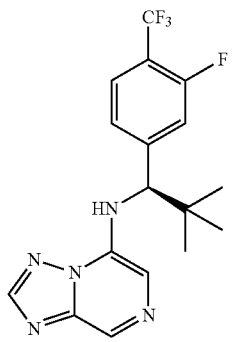 [SMILES: CC(C)(C)[C@@H](Nc1cncc2ncnn12)c1ccc(C(F)(F)F)c(F)c1]

Step 1: ((R)—N-(1-(3-Fluoro-4-(trifluoromethyl)phenyl)-2,2-dimethylpropyl)-[1,2,4]triazolo[1,5-a]pyrazin-5-amine To a solution of 5-bromo-[1,2,4]triazolo[1,5-a]pyrazine (100 mg, 0.502 mmol) in NMP (2 mL) was added (R)-1-(3-fluoro-4-(trifluoromethyl)phenyl)-2,2-dimethylpropan-1-amine (117 mg, 0.502 mmol) and DIEA (0.263 ml, 1.507 mmol) under $N_2$ and the resulting mixture stirred at 120° C. overnight. The mixture was filtered and purified by reverse phase HPLC (30-90% $CH_3CN/H_2O$ with 0.05% TFA) to afford the title compound as a solid. $^1$H NMR ($CDCl_3$, 500 MHz) δ: 8.72 (br s, 1H), 8.61 (s, 1H), 7.62 (m, 1H), 7.23 (m, 3H), 6.35 (m, 1H), 4.41 (m, 1H), 1.20 (s, 9H), LC/MS (m/z): 367.9 (M+H)$^+$.

The following compounds in Table 16 were prepared using procedures similar to those described in Example 284 using and the appropriate starting materials.

TABLE 16

| Example No. | Structure | IUPAC Name | Observed Exact Mass [M + H]$^+$ |
|---|---|---|---|
| 285 | 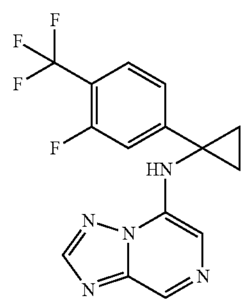 [SMILES: Fc1cc(C2(Nc3cncc4ncnn34)CC2)ccc1C(F)(F)F] | N-{1-[3-Fluoro-4-(trifluoromethyl)phenyl]cyclopropyl}[1,2,4]triazolo[1,5-a]pyrazin-5-amine | 338.1 |
| 286 | 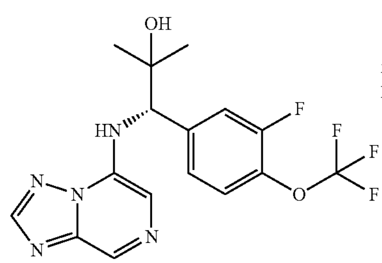 | (1S)-1-[3-Fluoro-4-(trifluoromethoxy)phenyl]-2-methyl-1-([1,2,4]triazolo[1,5-a]pyrazin-5-ylamino)propan-2-ol | 386.2 |
| 287 | 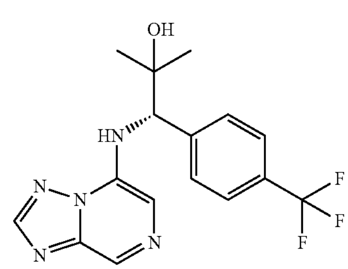 [SMILES: CC(C)(O)[C@@H](Nc1cncc2ncnn12)c1ccc(C(F)(F)F)cc1] | (1S)-2-Methyl-1-([1,2,4]triazolo[1,5-a]pyrazin-5-ylamino)-1-[4-(trifluoromethyl)phenyl]propan-2-ol | 352.1 |

TABLE 16-continued
| Example No. | Structure | IUPAC Name | Observed Exact Mass [M + H]+ |
|---|---|---|---|
| 288 | 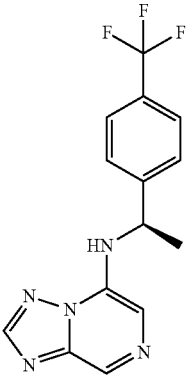 [SMILES: C[C@@H](Nc1cncc2ncnn12)c1ccc(C(F)(F)F)cc1] | N-{(1R)-1-[4-(Trifluoromethyl)phenyl]ethyl}[1,2,4]triazolo[1,5-a]pyridin-5-amine | 308.0 |
| 289 | 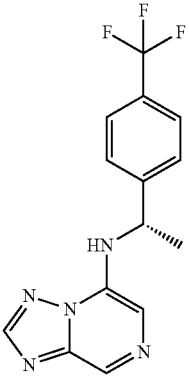 [SMILES: C[C@H](Nc1cncc2ncnn12)c1ccc(C(F)(F)F)cc1] | N-{(1S)-1-[4-(Trifluoromethyl)phenyl]ethyl}[1,2,4]triazolo[1,5-a]pyrazin-5-amine | 308.0 |
| 290 | 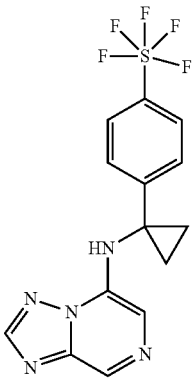 [SMILES: FS(F)(F)(F)(F)c1ccc(C2(Nc3cncc4ncnn34)CC2)cc1] | N-{1-[4-(Pentafluoro-$\lambda^6$-sulfanyl)phenyl]cyclopropyl}[1,2,4]triazolo[1,5-a]pyrazin-5-amine | 378.2 |

Examples 291 and 292

(R)-1-(3-Fluoro-4-(trifluoromethyl)phenyl)-2-methyl-1-((7-methyl-[1,2,4]triazolo[1,5-a]pyrimidin-5-yl)amino)propan-2-ol and (S)-1-(3-Fluoro-4-(trifluoromethyl)phenyl)-2-methyl-1-((7-methyl-[1,2,4]triazolo[1,5-a]pyrimidin-5-yl)amino)propan-2-ol

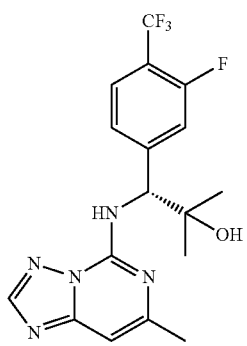

Step 1: 6-Methyl-4-thioxo-3,4-dihydropyrimidin-2(1H)-one

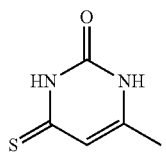

To a solution of phosphorus pentasulfide (3.59 g, 16.2 mmol) in pyridine (60 mL) was added 6-methylpyrimidine-2,4(1H,3H)-dione (3.40 g, 27.0 mmol) at 25° C. The reaction mixture was stirred at 120° C. for 16 h. The resulting mixture was cooled to 25° C. and solvent was evaporated under reduced pressure. The resulting mixture was quenched with water (200 mL). The mixture was filtered, washed with water (30 mL). The filter cake was re-crystallized from ethanol (50 mL). The title compound was obtained as a solid which was used in the next step without further purification. MS (+ESI) m/z=143.0.

Step 2: 4-Hydrazinyl-6-methylpyrimidin-2(1H)-one

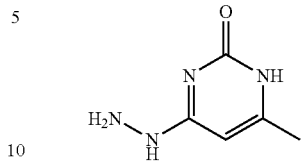

To a solution of 6-methyl-4-thioxo-3,4-dihydropyrimidin-2(1H)-one (1.00 g, 7.03 mmol) in EtOH (10 mL) was added hydrazine hydrate (2 mL) at room temperature. The reaction mixture was stirred at 80° C. for 2 h. On refrigeration, the filtrate deposited a solid which was washed with water and recrystallized from ethanol. The title compound was obtained as a solid and was used in the next step without further purification. MS (+ESI) m/z=141.0.

Step 3: 7-Methyl-[1,2,4]triazolo[1,5-a]pyrimidin-5(6H)-one

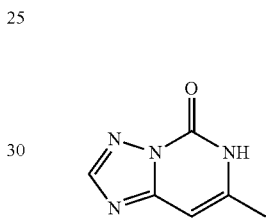

4-Hydrazinyl-6-methylpyrimidin-2(1H)-one (0.900 g, 6.42 mmol) in formic acid (13 mL) was heated at 110° C. for 3 h. The resulting mixture was cooled and concentrated under reduced pressure. The title compound was obtained as a solid which was used in the next step without further purification. MS (+ESI) m/z=150.9.

Step 4: 5-Chloro-7-methyl-[1,2,4]triazolo[1,5-a]pyrimidine

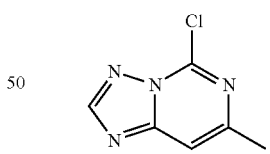

POCl₃ (15 mL) and N,N-diethylaniline (1.5 mL) were added to 7-methyl-[1,2,4]triazolo[1,5-a]pyrimidin-5(6H)-one (0.350 g, 2.33 mmol). The reaction mixture was stirred at 110° C. for 48 h. The resulting mixture was cooled to 25° C. and solvent was evaporated under reduced pressure. The residue was quenched with ice-water (20 mL) and extracted with ether (3×20 mL). The combined organic layers were washed with brine (3×30 mL), dried over anhydrous sodium sulfate and filtered. The filtrate was concentrated under vacuum. The residue was purified by column chromatography over silica gel using gradient 50-70% of ethyl acetate in petroleum ether as eluent. The title compound was obtained as a solid. MS (+ESI) m/z=168.9; 170.9.

Step 5: (R) and (S)-1-(3-fluoro-4-(trifluoromethyl)
phenyl)-2-methyl-1-((7-methyl-[1,2,4]triazolo[1,5-a]
pyrimidin-5-yl)amino)propan-2-ol

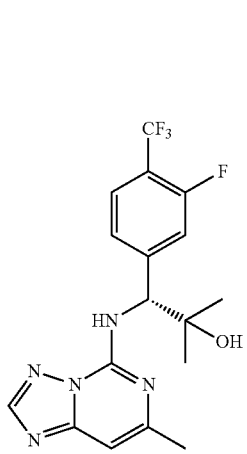

The title racemic compound was prepared as described in Step 1 of Example 191 using 5-chloro-7-methyl-[1,2,4]triazolo[1,5-a]pyrimidine, 1-amino-1-(3-fluoro-4-(trifluoromethyl)phenyl)-2-methylpropan-2-ol and DIEA in i-PrOH to give the title racemic compound as a solid. Then 1-(3-fluoro-4-(trifluoromethyl)phenyl)-2-methyl-1-((7-methyl-[1,2,4]triazolo[1,5-a]pyrimidin-5-yl) amino)propan-2-ol was separated by Chiral-Prep-HPLC with the following conditions: Chiralpak IA 2×25 cm, 5 um; Mobile Phase A: Hex-HPLC, Mobile Phase B: EtOH-HPLC; Flow rate: 20 mL/min; Gradient: isocratic 5% B in 17 min; 254/220 nm. The faster-eluting enantiomer of the title compound (Example 291) was obtained at 9.95 min as a solid. MS (+ESI) m/z=384.0. $^1$H NMR (300 MHz, DMSO-$d_6$) δ: 8.49 (s, 1H), 7.80 (d, J=8.7 Hz, 1H), 7.75-7.72 (m, 1H), 7.60 (br, 1H), 7.53 (d, J=8.1 Hz, 1H), 6.90 (s, 1H), 5.34 (s, 1H), 5.15 (d, J=8.4 Hz, 1H), 2.29 (s, 3H), 1.34 (s, 3H), 1.04 (s, 3H). The slower-eluting enantiomer of the title compound (Example 292) was obtained at 13.6 min as a solid. MS (+ESI) m/z=384.0. $^1$H NMR (300 MHz, DMSO-$d_6$) δ: 8.49 (s, 1H), 7.80 (d, J=8.7 Hz, 1H), 7.75-7.72 (m, 1H), 7.60 (br, 1H), 7.53 (d, J=8.1 Hz, 1H), 6.90 (s, 1H), 5.34 (s, 1H), 5.16 (d, J=8.7 Hz, 1H), 2.29 (s, 3H), 1.34 (s, 3H), 1.04 (s, 3H).

Example 293

N-{1-[3-Fluoro-4-(trifluoromethyl)phenyl]cyclopropyl}-7-methyl[1,2,4]triazolo[1,5-a]pyrimidin-5-amine

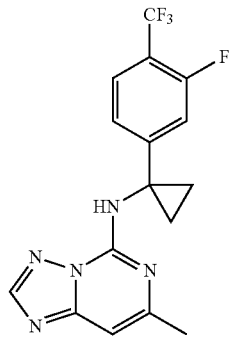 [SMILES: Cc1cc2ncnn2c(NC2(c3ccc(C(F)(F)F)c(F)c3)CC2)n1]

The following example was prepared using similar procedures as in Example 292 using the appropriate starting materials. LC-MS (+ESI) m/z=352.1.

Example 294

(S)-1-((2-Amino-7-(trifluoromethyl)-[1,2,4]triazolo[1,5-a]pyridin-5-yl)amino)-2-methyl-1-(4-(trifluoromethyl)phenyl)propan-2-ol

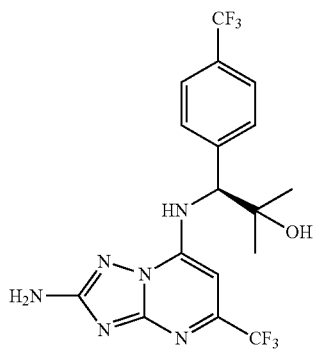 [SMILES: CC(C)(O)[C@@H](Nc1cc(C(F)(F)F)nc2nc(N)nn12)c1ccc(C(F)(F)F)cc1]

Step 1: tert-Butyl (5-chloro-7-(trifluoromethyl)-[1,2,4]triazolo[1,5-a]pyridin-2-yl)carbamate

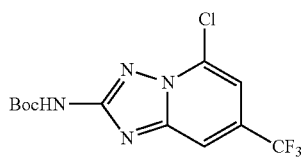 [SMILES: CC(C)(C)OC(=O)Nc1nc2cc(C(F)(F)F)cc(Cl)n2n1]

To a solution of 5-chloro-7-(trifluoromethyl)-[1,2,4]triazolo[1,5-a]pyridin-2-amine (1 g, 4.23 mmol) in DCM (40 mL) added BOCanhydride (1.963 ml, 8.45 mmol) and DMAP (0.052 g, 0.423 mmol), TEA (1.178 ml, 8.45 mmol) under N$_2$. The suspension mixture was stirred at rt overnight.

The mixture was diluted with water (50 mL) and extracted with DCM (100 mL×3). The organic layer was dried over Na₂SO₄ and concentrated in vacuo to afford crude product. Purification with ISCO (40 g biotage column, 0-100% EtOAc in Hexane) afforded the title compound. LC/MS (m/z): 336.9 (M+H)⁺.

Step 2: (S)-tert-Butyl (5-((2-hydroxy-2-methyl-1-(4-(trifluoromethyl)phenyl)propyl)amino)-7-(trifluoromethyl)-[1,2,4]triazolo[1,5-a]pyridin-2-yl)carbamate

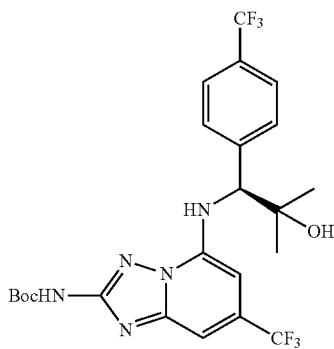 [SMILES: CC(C)(C)OC(=O)Nc1nc2cc(C(F)(F)F)cc(N[C@@H](c3ccc(C(F)(F)F)cc3)C(C)(C)O)n2n1]

To a solution of tert-butyl (5-chloro-7-(trifluoromethyl)-[1,2,4]triazolo[1,5-a]pyridin-2-yl)carbamate (100 mg, 0.297 mmol) in toluene (4 mL) added (S)-1-amino-2-methyl-1-(4-(trifluoromethyl)phenyl)propan-2-ol (104 mg, 0.446 mmol) and Pd(OAc)₂ (13.34 mg, 0.059 mmol), sodium tert-butoxide (57.1 mg, 0.594 mmol) and BINAP (37.0 mg, 0.059 mmol) under N₂. The mixture was stirred at 100° C. for 1.5 h. The mixture was directly purified with ISCO (10 g biotage column, 0-100% EtOAc in Hexane) to provide the title compound. LC/MS (m/z): 534.0 (M+H)⁺.

Step 3: (S)-1-((2-Amino-7-(trifluoromethyl)-[1,2,4]triazolo[1,5-a]pyridin-5-yl)amino)-2-methyl-1-((trifluoromethyl)phenyl)propan-2-ol

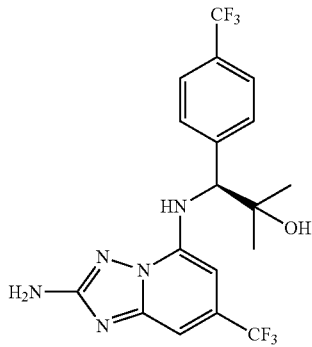 [SMILES: CC(C)(O)[C@@H](Nc1cc(C(F)(F)F)cc2nc(N)nn12)c1ccc(C(F)(F)F)cc1]

To a solution of (S)-tert-butyl (5-((2-hydroxy-2-methyl-1-(4-(trifluoromethyl) phenyl) propyl)amino)-7-(trifluoromethyl)-[1,2,4]triazolo[1,5-a]pyridin-2-yl)carbamate (crude) was in DCM (0.5 mL) and added TFA (0.2 mL). The mixture was stirred at rt for 1 h. The solvent was removed under vacuo and the residue was redissolved in CH₃CN (0.2 mL). Purification by reverse phase HPLC (30-90% CH₃CN/H₂O with 0.05% TFA) provided the title compound as a solid. ¹H NMR (CDCl₃, 500 MHz) δ: 7.67 (d, J=7.5 Hz, 2H), 7.48 (d, J=7.5 Hz, 2H), 7.09 (s, 1H), 6.01 (s, 1H), 4.43 (m, 1H), 1.59 (s, 3H), 1.21 (s, 3H). LC/MS (m/z): 433.9 (M+H)⁺.

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 μM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) aaccording to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 μL. Solutions of test compounds were prepared in DMSO and serially diluted with DMSO to yield 8 μL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 μM concentration for 100% inhibition. Bay 60-7550 was obtained from Axxora via Fisher Scientific (cat# ALX-270-421-M025/cat#NC9314773). Put another way, any compound with Ki of ~0.2 to about 2 nM could be used at 1 to 10 μM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM $MgCl_2$, 0.05% $NaN_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 μL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization $(mP)=1000*(S/So-P/Po)/(S/So+P/Po)$.

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \ mP - 100\% \ mP)(Imax - Imin)}{1+\left[\frac{[Drug]}{\left(10^{-pK_I}\left(1+\frac{[Substrate]}{K_M}\right)\right)}\right]^{nH}} + 100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1 (Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 μL. Solutions of test compounds were prepared in DMSO and serially diluted with DMSO to yield 30 μL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 μL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 μL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 μM. Many of compounds within the present invention had activity in inhibiting the human PDE2 enzyme in the aforementioned assays, with a Ki of less than about 1 μM, preferably less than or about 0.1 μM. Additional data is provided in the following Examples. Such a result is indicative of the intrinsic activity of the compounds in use as inhibitors of the PDE2 enzyme. In general, one of ordinary skill in the art would appreciate that a substance is considered to be particularly effective for inhibiting PDE2 activity if it has a Ki of less than or about 1 μM, preferably less than or about 0.1 μM. The present invention also includes compounds within the generic scope of the invention which possess activity as inhibitors of other phosphodiesterase enzymes.

In the following tables representative data for the compounds of formula I as PDE2 inhibitors as determined by the foregoing assays and as conducted in laboratory (Lab) A or B are shown. The PDE2 Ki is a measure of the ability of the test compound to inhibit the action of the PDE2 enzyme. Table 10. PDE2 Ki's (ND=Not determined)

TABLE 10

| Example No. | Rhesus PDE2 Ki (nM) Lab A | Human PDE2 Ki (nM) Lab A | Rhesus PDE2 Ki (nM) Lab B | Human PDE2 Ki (nM) Lab B |
|---|---|---|---|---|
| 1 | NA | NA | NA | 175 |
| 2 | NA | NA | NA | ~1545 |
| 3 | NA | NA | NA | 115 |
| 4 | NA | NA | NA | 108 |
| 5 | NA | NA | NA | 113 |
| 6 | NA | NA | NA | 482 |
| 7 | NA | NA | NA | 132 |
| 8 | NA | NA | NA | 57 |
| 9 | NA | NA | NA | 138 |
| 10 | NA | NA | NA | 21 |
| 11 | NA | NA | NA | 18 |
| 12 | NA | NA | NA | 68 |
| 13 | NA | NA | NA | 122 |
| 14 | NA | NA | NA | 48 |
| 15 | NA | NA | NA | 173 |
| 16 | NA | NA | NA | 61 |
| 17 | NA | NA | NA | 15 |
| 18 | NA | NA | NA | 15 |
| 19 | NA | NA | NA | 36 |
| 20 | NA | NA | NA | 28 |
| 21 | NA | NA | NA | 4.0 |
| 22 | NA | NA | NA | 13 |
| 23 | NA | NA | NA | 45 |
| 24 | NA | NA | NA | 26 |
| 25 | NA | NA | NA | 9.9 |
| 26 | NA | NA | NA | 11 |
| 27 | NA | NA | NA | 10 |
| 28 | NA | NA | NA | 7.1 |
| 29 | NA | NA | NA | 2.1 |
| 30 | NA | NA | NA | 4.4 |
| 31 | NA | NA | NA | 4.9 |
| 32 | NA | NA | NA | 6.6 |
| 33 | NA | NA | NA | 17 |
| 34 | NA | NA | NA | 15 |
| 35 | NA | NA | NA | 7.8 |
| 36 | NA | NA | NA | 6.3 |
| 37 | NA | NA | NA | 22 |
| 38 | NA | NA | NA | 20 |
| 39 | NA | NA | NA | 49 |
| 40 | NA | NA | NA | 14 |
| 41 | NA | NA | NA | 19 |
| 42 | NA | NA | NA | 20 |
| 43 | NA | NA | NA | 23 |
| 44 | NA | NA | NA | 18 |
| 45 | NA | NA | NA | 207 |
| 46 | NA | NA | NA | 48 |
| 47 | NA | NA | NA | 161 |
| 48 | NA | NA | NA | 474 |
| 49 | NA | NA | NA | 301 |
| 50 | NA | NA | NA | 182 |
| 51 | NA | NA | NA | 206 |
| 52 | NA | NA | NA | 78 |
| 53 | NA | NA | NA | 99 |
| 54 | NA | NA | NA | 342 |
| 55 | NA | NA | NA | 211 |
| 56 | NA | NA | 61 | 79 |
| 57 | NA | NA | 22 | 21 |
| 58 | NA | NA | NA | 52 |
| 59 | NA | NA | NA | 72 |
| 60 | NA | NA | NA | 32 |
| 61 | NA | NA | NA | 81 |
| 62 | NA | NA | NA | 162 |
| 63 | NA | NA | NA | 33 |
| 64 | NA | NA | NA | 77 |
| 65 | NA | NA | NA | 75 |
| 66 | NA | NA | NA | 108 |
| 67 | NA | NA | NA | 367 |
| 68 | NA | NA | 29 | 35 |
| 69 | NA | NA | NA | 29 |
| 70 | NA | NA | NA | 3.7 |
| 71 | NA | NA | NA | 25 |
| 72 | NA | NA | NA | 26 |
| 73 | NA | NA | NA | 72 |
| 74 | NA | NA | NA | 109 |
| 75 | NA | NA | NA | 201 |
| 76 | NA | NA | NA | 969 |
| 77 | NA | NA | NA | ~1178 |
| 78 | NA | NA | NA | 92 |
| 79 | NA | NA | NA | 208 |
| 80 | NA | NA | NA | 387 |
| 81 | NA | NA | NA | 31 |
| 82 | NA | NA | NA | 10 |
| 83 | 4681 | NA | NA | NA |
| 84 | 2771 | NA | NA | NA |
| 85 | NA | NA | NA | ~1157 |
| 86 | NA | NA | NA | ~1746 |
| 87 | NA | NA | NA | 132 |
| 88 | NA | NA | NA | 736 |
| 89 | NA | NA | NA | 82 |
| 90 | NA | NA | NA | ~1790 |
| 91 | NA | NA | NA | >2955 |
| 92 | NA | NA | 6.8 | 5.4 |
| 93 | NA | NA | NA | 742 |
| 94 | NA | NA | NA | 17 |
| 95 | NA | NA | NA | >2955 |
| 96 | NA | NA | NA | 15 |
| 97 | NA | NA | NA | >2955 |
| 98 | NA | NA | 12 | 10 |
| 99 | NA | NA | NA | 555 |
| 100 | NA | NA | NA | 4.3 |
| 101 | NA | NA | NA | 27 |
| 102 | NA | NA | NA | 14 |
| 103 | NA | NA | NA | 34 |
| 104 | NA | NA | NA | ~2775 |
| 105 | NA | NA | NA | 38 |
| 106 | NA | NA | NA | >1244 |
| 107 | NA | NA | NA | 13 |
| 108 | NA | NA | NA | 49 |
| 109 | NA | NA | NA | 905 |
| 110 | NA | NA | NA | >2955 |
| 111 | NA | NA | NA | 26 |
| 112 | NA | NA | NA | >2955 |
| 113 | NA | NA | NA | 93 |
| 114 | NA | NA | NA | >2955 |
| 115 | NA | NA | NA | 23 |
| 116 | NA | NA | NA | >2955 |
| 117 | NA | NA | 5.6 | 4.6 |
| 118 | NA | NA | NA | >2955 |
| 119 | NA | NA | NA | 15 |
| 120 | NA | NA | NA | >2955 |
| 121 | NA | NA | NA | 11 |
| 122 | NA | NA | NA | >2955 |
| 123 | NA | NA | NA | 35 |
| 124 | NA | NA | NA | 79 |
| 125 | NA | NA | NA | >2955 |
| 126 | NA | NA | NA | >2955 |
| 127 | NA | NA | NA | 21 |
| 128 | NA | NA | NA | >2955 |
| 129 | NA | NA | NA | 21 |
| 130 | NA | NA | NA | 2289 |
| 131 | NA | NA | NA | >2955 |
| 132 | NA | NA | NA | >2955 |
| 133 | NA | NA | NA | 18 |
| 134 | NA | NA | NA | >2955 |
| 135 | NA | NA | NA | 30 |
| 136 | NA | NA | NA | >2955 |
| 137 | NA | NA | NA | 436 |
| 138 | NA | NA | NA | ~1569 |
| 139 | NA | NA | NA | >2955 |
| 140 | NA | NA | NA | >2955 |
| 141 | NA | NA | NA | 877 |
| 142 | NA | NA | NA | >2955 |
| 143 | NA | NA | NA | 97 |
| 144 | NA | NA | NA | >2955 |
| 145 | NA | NA | NA | 25 |
| 146 | NA | NA | NA | >2955 |
| 147 | NA | NA | NA | >2955 |
| 148 | NA | NA | NA | >2955 |
| 149 | NA | NA | NA | >2955 |
| 150 | NA | NA | NA | >2955 |

TABLE 10-continued

| Example No. | Rhesus PDE2 Ki (nM) Lab A | Human PDE2 Ki (nM) Lab A | Rhesus PDE2 Ki (nM) Lab B | Human PDE2 Ki (nM) Lab B |
| --- | --- | --- | --- | --- |
| 151 | NA | NA | NA | >2955 |
| 152 | NA | NA | NA | 766 |
| 153 | NA | NA | NA | >2955 |
| 154 | NA | NA | NA | >2955 |
| 155 | NA | NA | NA | 525 |
| 156 | NA | NA | NA | 636 |
| 157 | NA | NA | NA | 37 |
| 158 | NA | NA | NA | ~2344 |
| 159 | NA | NA | NA | >2955 |
| 160 | NA | NA | NA | 81 |
| 161 | NA | NA | NA | 19 |
| 162 | NA | NA | NA | ~2052 |
| 163 | NA | NA | NA | 77 |
| 164 | NA | NA | NA | >2955 |
| 165 | NA | NA | NA | 52 |
| 166 | NA | NA | NA | ~2191 |
| 167 | NA | NA | NA | 184 |
| 168 | NA | NA | NA | >2955 |
| 169 | NA | NA | NA | 50 |
| 170 | NA | NA | NA | >2955 |
| 171 | NA | NA | NA | ~1559 |
| 172 | NA | NA | NA | 25 |
| 173 | NA | NA | NA | >2955 |
| 174 | NA | NA | NA | 29 |
| 175 | NA | NA | NA | 14 |
| 176 | NA | NA | NA | ~1306 |
| 177 | NA | NA | NA | 8.4 |
| 178 | NA | NA | NA | 421 |
| 179 | NA | NA | NA | >2955 |
| 180 | NA | NA | NA | 12 |
| 181 | NA | NA | NA | 32 |
| 182 | NA | NA | NA | >2955 |
| 183 | NA | NA | NA | 15 |
| 184 | NA | NA | NA | 68 |
| 185 | NA | NA | NA | 10 |
| 186 | NA | NA | NA | 1898 |
| 187 | NA | NA | NA | 5.5 |
| 188 | NA | NA | NA | >2955 |
| 189 | NA | NA | NA | 17 |
| 190 | NA | NA | NA | >2955 |
| 191 | NA | NA | NA | 67 |
| 192 | NA | NA | NA | 91 |
| 193 | NA | NA | NA | 142 |
| 194 | NA | NA | NA | 113 |
| 195 | NA | NA | NA | 144 |
| 196 | NA | NA | NA | 321 |
| 197 | NA | NA | NA | 80 |
| 198 | NA | NA | NA | 83 |
| 199 | NA | NA | NA | 167 |
| 200 | NA | NA | NA | >2955 |
| 201 | NA | NA | NA | 131 |
| 202 | NA | NA | NA | 56 |
| 203 | NA | NA | NA | 33 |
| 204 | NA | NA | NA | 17 |
| 205 | NA | NA | NA | 24 |
| 206 | NA | NA | NA | 184 |
| 207 | NA | NA | NA | 74 |
| 208 | NA | NA | NA | 2.7 |
| 209 | NA | NA | NA | >2955 |
| 210 | NA | NA | NA | 583 |
| 211 | NA | NA | NA | ~2483 |
| 212 | NA | NA | NA | 310 |
| 213 | NA | NA | NA | >2955 |
| 214 | NA | NA | NA | 25 |
| 215 | NA | NA | NA | >2955 |
| 216 | NA | NA | NA | 134 |
| 217 | NA | NA | NA | 329 |
| 218 | NA | NA | NA | >2955 |
| 219 | NA | NA | NA | 252 |
| 220 | NA | NA | NA | ~2107 |
| 221 | NA | NA | NA | >2955 |
| 222 | NA | NA | NA | 4.4 |
| 223 | NA | NA | NA | 1.1 |
| 224 | NA | NA | NA | 612 |
| 225 | NA | NA | NA | 258 |
| 226 | NA | NA | NA | 356 |
| 227 | NA | NA | NA | 7.6 |
| 228 | NA | NA | NA | >2955 |
| 229 | NA | NA | NA | 448 |
| 230 | NA | NA | NA | 167 |
| 231 | NA | NA | NA | 7.3 |
| 232 | NA | NA | NA | >2955 |
| 233 | NA | NA | NA | 256 |
| 234 | NA | NA | NA | 1226 |
| 235 | NA | NA | NA | 18 |
| 236 | NA | NA | NA | 210 |
| 237 | NA | NA | NA | 1694 |
| 238 | NA | NA | NA | 335 |
| 239 | NA | NA | NA | 13 |
| 240 | NA | NA | NA | 108 |
| 241 | NA | NA | NA | 375 |
| 242 | NA | NA | NA | 616 |
| 243 | NA | NA | NA | >2955 |
| 244 | NA | NA | NA | 377 |
| 245 | NA | NA | NA | 204 |
| 246 | NA | NA | NA | 46 |
| 247 | NA | NA | NA | 24 |
| 248 | NA | NA | NA | >2955 |
| 249 | NA | NA | NA | 40 |
| 250 | NA | NA | NA | 57 |
| 251 | NA | NA | NA | 140 |
| 252 | NA | NA | NA | 60 |
| 253 | NA | NA | NA | 83 |
| 254 | NA | NA | NA | >2955 |
| 255 | NA | NA | NA | 22 |
| 256 | NA | NA | NA | 608 |
| 257 | NA | NA | NA | 10 |
| 258 | NA | NA | NA | 6.0 |
| 259 | NA | NA | NA | 1431 |
| 260 | NA | NA | NA | 14 |
| 261 | NA | NA | NA | >2955 |
| 262 | NA | NA | NA | 137 |
| 263 | NA | NA | NA | 101 |
| 264 | NA | NA | NA | 292 |
| 265 | NA | NA | NA | 82 |
| 266 | NA | NA | NA | 13 |
| 267 | NA | NA | NA | 236 |
| 268 | NA | NA | NA | 2075 |
| 269 | NA | NA | NA | 181 |
| 270 | NA | NA | NA | 101 |
| 271 | NA | NA | NA | 530 |
| 272 | NA | NA | NA | 121 |
| 273 | NA | NA | NA | 102 |
| 274 | NA | NA | NA | 11 |
| 275 | NA | NA | NA | 111 |
| 276 | NA | NA | NA | 68 |
| 277 | NA | NA | NA | 87 |
| 278 | NA | NA | NA | 92 |
| 279 | NA | NA | NA | 41 |
| 280 | NA | NA | NA | 20 |
| 281 | NA | NA | NA | 40 |
| 282 | NA | NA | NA | 7.8 |
| 283 | NA | NA | NA | 498 |
| 284 | NA | NA | NA | 156 |
| 285 | NA | NA | NA | 22 |
| 286 | NA | NA | NA | 209 |
| 287 | NA | NA | NA | 150 |
| 288 | NA | NA | NA | 221 |
| 289 | NA | NA | NA | >2955 |
| 290 | NA | NA | NA | 90 |
| 291 | NA | NA | NA | 183 |
| 292 | NA | NA | NA | >2955 |
| 293 | NA | NA | NA | 172 |
| 294 | NA | NA | NA | 678 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound represented by structural formula Ia

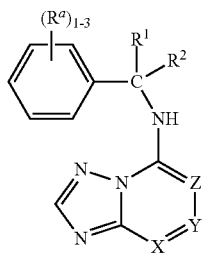

or a pharmaceutically acceptable salt thereof, wherein:
one of $R^1$ and $R^2$ is H and the other is $C_{1-6}$alkyl, said alkyl optionally substituted with 1 to 3 groups $R^a$;
or $R^1$ and $R^2$ can combine with the carbon to which they are attached to form $C_{3-10}$cycloalkyl or $C_{3-10}$-heterocycloalkyl selected from the group consisting of cyclopropyl, cyclobutyl, cyclopentyl, cyclohexyl, and oxetanyl, said cycloalkyl and heterocycloalkyl optionally substituted with 1 to 3 groups $R^a$;
$R^{4a}$ is selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl;
Rob is hydrogen or $CH_3$;
$R^a$ is selected from the group consisting of halo, CN, $C_{1-6}$alkyl, $(CH_2)_nOR$, $(O)_pC_{1-4}$haloalkyl, $NR_2$, $SCF_3$, and $SF_5$, said alkyl optionally substituted with one to three groups selected from halo, wherein halo is selected from the group consisting of fluorine and chlorine, and $C_{1-6}$alkyl; or
two adjacent $R^a$ groups on the phenyl together with the atoms to which they are attached can combine to form a cyclic ring, said ring optionally interrupted by 1 to 2 heteroatoms selected from N, S, and O;
R represents H or $C_{1-6}$alkyl,
n represents 0, 1, 2, 3, or 4;
p represents 0 or 1.

2. The compound according to claim 1 or a pharmaceutically acceptable salt thereof wherein one of $R^1$ and $R^2$ is H and the other is selected from the group consisting $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_n OCH_3$.

3. The compound according to claim 1 or a pharmaceutically acceptable salt thereof wherein $R^a$ is selected from halo, $(CH_2)_nCF_3$, $OCF_3$, $C(CH_3)_3$, $CHF_2$, $SF_5$, $SCF_3$, $OCHF_2$, $CH(CH_3)_2$, or when two adjacent $R^a$ on the phenyl along with the atoms to which they are attached combine the combination of two $R^a$ is selected from cyclopropyl or pyridyl, said cyclopropyl and pyridyl optionally substituted with 1 to 3 groups of $C_{1-6}$ alkyl,
X, Y and Z, respectively, represents X=N, Y=$CR^{4a}$, Z=$CR^{4b}$, wherein $R^{4a}$ and $R^{4b}$ are selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF_2CF_3$, $NH_2$, $N(CH_3)_2$, $NHCH_3$, $OCH_2CH_3$, $(CH_2)_nOCH_3$, halo and optionally substituted cyclopropyl, and
one of $R^1$ and $R^2$ is H and the other is selected from the group consisting H, $CH_3$, $CH(CH_3)_2$, $C(CH_3)_2OH$, $C(CH_3)_2CH_2OH$, $C(CH_3)_3$, $CH_2CH_3$, $CH(CH_3)OH$, $(CH_2)_nOH$, $C(CH_3)_2NH_2$, $C(CH_2CH_3)_2OH$, $N(CH_3)_2$, $NHCH_3$, $OCH_2CH_3$, and $(CH_2)_nOCH_3$.

4. The compound according to 36 or a pharmaceutically acceptable salt thereof wherein $R^a$ is selected from the group consisting of halo, (CH2)nCF3, and OCF3, one of $R^{4a}$ and $R^{4b}$ is hydrogen or $CH_3$ and the other is selected from the group consisting of H, $CH_3$, $CH(CH_3)_2$, $C(CH_3)_2OH$, $C(CH_3)_3$, $CH_2CH_3$, $CH(CH_3)OH$, $(CH_2)_nOH$, $CHF_2$, $CH_2F$, $CF_3$, $CF2CF3$, $NH_2$, $N(CH_3)_2$, $NHCH_3$, $OCH_2CH_3$, $(CH_2)_nOCH_3$, halo and optionally substituted cyclopropyl, and one of $R^1$ and $R^2$ is hydrogen and the other is selected from the group consisting of $CH_3$, $CH(CH_3)_2$, $C(CH_3)_2OH$, $C(CH_3)_3$, $(CH_2)_nOH$, and $(CH_2)_nOCH_3$.

5. The compound according to claim 3 or a pharmaceutically acceptable salt thereof wherein $R^a$ is selected from the group consisting of fluorine, chlorine, $CF_3$, and $OCF_3$, one of $R^{4a}$ and $R^{4b}$ is hydrogen and the other is selected from the group consisting of $CH_3$, $(CH_2)_nOH$, and $CF_3$, and one of $R^1$ and $R^2$ is hydrogen and the other is $CH_3$.

6. The compound according to claim 3 or a pharmaceutically acceptable salt thereof wherein $R^a$ is selected from the group consisting of fluorine, chlorine, $CF_3$, and $OCF_3$, one of $R^{4a}$ and $R^{4b}$ is hydrogen and the other is selected from the group consisting of $CH_3$, $(CH_2)_nOH$, and $CF_3$, and $R^1$ and $R^2$ combine with the carbon to which they are attached to form optionally substituted cyclopropyl, cyclobutyl, cyclopentyl, cyclohexyl, or oxetanyl.

7. A compound which is:
5-Methyl-N-{(1R)-1-[4-(trifluoromethyl)phenyl]ethyl}[1,2,4]triazolo[1,5-a]pyrimidin-7-amine,
5-Methyl-N-{(1S)-1-[4-(trifluoromethyl)phenyl]ethyl}[1,2,4]triazolo[1,5-a]pyrimidin-7-amine,
N-{(1R)-1-[3-Fluoro-4-(trifluoromethyl)phenyl]ethyl}-5-methyl[1,2,4]triazolo[1,5-a]pyrimidin-7-amine,
5-Methyl-N-{(1R)-1-[4-(2,2,2-trifluoroethyl)phenyl]ethyl}[1,2,4]triazolo[1,5-a]pyrimidin-7-amine,
N-{(1R)-1-[3-Chloro-4-(trifluoromethyl)phenyl]ethyl}-5-methyl[1,2,4]triazolo[1,5-a]pyrimidin-7-amine,
N-{(1R)-1-[2,5-Difluoro-4-(trifluoromethyl)phenyl]ethyl}-5-methyl[1,2,4]triazolo[1,5-a]pyrimidin-7-amine,
5-Methyl-N-{(1R)-1-[4-(trifluoromethoxy)phenyl]ethyl}[1,2,4]triazolo[1,5-a]pyrimidin-7-amine,
N-{(1R)-1-[3-Fluoro-4-(trifluoromethoxy)phenyl]ethyl}-5-methyl[1,2,4]triazolo[1,5-a]pyrimidin-7-amine,
N-{(1R)-1-[3-Chloro-4-(trifluoromethoxy)phenyl]ethyl}-5-methyl[1,2,4]triazolo[1,5-a]pyrimidin-7-amine,
5-Methyl-N-[(1R)-1-{4-[(trifluoromethyl)sulfanyl]phenyl}ethyl][1,2,4]triazolo[1,5-a]pyrimidin-7-amine,
N-[(1R)-1-{3-Fluoro-4-[(trifluoromethyl)sulfanyl]phenyl}ethyl]-5-methyl[1,2,4]triazolo[1,5-a]pyrimidin-7-amine,
5-Methyl-N-{(1R)-1-[4-(pentafluoro-$\lambda^6$-sulfanyl)phenyl]ethyl}[1,2,4]triazolo[1,5-a]pyrimidin-7-amine,
5-Methyl-N-{(1R)-1-[4-(1-methylethyl)phenyl]ethyl}[1,2,4]triazolo[1,5-a]pyrimidin-7-amine,
N-[(1R)-1-(4-Cyclopropyl-3-fluorophenyl)ethyl]-5-methyl[1,2,4]triazolo[1,5-a]pyrimidin-7-amine,
5-Methyl-N-{(1R)-1-[4-(1-methylcyclopropyl)phenyl]ethyl}[1,2,4]triazolo[1,5-a]pyrimidin-7-amine, N-{(1R)-1-[3-Fluoro-4-(trifluoromethyl)phenyl]propyl}-5-methyl[1,2,4]triazolo[1,5-a]pyrimidin-7-amine,
5-Methyl-N-[(1R)-1-{4-[(trifluoromethyl)sulfanyl]phenyl}propyl][1,2,4]triazolo[1,5-a]pyrimidin-7-amine,
N-[(1R)-1-{3-Fluoro-4-[(trifluoromethyl)sulfanyl]phenyl}propyl]-5-methyl[1,2,4]triazolo[1,5-a]pyrimidin-7-amine,
5-Methyl-N-{(1R)-2-methyl-1-[4-(trifluoromethyl)phenyl]propyl}[1,2,4]triazolo[1,5-a]pyrimidin-7-amine,
N-{(1R)-1-[3-Fluoro-4-(trifluoromethyl)phenyl]-2-methylpropyl]-5-methyl[1,2,4]triazolo[1,5-a]pyrimidin-7-amine,
N-[(1R)-1-{3-Fluoro-4-[(trifluoromethyl)sulfanyl]phenyl}-2-methylpropyl]-5-methyl[1,2,4]triazolo [1,5-a]pyrimidin-7-amine,
5-Methyl-N-{(1R)-2-methyl-1-[4-(pentafluoro-$\lambda^6$-sulfanyl)phenyl]propyl}[1,2,4]triazolo[1,5-a]pyrimidin-7-amine,
N-{(1R)-1-[4-(Difluoromethoxy)phenyl]-2-methylpropyl}-5-methyl[1,2,4]triazolo[1,5-a]pyrimidin-7-amine,
5-Methyl-N-{(1R)-2-methyl-1-[4-(1-methylcyclopropyl)phenyl]propyl}[1,2,4]triazolo[1,5-a]pyrimidin-7-amine,
N-[(1R)-1-(4-Cyclopropyl-3-fluorophenyl)-2-methylpropyl]-5-methyl[1,2,4]triazolo[1,5-a]pyrimidin-7-amine,
N-{(1R)-2,2-Dimethyl-1-[4-(trifluoromethyl)phenyl]propyl}-5-methyl[1,2,4]triazolo[1,5-a]pyrimidin-7-amine,
N-{(1R)-1-[3-Fluoro-4-(trifluoromethyl)phenyl]-2,2-dimethylpropyl}-5-methyl[1,2,4]triazolo[1,5-a]pyrimidin-7-amine,
N-{(1R)-1-[3-Fluoro-4-(trifluoromethoxy)phenyl]-2,2-dimethylpropyl}-5-methyl[1,2,4]triazolo [1,5-a]pyrimidin-7-amine,
N-[(1R)-2,2-Dimethyl-1-{4-[(trifluoromethyl)sulfanyl]phenyl}propyl]-5-methyl[1,2,4]triazolo [1,5-a]pyrimidin-7-amine,
N-[(1R)-1-(4-Cyclopropylphenyl)-2,2-dimethylpropyl]-5-methyl[1,2,4]triazolo[1,5-a]pyrimidin-7-amine,
N-[(1R)-1-(4-Cyclopropyl-3-fluorophenyl)-2,2-dimethylpropyl]-5-methyl[1,2,4]triazolo[1,5-a]pyrimidin-7-amine,
N-{(1R)-2,2-Dimethyl-1-[4-(trifluoromethoxy)phenyl]propyl}-5-methyl[1,2,4]triazolo[1,5-a]pyrimidin-7-amine,
N-{(1R)-1-[4-(Difluoromethoxy)phenyl]-2,2-dimethylpropyl}-5-methyl[1,2,4]triazolo[1,5-a]pyrimidin-7-amine,
N-{(1R)-1-[2-Fluoro-4-(trifluoromethyl)phenyl]-2,2-dimethylpropyl}-5-methyl[1,2,4]triazolo[1,5-a]pyrimidin-7-amine,
N-{(1R)-2,2-Dimethyl-1-[4-(2,2,2-trifluoroethyl)phenyl]propyl}-5-methyl[1,2,4]triazolo[1,5-a]pyrimidin-7-amine,
N-{(1R)-2,2-Dimethyl-1-[4-(pentafluoro-$\lambda^6$-sulfanyl)phenyl]propyl}-5-methyl[1,2,4]triazolo[1,5-a]pyrimidin-7-amine,
N—{(R)-Cyclopropyl[4-(pentafluoro-$\lambda^6$-sulfanyl)phenyl]methyl}-5-methyl[1,2,4]triazolo[1,5-a]pyrimidin-7-amine,
N—[(R)-Cyclopropyl(4-cyclopropyl-3-fluorophenyl)methyl]-5-methyl[1,2,4]triazolo[1,5-a]pyrimidin-7-amine,
N—{(R)-Cyclopropyl[3-fluoro-4-(trifluoromethyl)phenyl]methyl}-5-methyl[1,2,4]triazolo[1,5-a]pyrimidin-7-amine,
N—[(R)-Cyclopropyl{4-[(trifluoromethyl)sulfanyl]phenyl}methyl]-5-methyl[1,2,4]triazolo[1,5-a]pyrimidin-7-amine,
N—[(R)-Cyclopropyl{3-fluoro-4-[(trifluoromethyl)sulfanyl]phenyl}methyl]-5-methyl[1,2,4]triazolo[1,5-a]pyrimidin-7-amine,
N—[(R)-Cyclopropyl(4-cyclopropylphenyl)methyl]-5-methyl[1,2,4]triazolo[1,5-a]pyrimidin-7-amine,
N—[(R)-[3-Fluoro-4-(trifluoromethyl)phenyl](1-methylcyclopropyl)methyl]-5-methyl[1,2,4]triazolo [1,5-a]pyrimidin-7-amine,
5-Methyl-N—{(R)-(1-methylcyclopropyl)[4-(pentafluoro-$\lambda^6$-sulfanyl)phenyl]methyl}[1,2,4]triazolo [1,5-a]pyrimidin-7-amine,
N-{1-[3-Fluoro-4-(trifluoromethoxy)phenyl]-1-methylethyl}-5-methyl[1,2,4]triazolo[1,5-a]pyrimidin-7-amine,
N-{1-[3-Fluoro-4-(trifluoromethyl)phenyl]-1-methylethyl}-5-methyl[1,2,4]triazolo[1,5-a]pyrimidin-7-amine,
N-{1-[2-Chloro-4-(trifluoromethyl)phenyl]-1-methylethyl}-5-methyl[1,2,4]triazolo[1,5-a]pyrimidin-7-amine,
N-{1-[2-Methoxy-4-(trifluoromethyl)phenyl]-1-methylethyl}-5-methyl[1,2,4]triazolo[1,5-a]pyrimidin-7-amine,
5-Methyl-N-{1-methyl-1-[4-(trifluoromethoxy)phenyl]ethyl}[1,2,4]triazolo[1,5-a]pyrimidin-7-amine,
N-(1-{3-Fluoro-4-[(trifluoromethyl)sulfanyl]phenyl}-1-methylethyl)-5-methyl[1,2,4]triazolo[1,5-a]pyrimidin-7-amine,
N-{1-[2-Fluoro-4-(trifluoromethoxy)phenyl]-1-methylethyl}-5-methyl[1,2,4]triazolo[1,5-a]pyrimidin-7-amine,
N-{1-[2-Fluoro-4-(trifluoromethyl)phenyl]-1-methylethyl}-5-methyl[1,2,4]triazolo[1,5-a]pyrimidin-7-amine,
5-Methyl-N-{1-methyl-1-[4-(trifluoromethyl)phenyl]ethyl}[1,2,4]triazolo[1,5-a]pyrimidin-7-amine,
5-Methyl-N-{1-methyl-1-[2-methyl-4-(trifluoromethyl)phenyl]ethyl}[1,2,4]triazolo[1,5-a]pyrimidin-7-amine,
5-Methyl-N-(1-methyl-1-{4-[(trifluoromethyl)sulfanyl]phenyl}ethyl)[1,2,4]triazolo[1,5-a]pyrimidin-7-amine,
5-Methyl-N-{1-[4-(trifluoromethyl)phenyl]cyclopropyl}[1,2,4]triazolo[1,5-a]pyrimidin-7-amine,
N-{1-[3-Fluoro-4-(trifluoromethyl)phenyl]cyclopropyl}-5-methyl[1,2,4]triazolo[1,5-a]pyrimidin-7-amine,
5-Methyl-N-(1-{4-[(trifluoromethyl)sulfanyl]phenyl}cyclopropyl)[1,2,4]triazolo[1,5-a]pyrimidin-7-amine,
N-[1-(4-tert-Butylphenyl)cyclopropyl]-5-methyl[1,2,4]triazolo[1,5-a]pyrimidin-7-amine,
N-{1-[3-Fluoro-4-(trifluoromethoxy)phenyl]cyclopropyl}-5-methyl[1,2,4]triazolo[1,5-a]pyrimidin-7-amine,
5-Methyl-N-{1-[4-(pentafluoro-$\lambda^6$-sulfanyl)phenyl]cyclopropyl}[1,2,4]triazolo[1,5-a]pyrimidin-7-amine,
N-{1-[2-Fluoro-4-(trifluoromethyl)phenyl]cyclopropyl}-5-methyl[1,2,4]triazolo[1,5-a]pyrimidin-7-amine,
N-(1-{3-Fluoro-4-[(trifluoromethyl)sulfanyl]phenyl}cyclopropyl)-5-methyl[1,2,4]triazolo[1,5-a]pyrimidin-7-amine,
5-Methyl-N-{1-[4-(trifluoromethyl)phenyl]cyclobutyl}[1,2,4]triazolo[1,5-a]pyrimidin-7-amine,
5-Methyl-N-(1-{4-[(trifluoromethyl)sulfanyl]phenyl}cyclobutyl)[1,2,4]triazolo[1,5-a]pyrimidin-7-amine, N-(1-{3-Fluoro-4-[(trifluoromethyl)sulfanyl]phenyl}cyclobutyl)-5-methyl[1,2,4]triazolo[1,5-a]pyrimidin-7-amine,
5-Methyl-N-{1-[4-(trifluoromethyl)phenyl]cyclopentyl}[1,2,4]triazolo[1,5-a]pyrimidin-7-amine,
5-Ethyl-N-{1-[3-fluoro-4-(trifluoromethyl)phenyl]cyclopropyl}[1,2,4]triazolo[1,5-a]pyrimidin-7-amine,
N-{1-[3-Fluoro-4-(trifluoromethyl)phenyl]cyclopropyl}-5-(1-methylethyl)[1,2,4]triazolo[1,5-a]pyrimidin-7-amine,
5-Cyclopropyl-N-{1-[3-fluoro-4-(trifluoromethyl)phenyl]cyclopropyl}[1,2,4]triazolo[1,5-a]pyrimidin-7-amine,
5-Cyclopropyl-N-{1-[3-fluoro-4-(trifluoromethoxy)phenyl]cyclopropyl}[1,2,4]triazolo[1,5-a]pyrimidin-7-amine,
5-Cyclopropyl-N-{1-[4-(pentafluoro-$\lambda^6$-sulfanyl)phenyl]cyclopropyl}[1,2,4]triazolo[1,5-a]pyrimidin-7-amine,
5-tert-Butyl-N-{1-[3-fluoro-4-(trifluoromethyl)phenyl]cyclopropyl}[1,2,4]triazolo[1,5-a]pyrimidin-7-amine,
N-{1-[3-Fluoro-4-(trifluoromethyl)phenyl]cyclopropyl}-5-(pentafluoroethyl)[1,2,4]triazolo[1,5-a]pyrimidin-7-amine,
N-{1-[3-Fluoro-4-(trifluoromethyl)phenyl]cyclopropyl}-5-(methoxymethyl)[1,2,4]triazolo[1,5-a]pyrimidin-7-amine,
N-{(1R)-1-[3-Fluoro-4-(trifluoromethyl)phenyl]-2,2-dimethylpropyl}-5-(methoxymethyl)[1,2,4]triazolo[1,5-a]pyrimidin-7-amine,
N-{(1R)-1-[3-Fluoro-4-(trifluoromethyl)phenyl]ethyl}-5-(methoxymethyl)[1,2,4]triazolo[1,5-a]pyrimidin-7-amine,
[7-({1-[3-Fluoro-4-(trifluoromethyl)phenyl]cyclopropyl}amino)[1,2,4]triazolo[1,5-a]pyrimidin-5-yl]methanol,
[7-({(1R)-1-[3-Fluoro-4-(trifluoromethyl)phenyl]-2,2-dimethylpropyl}amino)[1,2,4]triazolo[1,5-a]pyrimidin-5-yl]methanol,
[7-({(1R)-1-[3-Fluoro-4-(trifluoromethyl)phenyl]ethyl}amino)[1,2,4]triazolo[1,5-a]pyrimidin-5-yl]methanol,
5-(Fluoromethyl)-N-{1-[3-fluoro-4-(trifluoromethyl)phenyl]cyclopropyl}[1,2,4]triazolo[1,5-a]pyrimidin-7-amine,
N-{1-[3-Fluoro-4-(trifluoromethyl)phenyl]cyclopropyl}-5-(trifluoromethyl)[1,2,4]triazolo[1,5-a]pyrimidin-7-amine,
N-{1-[4-(Trifluoromethyl)phenyl]ethyl}[1,2,4]triazolo[1,5-a]pyrimidin-7-amine,
N-{1-[4-(Trifluoromethoxy)phenyl]ethyl}[1,2,4]triazolo[1,5-a]pyrimidin-7-amine,
5,6-Dimethyl-N-{(1S)-1-[4-(trifluoromethyl)phenyl]ethyl}[1,2,4]triazolo[1,5-a]pyrimidin-7-amine,
5,6-Dimethyl-N-{(1R)-1-[4-(trifluoromethyl)phenyl]ethyl}[1,2,4]triazolo[1,5-a]pyrimidin-7-amine,
N-{1-[3-Fluoro-4-(trifluoromethyl)phenyl]cyclopropyl}-5,6-dimethyl[1,2,4]triazolo[1,5-a]pyrimidin-7-amine,
2-[(5-Methyl[1,2,4]triazolo[1,5-a]pyrimidin-7-yl)amino]-2-[4-(trifluoromethyl)phenyl]ethanol,
(1S,2R)-1-[(5-Methyl[1,2,4]triazolo[1,5-a]pyrimidin-7-yl)amino]-1-[4-(trifluoromethyl)phenyl]propan-2-ol,
(1S,2S)-1-[(5-Methyl[1,2,4]triazolo[1,5-a]pyrimidin-7-yl)amino]-1-[4-(trifluoromethyl)phenyl]propan-2-ol,
(1S)-1-[3-Fluoro-4-(trifluoromethoxy)phenyl]-2-methyl-1-[(5-methyl[1,2,4]triazolo[1,5-a]pyrimidin-7-yl)amino]propan-2-ol,
(1R)-1-[3-Fluoro-4-(trifluoromethoxy)phenyl]-2-methyl-1-[(5-methyl[1,2,4]triazolo[1,5-a]pyrimidin-7-yl)amino]propan-2-ol,
(1S)-1-[2-Fluoro-4-(trifluoromethoxy)phenyl]-2-methyl-1-[(5-methyl[1,2,4]triazolo[1,5-a]pyrimidin-7-yl)amino]propan-2-ol,
(1S)-2-Methyl-1-[(5-methyl[1,2,4]triazolo[1,5-a]pyrimidin-7-yl)amino]-1-[4-(trifluoromethyl)phenyl]propan-2-ol,
(1R)-2-Methyl-1-[(5-methyl[1,2,4]triazolo[1,5-a]pyrimidin-7-yl)amino]-1-[4-(trifluoromethyl)phenyl]propan-2-ol,
(1S)-2-Methyl-1-[(5-methyl[1,2,4]triazolo[1,5-a]pyrimidin-7-yl)amino]-1-[4-(trifluoromethoxy)phenyl]propan-2-ol,
(1R)-2-Methyl-1-[(5-methyl[1,2,4]triazolo[1,5-a]pyrimidin-7-yl)amino]-1-[4-(trifluoromethoxy)phenyl]propan-2-ol,
(1S)-1-[3-Fluoro-4-(trifluoromethyl)phenyl]-2-methyl-1-[(5-methyl[1,2,4]triazolo[1,5-a]pyrimidin-7-yl)amino]propan-2-ol,
(1R)-1-[3-Fluoro-4-(trifluoromethyl)phenyl]-2-methyl-1-[(5-methyl[1,2,4]triazolo[1,5-a]pyrimidin-7-yl)amino]propan-2-ol,
(1S)-1-[2-Chloro-4-(trifluoromethoxy)phenyl]-2-methyl-1-[(5-methyl[1,2,4]triazolo[1,5-a]pyrimidin-7-yl)amino]propan-2-ol,
(1S)-1-[2-Chloro-4-(trifluoromethoxy)phenyl]-2-methyl-1-{[5-(trifluoromethyl)[1,2,4]triazolo[1,5-a]pyrimidin-7-yl]amino}propan-2-ol,
(1S)-1-[3-Chloro-4-(trifluoromethoxy)phenyl]-2-methyl-1-[(5-methyl[1,2,4]triazolo[1,5-a]pyrimidin-7-yl)amino]propan-2-ol,
(1S)-1-[3-Chloro-4-(trifluoromethoxy)phenyl]-2-methyl-1-{[5-(trifluoromethyl)[1,2,4]triazolo[1,5-a]pyrimidin-7-yl]amino}propan-2-ol,
(1S)-1-[2-Chloro-4-(trifluoromethoxy)phenyl]-2-methyl-1-[(5-methyl[1,2,4]triazolo[1,5-a]pyrimidin-7-yl)amino]propan-2-ol,
(1R)-1-[2-Chloro-4-(trifluoromethyl)phenyl]-2-methyl-1-[(5-methyl[1,2,4]triazolo[1,5-a]pyrimidin-7-yl)amino]propan-2-ol,
(1S)-1-(4-tert-Butylphenyl)-2-methyl-1-[(5-methyl[1,2,4]triazolo[1,5-a]pyrimidin-7-yl)amino]propan-2-ol,
(1R)-1-(4-tert-Butylphenyl)-2-methyl-1-[(5-methyl[1,2,4]triazolo[1,5-a]pyrimidin-7-yl)amino]propan-2-ol,
(1S)-1-[4-(Difluoromethyl)phenyl]-2-methyl-1-[(5-methyl[1,2,4]triazolo[1,5-a]pyrimidin-7-yl)amino]propan-2-ol,
(1R)-1-[4-(Difluoromethyl)phenyl]-2-methyl-1-[(5-methyl[1,2,4]triazolo[1,5-a]pyrimidin-7-yl)amino]propan-2-ol,
(1S)-1-[4-(Difluoromethoxy)phenyl]-2-methyl-1-[(5-methyl[1,2,4]triazolo[1,5-a]pyrimidin-7-yl)amino]propan-2-ol,
(1R)-1-[4-(Difluoromethoxy)phenyl]-2-methyl-1-[(5-methyl[1,2,4]triazolo[1,5-a]pyrimidin-7-yl)amino]propan-2-ol,
(1S)-1-(2,2-Difluoro-1,3-benzodioxol-5-yl)-2-methyl-1-[(5-methyl[1,2,4]triazolo[1,5-a]pyrimidin-7-yl)amino]propan-2-ol,
(1R)-1-(2,2-Difluoro-1,3-benzodioxol-5-yl)-2-methyl-1-[(5-methyl[1,2,4]triazolo[1,5-a]pyrimidin-7-yl)amino]propan-2-ol,
(1S)-1-[2-Fluoro-4-(trifluoromethyl)phenyl]-2-methyl-1-[(5-methyl[1,2,4]triazolo[1,5-a]pyrimidin-7-yl)amino]propan-2-ol, (1R)-1-[2-Fluoro-4-(trifluoromethyl)phenyl]-2-methyl-1-[(5-methyl[1,2,4]triazolo[1,5-a]pyrimidin-7-yl)amino]propan-2-ol, (1S)-2-Methyl-1-[(5-methyl[1,2,4]triazolo[1,5-a]pyrimidin-7-yl)amino]-1-[4-(pentafluoro-$\lambda^6$-sulfanyl)phenyl]propan-2-ol, (1R)-2-Methyl-1-[(5-methyl[1,2,4]triazolo[1,5-a]pyrimidin-7-yl)amino]-1-[4-(pentafluoro-$\lambda^6$-sulfanyl)phenyl]propan-2-ol, (1S)-2-Methyl-1-[(5-methyl[1,2,4]triazolo[1,5-a]pyrimidin-7-yl)amino]-1-[4-(2,2,2-trifluoroethyl)phenyl]propan-2-ol, (1R)-2-Methyl-1-[(5-methyl[1,2,4]triazolo[1,5-a]pyrimidin-7-yl)amino]-1-[4-(2,2,2-trifluoroethyl)phenyl]propan-2-ol, (1S)-2-Methyl-1-[4-(1-methylcyclopropyl)phenyl]-1-[(5-methyl[1,2,4]triazolo[1,5-a]pyrimidin-7-yl)amino]propan-2-ol, (1R)-2-Methyl-1-[4-(1-methylcyclopropyl)phenyl]-1-[(5-methyl[1,2,4]triazolo[1,5-a]pyrimidin-7-yl)amino]propan-2-ol, (1S)-2-Methyl-1-[(5-methyl[1,2,4]triazolo[1,5-a]pyrimidin-7-yl)amino]-1-naphthalen-2-yl propan-2-ol, (1R)-2-Methyl-1-[(5-methyl[1,2,4]triazolo[1,5-a]pyrimidin-7-yl)amino]-1-naphthalen-2-yl propan-2-ol, (1S)-2-Methyl-1-(1-methyl-1H-indol-2-yl)-1-[(5-methyl[1,2,4]triazolo[1,5-a]pyrimidin-7-yl) amino]propan-2-ol, (1R)-2-Methyl-1-(1-methyl-1H-indol-2-yl)-1-[(5-methyl[1,2,4]triazolo[1,5-a]pyrimidin-7-yl) amino]propan-2-ol, (1S)-1-Biphenyl-4-yl-2-methyl-1-[(5-methyl[1,2,4]triazolo[1,5-a]pyrimidin-7-yl)amino]propan-2-ol, (1R)-1-Biphenyl-4-yl-2-methyl-1-[(5-methyl[1,2,4]triazolo[1,5-a]pyrimidin-7-yl)amino]propan-2-ol, (1S)-2-Methyl-1-[(5-methyl[1,2,4]triazolo[1,5-a]pyrimidin-7-yl)amino]-1-[2-methyl-4-(trifluoromethoxy)phenyl]propan-2-ol, (1R)-2-Methyl-1-[(5-methyl[1,2,4]triazolo[1,5-a]pyrimidin-7-yl)amino]-1-[2-methyl-4-(trifluoromethoxy)phenyl]propan-2-ol, (1S)-1-[4-fluoro-3-(Trifluoromethoxy)phenyl]-2-methyl-1-[(5-methyl[1,2,4]triazolo[1,5-a]pyrimidin-7-yl)amino]propan-2-ol, (1R)-1-[4-fluoro-3-(Trifluoromethoxy)phenyl]-2-methyl-1-[(5-methyl[1,2,4]triazolo[1,5-a]pyrimidin-7-yl)amino]propan-2-ol, (1S)-1-[(2,5-Dimethyl[1,2,4]triazolo[1,5-a]pyrimidin-7-yl)amino]-1-[3-fluoro-4-(trifluoromethoxy)phenyl]-2-methylpropan-2-ol, (1R)-1-[(2,5-Dimethyl[1,2,4]triazolo[1,5-a]pyrimidin-7-yl)amino]-1-[3-fluoro-4-(trifluoromethoxy)phenyl]-2-methylpropan-2-ol, (1S)-1-[(2,5-Dimethyl[1,2,4]triazolo[1,5-a]pyrimidin-7-yl)amino]-1-[2-fluoro-4-(trifluoromethoxy)phenyl]-2-methylpropan-2-ol, (1R)-1-[(2,5-Dimethyl[1,2,4]triazolo[1,5-a]pyrimidin-7-yl)amino]-1-[2-fluoro-4-(trifluoromethoxy)phenyl]-2-methylpropan-2-ol, (1S)-1-[2-Fluoro-4-(trifluoromethoxy)phenyl]-2-methyl-1-{[5-(1-methylethyl)[1,2,4]triazolo[1,5-a]pyrimidin-7-yl]amino}propan-2-ol, (1R)-1-[2-Fluoro-4-(trifluoromethoxy)phenyl]-2-methyl-1-{[5-(1-methylethyl)[1,2,4]triazolo[1,5-a]pyrimidin-7-yl]amino}propan-2-ol, (1S)-1-[3-Fluoro-4-(trifluoromethoxy)phenyl]-2-methyl-1-{[5-(1-methylethyl)[1,2,4]triazolo[1,5-a]pyrimidin-7-yl]amino}propan-2-ol, (1R)-1-[3-Fluoro-4-(trifluoromethoxy)phenyl]-2-methyl-1-{[5-(1-methylethyl)[1,2,4]triazolo[1,5-a]pyrimidin-7-yl]amino}propan-2-ol, (1S)-1-[(5-Cyclopropyl[1,2,4]triazolo[1,5-a]pyrimidin-7-yl)amino]-1-[3-fluoro-4-(trifluoromethoxy)phenyl]-2-methylpropan-2-ol, (1R)-1-[(5-Cyclopropyl[1,2,4]triazolo[1,5-a]pyrimidin-7-yl)amino]-1-[3-fluoro-4-(trifluoromethoxy)phenyl]-2-methylpropan-2-ol, (1S)-1-[(5-Cyclopropyl[1,2,4]triazolo[1,5-a]pyrimidin-7-yl)amino]-1-[2-fluoro-4-(trifluoromethoxy)phenyl]-2-methylpropan-2-ol, (1R)-1-[(5-Cyclopropyl[1,2,4]triazolo[1,5-a]pyrimidin-7-yl)amino]-1-[2-fluoro-4-(trifluoromethoxy)phenyl]-2-methylpropan-2-ol, (1S)-1-[(5-Cyclopropyl[1,2,4]triazolo[1,5-a]pyrimidin-7-yl)amino]-2-methyl-1-[4-(pentafluoro-$\lambda^6$-sulfanyl)phenyl]propan-2-ol, (1R)-1-[(5-Cyclopropyl[1,2,4]triazolo[1,5-a]pyrimidin-7-yl)amino]-2-methyl-1-[4-(pentafluoro-$\lambda^6$-sulfanyl)phenyl]propan-2-ol, (4R)-4-[3-Fluoro-4-(trifluoromethyl)phenyl]-2-methyl-4-[(5-methyl[1,2,4]triazolo[1,5-a]pyrimidin-7-yl)amino]butan-2-ol, (4S)-4-[3-Fluoro-4-(trifluoromethyl)phenyl]-2-methyl-4-[(5-methyl[1,2,4]triazolo[1,5-a]pyrimidin-7-yl)amino]butan-2-ol, (3R)-2-Methyl-3-[(5-methyl[1,2,4]triazolo[1,5-a]pyrimidin-7-yl)amino]-3[4-(trifluoromethoxy) phenyl]butan-2-ol, (3S)-2-Methyl-3-[(5-methyl[1,2,4]triazolo[1,5-a]pyrimidin-7-yl)amino]-3-[4-(trifluoromethoxy) phenyl]butan-2-ol, (1S)-2-Methyl-1-{[5-(1-methylethyl)[1,2,4]triazolo[1,5-a]pyrimidin-7-yl]amino}-1-[4-(trifluoromethyl)phenyl]propan-2-ol, (1S)-1-[(5-Cyclopropyl[1,2,4]triazolo[1,5-a]pyrimidin-7-yl)amino]-2-methyl-1-[4-(trifluoromethyl)phenyl]propan-2-ol, (1S)-1-[(5-tert-Butyl[1,2,4]triazolo[1,5-a]pyrimidin-7-yl)amino]-2-methyl-1-[4-(trifluoromethyl)phenyl]propan-2-ol, (1S)-1-[2-Chloro-4-(trifluoromethyl)phenyl]-2-methyl-1-{[5-(trifluoromethyl)[1,2,4]triazolo[1,5-a]pyrimidin-7-yl]amino}propan-2-ol, (1R)-1-[2-Chloro-4-(trifluoromethyl)phenyl]-2-methyl-1-{[5-(trifluoromethyl)[1,2,4]triazolo[1,5-a]pyrimidin-7-yl]amino}propan-2-ol, (1S)-1-(4-tert-Butylphenyl)-2-methyl-1-{[5-(trifluoromethyl)[1,2,4]triazolo[1,5-a]pyrimidin-7-yl]amino}propan-2-ol, (1R)-1-(4-tert-Butylphenyl)-2-methyl-1-{[5-(trifluoromethyl)[1,2,4]triazolo[1,5-a]pyrimidin-7-yl]amino}propan-2-ol, (1S)-1-[4-(Difluoromethyl)phenyl]-2-methyl-1-{[5-(trifluoromethyl)[1,2,4]triazolo[1,5-a]pyrimidin-7-yl]amino}propan-2-ol, (1R)-1-[4-(Difluoromethyl)phenyl]-2-methyl-1-{[5-(trifluoromethyl)[1,2,4]triazolo[1,5-a]pyrimidin-7-yl]amino}propan-2-ol, (1S)-1-[4-(Difluoromethoxy)phenyl]-2-methyl-1-{[5-(trifluoromethyl)[1,2,4]triazolo[1,5-a]pyrimidin-7-yl]amino}propan-2-ol, (1R)-1-[4-(Difluoromethoxy)phenyl]-2-methyl-1-{[5-(trifluoromethyl)[1,2,4]triazolo[1,5-a]pyrimidin-7-yl]amino}propan-2-ol,
(1S)-1-(2,2-Difluoro-1,3-benzodioxol-5-yl)-2-methyl-1-{[5-(trifluoromethyl)[1,2,4]triazolo[1,5-a]pyrimidin-7-yl]amino}propan-2-ol,
(1R)-1-(2,2-Difluoro-1,3-benzodioxol-5-yl)-2-methyl-1-{[5-(trifluoromethyl)[1,2,4]triazolo[1,5-a]pyrimidin-7-yl]amino}propan-2-ol,
(1S)-2-Methyl-1-[4-(2,2,2-trifluoroethyl)phenyl]-1-{[5-(trifluoromethyl)[1,2,4]triazolo[1,5-a]pyrimidin-7-yl]amino}propan-2-ol,
(1R)-2-Methyl-1-[4-(2,2,2-trifluoroethyl)phenyl]-1-{[5-(trifluoromethyl)[1,2,4]triazolo[1,5-a]pyrimidin-7-yl]amino}propan-2-ol,
(1S)-1-[2-Fluoro-4-(trifluoromethoxy)phenyl]-2-methyl-1-{[5-(trifluoromethyl)[1,2,4]triazolo [1,5-a]pyrimidin-7-yl]amino}propan-2-ol,
(1R)-1-[2-Fluoro-4-(trifluoromethoxy)phenyl]-2-methyl-1-{[5-(trifluoromethyl)[1,2,4]triazolo [1,5-a]pyrimidin-7-yl]amino}propan-2-ol,
(1S)-1-[2-Fluoro-4-(trifluoromethyl)phenyl]-2-methyl-1-{[5-(trifluoromethyl)[1,2,4]triazolo[1,5-a]pyrimidin-7-yl]amino}propan-2-ol,
(1R)-1-[2-Fluoro-4-(trifluoromethyl)phenyl]-2-methyl-1-{[5-(trifluoromethyl)[1,2,4]triazolo[1,5-a]pyrimidin-7-yl]amino}propan-2-ol,
(1S)-1-[3-Fluoro-4-(trifluoromethoxy)phenyl]-2-methyl-1-{[5-(trifluoromethyl)[1,2,4]triazolo [1,5-a]pyrimidin-7-yl]amino}propan-2-ol,
(1R)-1-[3-Fluoro-4-(trifluoromethoxy)phenyl]-2-methyl-1-{[5-(trifluoromethyl)[1,2,4]triazolo [1,5-a]pyrimidin-7-yl]amino}propan-2-ol,
(1S)-2-Methyl-1-[4-(pentafluoro-$\lambda^6$-sulfanyl)phenyl]-1-{[5-(trifluoromethyl)[1,2,4]triazolo[1,5-a]pyrimidin-7-yl]amino}propan-2-ol,
(1R)-2-Methyl-1-[4-(pentafluoro-$\lambda^6$-sulfanyl)phenyl]-1-{[5-(trifluoromethyl)[1,2,4]triazolo[1,5-a]pyrimidin-7-yl]amino}propan-2-ol,
(1S)-2-Methyl-1-[4-(1-methylcyclopropyl)phenyl]-1-{[5-(trifluoromethyl)[1,2,4]triazolo[1,5-a]pyrimidin-7-yl]amino}propan-2-ol,
(1R)-2-Methyl-1-[4-(1-methylcyclopropyl)phenyl]-1-{[5-(trifluoromethyl)[1,2,4]triazolo[1,5-a]pyrimidin-7-yl]amino}propan-2-ol,
(R)-1-[4-(Difluoromethoxy)-2-fluorophenyl]-1-{[5-(difluoromethyl)[1,2,4]triazolo[1,5-a]pyrimidin-7-yl]amino}-2-methylpropan-2-ol,
(S)-1-[4-(Difluoromethoxy)-2-fluorophenyl]-1-{[5-(difluoromethyl)[1,2,4]triazolo[1,5-a]pyrimidin-7-yl]amino}-2-methylpropan-2-ol,
(R)-1-[2-Chloro-4-(difluoromethoxy)phenyl]-1-{[5-(difluoromethyl)[1,2,4]triazolo[1,5-a]pyrimidin-7-yl]amino}-2-methylpropan-2-ol,
(S)-1-[2-Chloro-4-(difluoromethoxy)phenyl]-1-{[5-(difluoromethyl)[1,2,4]triazolo[1,5-a]pyrimidin-7-yl]amino}-2-methylpropan-2-ol,
(R)-1-{[5-(Difluoromethyl)[1,2,4]triazolo[1,5-a]pyrimidin-7-yl]amino}-1-[2-fluoro-4-(trifluoromethoxy)phenyl]-2-methylpropan-2-ol,
(S)-1-{[5-(Difluoromethyl)[1,2,4]triazolo[1,5-a]pyrimidin-7-yl]amino}-1-[2-fluoro-4-(trifluoromethoxy)phenyl]-2-methylpropan-2-ol,
(R)-1-{[5-(Difluoromethyl)[1,2,4]triazolo[1,5-a]pyrimidin-7-yl]amino}-1-[3-fluoro-4-(trifluoromethoxy)phenyl]-2-methylpropan-2-ol,
(S)-1-{[5-(Difluoromethyl)[1,2,4]triazolo[1,5-a]pyrimidin-7-yl]amino}-1-[3-fluoro-4-(trifluoromethoxy)phenyl]-2-methylpropan-2-ol,
(R)-1-[4-(Difluoromethoxy)-3-fluorophenyl]-1-{[5-(difluoromethyl)[1,2,4]triazolo[1,5-a]pyrimidin-7-yl]amino}-2-methylpropan-2-ol,
(S)-1-[4-(Difluoromethoxy)-3-fluorophenyl]-1-{[5-(difluoromethyl)[1,2,4]triazolo[1,5-a]pyrimidin-7-yl]amino}-2-methylpropan-2-ol,
2-(Fluoromethyl)-N-{(1R)-1-[3-fluoro-4-(trifluoromethyl)phenyl]-2,2-dimethylpropyl}-5-methyl[1,2,4]triazolo[1,5-a]pyrimidin-7-amine,
N-{1-[3-Fluoro-4-(trifluoromethyl)phenyl]cyclopropyl}-2,5-dimethyl[1,2,4]triazolo[1,5-a]pyrimidin-7-amine,
2-Ethyl-N-{1-[3-fluoro-4-(trifluoromethyl)phenyl]cyclopropyl}-5-methyl[1,2,4]triazolo[1,5-a]pyrimidin-7-amine,
N-{1-[3-Fluoro-4-(trifluoromethyl)phenyl]cyclopropyl}-5-methyl-2-propyl[1,2,4]triazolo[1,5-a]pyrimidin-7-amine,
2-Cyclopropyl-N-{1-[3-fluoro-4-(trifluoromethyl)phenyl]cyclopropyl}-5-methyl[1,2,4]triazolo [1,5-a]pyrimidin-7-amine,
[7-({1-[3-Fluoro-4-(trifluoromethyl)phenyl]cyclopropyl}amino)-5-methyl[1,2,4]triazolo[1,5-a]pyrimidin-2-yl]methanol,
2-(Fluoromethyl)-N-{1-[3-fluoro-4-(trifluoromethyl)phenyl]cyclopropyl}-5-methyl[1,2,4]triazolo [1,5-a]pyrimidin-7-amine,
N-{3-[3-Fluoro-4-(trifluoromethyl)phenyl]oxetan-3-yl}-5-methyl[1,2,4]triazolo[1,5-a]pyrimidin-7-amine
5-Methyl-N-{3 [4-(trifluoromethyl)phenyl]oxetan-3-yl}[1,2,4]triazolo[1,5-a]pyrimidin-7-amine,
2-(Difluoromethyl)-N-{1-[3-fluoro-4-(trifluoromethyl)phenyl]cyclopropyl}-5-methyl[1,2,4]triazolo [1,5-a]pyrimidin-7-amine,
N-{(1R)-1-[3-Fluoro-4-(trifluoromethyl)phenyl]-2,2-dimethylpropyl}-2,5-dimethyl[1,2,4]triazolo [1,5-a]pyrimidin-7-amine,
2-Ethyl-N-{(1R)-1-[3-fluoro-4-(trifluoromethyl)phenyl]-2,2-dimethylpropyl}-5-methyl [1,2,4]triazolo[1,5-a]pyrimidin-7-amine,
N-{(1R)-1-[3-Fluoro-4-(trifluoromethyl)phenyl]-2,2-dimethylpropyl}-5-methyl-2-propyl[1,2,4]triazolo[1,5-a]pyrimidin-7-amine,
2-Cyclopropyl-N-{(1R)-1-[3-fluoro-4-(trifluoromethyl)phenyl]-2,2-dimethylpropyl}-5-methyl [1,2,4]triazolo[1,5-a]pyrimidin-7-amine,
[7-({(1R)-1-[3-Fluoro-4-(trifluoromethyl)phenyl]-2,2-dimethylpropyl}amino)-5-methyl [1,2,4]triazolo[1,5-a]pyrimidin-2-yl]methanol,
2-(Difluoromethyl)-N-{(1R)-1-[3-fluoro-4-(trifluoromethyl)phenyl]-2,2-dimethylpropyl}-5-methyl [1,2,4]triazolo[1,5-a]pyrimidin-7-amine,
5-Chloro-N-{1-[3-fluoro-4-(trifluoromethyl)phenyl]cyclopropyl}[1,2,4]triazolo[1,5-a]pyrimidin-7-amine,
N-{(1S)-1-[3-Fluoro-4-(trifluoromethyl)phenyl]-2-methoxyethyl}-5-methyl[1,2,4]triazolo[1,5-a]pyrimidin-7-amine,
N-{(1R)-1-[3-Fluoro-4-(trifluoromethyl)phenyl]-2-methoxyethyl}-5-methyl[1,2,4]triazolo[1,5-a]pyrimidin-7-amine,
5-Methyl-N-{(1R)-2-methyl-1-[5-(trifluoromethyl)pyridin-2-yl]propyl}[1,2,4]triazolo[1,5-a]pyrimidin-7-amine, 5-Methyl-N-{(1S)-2-methyl-1-[5-(trifluoromethyl)pyridin-2-yl]propyl}[1,2,4]triazolo[1,5-a]pyrimidin-7-amine, (1R)-1-[3-Fluoro-4-(trifluoromethyl)phenyl]-2-methyl-1-{[5-(trifluoromethyl)[1,2,4]triazolo[1,5-a]pyrimidin-7-yl]amino}propan-2-ol, (1S)-1-[3-Fluoro-4-(trifluoromethyl)phenyl]-2-methyl-1-{[5-(trifluoromethyl)[1,2,4]triazolo[1,5-a]pyrimidin-7-yl]amino}propan-2-ol, 3-{(S)-[3-Fluoro-4-(trifluoromethyl)phenyl][(5-methyl[1,2,4]triazolo[1,5-a]pyrimidin-7-yl) amino]methyl}pentan-3-ol, 3-{(R)-[3-Fluoro-4-(trifluoromethyl)phenyl][(5-methyl[1,2,4]triazolo[1,5-a]pyrimidin-7-yl) amino]methyl}pentan-3-ol, N-{(1S)-1-[3-Fluoro-4-(trifluoromethyl)phenyl]-2-methoxyethyl}-5-(trifluoromethyl) [1,2,4]triazolo[1,5-a]pyrimidin-7-amine, N-{(1R)-1-[3-Fluoro-4-(trifluoromethyl)phenyl]-2-methoxyethyl}-5-(trifluoromethyl) [1,2,4]triazolo[1,5-a]pyrimidin-7-amine, 3-[(S)-[3-Fluoro-4-(trifluoromethyl)phenyl]{[5-(trifluoromethyl)[1,2,4]triazolo[1,5-a]pyrimidin-7-yl]amino}methyl]pentan-3-ol, 3-[(R)-[3-Fluoro-4-(trifluoromethyl)phenyl]{[5-(trifluoromethyl)[1,2,4]triazolo[1,5-a]pyrimidin-7-yl]amino}methyl]pentan-3-ol, (1S)-2-Methyl-1-{4-[(trifluoromethyl)sulfanyl]phenyl}-1-{[5-(trifluoromethyl)[1,2,4]triazolo[1,5-a]pyrimidin-7-yl]amino}propan-2-ol, (1R)-2-Methyl-1-{4-[(trifluoromethyl)sulfanyl]phenyl}-1-{[5-(trifluoromethyl)[1,2,4]triazolo [1,5-a]pyrimidin-7-yl]amino}propan-2-ol, (1R)-1-[(5-Chloro[1,2,4]triazolo[1,5-a]pyrimidin-7-yl)amino]-1-[3-fluoro-4-(trifluoromethyl)phenyl]-2-methylpropan-2-ol, (1S)-1-[(5-Chloro[1,2,4]triazolo[1,5-a]pyrimidin-7-yl)amino]-1-[3-fluoro-4-(trifluoromethyl) phenyl]-2-methylpropan-2-ol, (1S)-2-Methyl-1-[(5-methyl[1,2,4]triazolo[1,5-a]pyrimidin-7-yl)amino]-1-[6-(trifluoromethyl) pyridin-3-yl]propan-2-ol, (1R)-2-Methyl-1-[(5-methyl[1,2,4]triazolo[1,5-a]pyrimidin-7-yl)amino]-1-[6-(trifluoromethyl) pyridin-3-yl]propan-2-ol, (1S)-1-{[5-(Difluoromethyl)[1,2,4]triazolo[1,5-a]pyrimidin-7-yl]amino}-1-[3-fluoro-4-(trifluoromethyl)phenyl]-2-methylpropan-2-ol, (1R)-1-{[5-(Difluoromethyl)[1,2,4]triazolo[1,5-a]pyrimidin-7-yl]amino}-1-[3-fluoro-4-(trifluoromethyl)phenyl]-2-methylpropan-2-ol, N—[(R)-[3-Fluoro-4-(trifluoromethoxy)phenyl](oxetan-3-yl)methyl]-5-methyl[1,2,4]triazolo[1,5-a]pyrimidin-7-amine, N—[(S)-[3-Fluoro-4-(trifluoromethoxy)phenyl](oxetan-3-yl)methyl]-5-methyl[1,2,4]triazolo[1,5-a]pyrimidin-7-amine, (R)-3-[3-Fluoro-4-(trifluoromethoxy)phenyl]-2,2-dimethyl-3-[(5-methyl[1,2,4]triazolo[1,5-a]pyrimidin-7-yl)amino]propan-1-ol, (S)-3-[3-Fluoro-4-(trifluoromethoxy)phenyl]-2,2-dimethyl-3-[(5-methyl[1,2,4]triazolo[1,5-a]pyrimidin-7-yl)amino]propan-1-ol, N-{(1R)-1-[3-Fluoro-4-(trifluoromethyl)phenyl]-2,2-dimethylpropyl}-5-methoxy[1,2,4]triazolo [1,5-a]pyrimidin-7-amine, 5-Ethoxy-N-{(1R)-1-[3-fluoro-4-(trifluoromethyl)phenyl]-2,2-dimethylpropyl}[1,2,4]triazolo [1,5-a]pyrimidin-7-amine, N-{1-[3-Fluoro-4-(trifluoromethyl)phenyl]cyclopropyl}-5-methoxy[1,2,4]triazolo[1,5-a]pyrimidin-7-amine, (1S)-1-[3-Fluoro-4-(trifluoromethyl)phenyl]-1-[(5-methoxy[1,2,4]triazolo[1,5-a]pyrimidin-7-yl) amino]-2-methylpropan-2-ol, (1R)-1-[3-Fluoro-4-(trifluoromethyl)phenyl]-1-[(5-methoxy[1,2,4]triazolo[1,5-a]pyrimidin-7-yl) amino]-2-methylpropan-2-ol, 7-({(1R)-1-[3-Fluoro-4-(trifluoromethyl)phenyl]-2,2-dimethylpropyl}amino)[1,2,4]triazolo[1,5-a]pyrimidin-5-ol, $N^7$-{1-[3-Fluoro-4-(trifluoromethyl)phenyl]cyclopropyl}-$N^5$~,$N$~5~-dimethyl[1,2,4]triazolo [1,5-a]pyrimidine-5,7-diamine, $N^7$-{(1R)-1-[3-Fluoro-4-(trifluoromethyl)phenyl]-2,2-dimethylpropyl}[1,2,4]triazolo[1,5-a]pyrimidine-5,7-diamine, $N^7$-{(1R)-1-[3-Fluoro-4-(trifluoromethyl)phenyl]-2,2-dimethylpropyl}-$N^5$-methyl[1,2,4]triazolo [1,5-a]pyrimidine-5,7-diamine, $N^7$-{(1R)-1-[3-Fluoro-4-(trifluoromethyl)phenyl]-2,2-dimethylpropyl}-$N^5$,$N^5$-dimethyl [1,2,4]triazolo[1,5-a]pyrimidine-5,7-diamine, (1S)-1-{[5-(Dimethylamino)[1,2,4]triazolo[1,5-a]pyrimidin-7-yl]amino}-1-[3-fluoro-4-(trifluoromethyl)phenyl]-2-methylpropan-2-ol, (1R)-1-{[5-(Dimethylamino)[1,2,4]triazolo[1,5-a]pyrimidin-7-yl]amino}-1-[3-fluoro-4-(trifluoromethyl)phenyl]-2-methylpropan-2-ol, 3-[7-({1-[3-Fluoro-4-(trifluoromethyl)phenyl]cyclopropyl}amino)[1,2,4]triazolo[1,5-a]pyrimidin-5-yl]propan-1-01, N-{1-[3-Fluoro-4-(trifluoromethyl)phenyl]cyclopropyl}-N, 5-dimethyl[1,2,4]triazolo[1,5-a]pyrimidin-7-amine, (R)-1-[3-Fluoro-4-(trifluoromethoxy)phenyl]-2-methyl-1-[methyl(5-methyl[1,2,4]triazolo[1,5-a]pyrimidin-7-yl)amino]propan-2-ol, (S)-1-[3-Fluoro-4-(trifluoromethoxy)phenyl]-2-methyl-1-[methyl(5-methyl[1,2,4]triazolo[1,5-a]pyrimidin-7-yl)amino]propan-2-ol, 3[7-({(1R)-1-[3-Fluoro-4-(trifluoromethyl)phenyl]-2,2-dimethylpropyl}amino)-5-methyl [1,2,4]triazolo[1,5-a]pyrimidin-2-yl]propan-1-ol, 2-[7-({(1R)-1-[3-Fluoro-4-(trifluoromethyl)phenyl]-2,2-dimethylpropyl}amino)-5-methyl [1,2,4]triazolo[1,5-a]pyrimidin-2-yl]ethanol, 2-[7-({1-[3-Fluoro-4-(trifluoromethyl)phenyl]cyclopropyl}amino)[1,2,4]triazolo[1,5-a]pyrimidin-5-yl]ethanol, 1-[3-Fluoro-4-(trifluoromethyl)phenyl]-2-methyl-M--(5-methyl[1,2,4]triazolo[1,5-a]pyrimidin-7-yl) propane-1, 2-diamine, (1S)-1-[3-Fluoro-4-(trifluoromethyl)phenyl]-2-methyl-$N^1$-[5-(trifluoromethyl)[1,2,4]triazolo[1,5-a]pyrimidin-7-yl]propane-1,2-diamine, (1R)-1-[3-Fluoro-4-(trifluoromethyl)phenyl]-2-methyl-$N^1$-[5-(trifluoromethyl)[1,2,4]triazolo[1,5-a]pyrimidin-7-yl]propane-1,2-diamine, $N^7$-{1-[3-Fluoro-4-(trifluoromethyl)phenyl]cyclopropyl}-5-methyl[1,2,4]triazolo[1,5-a]pyrimidine-2,7-diamine, $N^7$-{1-[3-Fluoro-4-(trifluoromethyl)phenyl]cyclopropyl}-$N^2$,$N^2$, 5-trimethyl[1,2,4]triazolo[1,5-a]pyrimidine-2,7-diamine, N⁷-{1-[3-Fluoro-4-(trifluoromethyl)phenyl]cyclopropyl}-N²,5-dimethyl[1,2,4]triazolo[1,5-a]pyrimidine-2,7-diamine,
(1S)-1-[(2-Amino-5-methyl[1,2,4]triazolo[1,5-a]pyrimidin-7-yl)amino]-1-[2-fluoro-4-(trifluoromethoxy)phenyl]-2-methylpropan-2-ol,
N-{(1R)-1-[4-(Pentafluoro-λ⁶-sulfanyl)phenyl]ethyl}[1,2,4]triazolo[5,1-a][1,2,4]triazin-4-amine,
(R)-7-{2,2-Dimethyl-1-[4-(trifluoromethyl)phenyl]propoxy}-5-methyl[1,2,4]triazolo[1,5-a]pyrimidine,
(R)-7-{2,2-Dimethyl-1-[4-(trifluoromethyl)phenyl]propoxy}-5-methyl[1,2,4]triazolo[1,5-a]pyrimidine,
5-Methyl-7-({1-[4-(trifluoromethyl)phenyl]cyclopropyl}oxy)[1,2,4]triazolo[1,5-a]pyrimidine,
N-{1-[3-Fluoro-4-(trifluoromethyl)phenyl]cyclopropyl}-7-methyl[1,2,4]triazolo[1,5-a]pyridin-5-amine,
N-{(1R)-1-[3-Fluoro-4-(trifluoromethyl)phenyl]-2,2-dimethylpropyl}-7-methyl[1,2,4]triazolo [1,5-a]pyridin-5-amine,
(1S)-2-Methyl-1-[(7-methyl[1,2,4]triazolo[1,5-a]pyridin-5-yl)amino]-1-[4-(trifluoromethyl) phenyl]propan-2-ol,
[5-({1-[3-Fluoro-4-(trifluoromethyl)phenyl]cyclopropyl}amino)[1,2,4]triazolo[1,5-a]pyridin-7-yl]methanol,
[5-({(1R)-1-[4-(Trifluoromethyl)phenyl]ethyl}amino)[1,2,4]triazolo[1,5-a]pyridin-7-yl]methanol,
[5-({(1S)-1-[4-(Trifluoromethyl)phenyl]ethyl}amino)[1,2,4]triazolo[1,5-a]pyridin-7-yl]methanol,
[5-({(1R)-1-[3-Fluoro-4-(trifluoromethyl)phenyl]propyl}amino)[1,2,4]triazolo[1,5-a]pyridin-7-yl]methanol,
[5-({1-[2-Fluoro-4-(trifluoromethyl)phenyl]cyclopropyl}amino)[1,2,4]triazolo[1,5-a]pyridin-7-yl]methanol,
[5-({(1R)-1-[4-(Trifluoromethoxy)phenyl]ethyl}amino)[1,2,4]triazolo[1,5-a]pyridin-7-yl]methanol,
[5-({(1R)-1-[3-Fluoro-4-(trifluoromethyl)phenyl]ethyl}amino)[1,2,4]triazolo[1,5-a]pyridin-7-yl]methanol,
(1S)-1-[2-Fluoro-4-(trifluoromethoxy)phenyl]-1-{[7-(hydroxymethyl) [1,2,4]triazolo[1,5-a]pyridin-5-yl]amino}-2-methylpropan-2-ol,
7-(Difluoromethyl)-N-{1-[3-fluoro-4-(trifluoromethyl)phenyl]cyclopropyl}[1,2,4]triazolo[1,5-a]pyridin-5-amine,
1-[5-({1-[3-Fluoro-4-(trifluoromethyl)phenyl]cyclopropyl}amino)[1,2,4]triazolo[1,5-a]pyridin-7-yl]ethanol,
N-{1-[3-Fluoro-4-(trifluoromethyl)phenyl]cyclopropyl}-7-(trifluoromethyl)[1,2,4]triazolo[1,5-a]pyridin-5-amine,
(1S)-2-Methyl-1-[4-(trifluoromethyl)phenyl]-1-{[7-(trifluoromethyl)[1,2,4]triazolo[1,5-a]pyridin-5-yl]amino}propan-2-ol,
(1S)-1-[2-Fluoro-4-(trifluoromethoxy)phenyl]-2-methyl-1-{[7-(trifluoromethyl)[1,2,4]triazolo [1,5-a]pyridin-5-yl]amino}propan-2-ol,
(1S)-1-{[7-(Difluoromethyl)[1,2,4]triazolo[1,5-a]pyridin-5-yl]amino}-1-[3-fluoro-4-(trifluoromethoxy)phenyl]-2-methylpropan-2-ol,
(1S)-1-{[7-(Difluoromethyl)[1,2,4]triazolo[1,5-a]pyridin-5-yl]amino}-2-methyl-1-[4-(trifluoromethyl)phenyl]propan-2-ol,
(1S)-1-{[7-(Difluoromethyl)[1,2,4]triazolo[1,5-a]pyridin-5-yl]amino}-1-[2-fluoro-4-(trifluoromethoxy)phenyl]-2-methylpropan-2-ol,
(1S)-1-{[7-(Difluoromethyl)[1,2,4]triazolo[1,5-a]pyridin-5-yl]amino}-2-methyl-1-[4-(pentafluoro-λ⁶-sulfanyl)phenyl]propan-2-ol,
(1R)-1-{[7-(Difluoromethyl)[1,2,4]triazolo[1,5-a]pyridin-5-yl]amino}-2-methyl-1-[4-(pentafluoro-λ⁶-sulfanyl)phenyl]propan-2-ol,
N{-(1R)-1-[3-Fluoro-4-(trifluoromethyl)phenyl]-2,2-dimethylpropyl}[1,2,4]triazolo[1,5-a]pyrazin-5-amine,
N-{1-[3-Fluoro-4-(trifluoromethyl)phenyl]cyclopropyl}[1,2,4]triazolo[1,5-a]pyrazin-5-amine,
(1S)-1-[3-Fluoro-4-(trifluoromethoxy)phenyl]-2-methyl-1-([1,2,4]triazolo[1,5-a]pyrazin-5-ylamino)propan-2-ol,
(1S)-2-Methyl-1-([1,2,4]triazolo[1,5-a]pyrazin-5-ylamino)-1-[4-(trifluoromethyl)phenyl]propan-2-ol,
N-{(1R)-1-[4-(Trifluoromethyl)phenyl]ethyl}[1,2,4]triazolo[1,5-a]pyrazin-5-amine,
N-{1-[4-(Pentafluoro-λ⁶-sulfanyl)phenyl]cyclopropyl}[1,2,4]triazolo[1,5-a]pyrazin-5-amine,
(1S)-1-[3-Fluoro-4-(trifluoromethyl)phenyl]-2-methyl-1-[(7-methyl[1,2,4]triazolo[1,5-a]pyrimidin-5-yl)amino]propan-2-ol,
(1R)-1-[3-Fluoro-4-(trifluoromethyl)phenyl]-2-methyl-1-[(7-methyl[1,2,4]triazolo[1,5-a]pyrimidin-5-yl)amino]propan-2-ol,
N-{1-[3-Fluoro-4-(trifluoromethyl)phenyl]cyclopropyl}-7-methyl[1,2,4]triazolo[1,5-a]pyrimidin-5-amine,
(1S)-14 [2-Amino-7-(trifluoromethyl)[1,2,4]triazolo[1,5-a]pyridin-5-yl]amino-2-methyl-1-[4-(trifluoromethyl)phenyl]propan-2-ol,
or a pharmaceutically acceptable salt thereof.

8. A pharmaceutical composition which comprises a pharmaceutically acceptable carrier and a compound of claim 1 or a pharmaceutically acceptable salt thereof.

* * * * *